United States Patent
Fan et al.

(10) Patent No.: US 10,287,292 B2
(45) Date of Patent: *May 14, 2019

(54) CXCR7 ANTAGONISTS

(71) Applicant: CHEMOCENTRYX, INC., Mountain View, CA (US)

(72) Inventors: Junfa Fan, Foster City, CA (US); Antoni Krasinski, Sunnyvale, CA (US); Christopher W. Lange, El Cerrito, CA (US); Rebecca M. Lui, Santa Clara, CA (US); Jeffrey P. McMahon, San Francisco, CA (US); Jay P. Powers, Pacifica, CA (US); Yibin Zeng, Foster City, CA (US); Penglie Zhang, Foster City, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/692,739

(22) Filed: Aug. 31, 2017

(65) Prior Publication Data

US 2018/0086766 A1    Mar. 29, 2018

Related U.S. Application Data

(63) Continuation of application No. 14/836,172, filed on Aug. 26, 2015, now Pat. No. 9,783,544, which is a continuation of application No. 14/091,641, filed on Nov. 27, 2013, now Pat. No. 9,169,261.

(60) Provisional application No. 61/731,463, filed on Nov. 29, 2012.

(51) Int. Cl.
C07D 487/04 (2006.01)
A61K 51/04 (2006.01)
G01N 33/574 (2006.01)

(52) U.S. Cl.
CPC ........ *C07D 487/04* (2013.01); *A61K 51/0459* (2013.01); *G01N 33/57492* (2013.01); *G01N 2333/7158* (2013.01)

(58) Field of Classification Search
CPC .............. A61K 31/4709; A61K 31/454; A61K 31/4162; A61K 49/10; A61K 51/0459
See application file for complete search history.

(56) References Cited

U.S. PATENT DOCUMENTS

| | | |
|---|---|---|
| 9,169,261 B2 | 10/2015 | Fan et al. |
| 9,783,544 B2 | 10/2017 | Fan et al. |
| 2005/0043367 A1 | 2/2005 | Bridger et al. |
| 2006/0074071 A1 | 4/2006 | Melikian et al. |
| 2007/0021484 A1 | 1/2007 | Melikian et al. |
| 2007/0167443 A1 | 7/2007 | Melikian et al. |
| 2007/0254915 A1 | 11/2007 | Leleti et al. |
| 2007/0275965 A1 | 11/2007 | Thomas et al. |
| 2009/0022717 A1 | 1/2009 | Premack et al. |
| 2010/0150831 A1 | 6/2010 | Chen et al. |

FOREIGN PATENT DOCUMENTS

| | | |
|---|---|---|
| WO | 97/36893 A1 | 10/1997 |
| WO | 2001/002392 A1 | 1/2001 |
| WO | 2008/020229 A2 | 2/2008 |
| WO | 2008/020229 A3 | 2/2008 |
| WO | 2010/069684 A1 | 6/2010 |
| WO | 2012/022265 A1 | 2/2012 |

OTHER PUBLICATIONS

International Search Report and Written Opinion corresponding to PCT Application No. PCT/US2013/072067 dated Apr. 4, 2014; 12 pages.
Extended European Search Report corresponding to EP Application No. 13859147.4 dated May 17, 2016; 7 pages.

*Primary Examiner* — Michael G. Hartley
*Assistant Examiner* — Jagadishwar R Samala
(74) *Attorney, Agent, or Firm* — Mintz Levin Cohn Ferris Glovsky and Popeo PC

(57) ABSTRACT

Compounds having formula I,

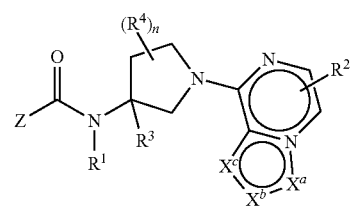

or pharmaceutically acceptable salts, hydrates or N-oxides thereof are provided and are useful for binding to CXCR7, and treating diseases that are dependent, at least in part, on CXCR7 activity. Accordingly, the present invention provides in further aspects, compositions containing one or more of the above-noted compounds in admixture with a pharmaceutically acceptable excipient.

7 Claims, No Drawings

Specification includes a Sequence Listing.

CXCR7 ANTAGONISTS

CROSS-REFERENCES TO RELATED APPLICATIONS

This application is a continuation of U.S. application Ser. No. 14/836,172 filed Aug. 26, 2015, which application is a continuation of U.S. patent application Ser. No. 14/091,641 filed Nov. 27, 2013 (now U.S. Pat. No. 9,169,261), which application claims the benefit of priority to U.S. Provisional Application Ser. No. 61/731,463 filed Nov. 29, 2012, each of which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

The Sequence Listing written in file-SequenceListing_085236-009911US-0956502.txt, created on Jan. 28, 2016, 4,447 bytes, machine format IBM-PC, MS-Windows operating system, is hereby incorporated by reference in its entirety for all purposes.

BACKGROUND OF THE INVENTION

The present invention is directed to novel compounds and pharmaceutical compositions that inhibit the binding of the SDF-1 chemokine (also known as the CXCL12 chemokine) or I-TAC (also known as CXCL11) to the chemokine receptor CXCR7. These compounds are useful in preventing tumor cell proliferation, tumor formation, tumor vascularization, metastasis, inflammatory diseases including, but not limited to arthritis, renal inflammatory disorders and multiple sclerosis, conditions of improper vascularization including, but not limited to wound healing, treatment of HIV infectivity, and treatment of stem cell differentiation and mobilization disorders (see also, co-pending U.S. Ser. Nos. 10/912,638, 11/407,729 and 11/050,345).

Chemokines are a superfamily of small, cytokine-like proteins that induce cytoskeletal rearrangement, firm adhesion to endothelial cells, and directional migration and may also effect cell activation and proliferation. Chemokines act in a coordinated fashion with cell surface proteins to direct the specific homing of various subsets of cells to specific anatomical sites.

Early research efforts by a number of groups have indicated a role for the chemokine receptor CXCR4 in metastasis and tumor growth. Muller, et al., "Involvement of Chemokine Receptors in Breast Cancer Metastasis," Nature, 410:50-56 (2001) demonstrated that breast tumor cells use chemokine-mediated mechanisms, such as those regulating leukocyte trafficking, during the process of metastasis. Tumor cells express a distinct, non-random pattern of functionally active chemokine receptors. Signaling through CXCR4 mediates actin polymerization and pseudopodia formation in breast cancer cells, and induces chemotactic and invasive responses. Additionally, the organs representing the main sites of breast cancer metastasis (such as lymph nodes, bone marrow, and lungs) are the most abundant sources of ligand for the CXCR4 receptor.

Using immunodeficient mice, Muller and colleagues succeeded in reducing the metastasis of injected human breast cancer cells by treating mice with an antibody known to bind CXCR4. Their finding suggests that breast cancer metastasis could be reduced by treating a patient with a CXCR4 antagonist.

Bertolini, et al., "CXCR4 Neutralization, a Novel Therapeutic Approach for Non-Hodgkin's Lymphoma," Cancer Research, 62:3106-3112 (2002) demonstrated a reduction of tumor volume as well as prolonged survival of immunodeficient mice injected with human lymphoma cells treated with anti-CXCR4 antibodies. They interpreted their finding to mean that tumor volume could be reduced by treating a patient with a CXCR4 antagonist.

More recent studies suggest that another chemokine receptor, CXCR7, may also be a target in the treatment of cancer. CXCR7 is preferentially expressed in transformed cells over normal cells, with detectable expression in a number of human cancers. In vitro studies indicate that proliferation of CXCR7 expressing cells can be inhibited by an antagonist of CXCR7. In vivo studies in mice indicate that CXCR7 antagonists can inhibit tumor formation and tumor growth.

The potential importance of CXCR7 is illustrated by an alternative interpretation of the reduction in tumor volume seen by Bertolini and colleagues. This reduction could clearly be the result of an antibody-mediated clearance, and not the result of the anti-CXCR4 antibody as originally believed. In an antibody-mediated clearance, any antibody that recognized a protein on the cell surface of the lymphoma cells would have had the same effect as that attributed to the anti-CXCR4 antibody. Unfortunately, Bertolini and colleagues studies are inconclusive as to whether the observed tumor response was due to antibody-mediated clearance or interaction with CXCR4.

However it is now known that the lymphoma cells used by Bertolini and colleagues express both CXCR4 and CXCR7. SDF-1 is the only ligand for CXCR4. SDF-1 and I-TAC both bind CXCR7. Using anti-SDF-1 antibody, it has now been shown that antagonists of CXCR7 are responsible for the reduction in tumor load and increased survival rate. Because SDF-1 is the only ligand for CXCR4, one would expect neutralization of SDF-1 with anti-SDF-1 antibody would be equivalent to the neutralization of CXCR4 with anti-CXCR4 antibody. However, experiments using an anti-SDF-1 antibody demonstrated only a partial reduction in tumor load and an increased survival rate. As a result, CXCR7 is the likely target, as the continued activity appears due to the interactions of the second ligand, I-TAC, with CXCR7.

Until recently, the possible importance of CXCR7 in tumor cell proliferation, tumor growth, and metastasis was unknown. Now, evidence points to the ability of certain CXCR7 antagonists to prevent the growth and spread of cancer, and expression patterns indicate a limited tissue distribution for the CXCR7 receptor which correlates to tumorigenesis.

Moreover, it has been discovered that CXCR7 can serve as a co-receptor for certain genetically divergent human immunodeficiency virus (HIV) and simian immunodeficiency virus (SIV), in particular for the HIV-2-ROD, an X4-tropic isolate (Shimizu. N. et al., *J Virol.*, (2000) 74: 619-626; Balabanian, K., et al., *J. Biol. Chem.*, in press; published on Aug. 17, 2005 as Manuscript M508234200).

Still further, SDF-1, has been described to have a role in the mobilization of hematopoietic progenitor cells and stem cells, and in particular of those cells bearing the CXCR4 receptor, from specific hematopoietic tissues including bone marrow has been described (Hattori, K., et al., *Blood*, (2000) 97:3354-3360; WO 2005/000333, the disclosure of which are incorporated herein by reference). More recent studies suggest that the CXCR7 receptor may also play a part in stem cell mobilization processes.

In view of the above, it is apparent that compounds that are able to bind specifically to CXCR7 receptors can be useful for treating diseases and other biological conditions that may benefit from such interactions. The present invention provides such compounds along with pharmaceutical compositions and related methods for treatment.

BRIEF SUMMARY OF THE INVENTION

The present invention provides, in one aspect, compounds having formula I,

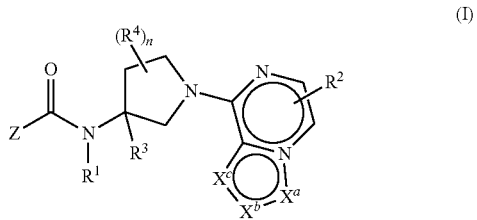

or pharmaceutically acceptable salts, hydrates or N-oxides thereof. The various groups (e.g., $R^1$, $R^2$, $R^3$, $R^4$, Z, $X^a$, $X^b$, $X^c$ and the subscript n) are described in the Detailed Description of the Invention.

The compounds provided herein are useful for binding to CXCR7, and treating diseases that are dependent, at least in part, on CXCR7 activity. Accordingly, the present invention provides in further aspects, compositions containing one or more of the above-noted compounds in admixture with a pharmaceutically acceptable excipient.

In still another aspect, the present invention provides methods for treating various diseases, discussed further herein, comprising administering to a subject in need to such treatment a therapeutically effective amount of a compound of the above formula for a period of time sufficient to treat the disease.

In yet another aspect, the present invention provides methods of diagnosing disease in an individual. In these methods, the compounds provided herein are administered in labeled form to a subject, followed by diagnostic imaging to determine the presence or absence of CXCR7. In a related aspect, a method of diagnosing disease is carried out by contacting a tissue or blood sample with a labeled compound as provided herein and determining the presence, absence, or amount of CXCR7 in the sample.

In some embodiments, an amount of a chemotherapeutic agent or radiation is administered to the subject prior to, subsequent to or in combination with the compounds of the present invention. In some embodiments, the amount is sub-therapeutic when the chemotherapeutic agent or radiation is administered alone.

BRIEF DESCRIPTION OF THE DRAWINGS

Not Applicable

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "cycloalkenyl" refers to a cycloalkyl group having at least one double bond between ring vertices. Examples of cycloalkenyl are cyclopentenyl and cyclohexenyl. The term "spirocycloalkyl" refers to a cycloalkyl group in which a single ring vertex is attached to two other non-hydrogen portions of the molecule. A spirocycloalkyl substituent is one in which two carbon atoms of an alkylene chain (typically the termini of the alkylene chain) are attached to the same carbon atom in the remainder of the molecule. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

Similarly, "alkenylene" and "alkynylene" refer to the unsaturated forms of "alkylene" having double or triple bonds, respectively.

As used herein, a wavy line, "〜", that intersects a single, double or triple bond in any chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroaryl-alkyl" is meant to include those radicals in which a heteroaryl group is attached to an alkyl group (e.g., pyridylmethyl, thiazolylethyl, and the like).

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

As used herein, the term "progenitor cells" and "stem cells" are used interchangeably. "Progenitor cells" and "stem cells" refer to cells that, in response to certain stimuli, can form differentiated cell lineages, including but not limited to hematopoietic, mesenchymal, epithelial, neuronal, renal or myeloid cells. The presence of progenitor/stem cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies which can be obtained in culture using known protocols. Hematopoetic progenitor/stem cells are often positive for CD34. Some stem cells do not contain this marker, however. These CD34+ cells can be assayed using fluorescence activated cell sorting (FACS) and thus their presence can be assessed in a sample using this technique. Alternatively, such cells can be assayed by FACS for the presence of c-kit receptor (CD117), absence of lineage specific markers (e.g., CD2, CD3, CD4, CD5, CD8, NK1.1, B220, TER-119, and Gr-1 in mice and CD3, CD14, CD16, CD19, CD20 and CD56 in humans).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge. S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. In some embodiments, the compounds of the invention are present in an enantiomerically enriched form, wherein the amount of enantiomeric excess for a particular enantiomer is calculated by known methods. The preparation of enantiomerically enriched forms is also well known in the art and can be accomplished using, for example, chiral resolution via chromatography or via chiral salt formation. Additionally, different conformers are contemplated by the present invention, as well as distinct rotamers. Conformers are conformational isomers that can differ by rotations about one or more a bonds. Rotamers are conformers that differ by rotation about only a single a bond. Still further, the compounds of the present invention may also contain unnatural proportions of atomic isotopes at one or more of the atoms that constitute such compounds. Accordingly, in some embodiments, the compounds of the invention are present in isotopically enriched form. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

"CXCR7" also referred to as "RDC1" or "CCXCKR2" refers to a seven-transmembrane domain presumed G-protein coupled receptor (GPCR). The CXCR7 dog ortholog was originally identified in 1991. See, Libert et al. *Science* 244:569-572 (1989). The dog sequence is described in Libert et al., *Nuc. Acids Res.* 18(7):1917 (1990). The mouse sequence is described in, e.g., Heesen et al., *Immunogenetics* 47:364-370 (1998). The human sequence is described in, e.g., Sreedharan et al., *Proc. Natl. Acad Sci. USA* 88:4986-4990 (1991), which mistakenly described the protein as a receptor of vasoactive intestinal peptide. "CXCR7" includes sequences that are substantially similar to or conservatively modified variants of SEQ ID NO:1. SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO: 10.

II. General

Compounds of the present invention can inhibit the binding of ligands to the CXCR7 receptor and are useful in the treatment of various diseases, including cancer, particularly solid tumor cancers and lymphomas. More recently, the inhibition of ligand binding to CXCR7 was noted to reduce the severity of rheumatoid arthritis in an animal model.

Those of skill in the art will understand that agents that modulate CCX-CKR2 activity (CXCR7 activity) can be combined in treatment regimens with other anti-angiogenesis agents and/or with chemotherapeutic agents or radiation and/or other anti-arthritis agents. In some cases, the amount of chemotherapeutic agent or radiation is an amount which would be sub-therapeutic if provided without combination with an anti-angiogenic agent. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current invention may be administered prior to or subsequent to a second therapeutic regimen, for instance prior to or subsequent to a dose of chemotherapy or irradiaition.

III. Embodiments of the Invention

A. Compounds

The present invention provides, in one aspect, compounds having formula I,

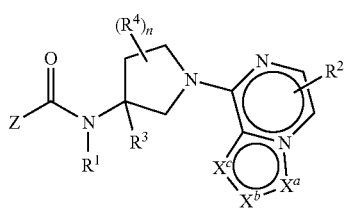

(I)

or pharmaceutically acceptable salts, hydrates, N-oxides, isotopically enriched or enantiomerically enriched versions and rotamers thereof. In formula I, each of ring vertices $X^a$, $X^b$ and $X^c$ is independently selected from N, NH, N($R^2$), O, CH and C($R^2$). Additionally, the subscript n is 0, 1 or 2. The letter Z represents a group selected from:
  (i) monocyclic or fused-bicyclic aryl and heteroaryl, wherein the heteroaryl group has from 1-4 heteroatoms as ring members selected from N, O and S; and wherein said aryl and heteroaryl groups are optionally substituted with from 1 to 5 $R^5$ substituents;
  (ii) monocyclic four-, five-, six- or seven-membered ring selected from the group consisting of cycloalkane, and heterocycloalkane, wherein the heterocycloalkane rings have from 1-3 heteroatoms as ring members selected from N, O and S; and wherein each of said monocyclic Z rings are optionally substituted with from 1 to 3 $R^5$ substituents.

$R^1$ is a member selected from H and $C_{1-8}$ alkyl, wherein the alkyl portion is optionally substituted with halogen, $-NR^aR^b$, $-OR^a$, $-CO_2R^a$, and $-CONR^aR^b$.

Each $R^2$ is independently selected from H, halogen, CN, $C_{1-8}$ alkyl, $C_{1-8}$ haloalkyl, $C_{1-8}$ hydroxyalkyl, $-OR^a$, $-CO_2R^a$, $-X-CO_2R^a$, $-NR^aR^b$, $-CONR^aR^b$ and $-X-CONR^aR^b$.

$R^3$ is selected from H, $C_{1-8}$ alkyl, $C_{1-8}$ haloalkyl, $C_{1-8}$ hydroxyalkyl, $-CO_2R^a$, $-X-CO_2R^a$, $-CONR^aR^b$ and $-X-CONR^aR^b$.

Each $R^4$, when present, is independently selected from $C_{1-8}$ alkyl, $C_{1-8}$ haloalkyl, $C_{1-8}$ hydroxyalkyl, $-OR^a$, $-CO_2R^a$, $-X-CO_2R^a$, $-NR^aR^b$, $-CONR^aR^b$ and $-X-CONR^aR^b$.

Each $R^5$ is independently selected from halogen, CN, $-X-CN$, $C_{1-8}$ alkyl, $C_{3-8}$ cycloalkyl, $C_{3-8}$ cycloalkenyl, $C_{3-5}$ spirocycloalkyl, $C_{2-8}$ alkenyl, $C_{2-8}$ alkynyl, $C_{1-8}$ haloalkyl, $C_{1-8}$ hydroxyalkyl, $-OR^a$, $-CO_2R^a$, $-X-CO_2R^a$, $-NR^aR^b$, $-CONR^aR^b$, $-X-CONR^aR^b$, aryl, 5- or 6-membered heteroaryl, and 3-, 4-, 5- or 6-membered heterocyclic wherein the heteroatoms present as ring vertices of the heteroaryl and heterocyclic rings are selected from N, O and S, and wherein the aryl, heteroaryl and heterocyclic portions of $R^5$ are optionally further substituted with 1-3 $R^a$.

Each $R^a$ and $R^b$ is independently selected from hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and $-SO_2-C_{1-8}$ alkyl.

Each X is a $C_{1-4}$ alkylene linking group or a linking group having the formula $-(CH_2)_mO(CH_2)_p-$, wherein the subscripts m and p are integer of from 0 to 5, and m+p is from 0 to 6, wherein any of the methylene portions of X are optionally substituted with one or two methyl groups. In one group of embodiments, each X is independently selected from $-OCH_2-$, $-OCH_2CH_2-$, $-OCH_2CH_2CH_2-$, $-OC(CH_3)_2-$, $-OCH_2C(CH_3)_2-$, $-OCH_2CH_2C(CH_3)_2-$, $-CH_2-$, $-C(CH_3)_2-$ and $-CH_2CH_2-$. In another group of embodiments, each X is selected from $-O-$, $-CH_2-$, $-OCH_2-$, $-OCH_2CH_2-$, $-C(CH_3)_2-$ and $-CH_2CH_2-$.

A number of embodiments are provided in the present invention.

(A) In one group of embodiments. Z is monocyclic or fused-bicyclic heteroaryl, having 1-3 heteroatoms as ring members selected from N, O and S; and wherein said heteroaryl group is optionally substituted with from 1 to 5 $R^5$ substituents.

(B) In another group of embodiments, Z is monocyclic or fused-bicyclic heteroaryl selected from the group consisting of imidazole, pyrazole, 1,2,3-triazole, 1,2,4-triazole, tetrazole, thiazole, oxazole, oxadiazole, pyrimidine, pyrazine, pyridazine, and quinazoline, each of which is optionally substituted with from 1-2 $R^5$ substituents.

(C) In still another group of embodiments, Z is is a 5-membered heteroaryl group substituted with one $R^5$ group selected from an optionally substituted aryl, heteroaryl, cycloalkyl, or heterocycloalkyl ring, and optionally with up to two additional $R^5$ groups which are selected from halogen, $C_{1-4}$ alkyl, $C_{1-4}$ haloalkyl, and $CH_2CN$.

(D) In other embodiments, Z is selected from:

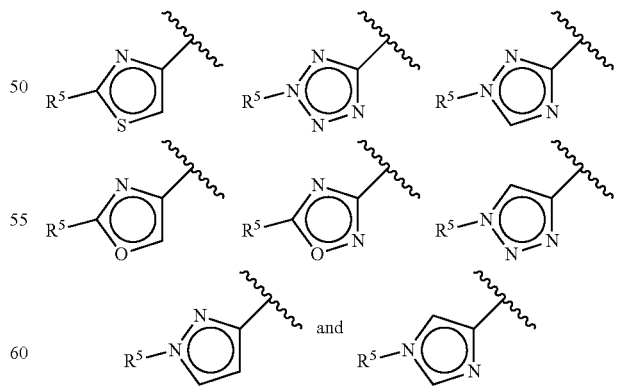

wherein $R^5$ has the meaning provided with reference to formula I above.

(E) In yet another group of embodiments, the compounds of formula I are those in which Z is

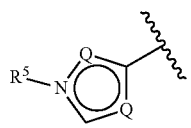

wherein each Q is independently selected from the group consisting of N, CH, and C(R$^5$), and R$^5$ has the meaning provided with reference to formula I above.

Within any of the embodiments provided in (A) through (E) or with reference to formula I, are other selected embodiments.

(1) In one group of embodiments, n is zero.
(2) In another group of embodiments, R$^1$ is H.

In another group of embodiments, the compounds of formula I are represented by:

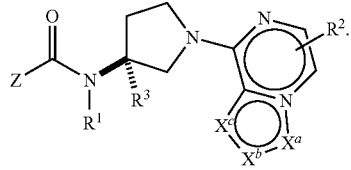

Ia

Selected embodiments of formula Ia, include each of the embodiments for Z, identified in (A) through (E) above, In one specific group of embodiments of formula I or Ia.
(F) The bicyclic portion having X$^a$, X$^b$ and X$^c$ as ring vertices is selected from:

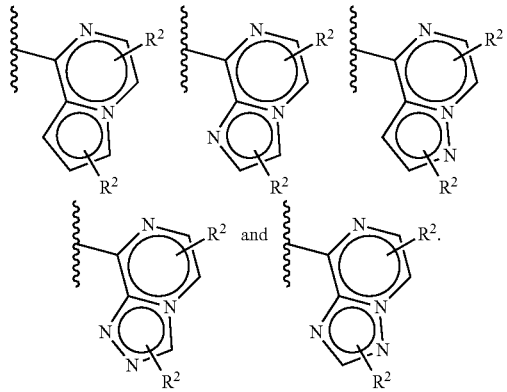

In another specific group of embodiments of formula Ia,
(G) The bicyclic portion having X$^a$, X$^b$ and X$^c$ as ring vertices is selected from:

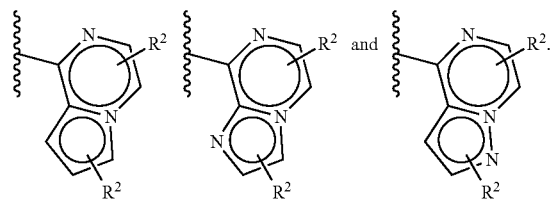

In still another specific group of embodiments of formula Ia, (H) The bicyclic portion having X$^a$, X$^b$ and X$^c$ as ring vertices is selected from:

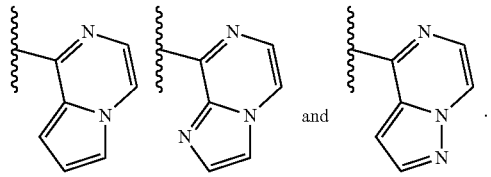

In one specific group of embodiments of formula Ia,
(I) The bicyclic portion having X$^a$, X$^b$ and X$^c$ as ring vertices is selected from:

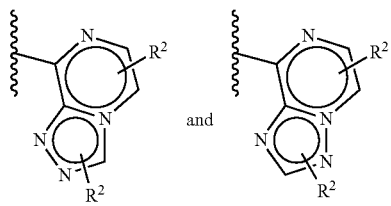

In another specific group of embodiments of formula Ia,
(J) The bicyclic portion having X$^a$, X$^b$ and X$^c$ as ring vertices is selected from:

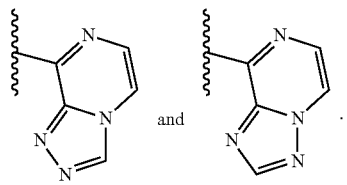 [SMILES: *c1nccn2cnnc12 ; "and" ; *c1nccn2ncnc12 ; "."]

In certain selected embodiments, the compounds of formula Ia. and the embodiments identified as (F), (G), (H), (I), and (J) are compounds in which Z is selected from the embodiments identified as (A) through (E), above, particularly those wherein Z is a 5-membered heteroaryl group substituted with one R$^5$ group selected from an optionally substituted aryl, heteroaryl, cycloalkyl, or a heterocycloalkyl ring, and optionally with up to two additional R$^5$ groups which are selected from halogen, C$_{1-4}$ alkyl, C$_{1-4}$ haloalkyl, and CH$_2$CN.

In yet another specific group of embodiments, for formula I or Ia, and embodiments identified as (F), (G), (H), (I), and (J), Z is selected from the group consisting of:

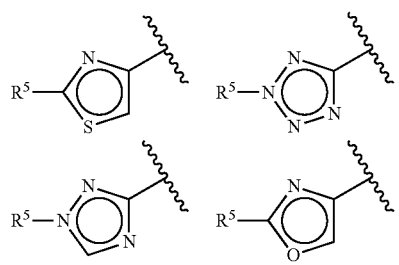

-continued

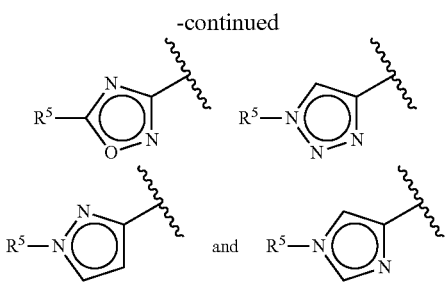

wherein R⁵ has the meaning provided with reference to formula I above.

In still another specific group of embodiments, with reference to formula I or Ia, and embodiments identified as (F), (G), (H), (I), and (J), Z has the formula:

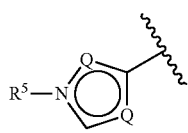

wherein each Q is independently selected from the group consisting of N, CH, and C(R⁵).

In one specific group of embodiments, the compounds have the formula:

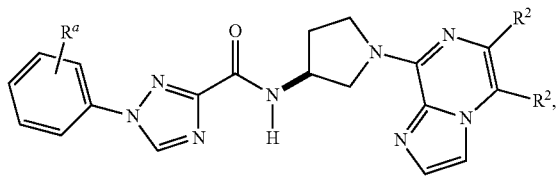

wherein Rᵃ and each R² have the meanings provided with reference to formula I.

Within any of the embodiments provided in (A) through (J), as well as the embodiments which are combinations (for example (A) and (F); (B) and (G); (A) and (H), and the like), are still other selected embodiments:

(a) wherein the subscript n is 0;
(b) wherein n is 0, and R¹ is H or methyl:
(c) wherein n is 0, and R¹ is H or methyl and R² is H or C₁₋₈ alkyl and R³ is hydrogen;
(d) wherein n is 0, and each of R² and R³ is hydrogen:
(e) wherein n is 0, each R² is hydrogen and R³ is selected from the group consisting of methyl, ethyl, —CONH₂, and —CH₂OH;
(f) wherein each R² is hydrogen.

One of skill in the art will appreciate that specific embodiments of the invention are compounds of formula I or Ia, wherein features of the compound are further defined by the combinations of embodiments, including (A)+(F); (A)+(G); (A)+(H); (A)+(I); and (A)+(J); each of which, in further selected embodiments is independently combined with each of selected embodiments (a) through (f). Similarly, selected compounds of formula I or Ia, are those wherein features of the compound are further defined by the combinations of embodiments, including (B)+(F); (B)+(G); (B)+(H); (B)+(I); and (B)+(J); each of which, in further selected embodiments is independently combined with each of selected embodiments (a) through (f). Still other selected compounds of formula I or Ia, are those wherein features of the compound are further defined by the combinations of embodiments, including (C)+(F); (C)+(G); (C)+(H); (C)+(I); and (C)+(J); each of which, in further selected embodiments is independently combined with each of selected embodiments (a) through (f). Other selected compounds of formula I or Ia, are those wherein features of the compound are further defined by the combinations of embodiments, including (D)+(F); (D)+(G); (D)+(H); (D)+(I); and (D)+(J); each of which, in further selected embodiments is independently combined with each of selected embodiments (a) through (f). Still other selected compounds of formula I or Ia, are those wherein features of the compound are further defined by the combinations of embodiments, including (E)+(F); (E)+(G); (E)+(H); (E)+(I); and (E)+(J); each of which, in further selected embodiments is independently combined with each of selected embodiments (a) through (f).

In one selected group of embodiments, the compound is selected from those provided in the Examples below, or in Table 1.

In each of the selected embodiments, the noted compounds may be present in a pharmaceutically acceptable salt or hydrate form.

Still further, for those compounds shown above without stereochemistry, the present invention is also directed to chiral forms of each of the compounds, as well as enantiomerically enriched forms of the noted compounds. Enantiomerically enriched forms can be prepared using chiral chromatography according to well known methods practiced in the art or, for example, by chiral resolution with a chiral salt form. In some embodiments, the enantiomeric excess for an enantiomerically enriched form is at least 10%, 20%, 30%, 40%, 50%, 60% or more. In still other embodiments, an enantiomerically enriched form is provided that is at least 70%, 80%, 90%, 95%, or more.

Preparation of Compounds

Certain compounds of the invention can be prepared following methodology as described in the Examples section of this document. In addition the syntheses of certain intermediate compounds that are useful in the preparation of compounds of the invention are also described.

B. Compositions

In addition to the compounds provided above, compositions for modulating CXCR7 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

C. Methods of Use

While not wishing to be bound by any particular theory, the compounds and compositions of the present invention are considered to provide a therapeutic effect by inhibiting the binding of SDF-1 and/or I-TAC to the CXCR7 receptor. Therefore, the compounds and compositions of the present invention can be used in the treatment or prevention of diseases or disorders in a mammal in which the inhibition of binding of SDF-1 and/or I-TAC to the CXCR7 receptor would provide a therapeutic effect.

In one embodiment, a preferred method of inhibiting the binding of the chemokines SDF-1 and/or I-TAC to a CXCR7 receptor includes contacting one or more of the previously mentioned compounds with a cell that expresses the CXCR7 receptor for a time sufficient to inhibit the binding of these chemokines to the CXCR7 receptor.

In some embodiments, the compounds and compositions of the invention are administered to a subject having cancer. In some cases, CXCR7 modulators are administered to treat cancer, e.g., carcinomas, gliomas, mesotheliomas, melanomas, lymphomas, leukemias (including acute lymphocytic leukemias), adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, renal cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER:PRINCIPLES AND PRACTICE (DeVita, V. T. et al. eds 1997) for additional cancers); as well as brain and neuronal dysfunction, such as Alzheimer's disease, multiple sclerosis and demyelinating diseases; hypertensive disorders such as pulmonary arterial hypertension; kidney dysfunction; renal dysfunction; rheumatoid arthritis; allograft rejection; atherosclerosis (and elevated cholesterol levels); asthma; glomerulonephritis; contact dermatitis; inflammatory bowel disease; colitis; psoriasis; reperfusion injury; as well as other disorders and diseases described herein. In some embodiments, the subject does not have Kaposi's sarcoma, multicentric Castleman's disease or AIDS-associated primary effusion lymphoma.

The present invention also encompasses decreasing angiogenesis in any subject in need thereof by administering the compounds and compositions of the invention. For example, decreasing CXCR7 activity by contacting CXCR7 with a compound of the invention, thereby decreasing angiogenesis, is useful to inhibit formation, growth and/or metastasis of tumors, especially solid tumors. Description of embodiments relating to modulated CXCR7 and angiogenesis are described in, e.g., U.S. patent application Ser. No. 11/050,345.

Other disorders involving unwanted or problematic angiogenesis include rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; disease of excessive or abnormal stimulation of endothelial cells, including intestinal adhesions, Crohn's disease, skin diseases such as psoriasis, excema, and scleroderma, diabetes, diabetic retinopathy, retinopathy of prematurity, age-related macular degeneration, atherosclerosis, scleroderma, wound granulation and hypertrophic scars, i.e., keloids, and diseases that have angiogenesis as a pathologic consequence such as cat scratch disease and ulcers (*Helicobacter pylori*), can also be treated with antibodies of the invention. Angiogenic inhibitors can be used to prevent or inhibit adhesions, especially intra-peritoneal or pelvic adhesions such as those resulting after open or laproscopic surgery, and burn contractions. Other conditions which should be beneficially treated using the angiogenesis inhibitors include prevention of scarring following transplantation, cirrhosis of the liver, pulmonary fibrosis following acute respiratory distress syndrome or other pulmonary fibrosis of the newborn, implantation of temporary prosthetics, and adhesions after surgery between the brain and the dura. Endometriosis, polyposis, cardiac hypertrophy, as well as obesity, may also be treated by inhibition of angiogenesis. These disorders may involve increases in size or growth of other types of normal tissue, such as uterine fibroids, prostatic hypertrophy, and amyloidosis. Compounds and compositions of the present invention may be used prophylactically or therapeutically for any of the disorders or diseases described herein.

Decreasing CXCR7 activity with the compounds and compositions of the present invention can also be used in the prevention of neovascularization to effectively treat a host of disorders. Thus, for example, the decreasing angiogenesis can be used as part of a treatment for disorders of blood vessels (e.g., hemangiomas and capillary proliferation within atherosclerotic plaques), muscle diseases (e.g., myocardial angiogenesis, myocardial infarction or angiogenesis within smooth muscles), joints (e.g., arthritis, hemophiliac joints, etc.), and other disorders associated with angiogenesis. Promotion of angiogenesis can also aid in accelerating various physiological processes and treatment of diseases requiring increased vascularization such as the healing of wounds, fractures, and burns, inflammatory diseases, ischeric heart, and peripheral vascular diseases. The compounds of the present invention can also provide benefit in conditions in which normal blood flow is restricted, such as pulmonary hypertension.

The compounds and compositions of the present invention may also be used to enhance wound healing. Without intending to limit the invention to a particular mechanism of action, it may be that antagonism of CXCR7 allows for endogenous ligands to instead bind to lower affinity receptors, thereby triggering enhanced wound healing. For example, SDF-1 binds to both CXCR7 and CXCR4, but binds to CXCR4 with a lower affinity. Similarly, I-TAC binds to CXCR3 with a lower affinity than I-TAC binds to CXCR7. By preventing binding of these ligands to CXCR7, CXCR7 antagonists may allow the ligands to bind to the other receptors, thereby enhancing wound healing. Thus, the antagonism of CXCR7 to enhance wound healing may be mediated by a different mechanism than enhancing wound healing by stimulating CXCR7 activity with an agonist.

Aside from treating disorders and symptoms associated with neovascularization, the inhibition of angiogenesis can be used to modulate or prevent the occurrence of normal physiological conditions associated with neovascularization. Thus, for example the compounds and compositions can be used as a birth control. In accordance with the present invention, decreasing CXCR7 activity within the ovaries or endometrium can attenuate neovascularization associated with ovulation, implantation of an embryo, placenta formation, etc.

Inhibitors of angiogenesis have yet other therapeutic uses. For example, the compounds and compositions of the present invention may be used for the following:
(a) Adipose tissue ablation and treatment of obesity. See. e.g. Kolonin et al., *Nature Medicine* 10(6):625-632 (2004);
(b) Treatment of preclampsia. See, e.g., Levine et al., *N. Engl. J. Med.* 350(7): 672-683 (2004); Maynard, et al., *J. Clin. Invest.* 111(5): 649-658 (2003); and
(c) Treatment of cardiovascular disease. See, e.g., March. et al., *Am. J. Physiol. Heart Circ. Physiol.* 287:H458-H463 (2004); Rehman et al., *Circulation* 109: 1292-1298 (2004).

Methods of Treating Cancer

More specifically, the present invention also provides a method of treating cancer. A preferred method of treating cancer, includes administering a therapeutically effective amount of one or more of the previously mentioned compounds (or salts thereof) to a cancer patient for a time sufficient to treat the cancer.

For treatment, the compositions of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In some embodiments, CXCR7 modulators of the present invention can be administered in combination with other appropriate therapeutic agents, including, e.g., chemotherapeutic agents, radiation, etc. It is understood that such administration may be prior to, subsequent to or in unison with the second therapeutic agent, such that the therapeutic effects of the second agent are enhanced when compared to administration of the second agent in the absence of the CXCR7 modulator. Selection of the appropriate agents for use in combination therapy may be made by one of ordinary skill in the art, according to conventional pharmaceutical principles. The combination of therapeutic agents may act synergistically to effect the treatment or prevention of the various disorders such as, e.g., cancer, wounds, kidney dysfunction, brain dysfunction or neuronal dysfunction. Using this approach, one may be able to achieve therapeutic efficacy with lower dosages of each agent, thus reducing the potential for adverse side effects.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Standard in vivo assays demonstrating that the compositions of the present invention are useful for treating cancer include those described in Bertolini, F., et al., *Endostatin, an antiangiogenic drug, induces tumor stabilization after chemotherapy or anti-CD20 therapy in a NOD/SCID mouse model of human high-grade non-Hodgkin lymphoma*. Blood, No. 1, Vol. 96, pp. 282-87 (1 Jul. 2000); Pengnian, L., *Antiangiogenic gene therapy targeting the endothelium-specific receptor tyrosine kinase Tie2*. Proc. Natl. Acad. Sci. USA, Vol. 95, pp. 8829-34 (July 1998); and Pulaski, B. *Cooperativity of Staphylococcal aureus Enterotoxin B Superantigen, Major Histocompatibility Complex Class II, and CD80 for Immunotherapy of Advanced Spontaneous Metastases in a Clinically Relevant Postoperative Mouse Breast Cancer Model*. Cancer Research, Vol. 60, pp. 2710-15 (May 15, 2000).

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

The compounds and compositions of the present invention can be combined with other compounds and compositions having related utilities to prevent and treat cancer and diseases or conditions associated with CXCR7 signaling. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: cisplatin, paclitaxel, methotrexate, cyclophosphamide, ifosfamide, chlorambucil, carmustine, carboplatin, vincristine, vinblastine, thiotepa, lomustine, semustine, 5-fluorouracil and cytarabine. The weight ratio of the compound of the present invention to the second active ingredient may be varied and will depend upon the effective dose of each ingredient. Generally, an effective dose of each will be used. Thus, for example, when a compound of the present invention is combined with a second anticancer agent, the weight ratio of the compound of the present invention to the second agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating Inflammation

Still further, the compounds and compositions of the present invention are useful for the treatment of inflammation, and can be combined with other compounds and compositions having therapeutic utilities that may require treatment either before, after or simultaneously with the treatment of cancer or inflammation with the present compounds. Accordingly, combination methods and compositions are also a component of the present invention to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

As noted, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin D$_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Method of Inducing Progenitor/Stem Cell Mobilization

Still further, the compounds and compositions of the present invention can be useful for mobilizing progenitor/stem cells and thus for treating or ameliorating disorders or conditions for which progenitor/stem cell mobilization is efficacious or desirable, optionally using the compounds of the present invention according to the procedures and protocols as described in WO05/000333, incorporated herein by reference in its entirety for all purposes. Conditions that may be ameliorated or otherwise benefited include, for example, hematopoietic disorders, such as aplastic anemia, leukemias, drug-induced anemias, and hematopoietic deficits from chemotherapy or radiation therapy. Still further, the compounds and compositions of the invention can be used in enhancing the success of transplantation during and following immunosuppressive treatments as well as in effecting more efficient wound he Still further, the compounds and compositions of the present invention can be useful for mobilizing progenitor/stem cells and thus for treating or ameliorating disorders or conditions for which progenitor/stem cell mobilization is efficacious or desirable, optionally using the compounds of the present invention according to the procedures and protocols as described in WO05/000333, incorporated herein by reference in its entirety for all purposes. Conditions that may be ameliorated or otherwise benefited include, for example, hematopoietic disorders, such as aplastic anemia, leukemias, drug-induced anemias, and hematopoietic deficits from chemotherapy or radiation therapy. Still further, the compounds and compositions of the invention can be used in enhancing the success of transplantation during and following immunosuppressive treatments as well as in effecting more efficient wound healing and treatment of bacterial infections. Optionally, following administration of the compounds of the invention, and following progenitor/stem cell mobilization, blood comprising the mobilized cells is collected and optionally, the mobilized cells are purified and optionally expanded, and where desired, reintroduced into the same person or into a second person (e.g., a matched donor).

A number of different types of cells can be mobilized as desired. In some embodiments, hematopoietic progenitor cells (HSCs) are mobilized following administration of the compounds or compositions of the invention, and optionally harvested and purified from other blood components. Optionally, HSC mobilization is induced by administration of at least one compound of the invention in conjunction with one or more of granulocyte-colony stimulating factor (G-CSF) or AMD3100 (1,1'-[1,4-Phenylenebis(methylene)] bis [1,4,8,11-tetraazacyclotetradecane] octohydrobromide dihydrate) or salts, racemates, or isomers thereof.

In some embodiments, endothelial progenitor cells (EPCs) are mobilized following administration of the compounds or compositions of the invention, and optionally harvest and purified from other blood components. Optionally, EPC mobilization is induced by administration of at least one compound of the invention in conjunction with one or more of vascular endothelial growth factor (VEGF), a VEGF agonist (including but not limited to a VEGF agonist antibody) or AMD3100 or salts, racemates, or isomers thereof.

In some embodiments, mesenchymal stem cells (MSCs) or stromal progenitor cells (SPCs) are mobilized following administration of the compounds or compositions of the invention, and optionally harvest and purified from other blood components. Optionally, such mobilization is induced by administration of at least one compound of the invention in conjunction with one or more of G-CSF, VEGF, a VEGF agonist (including but not limited to a VEGF agonist antibody), AMD3100, or salts, racemates, or isomers thereof.

For immobilizing progenitor or stem cells, an appropriate dosage level will generally be about 0.001 to 100 mg per kg patient body weight per day which can be administered in single or multiple doses. The compounds may be administered as a single dose, a dose over time, as in i.v., or transdermal administration, or in multiple doses. The compounds of the invention can also be used in ex vivo treatment protocols to prepare cell cultures which are then used to replenish the blood cells of the subject. Ex vivo treatment can be conducted on autologous cells harvested from the peripheral blood or bone marrow or from allografts from matched donors.

The present compounds can be combined with other compounds and compositions that induce activation, proliferation or mobilization of progenitor/stem cells. In addition to those described above, these include but are not limited to Fms-related tyrosine kinase 3 ligand (Flt3 ligand), interleukin 3 (IL-3), interleukin 7 (IL-7), interleukin 20 (IL-20), Steel factor (SF) and granulocyte macrophage colony-stimulating factor (GM-CSF) and may provide therapeutic utilities that may require or benefit from treatment either before, after or simultaneously with mobilization of progenitor/stem cells. Accordingly, combination methods and compositions are also a component of the present invention to prevent and treat the condition or disease of interest. Additionally, the compounds of the present invention can provide benefit in conditions in which disregulation of stem cell mobilization may play a role, such as heart disease and pulmonary hypertension.

Method of Diagnosing Diseases and Disorders Associated with CKCR7

Still further, the compounds and compositions of the present invention are useful for the diagnosis of diseases and disorders associated with CXCR7. In particular, the compounds of the present invention can be prepared in a labeled form (e.g., radiolabeled) and used for the diagnosis of, for example, cancer. Labeled compounds of the present invention that bind to CXCR7 (e.g., antagonists or agonists) can be used to determine levels of CXCR7 in a mammalian subject. In some embodiments, the CXCR7 modulators are administered to a subject having cancer. In some cases, labeled compounds are administered to detect developing cancers, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER:PRINCIPLES AND PRACTICE (DeVita, V. T. et al. eds 1997) for additional cancers); as well as brain and neuronal dysfunction, such as Alzheimer's disease and multiple sclerosis; kidney dysfunction; rheumatoid arthritis; cardiac allograft rejection; atherosclerosis (and elevated cholesterol levels); asthma; glomerulonephritis; contact dermatitis; inflammatory bowel disease; colitis; psoriasis; reperfusion injury; as well as other disorders and diseases described herein. In some embodiments, the subject does not have Kaposi's sarcoma, multicentric Castleman's disease or AIDS-associated primary effusion lymphoma. Since CXCR7 is often expressed in cancer cells but not non-cancer cells, it is typically desirable to administer antagonists of CXCR7 to subjects at risk of having cancer.

A variety of imaging and detection methods can be used for the detection of cancers. In some embodiments, direct methods are available to evaluate CXCR7 biodistribution in the body such as magnetic resonance imaging ("MRI"), positron emission tomography ("PET"), and single photon emission computed tomography ("SPECT"). Each of these methods can detect the distribution of a suitably labeled compound (generally as bound to CXCR7) within the body if that compound contains an atom with the appropriate nuclear properties. MRI detects paramagnetic nuclei; PET and SPECT detect the emission of particles from the decay of radionuclei.

For methods involving PET, it is necessary to incorporate an appropriate positron-emitting radionuclide. There are relatively few positron-emitting isotopes that are suitable for labeling a therapeutic agent. The carbon isotope, $^{11}C$, has been used for PET, but has a short half-life of 20.5 minutes. Accordingly, the facilities for synthesis and use are typically near to a cyclotron where the precursor $^{11}C$ starting material is generated. Another useful isotope, $^{18}F$, has a half-life of 110 minutes. This allows sufficient time for incorporation into a radiolabeled tracer, for purification and for administration into a human or animal subject. Other isotopes have even shorter half-lives. $^{13}N$ has a half-life of 10 minutes and $^{15}O$ has an even shorter half-life of 2 minutes. The emissions of both are more energetic, however, than those of $^{11}C$ and PET studies have been carried out with these isotopes (see, Clinical Positron Emission Tomography, Mosby Year Book, 1992, K. F. Hubner, et al., Chapter 2).

SPECT imaging employs isotope tracers that are γ-emitters. While the range of useful isotopes is greater than for PET, imaging with SPECT provides lower three-dimensional resolution. However, in some instances, SPECT is used to obtain clinically significant information about compound binding, localization and clearance rates. One useful isotope for SPECT imaging is $^{123}I$, a γ-emitter with a 13.3 hour half life. Compounds labeled with $^{123}I$ can be shipped up to about 1000 miles from the manufacturing site, or the isotope itself can be transported for on-site synthesis. Eighty-five percent of the isotope's emissions are 159 KeV photons, which are readily measured by SPECT instrumentation currently in use. Other halogen isotopes can serve for PET or SPECT imaging, or for conventional tracer labeling. These include $^{75}Br$, $^{76}Br$, $^{77}Br$ and $^{82}Br$ as having usable half-lives and emission characteristics.

In view of the above, the present invention provides methods for imaging a tumor, organ, or tissue, said method comprising:
  (a) administering to a subject in need of such imaging, a radiolabeled or detectable form of a compound of Formula I; and
  (b) detecting said compound to determine where said compound is concentrated in said subject.

Additionally, the present invention provides methods for detecting elevated levels of CXCR7 in a sample, said method comprising:
  (a) contacting a sample suspected of having elevated levels of CXCR7 with a radiolabeled or detectable form of a compound of Formula I;
  (b) determining a level of compound that is bound to CXCR7 present in said sample to determine the level of CXCR7 present in said sample; and
  (c) comparing the level determined in step (b) with a control sample to determine if elevated levels of CXCR7 are present in said sample.

As with the treatment methods described herein, administration of the labeled compounds can be by any of the routes normally used for introducing a compound into ultimate contact with the tissue to be evaluated and is well known to those of skill in the art. Although more than one route can be used to administer a particular composition, a particular route can often provide a more immediate and more effective diagnosis than another route.

Combination Therapies

Inhibitors of CXCR7 can be supplied alone or in conjunction with one or more other drugs. Possible combination partners can include, e.g., additional anti-angiogenic factors and/or chemotherapeutic agents (e.g., cytotoxic agents) or radiation, a cancer vaccine, an immunomodulatory agent, an anti-vascular agent, a signal transduction inhibitor, an anti-proliferative agent, or an apoptosis inducer.

IV. Examples

The following examples are offered to illustrate, but not to limit the claimed invention.

Reagents and solvents used below can be obtained from commercial sources such as Aldrich Chemical Co. (Milwaukee, Wis., USA). $^{1}$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP 1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention: rt, room temperature; HPLC, high pressure liquid chromatography; TFA, trifluoroacetic acid; LC-MSD, liquid chromatograph/mass selective detector; LC-MS, liquid chromatograph/mass spectrometer; Pd$_2$dba$_3$, tris(dibenzylideneacetone) dipalladium; THF, tetrahydrofuran; DMF, dimethylformamide or N,N-dimethylformamide; DCM, dichloromethane; DMSO, dimethyl sulfoxide; TLC, thin-layer chromatography; KHMDS, potassium hexamethyldisilazane; ES, electrospray; sat., saturated.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: Synthesis of ethyl 1-(4-fluorophenyl)-1,2,4-triazole-3-carboxylate

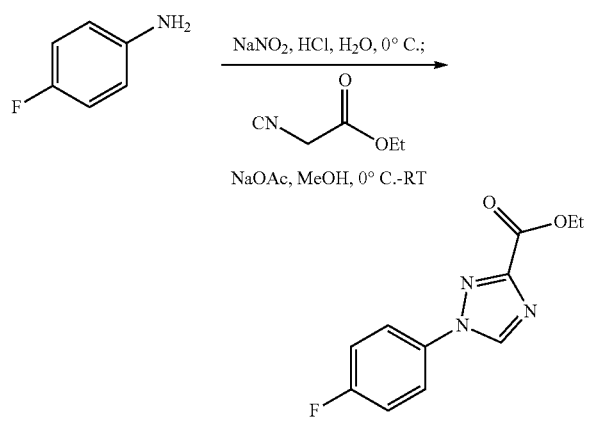

4-Fluoroaniline (2.8 g, 26 mmol) was dissolved in 10% HCl and cooled to 0° C. To this solution was carefully added NaNO$_2$ (1.8 g, 26 mmol) dissolved in 10 mL water. In a separate flask, NaOAc (13 g, 96 mmol), and water (25 mL) were added to a solution of ethyl isocyanoacetate (2.0 g, 18 mmol) in methanol (80 mL). This solution was cooled to 0° C. and the diazonium salt of 4-fluoroaniline was carefully added over the course of 15 minutes. Stirring was continued at 0° C. for an additional 15 minutes, after which the flask was removed from the ice bath and stirring was continued for an additional 2 hours. The reaction mixture was then added to 500 mL water and the resulting brown precipitate was collected by filtration and dried in vacuo to obtain 3.8 g of the desired ester (90% yield).

Example 2: Synthesis of 1-(4-fluorophenyl)-1,2,4-triazole-3-carboxylic acid

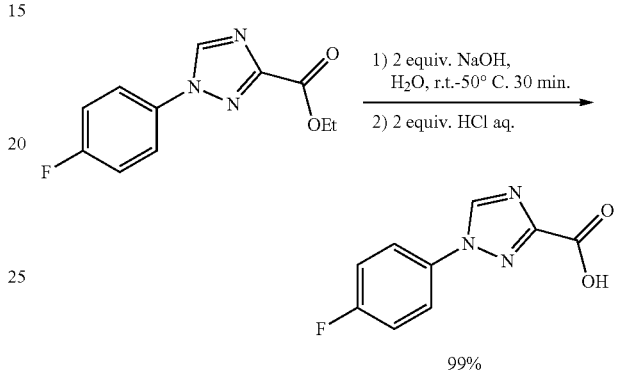

1.84 g of ethyl 1-(4-fluorophenyl)-1,2,4-triazole-3-carboxylate (7.83 mmol) was suspended in a solution of 0.63 g of sodium hydroxide (2 equiv.) in 110 mL of water. The mixture was vigorously stirred and slowly brought up to 50° C., whereupon all solids have dissolved. The solution was cooled down to r.t and diluted with water to a total volume of 400 mL, 1.31 mL of concentrated HCl (2 equiv.) was added while the mixture was vigorously stirred. The stirring was continued for 15 minutes, letting all the solids to disperse evenly. The white solids were filtered off and thoroughly washed on the funnel with 15 mL of water and then dried in a vacuum oven at 50° C. to obtain 1.6 g of the acid product as a white powder (99% yield).

Example 3: Synthesis of 1-(4-fluorophenyl)-1,2,4-triazole-3-acetyl chloride

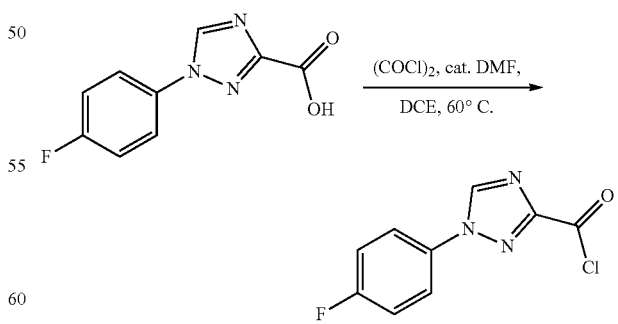

1.71 g (8.24 mmol) of 1-(4-fluorophenyl)-1,2,4-triazole-3-carboxylic acid was suspended in 15 mL of 1,2-dichloroethane and then 1.24 mL (12.4 mmol) of oxalyl chloride was added dropwise at r.t., followed by 1.6 µL (0.021 mmol) of DMF. The mixture was stirred at r.t. and then slowly brought up to 60° C. Another 1.6 µL portion of DMF was added, resulting in full dissolution of the material after 5 minutes. The solution was concentrated in vacuo to obtain 1.86 g of the desired product as a light yellow solid (100% yield). The product was used in subsequent steps without purification.

Example 4: Synthesis of ethyl 1-(4-Chloro-3-fluorophenyl)pyrazole-3-carboxylate

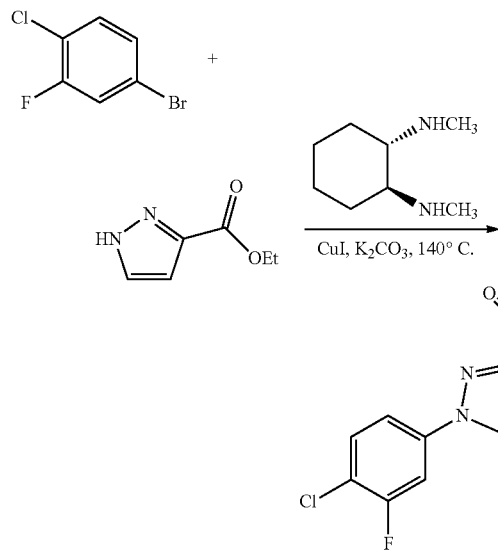

A 50 mL of flask was charged with 3.00 g of 4-chloro-3-fluorobenzenebromide (15 mmol), 1.40 g of ethyl 1-H-pyrazole-3-carboxylate (10 mmol), 400 mg of CuI (2.0 mmol), 4.5 g of K₂CO₃ (3.3 mmol) and 0.9 mL of trans-N,N'-dimethylcyclohexayldiamine (2.0 mmol). The resulting mixture was stirred at 140° C. for 3 h. After the mixture was cooled down to room temperature, it was diluted with 200 mL EtOAc and then was washed with water (2×50 mL), brine (2×50 mL). The organics was dried over MgSO₄ and concentrated under reduced pressure. The residued was purified via flash column chromatography on silica gel (0-25% EtOAc in hexanes) to get the desired product (1.2 g, 50%).

Example 5: Synthesis of 1-(4-chloro-3-fluorophenyl)pyrazole-3-carboxylic acid

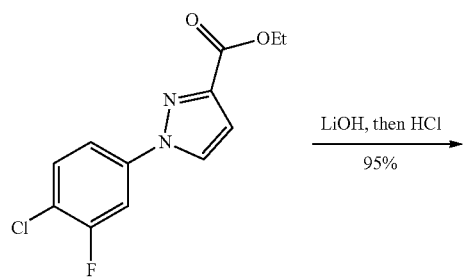

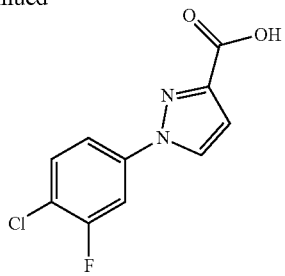

To a solution of ethyl 1-(4-chloro-3-fluorophenyl)pyrazole-3-carboxylate (268 mg, 1 mmol) in THF was added 3.0 mL of 1.0M of LiOH (3.0 mmol). The resulting mixture was stirred at room temperature for 3 h at which time 1.0 M of HCl was added to adjust pH to 1.0. The organics were extracted with EtOAc (2×100 mL), followed by drying over MgSO₄ and concentrated under reduced pressure to give a white solid (230 mg, 96%), which was used for next step without further purification.

Example 6: Synthesis of ethyl 1-(4-chlorophenyl)pyrazole-3-carboxylate

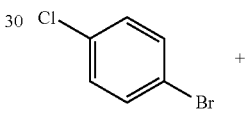

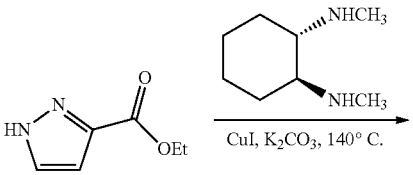

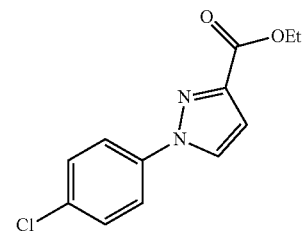

A 50 mL of flask was charged with 2.87 g of 4-chlorobenzenebromide (15 mmol), 1.40 g of ethyl 1-H-pyrazole-3-carboxylate (10 mmol), 400 mg of CuI (2.0 mmol), 4.5 g of K₂CO₃ (3.3 mmol) and 0.9 mL of trans-N,N'-dimethylcyclohexayldiamine (2.0 mmol). The resulting mixture was stirred at 140° C. for 3 h. After the mixture was cooled down to room temperature, it was diluted with 200 mL EtOAc and then was washed with water (2×50 mL) and brine (2×50 mL). The organics were dried over MgSO₄ and concentrated under reduced pressure. The residued was purified via flash column chromatography on silica gel (0-25% EtOAc in hexanes) to get the desired product (1.25 g, 50%).

Example 7: Synthesis of 1-(4-chlorophenyl)pyrazole-3-carboxylic acid

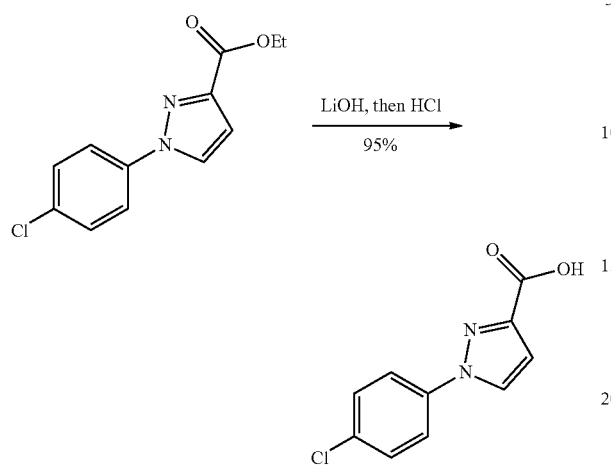

To a solution of ethyl 1-(4-chlorophenyl)pyrazole-3-carboxylate (250 mg, 1 mmol) in THF was added 3.0 mL of 1.0 M of LiOH (3.0 mmol). The resulting mixture was stirred at room temperature for 3 h at which time 1.0 M HCl was added to adjust the pH to 1.0. The organics were extracted with EtOAc (2×100 mL), dried over MgSO$_4$, and concentrated under reduced pressure to give a white solid (213 mg, 96%), which was used for next step without further purification.

Example 8: Synthesis of ethyl 1-(3-fluorophenyl)pyrazole-3-carboxylate

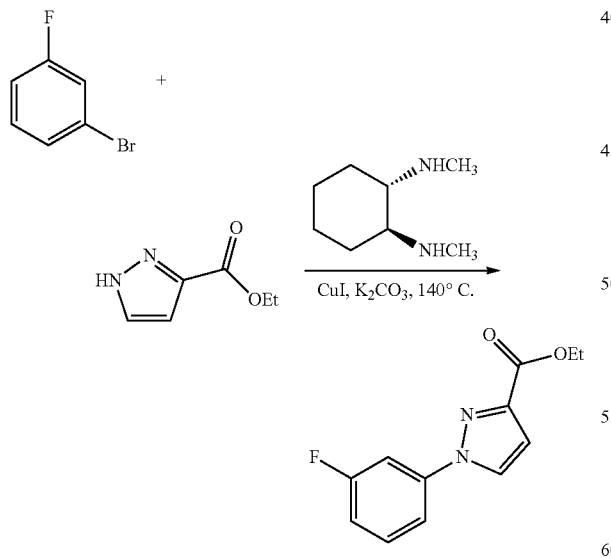

A 50 mL of flask was charged with 2.62 g of 3-fluorobenzenebromide (15 mmol), 1.40 g of ethyl 1-H-pyrazole-3-carboxylate (10 mmol), 400 mg of CuI (2.0 mmol), 4.5 g of K$_2$CO$_3$ (3.3 mmol) and 0.9 mL of trans-N,N'-dimethylcyclohexayldiamine (2.0 mmol). The resulting mixture was stirred at 140° C. for 3 h. After the mixture was cooled down to room temperature, it was diluted with 200 mL EtOAc and then was washed with water (2×50 mL), and brine (2×50 mL). The organics were dried over MgSO$_4$ and concentrated under reduced pressure. The residue was purified via flash column chromatography on silica gel (0-25% EtOAc in hexanes) to give the desired product (1.17 g, 50%).

Example 9: Synthesis of 1-(3-fluorophenyl)pyrazole-3-carboxylic acid

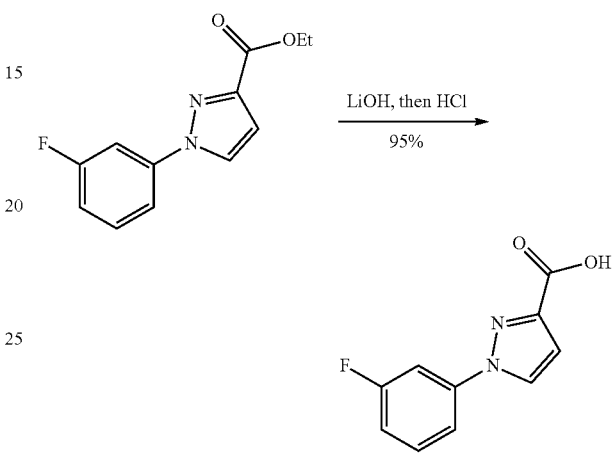

To a solution of ethyl 1-(3-fluorophenyl)pyrazole-3-carboxylate (234 mg, 1 mmol) in THF was added 3.0 mL of 1.0M of LiOH (3.0 mmol). The resulting mixture was stirred at room temperature for 3 h and then 1.0 M of HCl was added to adjust pH to 1.0. The organics were extracted with EtOAc (2×100 mL), followed by drying over MgSO$_4$ and concentrated under reduced pressure to give a white solid (198 mg, 96%), which was used for next step without further purification.

Example 10: Synthesis of ethyl 1-(4-fluorophenyl)-1,2,4-triazole-5-methyl-3-carboxylate

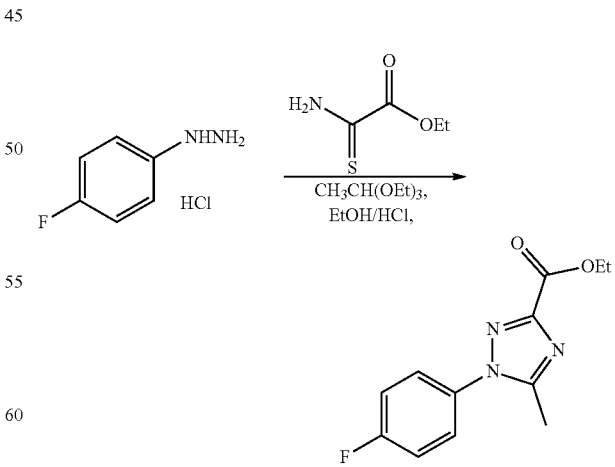

4-Fluorohydrazine hydrochloride (12.8 g, 7.7 mmol) and ethyl thiooxamte (10 g, 7.7 mmol) was suspended in water (80 ml) and then the mixture was cooled to 0° C. To this mixture was dropwise added triethylamine (10.77 ml, 7.7 mmol). The resulting mixture was stirred at room temperature for 2 hr. The solid as filtered was then washed with water (2×200 ml) to get a yellow solid (13.8 g, 6.1 mmol). 11.25 g of this yellow solid (50 mmol) was dissolved in EtOH (50 ml) and 4 M HCl (0.5 ml) followed by the addition of triethyl orthoacetate (8.9 g, 55 mmol). The resulting mixture was heated at 80° C. for 2 h and the solid (10 g, 85%) was collected after it was cooled own to room temperature.

Example 11: Synthesis of 1-(4-fluorophenyl)-1,2,4-triazole-5-methyl-3-carboxylic acid

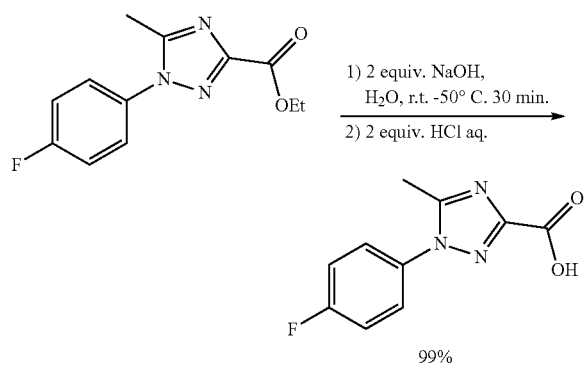

1.94 g of ethyl 1-(4-fluorophenyl)-1,2,4-triazole-5-methyl-3-carboxylate (7.83 mmol) was suspended in a solution of 0.63 g of sodium hydroxide (2 equiv.) in 110 mL of water. The mixture was vigorously stirred and slowly brought up to 50° C., whereupon all solids had dissolved. The solution was cooled down to rt and diluted with water to a total volume of 400 mL, 1.31 mL of concentrated HCl (2 equiv.) was added while the mixture was vigorously stirred. The stirring was continued for 15 minutes. The white solids were then filtered off and thoroughly washed with 15 mL of, then dried in a vacuum oven at 50° C. to obtain 1.7 g of the desired acid product as a white powder (99% yield).

Example 12: Synthesis of ethyl 2-pyrrolidinethiazole-4-carboxylate

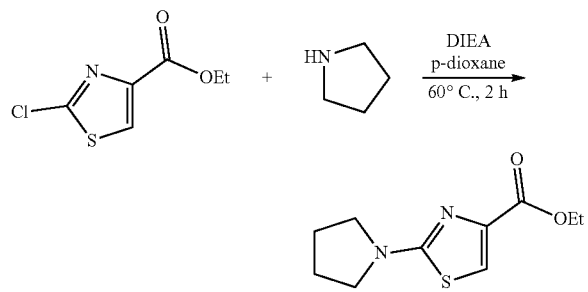

A mixture of ethyl 2-chlorothiazole-4-carboxylate (500 mg, 2.6 mmol), pyrrolidine (210 mg, 2.98 mmol) and diethylisopropyl amine (1 mL) in p-dioxane (5 mL) was heated to 60° C. for 2 h. After cooling to room temperature, the solution was concentrated in vacuo and the residue purified by flash chromatography (SiO$_2$, 2 to 5% MeOH in CH$_2$Cl$_2$ as eluent) to give the desired compound as a foam (400 mg, 68% yield, which was used directly for the next step). MS: (ES) m/z 227.1 (M+H$^+$).

Example 13: Synthesis of 2-pyrrolidinethiazole-4-carboxylic acid

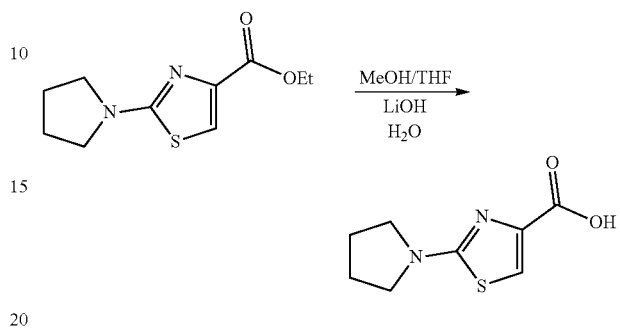

To the mixture of the above ester (400 mg, 1.8 mmol), MeOH (3 mL), THF (5 mL) and DI H$_2$O (2 mL) was added LiOH monohydrate (210 mg, 5 mmol). The resulting mixture was stirred at room temperature overnight. The mixture was diluted with ice-water. pH adjusted to pH 3 with 1 N HCl, and extracted with 20% MeOH in CH$_2$Cl$_2$. The organic layer was dried (Na$_2$SO$_4$), filtered and concentrated in vacuo to give the desired compound as an off-white solid (300 mg, 89% yield, which was used directly for the next step). MS: (ES) m/z 199.1 (M+H$^+$).

Example 14: Synthesis of 2-(4-hydroxy-piperidin-1-yl)-thiazole-4-carboxylic acid

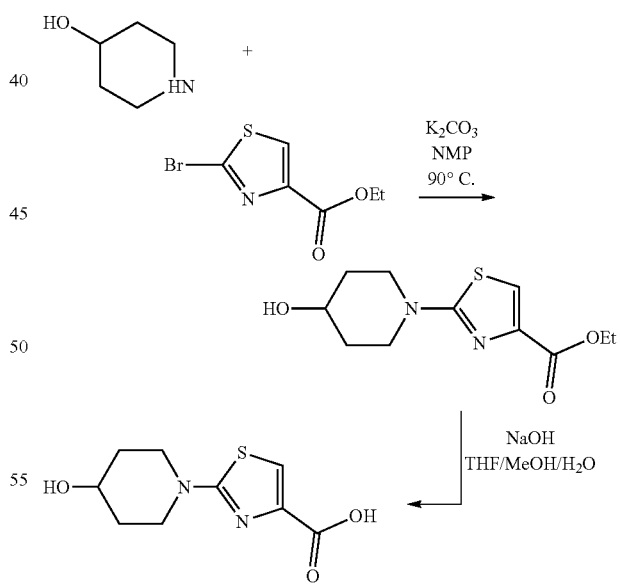

a) A flask was charged 4-hydroxypiperidine (236 mg, 2.33 mmol), ethyl 2-bromothiazole-4-carboxylate (500 mg, 2.12 mmol), K$_2$CO$_3$ (879 mg, 6.36 mmol), and N-methylpyrrolidine (3.5 mL). The reaction mixture was heated to 90° C. and stirred overnight. The reaction was then diluted with EtOAc (30 mL) and washed with water (5×30 mL). The organic layer was dried over Na$_2$SO$_4$, filtered, and concentrated. The crude material was purified on silica gel (95:5-20:80 hexanes:EtOAc) to give the product mixed with 2 equivalents of N-methylpyrrolidine (883 mg) as a clear colorless oil.

b) The 2-(4-hydroxy-piperidin-1-yl)-thiazole-4-carboxylic acid ethyl ester mixture from step a was dissolved in MeOH (10 mL). To this was added NaOH (2 M, 5.00 mL). The reaction mixture was stirred overnight, then diluted 1M NaHSO$_4$ (30 mL). This solution was extracted with EtOAc (3×50 mL), and the combined organic layers were dried over Na$_2$SO$_4$, filtered, and concentrated to give the product (433 mg, 1.90 mmol, 90%) as a white solid.

Example 15: Synthesis of 2-(pyrrolidin-1-yl)thiazole-4-carboxylic acid

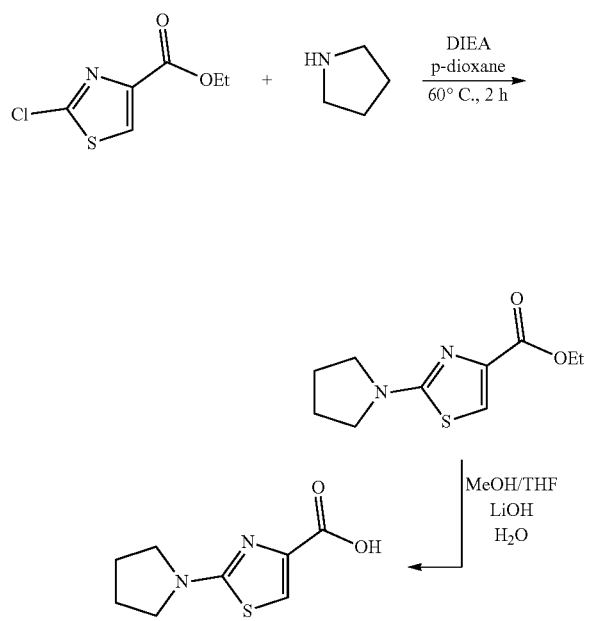

a) A mixture of ethyl 2-chlorothiazole-4-carboxylate (500 mg, 2.6 mmol), pyrrolidine (210 mg, 2.98 mmol) and diethylisopropyl amine (1 mL) in p-dioxane (5 mL) was heated to 60° C. for 2 h. After cooling to room temperature, the solvent was concentrated in vacuo and the residue purified by flash chromatography (SiO$_2$, 2 to 5% MeOH in CH$_2$Cl$_2$ as eluent) to give the desired compound as a foam (400 mg, 68% yield, which was used directly for the next step). MS: (ES) m/z 227.1 (M+H$^+$).

b) To the mixture of the above ester (400 mg, 1.8 mmol), MeOH (3 mL), THF (5 mL) and DI H$_2$O (2 mL) was added LiOH monohydrate (210 mg, 5 mmol). The resulting mixture was stirred at room temperature overnight. The mixture was diluted with ice-water, pH was adjusted to 3 with 1 N HCl, and the solution was extracted with 20% MeOH in CH$_2$Cl$_2$. The organic layer was dried (Na$_2$SO$_4$), filtered and concentrated in vacuo give the desired compound as an off-white solid (300 mg, 89% yield, which was used directly for the next step). MS: (ES) m/z 199.1 (M+H$^+$).

Example 16: Synthesis of methyl 1-(o-fluorophenyl)-1,2,4-triazole-3-carboxylate

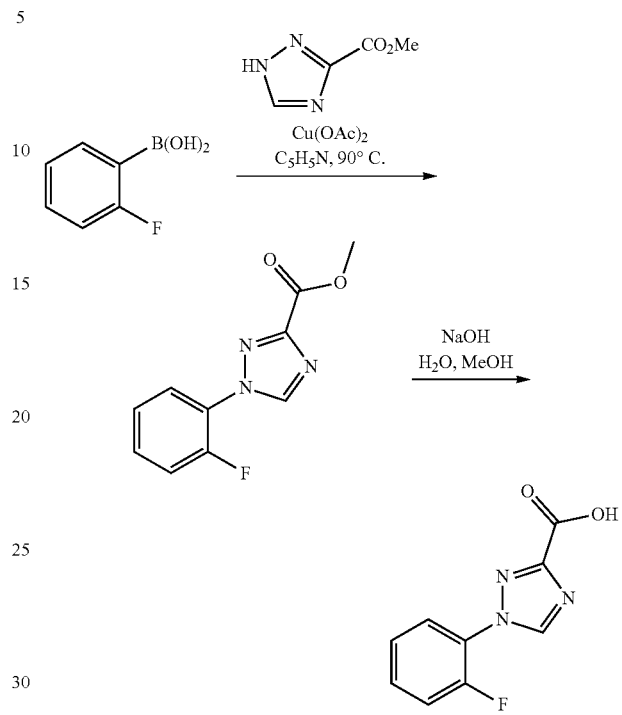

a) To a solution of methyl 1,2,4-triazole-3-carboxylate (1.0 g, 7.9 mmol) in 10 mL DMF was added o-fluorophenylboronic acid (1.1 g, 7.9 mmol), Cu(OAc)$_2$ (1.6 g, 8.8 mmol), and pyridine (0.70 mmol, 8.7 mmol). The mixture was placed in a 90° C. oil bath and stirred vigorously for 3.5 hours. Afterward the mixture was diluted with 100 mL EtOAc, filtered, and washed with 1:3 v/v conc. NH$_4$OH-saturated NH$_4$Cl. After removal of solvent under reduced pressure, the residue was purified by flash chromatography (SiO$_2$, 20-80% EtOAc/hexanes) to obtain 280 mg of white powder (16% yield).

b) To a solution of the ester from step a (280 mg, 1.3 mmol) dissolved in 4 mL MeOH was added 2.5 mL of 1.0 M NaOH. After stirring 15 minutes, 6.0 m HCl was added (0.42 mmol, 2.5 mmol), MeOH was removed under reduced pressure, and the white precipitate was collected by filtration and dried in vacuo to obtain 150 mg of the desired acid (57% yield).

Example 17: Synthesis of 1-(o-tolyl)-1,2,4-triazole-3-carboxylic acid

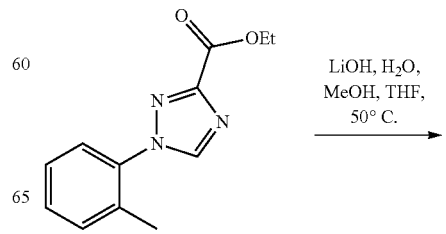

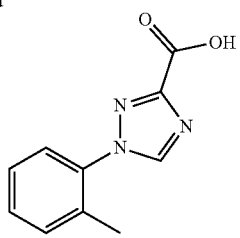

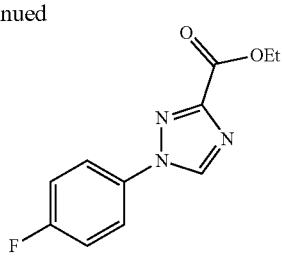

To a solution of ethyl 1-(o-tolyl)-1,2,4-triazole-3-carboxylate (400 mg, 1.7 mmol) in 3 mL THF was added 4 M LiOH (2 mL, 8 mmol) followed by 3 mL of MeOH. The reaction mixture was stirred at 50° C. for 5 minutes, after which the pH was adjusted to 4 with the addition of conc. HCl. After extraction, drying (MgSO$_4$), filtration and drying under reduced pressure, 43 mg of residue was recovered (12%) and used in the subsequent step without further purification.

4-Fluoroaniline (2.8 g, 26 mmol) was dissolved in 10% HCl and cooled to 0° C. To this solution was carefully added NaNO$_2$ (1.8 g, 26 mmol) dissolved in 10 mL water. In a separate flask, NaOAc (13 g, 96 mmol), and water (25 mL) were added to a solution of ethyl isocyanoacetate (2.0 g, 18 mmol) in methanol (80 mL). This solution was cooled to 0° C. and the diazonium salt of 4-fluoroaniline was carefully added over the course of 15 minutes. Stirring was continued at 0° C. for an additional 15 minutes, after which the flask was removed from the ice bath and stirring was continued for an additional 2 hours. The reaction mixture was then added to 500 mL water and the resulting brown precipitate was collected by filtration and dried in vacuo to obtain 3.8 g of the desired ester (90% yield).

Example 18: Synthesis of 1-(p-fluorophenyl)-1,2,4-triazole-3-carboxylic acid

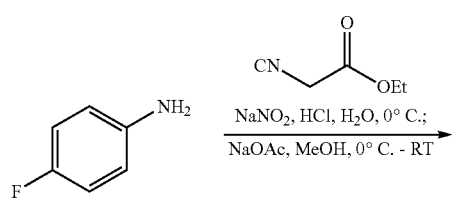

Example 19: Synthesis of N-[(3S)-1-(8-methylpyrrolo[1,2-a]pyrazin-1-yl)pyrrolidin-3-yl]-2-phenyl-thiazole-4-carboxamide

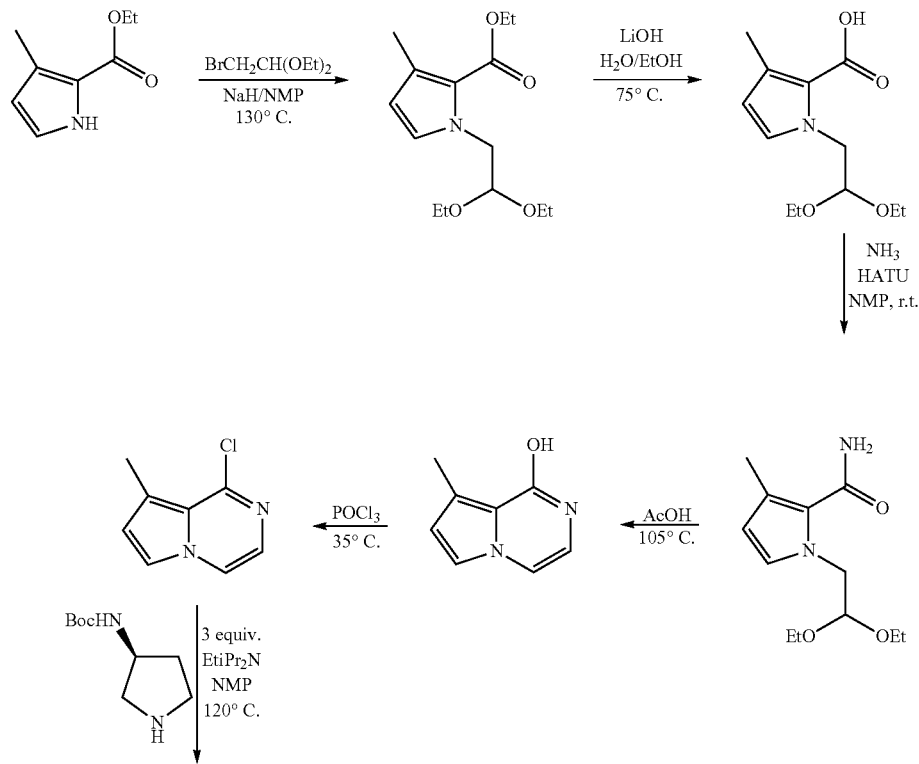

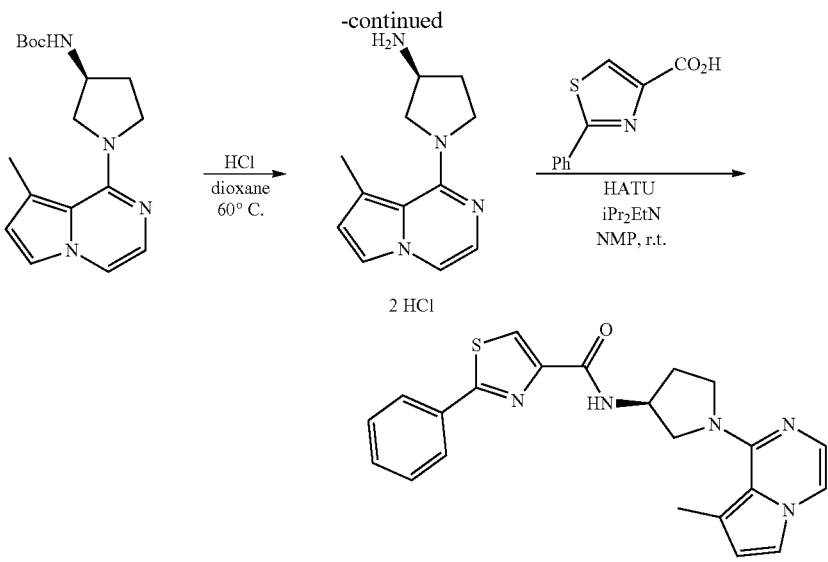

a) Ethyl 3-methyl-H-pyrrole-2-carboxylate (2.45 g, 16.0 mmol) was dissolved in a mixture of 8 mL of NMP and 2-bromo-1,1-diethoxyethane (3.23 mL, 20.8 mmol). 60% Sodium hydride (0.77 g, 19.2 mmol) was added portionwise at rt. The resulting solution was heated to 130° C. for 5 hours and then cooled down to rt. The solution was then diluted with 100 mL of water and the resulting mixture was extracted with one 100 mL portion of MTBE. The organic layer was evaporated in vacuo and purified via flash chromatography (SiO$_2$, 10-40% EtOAc/hexanes) to yield 1.90 g of the desired compound as a colorless oil (44% yield).

b) 1.90 g (7.06 mmol) Of ethyl 1-(2,2-diethoxyethyl)-3-methyl-1H-pyrrole-2-carboxylate (prepared in step a above) was dissolved in 40 mL of ethanol-water mixture (1:1). Following the addition of 1.48 g (35.3 mmol) of lithium hydroxide monohydrate, the mixture was heated to 75° C. for 8 hours. After cooling, the majority of the ethanol was evaporated in vacuo. The resulting solution was diluted with 30 mL of water and neutralized with 2.33 g of acetic acid (38.8 mmol), then extracted with two 30 mL portions of dichloromethane. The organic phase was dried over anhydrous magnesium sulfate, filtered, and concentrated in vacuo to yield 1.68 g of a colorless solid (99% yield).

c) 1.68 g (6.97 mmol) of 1-(2,2-diethoxyethyl)-3-methyl-1H-pyrrole-2-carboxylic acid (prepared in step b above) was dissolved in a mixture of 15 mL NMP and 45 mL of a 0.5 M solution of ammonia gas in dioxane. 3.18 g of HATU (8.36 mmol) was added and the mixture was stirred overnight at rt. To this mixture 10 mL of NMP was added and the dioxane was evaporated in vacuo. Another portion of HATU was added (1.59 g, 4.18 mmol) and ammonia gas was bubbled through the mixture and until no more reaction progress was observed. The mixture was then diluted with 300 mL of brine and extracted with one 150 mL portion of MTBE. The organic layer was evaporated in vacuo and purified via flash chromatography (SiO$_2$, 20-100% EtOAc/ hexanes) to give 1.26 g of the desired compound as a colorless oil (75% yield).

d) 1.25 g (5.21 mmol) of 1-(2,2-diethoxyethyl)-3-methyl-1H-pyrrole-2-carboxamide (prepared in step c above) was dissolved in 30 mL of glacial acetic acid and heated to 105° C. for 4 hours, then evaporated to dryness in vacuo. The residue was dissolved in 25 mL of hot dichloromethane, then diluted with 30 mL of hexanes while evaporating most of the dichloromethane. The solids were filtered off, washed with 5 mL of hexanes, and dried to give 730 mg of the pure desired compound as a tan powder (95% yield).

e) 725 mg (4.90 mmol) of 8-methyl-2H-pyrrolo[1,2-a] pyrazin-1-one (prepared in step d above) was suspended in 7 mL of phosphoryl chloride and stirred at r.t. overnight, followed by heating to 35° C. for 4 hours. The resulting solution was then evaporated to dryness in vacuo. The residue was taken up in a mixture of 10 mL of dichloromethane and 10 mL of aqueous sodium bicarbonate and stirred until gas evolution had ceased. The separated organic layer was dried over anhydrous magnesium sulfate, filtered and concentrated in vacuo. The residue was dissolved in 9 mL of hot n-heptane. The solution was decanted off the insoluble black tars and concentrated in vacuo to give 774 mg of the desired product as an off-white solid (95% yield).

f) 646 mg (3.87 mmol) Of 1-chloro-8-methyl-pyrrolo[1, 2-a]pyrazine (prepared in step e above), 2.16 g (11.6 mmol) of (S)-3-(Boc-amino)pyrrolidine, 1 mL of N,N-diisopropylethylamine and 1 mL of NMP were combined and heated to 120° C. for 1 hour. The mixture was cooled down, diluted with 50 mL of water and extracted with three 50 mL portions of ethyl acetate. Solid sodium bicarbonate was added to the aqueous layer and it was extracted again with 50 mL of ethyl acetate. The combined organic layers were washed with aqueous sodium bicarbonate, evaporated in vacuo and purified using flash chromatography (SiO$_2$, 20-60% EtOAc/ hexanes) to yield 872 mg of the desired compound as a colorless oil (71% yield).

g) 872 mg (2.75 mmol) of tert-butyl N-[(3S)-1-(8-methylpyrrolo[1,2-a]pyrazin-1-yl)pyrrolidin-3-yl]carbamate (prepared in step f above) was dissolved in 3.5 mL of dioxane. To this solution 3.5 mL of a hydrogen chloride solution in dioxane (4 M) was added and the mixture was stirred at 60° C. for 1 hour, during which precipitation of colorless solids was observed. The volatiles were removed in vacuo to give 739 mg of the desired compound without further purification (93% yield).

h) 39 mg (0.135 mmol) of (3S)-1-(8-methylpyrrolo[1,2-a]pyrazin-1-yl)pyrrolidin-3-amine dihydrochloride (prepared in step g above) and 28 mg (0.135 mmol) of 2-phenylthiazole-4-carboxylic acid were dissolved in 0.5 mL of NMP. To this mixture were added 77 mg (0.203 mmol) of HATU and 0.117 mL (0.675 mmol) of N,N-diisopropylethylamine. The mixture was stirred at r.t. for 1 hour, then diluted with 3 mL of DMSO and injected directly onto a reverse-phase semi-preparative HPLC system (5-60% acetonitrile/water, 0.1%6 TFA). Pure fractions were concentrated in vacuo to give 66 mg of the desired product as a TFA salt (95% yield). $^1$H NMR (400 MHz, DMSO) δ 11.28 (s, 1H), 8.82 (d, J=7.0 Hz, 1H), 8.33 (s, 1H), 8.04-8.01 (m, 2H), 7.82 (m, 2H), 7.54-7.50 (m, 3H), 6.86 (d, J=5.5 Hz, 1H), 6.76 (d, J=2.2 Hz, 1H), 4.75-4.65 (m, 1H), 4.20-3.60 (m, 4H), 2.48 (s, 3H), 2.40-2.20 (m, 2H); MS: (ES) m/z calculated for $C_{22}H_{21}N_5OS$ [M+H]$^+$ 404.2, found 404.

Example 20: Synthesis of 1-(4-chlorophenyl)-N-[(3S)-1-(8-methylpyrrolo[1,2-a]pyrazin-1-yl)pyrrolidin-3-yl]pyrazole-3-carboxamide

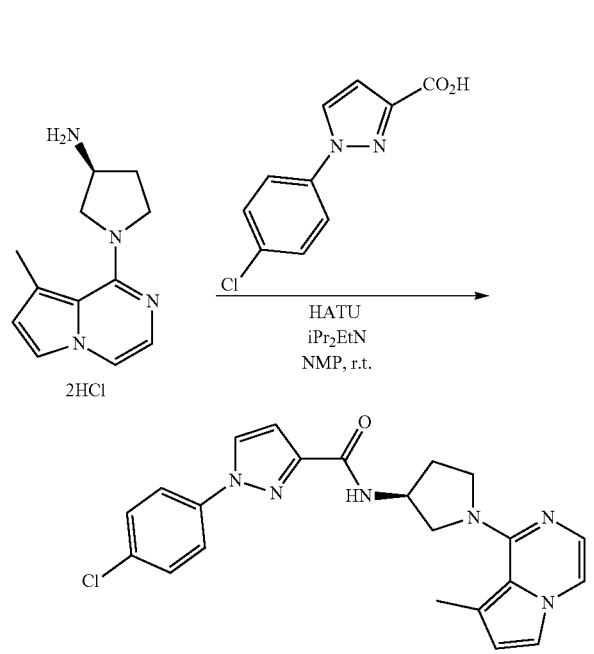

40 mg (0.138 mmol) of (3S)-1-(8-methylpyrrolo[1,2-a]pyrazin-1-yl)pyrrolidin-3-amine dihydrochloride and 31 mg (0.138 mmol) of 1-(4-chlorophenyl)pyrazole-3-carboxylic acid were dissolved in 0.5 mL of NMP. To this mixture were added 79 mg (0.207 mmol) of HATU and 0.120 mL (0.690 mmol) of N,N-diisopropylethylamine. The mixture was stirred at rt for 1 hour, then diluted with 3 mL of DMSO and injected directly onto a reverse-phase semi-preparative HPLC system (5-60% acetonitrile/water, 0.1% TFA). Pure fractions were concentrated in vacuo, dissolved in 1 mL of methanol and passed through a bicarbonate resin cartridge (PL-HCO3 MP SPE 500 mg/6 mL). To the resulting solution 15 µL of concentrated hydrochloric acid was added and the volatiles were removed in vacuo to give 49 mg of the desired product as an HCl salt (78% yield). $^1$H NMR (400 MHz, DMSO) δ 11.38 (s, 1H), 8.78 (d, J=7.0 Hz, 1H), 8.59 (d, J=3.0 Hz, 1H), 7.95 (d, J=7.0, 2H), 7.81 (m, 2H), 7.61 (d, J=8.8 Hz, 2H), 6.92 (s, 1H), 6.85 (d, J=5.5 Hz, 1H), 6.76 (d, J=2.2 Hz, 1H), 4.70-4.65 (m, 1H), 4.18-3.80 (m, 4H), 2.48 (s, 3H), 2.38-2.18 (m, 2H); MS: (ES) m/z calculated for $C_{22}H_{21}ClN_6O$ [M+H]+ 421.2, found 421.

Example 21: Synthesis of 6-methyl-N-[(3S)-1-pyrrolo[1,2-a]pyrazin-1-ylpyrrolidin-3-yl]quinazoline-2-carboxamide

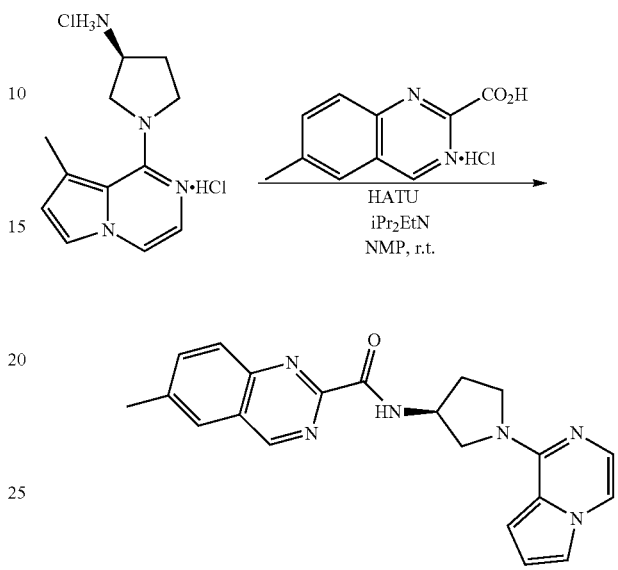

43 mg (0.156 mmol) of (3S)-1-pyrrolo[1,2-a]pyrazin-1-ylpyrrolidin-3-amine dihydrochloride and 33 mg (0.156 mmol) of 6-methylquinazoline-2-carboxylic acid hydrochloride were dissolved in 0.4 mL of NMP. To this mixture was added 85 mg (0.224 mmol) of HATU and 155 µL (0.892 mmol) of N,N-diisopropylethylamine. The mixture was stirred at rt for 30 minutes, then diluted with 3 mL of DMSO and injected directly onto a reverse-phase semi-preparative HPLC system (5-40% acetonitrile/water, 0.1% TFA). Pure fractions were concentrated in vacuo to give 39 mg of the desired product as a TFA salt (51% yield). $^1$H NMR (400 MHz, CD$_3$OD) δ 9.49 (s, 1H), 8.04 (d, J=9.1 Hz, 1H), 7.93 (d, J=6.9 Hz, 2H), 7.75 (d, J=1.5 Hz, 1H), 7.70 (d, J=5.9 Hz, 1H), 7.55 (s, 1H), 6.92 (s, 1H), 6.85 (d, J=5.5 Hz, 1H), 5.00-3.70 (m, 5H), 3.30 (s, 3H), 2.60-2.30 (m, 2H), MS: (ES) m/z calculated for $C_{21}H_{20}N_6O$ [M+H]+ 373.2, found 373.

Example 22: Synthesis of 1-(4-chlorophenyl)-N-[(3S)-1-pyrrolo[1,2-a]pyrazin-1-ylpyrrolidin-3-yl]pyrazole-3-carboxamide.trifluoroacetate salt

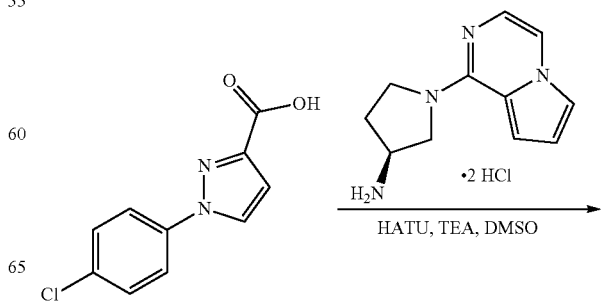

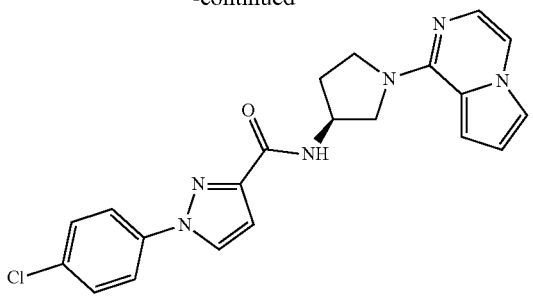

To a solution of 1-(4-chlorophenyl)pyrazole-3-carboxylic acid (49 mg, 0.22 mmol) in 0.80 mL DMSO was added (3S)-1-pyrrolo[1,2-a]pyrazin-1-ylpyrrolidin-3-amine dihydrochloride (74 mg, 0.27 mmol), followed by triethylamine (0.12 mL, 0.86 mmol) and HATU (92 mg, 0.24 mmol). After 1.5 hours the reaction mixture was diluted with 1 mL water, filtered, purified by reverse phase preparative HPLC (22-36% gradient of CH$_3$CN/H$_2$O with 0.1% TFA modifier) and dried (lyophilizer) to give the product. $^1$H NMR (400 MHz, CD$_3$OD) δ 8.76 (d, J=6.2 Hz, 1H), 8.31 (s, 1H), 7.86 (d, J=8.8 Hz, 2H), 7.77 (d, J=2.5 Hz, 1H), 7.72 (d, J=5.5 Hz, 1H), 7.57 (d, J=5.5 Hz, 1H), 7.50 (d, J=8.8 Hz, 2H), 6.96 (d, J=2.5, 1H), 6.93 (dd, J=2.6, 7.0 Hz, 1H), 6.84 (d, J=5.9 Hz, 1H), 4.95-4.80 (m, 1H), 4.70-3.70 (br, 4H), 2.60-2.30 (m, 2H). MS: (ES) 407.2 (M+H$^+$).

Example 23: Synthesis of 1-(o-tolyl)-N-[(3S)-1-pyrrolo[1,2-a]pyrazin-1-ylpyrrolidin-3-yl]pyrazole-3-carboxamide.trifluoroacetate salt

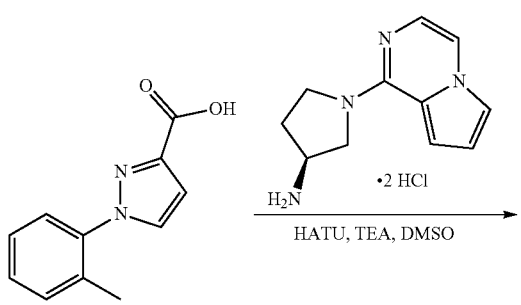

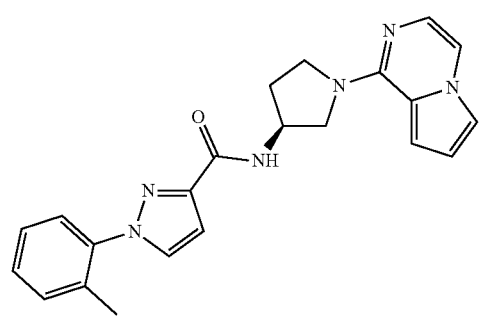

To a solution of 1-(o-tolyl)pyrazole-3-carboxylic acid (35 mg, 0.17 mmol) in 0.80 mL DMSO was added added (3S)-1-pyrrolo[1,2-a]pyrazin-1-ylpyrrolidin-3-amine dihydrochloride (46 mg, 0.17 mmol), followed by triethylamine (0.10 mL, 0.70 mmol) and HATU (80 mg, 0.21 mmol). After 1 hour the reaction mixture was diluted in dichloromethane (70 mL), washed with water (20 mL) and concentrated under reduced pressure. The residue was purified by reverse phase preparative HPLC (20-40% gradient of CH$_3$CN/H$_2$O with 0.1% TFA modifier) and dried (lyophilizer) to give the desired compound. $^1$H NMR (400 MHz, CD$_3$OD) δ 8.62 (d, J=5.9 Hz, 1H), 7.88 (d, J=2.5 Hz, 1H), 7.75 (s, 1H), 7.70 (d, J=5.9 Hz, 1H), 7.54 (d, J=3.6 Hz, 1H), 7.40-7.25 (m, 4H), 6.94 (d, J=2.2 Hz, 1H), 6.91 (dd, J=2.6, 4.4 Hz, 1H), 6.82 (d, J=5.5 Hz, 1H), 4.95-3.65 (br, 5H), 2.58-2.30 (m, 2H), 2.20 (s, 3H). MS: (ES) 387.2 (M+H$^+$).

Example 24: Synthesis of 1-(o-tolyl)-N-[(3S)-1-pyrrolo[1,2-a]pyrazin-1-ylpyrrolidin-3-yl]-1,2,4-triazole-3-carboxamide.trifluoroacetate salt

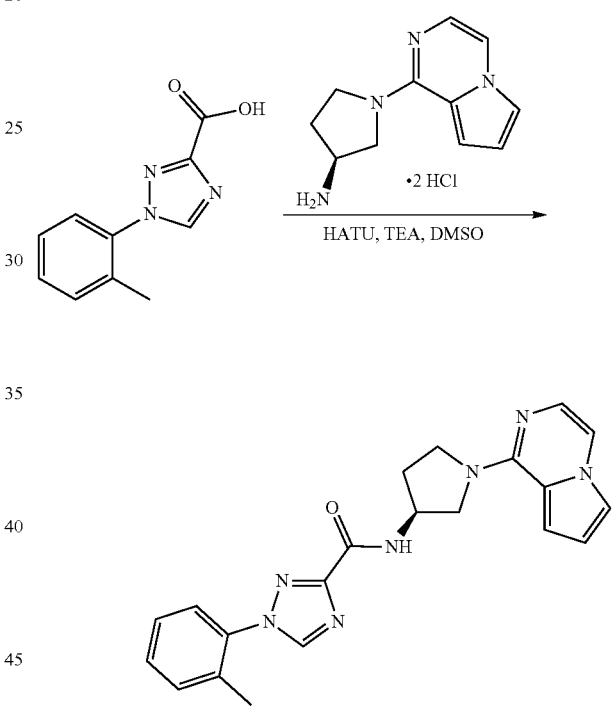

To a solution of 1-(o-tolyl)-1,2,4-triazole-3-carboxylic acid (43 mg, 0.21 mmol) in 1 mL DMSO was added (3S)-1-pyrrolo[1,2-a]pyrazin-1-ylpyrrolidin-3-amine dihydrochloride (60 mg, 0.22 mmol), followed by triethylamine (0.12 mL, 0.89 mmol) and HATU (80 mg, 0.21 mmol). After 20 minutes, the reaction mixture was quenched with 10 mL water and extracted with dichloromethane. The organic layer was separated and concentrated under reduced pressure. The residue was purified by reverse phase preparative HPLC (20-40% gradient of CH$_3$CN/H$_2$O with 0.1% TFA modifier) and dried (lyophilizer) to give 20 mg of the desired compound (19% yield). $^1$H NMR (400 MHz, CD$_3$OD) δ 8.73 (s, 1H), 7.76 (d, J=2.6 Hz, 1H), 7.70 (d, J=5.5 Hz, 1H), 7.55 (d, J=4.0 Hz, 1H), 7.50-7.32 (m, 4H), 6.92 (dd, J=2.5, 4.4 Hz, 1H), 6.83 (d, J=5.9 Hz, 1H), 4.95-4.80 (m, 1H), 4.70-3.70 (br, 5H), 2.60-2.30 (m, 2H), 2.22 (s, 3H). MS: (ES) 388.2 (M+H$^+$).

Example 25: Synthesis of N-[(3S)-1-(8-methylpyrrolo[1,2-a]pyrazin-1-yl)pyrrolidin-3-yl]-5-phenyl-pyrimidine-2-carboxamide.trifluoroacetate salt

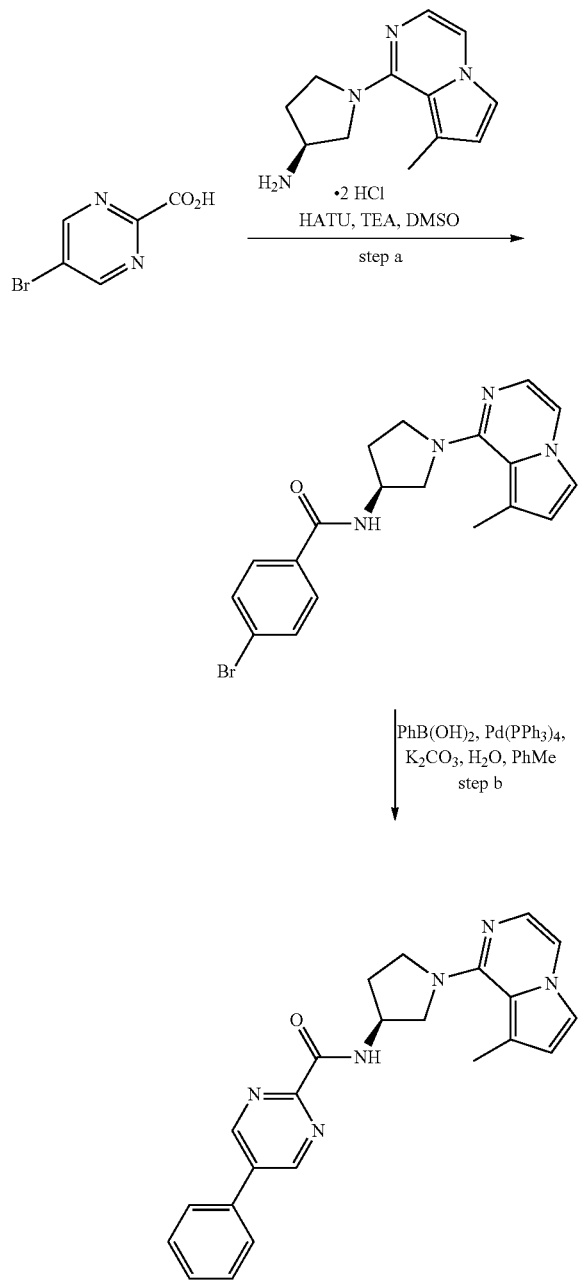

a) To a solution of 5-bromopyrimidine-2-carboxylic acid (41 mg, 0.20 mmol) in 0.80 mL DMSO was added (3S)-1-(8-methylpyrrolo[1,2-a]pyrazin-1-yl)pyrrolidin-3-amine dihydrochloride (61 mg, 0.21 mmol), followed by triethylamine (0.12 mL, 0.86 mmol) and HATU (81 mg, 0.21 mmol). After 20 minutes, the reaction mixture was quenched with 10 mL water and extracted with dichloromethane. The organic layer was separated and concentrated under reduced pressure. The residue was purified by flash chromatography (SiO$_2$, 2% 7 M NH$_3$ in MeOH/dichloromethane). MS: (ES) 402.2 (M+H$^+$).

b) In a 4 mL vial, the product from step a was combined with phenylboronic acid (24 mg, 0.2 mmol), Pd(PPh$_3$)$_4$ (23 mg, 0.020 mmol), degassed toluene (2 mL), and degassed 2 M K$_2$CO$_3$ (0.3 mL, 0.6 mmol). The vial was sealed and the reaction mixture was stirred on a preheated hot plate at 100° C. for 1 hour. The reaction mixture was concentrated under reduced pressure and purified by reverse phase preparative HPLC (20-30% gradient of CH$_3$CN/H$_2$O with 0.1% TFA modifier) and dried (lyophilizer) to give the desired product. $^1$H NMR (400 MHz, CD$_3$OD) δ 9.18 (s, 2H), 7.77 (d, J=7.0 Hz, 2H), 7.67 (d, J=5.9 Hz, 2H), 7.57-7.48 (m, 3H), 6.76-6.72 (m, 2H), 4.95-4.80 (m, 1H), 4.32-4.24 (m, 1H), 4.10-3.90 (m, 3H), 2.64 (s, 3H), 2.50-2.35 (m, 2H). MS: (ES) 389.2 (M+H$^+$).

Example 26: Synthesis of N-[(3S)-1-(8-methylpyrrolo[1,2-a]pyrazin-1-yl)pyrrolidin-3-yl]-1-(o-tolyl)pyrazole-3-carboxamide.trifluoroacetate salt

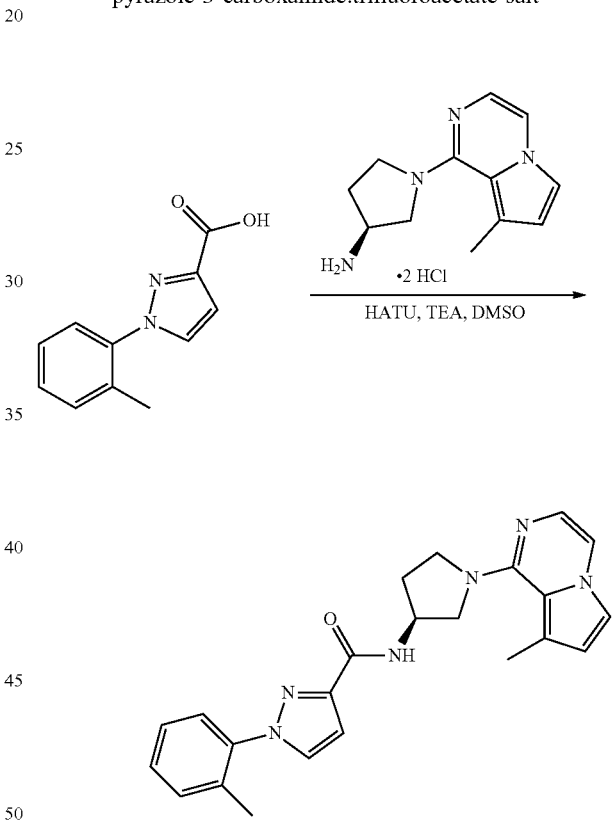

To a solution of 1-(o-tolyl)pyrazole-3-carboxylic acid (27 mg, 0.13 mmol) in 0.60 mL DMSO was added (3S)-1-(8-methylpyrrolo[1,2-a]pyrazin-1-yl)pyrrolidin-3-amine dihydrochloride (39 mg, 0.13 mmol), followed by triethylamine (0.080 mL, 0.58 mmol) and HATU (53 mg, 0.14 mmol). After 15 minutes, acetic acid (0.060 mL, 1 mmol) was added to the reaction mixture, followed by CH$_3$OH (0.60 mL) and water (0.70 mL). The mixture was filtered and purified by reverse phase preparative HPLC (20-40% gradient of CH$_3$CN/H$_2$O with 0.1% TFA modifier) and dried (lyophilizer) to give the desired product. $^1$H NMR (400 MHz, CD$_3$OD) δ 7.87 (s, 1H), 7.64 (m, 2H), 7.40-7.28 (m, 4H), 6.93 (s, 1H), 6.74-6.70 (m, 2H), 4.80-4.70 (m, 1H), 4.30-4.20 (m, 1H), 4.10-3.85 (m, 3H), 2.61 (s, 3H), 2.50-2.35 (m, 2H), 2.20 (s, 3H). MS: (ES) 401.2 (M+H$^+$).

Example 27: Synthesis of N-[(3S)-1-(8-methylpyrrolo[1,2-a]pyrazin-1-yl)pyrrolidin-3-yl]-2-phenyloxazole-4-carboxamide.trifluoroacetate salt

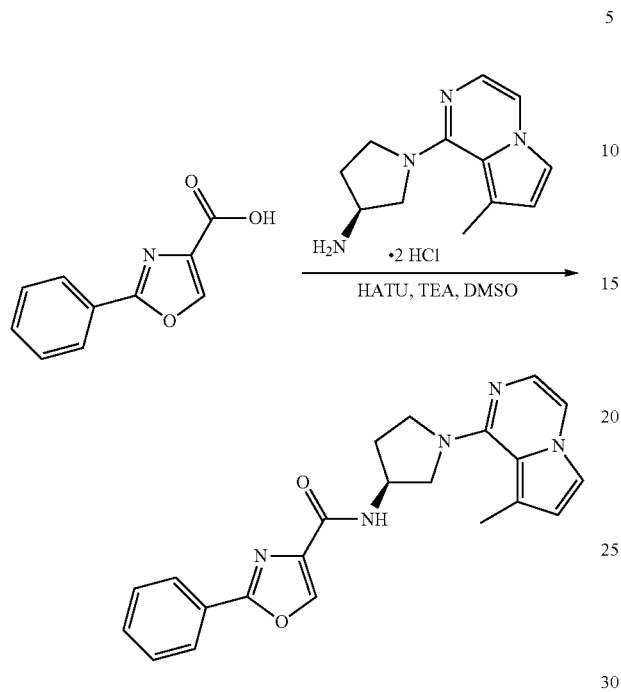

To a solution of 2-phenyloxazole-4-carboxylic acid (24 mg, 0.13 mmol) in 0.5 mL DMSO was added (3S)-1-(8-methylpyrrolo[1,2-a]pyrazin-1-yl)pyrrolidin-3-amine dihydrochloride (41 mg, 0.14 mmol), followed by triethylamine (0.080 mL, 0.58 mmol) and HATU (53 mg, 0.14 mmol). After 15 minutes, acetic acid (0.060 mL, 1 mmol) was added to the reaction mixture, followed by $CH_3OH$ (0.60 mL) and water (0.70 mL). The mixture was filtered and purified by reverse phase preparative HPLC (20-40% gradient of $CH_3CN/H_2O$ with 0.1% TFA modifier) and dried (lyophilizer) to give the desired product. $^1H$ NMR (400 MHz, $CD_3OD$) δ 8.72 (d, J=8.1 Hz, 1H), 8.45 (s, 1H), 8.06 (d, J=8.1 Hz, 2H), 7.67 (d, J=5.5 Hz, 2H), 7.52 (m, 3H), 6.76-6.73 (m, 2H), 4.85-4.75 (m, 1H), 4.30-4.22 (m, 1H), 4.10-3.90 (m, 3H), 2.64 (s, 3H), 2.55-2.35 (m, 2H). MS: (ES) 388.2 (M+H$^+$).

Example 28: Synthesis of 5-phenyl-N-[(3S)-1-pyrrolo[1,2-a]pyrazin-1-ylpyrrolidin-3-yl]pyrimidine-2-carboxamide.trifluoroacetate salt

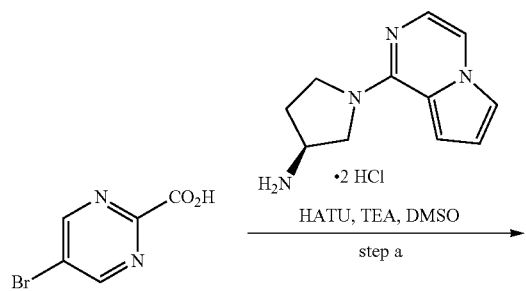

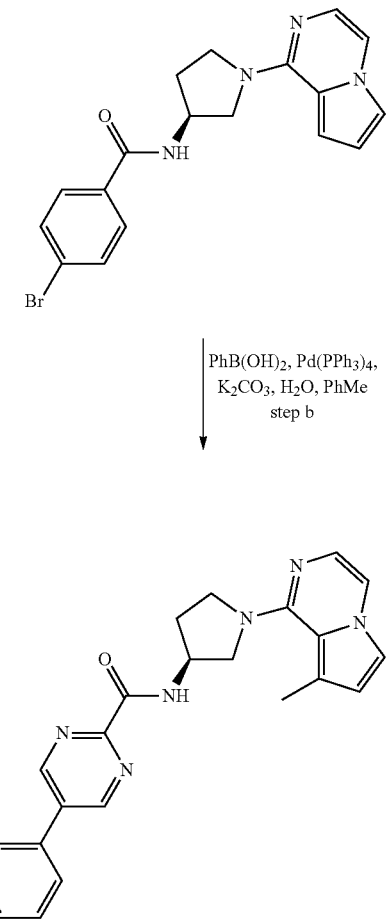

a) To a solution of 5-bromopyrimidine-2-carboxylic acid (120 mg, 0.59 mmol) in 2.0 mL DMSO was added (3S)-1-pyrrolo[1,2-a]pyrazin-1-ylpyrrolidin-3-amine dihydrochloride (160 mg, 0.58 mmol), followed by triethylamine (0.30 mL, 2.2 mmol) and HATU (228 mg, 0.60 mmol). After stirring overnight, the reaction mixture was quenched with 10 mL water and extracted with dichloromethane. The organic layer was separated and concentrated under reduced pressure. The residue was purified by flash chromatography ($SiO_2$, 2% 7 M $NH_3$ in MeOH/dichloromethane). MS: (ES) 388.2 (M+H$^+$).

b) In a 4 mL vial, the product from step a (80 mg, 0.21 mmol) was combined with phenylboronic acid (29 mg, 0.24 mmol), Pd(PPh$_3$)$_4$ (25 mg, 0.021 mmol), degassed toluene (2 mL), and degassed 2 M $K_2CO_3$ (0.35 mL, 0.7 mmol). The vial was sealed and the reaction mixture was stirred on a preheated hot plate at 100° C. for 30 minutes. The reaction mixture was concentrated under reduced pressure and purified by reverse phase preparative HPLC (20-40% gradient of $CH_3CN/H_2O$ with 0.1% TFA modifier) and dried (lyophilizer) to give the desired product. $^1H$ NMR (400 MHz, $CD_3OD$) δ 9.42 (d, J=7.0 Hz, 0.8H), 9.18 (s, 2H), 7.77-7.70 (m, 4H), 7.58-7.48 (m, 4H), 6.93 (dd, J=2.6, 4.4 Hz, 1H), 6.85 (d, J=5.5 Hz, 1H), 5.00-3.65 (br, 5H), 2.65-2.40 (m, 2H). MS: (ES) 385.1 (M+H$^+$).

Example 29: Synthesis of 5-phenyl-N-[(3)-1-pyrrolo[1,2-a]pyrazin-1-ylpyrrolidin-3-yl]-4H-1,2,4-triazole-3-carboxamide.trifluoroacetate salt

Example 30: Synthesis of 5-(dimethylamino)-N-[(3S)-1-pyrrolo[1,2-a]pyrazin-1-ylpyrrolidin-3-yl]pyrimidine-2-carboxamide.trifluoroacetate salt

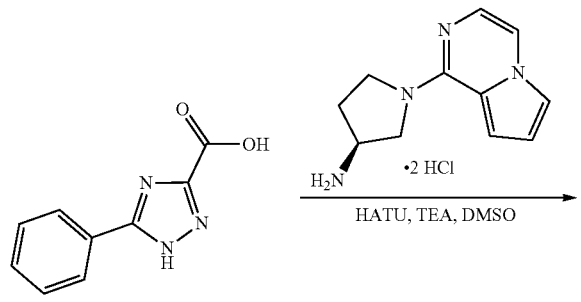

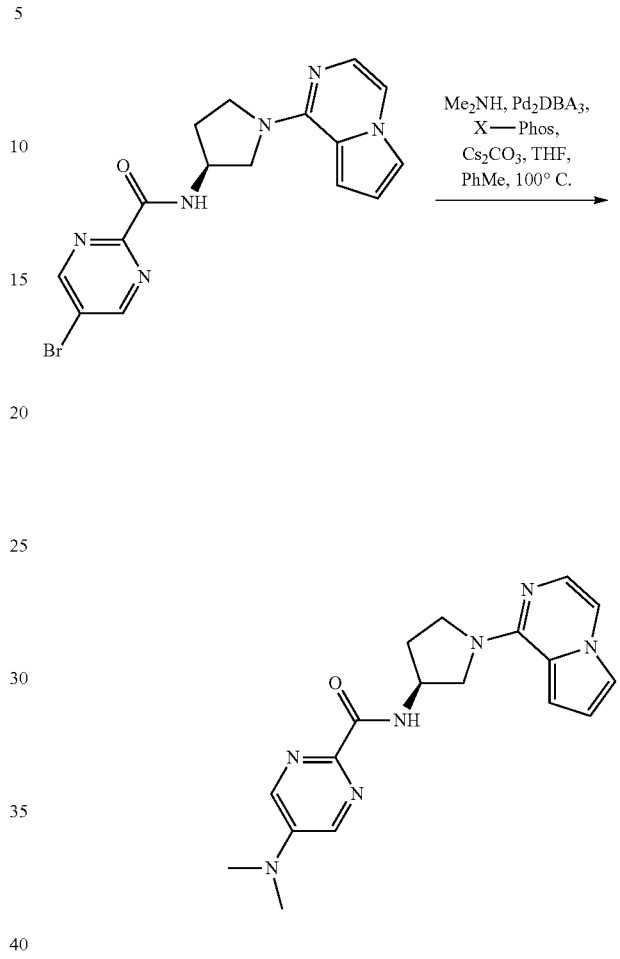

To a solution of sodium 5-phenyl-4H-1,2,4-triazole-3-carboxylate (50 mg, 0.24 mmol) in 0.70 mL DMSO was added (3. S)-1-pyrrolo[1,2-a]pyrazin-1-ylpyrrolidin-3-amine dihydrochloride (80 mg, 0.29 mmol), followed by triethylamine (0.14 mL, 1.0 mmol) and HATU (105 mg, 0.28 mmol). After stirring the reaction mixture overnight, it was purified directly by reverse phase preparative HPLC (20-30% gradient of $CH_3CN/H_2O$ with 0.1% TFA modifier) and dried (lyophilizer) to give the desired product. $^1$H NMR (400 MHz, DMSO) δ 11.40 (s, 1H), 8.05 (d, J=7.0 Hz, 2H), 7.91 (s, 1H), 7.84 (d, J=4.4 Hz, 1H), 7.60-7.40 (m, 4H), 7.00-6.90 (m, 2H), 4.85-3.50 (br, 5H), 2.45-2.20 (m, 2H). MS: (ES) 374.2 (M+H$^+$).

In a 4 mL vial, 4-bromo-N-[(3S)-1-pyrrolo[1,2-a]pyrazin-1-ylpyrrolidin-3-yl]benzamide (57 mg, 0.15 mmol) was combined with tris(dibenzylideneacetone)dipalladium (26 mg, 0.023 mmol), 2-dicyclohexylphosphino-2',4',6'-triisopropylbiphenyl ("X-Phos", 49 mg, 0.10 mmol), $Cs_2CO_3$ (250 mg, 0.77 mmol), degassed toluene (1.0 mL), and 2 M dimethylamine in THF (1 mL, 2 mmol). The vial was sealed and the reaction mixture was stirred for 22 hours at 100° C. It was adsorbed onto silica gel and purified by flash chromatography ($SiO_2$, 2-5% 7 M $NH_3$ in MeOH/dichloromethane), followed by reverse phase preparative HPLC (20-30% gradient of $CH_3CN/H_2O$ with 0.1% TFA modifier) and dried (lyophilizer) to give the desired product. $^1$H NMR (400 MHz, $CD_3OD$) δ 8.27 (s, 2H), 7.75 (t, J=1.1, 1H), 7.70 (d, J=5.5, 1H), 7.55 (s, 1H), 6.91 (dt, J=1.8, 2.6 Hz, 1H), 6.83 (d, J=5.5 Hz, 1H), 5.00-4.80 (m, 1H), 4.65-3.70 (br, 4H), 3.10 (s, 6H), 2.60-2.30 (m, 2H). MS: (ES) 352.2 (M+H$^+$).

Example 31: Synthesis of 5-(1-hydroxyethyl)-N-[(3S)-1-pyrrolo[1,2-a]pyrazin-1-ylpyrrolidin-3-yl]pyrimidine-2-carboxamide.trifluoroacetate salt

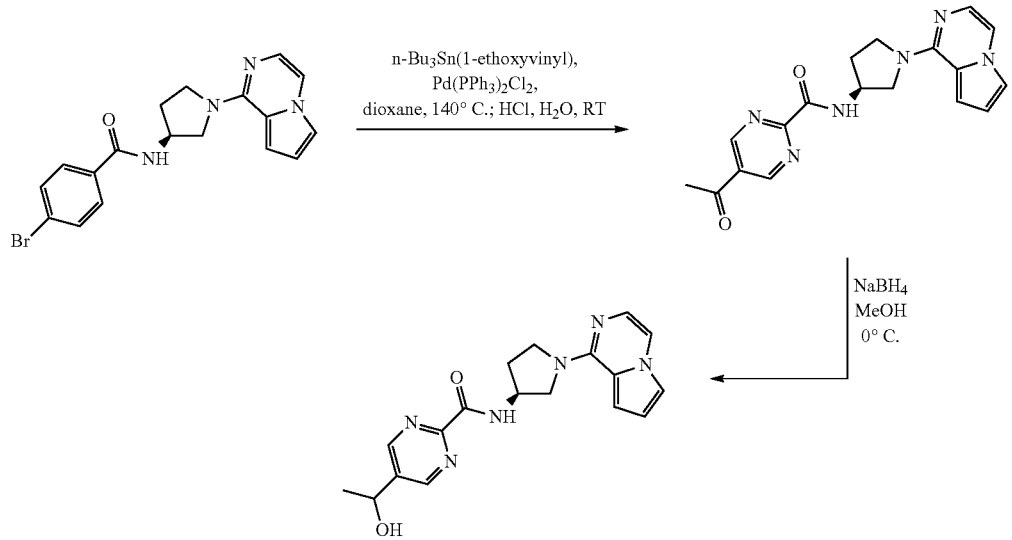 [SMILES: O=C(N[C@H]1CCN(c2nccn3cccc23)C1)c1ccc(Br)cc1 ; CC(=O)c1cnc(C(=O)N[C@H]2CCN(c3nccn4cccc34)C2)nc1 ; CC(O)c1cnc(C(=O)N[C@H]2CCN(c3nccn4cccc34)C2)nc1]

a) To a 15 mL heavy-walled pressure vessel was added 4-bromo-N-[(3S)-1-pyrrolo[1,2-a]pyrazin-1-ylpyrrolidin-3-yl]benzamide (289 mg, 0.747 mmol), tri-n-butyl(1-ethoxyvinyl)tin (0.35 mL, 1.0 mmol), dichlorobis(triphenylphosphine)palladium (30 mg, 0.042 mmol), and degassed dioxane (4 mL). The vessel was sealed and immersed into a preheated (140° C.) oil bath. After 25 minutes, the vessel was removed from the oil bath, allowed to cool to room temperature, and treated with 6 M HCl (0.40 mL, 2.4 mmol), and stirred overnight. The reaction mixture was diluted with 200 mL dichloromethane and 20 mL water. The organic layer was separated and set aside, while the aqueous phase was basified with NaOH and extracted with dichloromethane. The combined organic layers were concentrated under reduced pressure and the remaining residue was purified by flash chromatography ($SiO_2$; 2-5% $CH_3OH$/dichloromethane) to obtain 209 mg of the desired compound (80% yield). MS: (ES) 351.2 (M+H$^+$).

b) The ketone prepared in step a (56 mg, 0.16 mmol) was dissolved in 5 mL MeOH and cooled to 0° C. on an ice bath. Sodium borohydride (7.2 mg, 0.19 mmol) was added, and the reaction was stirred for 20 minutes at 0° C. The reaction was quenched with 6 M HCl, concentrated under reduced pressure, and directly purified by reverse phase preparative HPLC (20-30% gradient of $CH_3CN$/$H_2O$ with 0.1% TFA modifier) and dried (lyophilizer) to give the desired compound. $^1$H NMR (400 MHz, $CD_3OD$) δ 8.93 (s, 2H), 7.79 (dd, J=1.2, 2.7 Hz, 1H), 7.74 (d, J=5.9 Hz, 1H), 7.58 (d, J=3.5 Hz, 1H), 6.94 (dd, J=2.7, 5.7 Hz, 1H), 6.87 (d, J=5.9 Hz, 1H), 5.02-4.95 (q, J=6.6 Hz, 1H), 4.80-3.60 (br, 5H), 2.62-2.38 (m, 2H), 1.53 (d, J=6.6 Hz, 3H). MS: (ES) 353.2 (M+H+).

Example 32: Synthesis of N-[(3R)-1-imidazo[1,2-a]pyrazin-8-ylpyrrolidin-3-yl]-1-phenyl-1,2,4-triazole-3-carboxamide

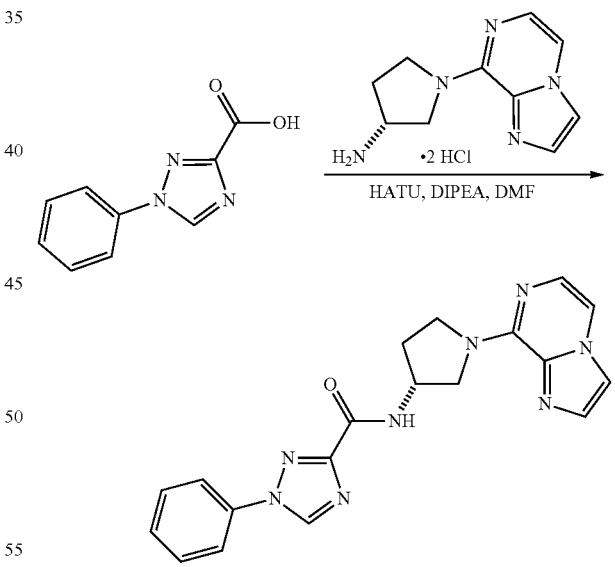

1-Phenyl-1,2,4-triazole-3-carboxylic acid (1.2 g, 6.3 mmol), (3R)-1-imidazo[1,2-a]pyrazin-8-ylpyrrolidin-3-amine dihydrochloride (2.0 g, 7.4 mmol), and diisopropylethylamine (13 mL, 75 mmol) were combined together in 50 mL DMF. To this mixture was added HATU (2.5 g, 6.6 mmol). After stirring 3 minutes, LCMS of an aliquot indicated the reaction was complete. DIPEA and most of the DMF were removed under reduced pressure. The residue was diluted in 400 mL EtOAc and washed with 50 mL saturated $NaH_2PO_4$. It was determined that a large amount of the desired product was present in the organic phase, therefore it was extracted with 400 mL 10 vol % i-PrOH/CHCl₃. The combined organic layers were dried (Na₂SO₄), filtered and concentrated. The crude product was purified by flash chromatography (SiO₂, 2-5% MeOH/dichloromethane) to provide 936 mg of the desired product (39% yield). $^1$H NMR (400 MHz, CDCl₃) δ 8.54 (s, 1H), 7.74 (td, J=1.1, 7.5 Hz, 2H), 7.56-7.48 (m, 4H), 7.47-7.40 (m, 2H), 7.37 (d, J=8.2 Hz, 1H), 7.33 (d, J=4.3 Hz, 1H), 5.00-4.80 (m, 1H), 4.50-4.35 (br, 1H), 4.30-4.15 (br, 3H), 3.45-3.30 (m, 1H), 2.90-2.75 (m, 1H), 2.50-2.38 (m, 1H), 2.25-2.15 (m, 1H). MS: (ES) 375.2 (M+H⁺).

Example 33: Synthesis of N-[(3S)-1-(3-ethylpyrrolo[1,2-a]pyrazin-1-yl)pyrrolidin-3-yl]-1-phenyl-1,2,4-triazole-3-carboxamide.trifluoroacetate salt

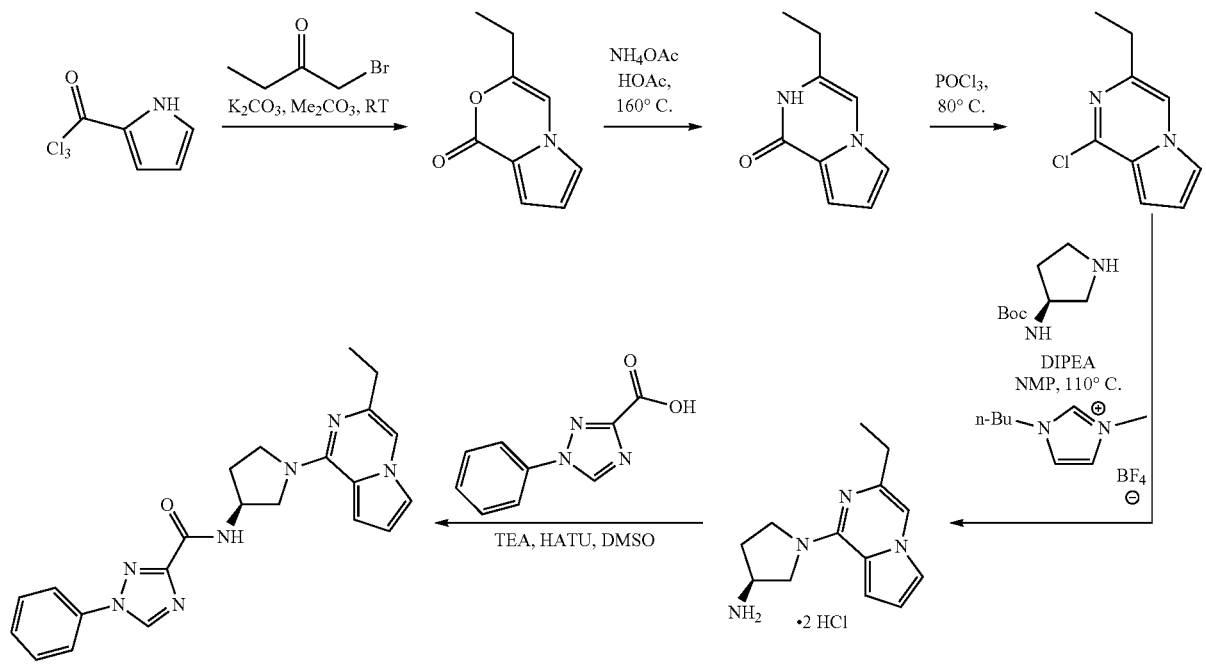

a) To a slurry of 2-(trichloroacetyl)pyrrole (380 mg, 1.79 mmol) and K₂CO₃ (780 mg, 5.7 mmol) in 5 mL acetone was added a solution of 1-bromo-2-butanone (400 mg, 2.7 mmol) in 2 mL acetone. The mixture was stirred for 19 hours at room temperature before filtering and concentrating under reduced pressure to obtain 3-ethyl-1H-pyrrolo[2,1-c][1,4]oxazin-1-one (298 mg, quantitative), which was used in the following step without purification.

b) To a 150 mL heavy wall glass pressure vessel were added the lactone from step a, 3-ethyl-1H-pyrrolo[2,1-c][1,4]oxazin-1-one (2.6 g, 16 mmol), NH₄OAc (6.0 g, 78 mmol), and acetic acid (40 mL). The vessel was sealed, immersed in a preheated oil bath set to 160° C., and stirred for 3 hours. Afterward, acetic acid was removed under reduced pressure and the residue was purified by flash chromatography (SiO₂, 2% MeOH/dichloromethane) to obtain 3-ethylpyrrolo[1,2-a]pyrazin-1(2H)-one (760 mg, 29% yield). MS: (ES) 163.1 (M+H⁺).

c) 3-Ethylpyrrolo[1,2-a]pyrazin-1(2H)-one from step b (760 mg, 4.7 mmol) was combined with POCl₃ (20 mL) and stirred at 80° C. for 20 minutes. POCl₃ was removed under reduced pressure. The residue was taken up in DCM and washed twice with saturated sodium bicarbonate. Afterward the organic phase was dried over magnesium sulfate, filtered, and concentrated under reduced pressure. The residue was used in the following step without purification.

d) In a 20 mL vial were combined tert-butyl N-[(3S)-pyrrolidin-3-yl]carbamate (610 mg, 3.3 mmol), 1-chloro-3-ethylpyrrolo[1,2-a]pyrazine from step c (470 mg, 2.6 mmol). DIPEA (2.0 mmol, 11 mmol), and 1-butyl-3-methylimidazolium tetrafluoroborate (100 mg, 0.4 mmol), and the mixture was heated for 45 minutes at 110° C. 1-methylpyrrolidinone (1 mL) was added, followed by additional tert-butyl N-[(3S)-pyrrolidin-3-yl]carbamate (200 mg, 1.1 mmol), and the reaction was stirred for an additional hour at 110° C. An extra 400 mg (2.2 mmol) of the aminopyrroldine was then added, and the mixture was stirred at 110° C. for an additional 20 minutes. The reaction mixture was dried in vacuo and purified by flash chromatography (SiO₂, 2% 7 M NH₃ in MeOH/dichloromethane). The desired Boc-protected intermediate was obtained after drying. The residue was taken up in a minimal amount of methanol and dichloromethane and treated with 4 M HCl in dioxane (3 mL, 12 mmol). The mixture was heated at 50° C. and stirred for 30 minutes, after which time the flask was removed from heat, allowed to cool to room temperature, and ether was added. The resulting brown precipitate, (3S)-1-(3-ethylpyrrolo[1,2-a]pyrazin-1-yl)pyrrolidin-3-amine dihydrochloride was collected by filtration and dried in vacuo; 638 mg, 86% yield.

e) 1-Phenyl-1,2,4-triazole-3-carboxylic acid (34 mg 0.18 mmol), (3S)-1-(3-ethylpyrrolo[1,2-a]pyrazin-1-yl)pyrrolidin-3-amine dihydrochloride (63 mg, 0.21 mmol) and triethylamine (0.13 mL, 0.93 mmol) were combined in 1 mL DMSO. HATU (74 mg, 0.19 mmol) was added and the mixture was stirred for 40 minutes. DMSO was removed under reduced pressure and the residue was purified by reverse phase preparative HPLC (10-30% gradient of CH₃CN/H₂O with 0.1% TFA modifier) and dried (lyophilizer) to give the desired compound. $^1$H NMR (400

MHz, CD$_3$OD) δ 9.14 (s, 1H), 9.05 (d, J=6.7 Hz, 1H), 7.88 (d, J=7.4 Hz, 2H), 7.71 (s, 1H), 7.60-7.46 (m, 5H), 6.89 (dd, J=2.8, 4.7 Hz, 1H), 4.95-4.80 (m, 1H), 4.78-3.80 (br, 4H), 2.68 (q, J=7.4 Hz, 2H), 2.60-2.40 (m, 2H), 1.33 (t, J=7.4 Hz, 3H). MS: (ES) 402.2 (M+H$^+$).

Example 34: Synthesis of N-[(3S)-1-(3-ethylpyrrolo[1,2-a]pyrazin-1-yl)pyrrolidin-3-yl]-1-(4-fluorophenyl)-1,2,4-triazole-3-carboxamide.trifluoroacetate salt

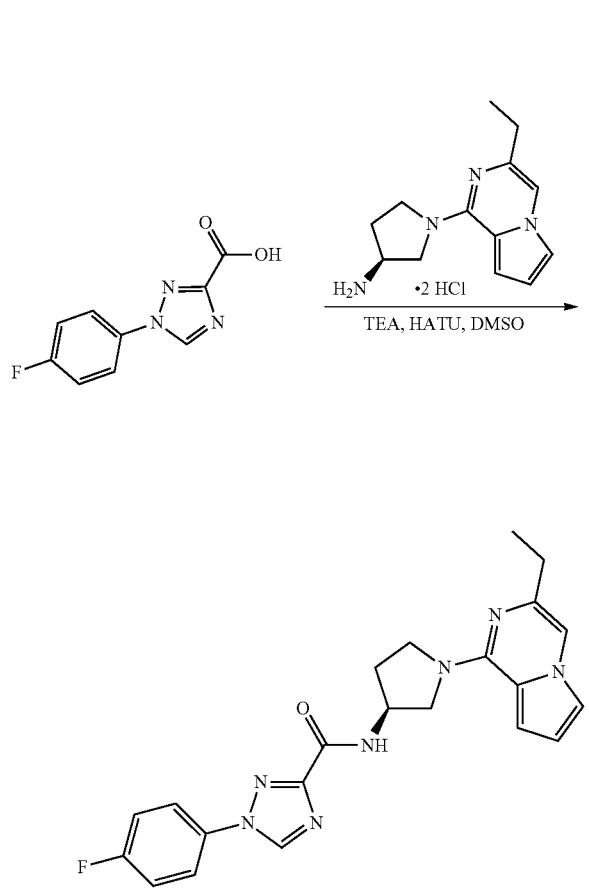

1-(4-fluorophenyl)-1,2,4-triazole-3-carboxylic acid (35 mg 0.17 mmol), (3S)-1-(3-ethylpyrrolo[1,2-a]pyrazin-1-yl)pyrrolidin-3-amine dihydrochloride (60 mg, 0.20 mmol) and triethylamine (0.12 mL, 0.86 mmol) were combined in 1 mL DMSO. HATU (72 mg, 0.19 mmol) was added and the mixture was stirred for 50 minutes. DMSO was removed under reduced pressure and the residue was purified by reverse phase preparative HPLC (10-30% gradient of CH$_3$CN/H$_2$O with 0.1% TFA modifier) and dried (lyophilizer) to give the desired compound. $^1$H NMR (400 MHz, CD$_3$OD) δ 9.10 (s, 1H), 7.92-7.88 (m, 2H), 7.71 (s, 1H), 7.53 (s, 2H), 7.35 (t, J=8.8 Hz, 2H), 6.89 (dd, J=2.4, 4.7 Hz, 1H), 4.95-4.80 (m, 1H), 4.78-3.80 (br, 4H), 2.68 (q, J=7.4 Hz, 2H), 2.60-2.35 (m, 2H), 1.33 (t, J=7.4 Hz, 3H). MS: (ES) 420.2 (M+H$^+$).

Example 35: Synthesis of N-[(3S)-1-(3-ethylpyrrolo[1,2-a]pyrazin-1-yl)pyrrolidin-3-yl]-2-(4-hydroxy-1-piperidyl)thiazole-4-carboxamide.trifluoroacetate salt

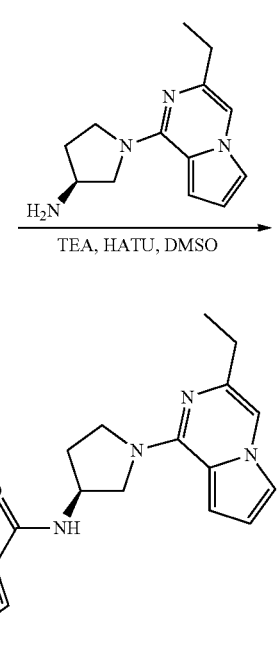

2-(4-Hydroxy-1-piperidyl)thiazole-4-carboxylic acid (40 mg 0.18 mmol), (3S)-1-(3-ethylpyrrolo[1,2-a]pyrazin-1-yl)pyrrolidin-3-amine dihydrochloride (60 mg, 0.20 mmol) and triethylamine (0.13 mL, 0.93 mmol) were combined in 1 mL DMSO. HATU (77 mg, 0.20 mmol) was added and the mixture was stirred for 40 minutes. DMSO was removed under reduced pressure and the residue was purified by reverse phase preparative HPLC (10-30% gradient of CH$_3$CN/H$_2$O with 0.1% TFA modifier) and dried (lyophilizer) to give the desired compound. $^1$H NMR (400 MHz, CD$_3$OD) δ 7.70 (d, J=2.4 Hz, 1H), 7.52-7.50 (m, 2H), 7.41 (s, 1H), 6.89 (dd, J=2.4, 4.3 Hz, 1H), 4.95-4.78 (m, 2H), 4.60-3.70 (br, 4H), 3.95-3.80 (m, 2H), 3.36-3.20 (m, 2H), 2.68 (q, J=7.4 Hz, 2H), 2.60-2.30 (m, 2H), 1.98-1.90 (m, 2H), 1.62-1.55 (m, 2H), 1.33 (t, J=7.4 Hz, 3H). MS: (ES) 441.2 (M+H$^+$).

Example 36: 1-(4-fluorophenyl)-N-[(3R)-1-imidazo[1,2-a]pyrazin-8-ylpyrrolidin-3-yl]-1,2,4-triazole-3-carboxamide

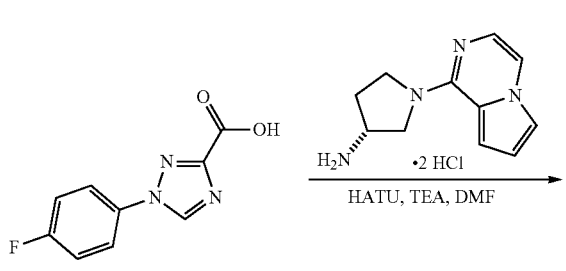

-continued

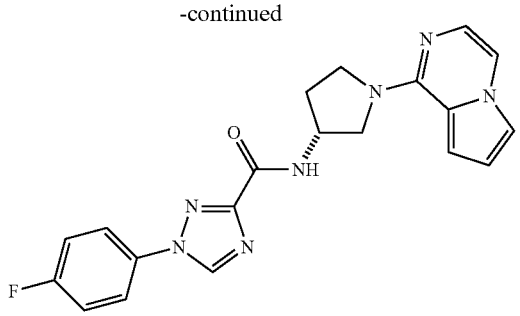

A mixture of 1-(4-fluorophenyl)-1,2,4-triazole-3-carboxylic acid (300 mg 1.4 mmol), (3R)-1-pyrrolo[1,2-a]pyrazin-1-ylpyrrolidin-3-amine dihydrochloride (400 mg, 1.4 mmol) and triethylamine (1.5 mL, 11 mmol) were combined in 8 mL DMF. The mixture was stirred for 30 minutes before HATU (576 mg, 1.5 mmol) was added and the mixture was then stirred at 60° C. for 1 hour. The mixture was chromatographed ($SiO_2$, 5-20% MeOH/EtOAc). A portion of the residue recovered from flash chromatography was purified by reverse phase preparative HPLC (10-30% gradient of $CH_3CN/H_2O$ with 0.1% TFA modifier and concentrated under reduced pressure to give 70 mg of a TFA salt of the desired compound. The TFA salt was converted to the free base by suspending it in saturated NaCl (1 mL), adding 1 M NaOH (0.6 mL, 0.6 mmol), and extracting with dichloromethane. Removal of dichloromethane resulted in a glassy residue. The sample was dissolved in $CH_3CN/H_2O$ and dried (lyophilizer) to obtain a white powder (28 mg, 5% yield). $^1$H NMR (400 MHz, DMSO) δ 9.31 (s, 1H), 8.92 (d, J=5.9 Hz, 1H), 7.92-7.85 (m, 3H), 7.76 (s, 1H), 7.53 (s, 1H), 7.41 (t, J=9.0 Hz, 2H), 7.21 (d, J=4.7 Hz, 1H), 4.65-4.50 (m, 1H), 4.48-3.65 (br, 4H), 2.30-2.05 (m, 2H). MS: (ES) 393.2 (M+H$^+$).

Example 37: Synthesis of N-[(3S)-1-(3-isopropylpyrrolo[1,2-a]pyrazin-1-yl)pyrrolidin-3-yl]-1-phenyl-1,2,4-triazole-3-carboxamide.trifluoroacetate salt a) To a slurry of 2-(trichloroacetyl)pyrrole (5.3 g, 25 mmol) and $K_2CO_3$ (11 g, 76 mmol) in 100 mL acetone was added a solution of 1-bromo-3-methylbutan-2-one (4.5 g, 27 mmol) in 30 mL acetone. The mixture was stirred for 1 hour at 50° C. before filtering and concentrating under reduced pressure to obtain 3-isopropyl-1H-pyrrolo[2,1-c][1,4]oxazin-1-one (4.1 g, 93%), which was used in the following step without purification.

b) To a 150 mL heavy wall glass pressure tube were added the lactone from step a, 3-isopropyl-1H-pyrrolo[2,1-c][1,4]oxazin-1-one (4.1 g, 23 mmol), $NH_4OAc$ (9.4 g, 122 mmol), and acetic acid (25 mL). The tube was sealed with a teflon bushing, immersed in a preheated oil bath set to 160° C., and stirred for 9 hours at this temperature. The tube was removed from the bath, an additional 10 g (130 mmol) of $NH_4OAc$ was added, and the reaction was stirred at 160° C. for an additional 3 hours. Afterward, acetic acid was removed under reduced pressure, and the residue was taken up in 150 mL DCM and 30 mL saturated $NaHCO_3$. After filtration through celite, the aqueous phase was separated and discarded, the organic phase was concentrated and purified by flash chromatography ($SiO_2$, 1% MeOH/dichloromethane) to provide 2.0 grams of 3-isopropylpyrrolo[1,2-a]pyrazin-1(2H)-one (49% yield). MS: (ES) 177.2 (M+H$^+$).

c) 3-isopropylpyrrolo[1,2-a]pyrazin-1(2H)-one from step b (1.6 g, 4.7 mmol) was combined with $POCl_3$ (20 mL) and stirred at 70° C. for 20 minutes. $POCl_3$ was removed under reduced pressure. The residue was taken up in DCM and washed twice with saturated sodium bicarbonate. Afterward the organic phase was dried over sodium sulfate, filtered, and concentrated under reduced pressure. The residue was purified by flash chromatography ($SiO_2$, 5-10% MTBE/hexanes) to provide chloro-3-isopropylpyrrolo[1,2-a]pyrazine (1.09 g, 62% yield).

d) In a 20 mL vial were combined tert-butyl N-[(3S)-pyrrolidin-3-yl]carbamate (2.06 g, 11.1 mmol), 1-chloro-3-isopropylpyrrolo[1,2-a]pyrazine from step c (1.09 g, 5.6 mmol), DIPEA (4.0 mmol, 23 mmol), and 1-methylpyrrolidinone (1 mL) and the mixture was heated with stirring in a vial at 110° C. for 1 hour. Temperature was decreased to 90° C. and the reaction was stirred for another 16 hours. Afterward the organic reaction mixture was diluted in DCM

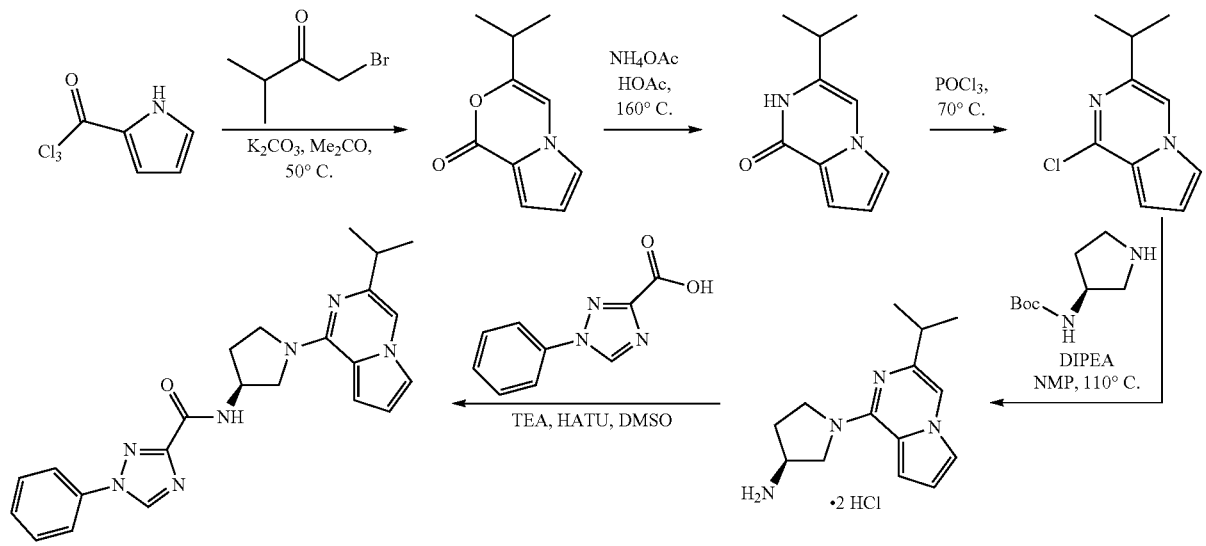

(100 mL), washed with water (20 mL), dried (Na₂SO₄), filtered and concentrated under reduced pressure. The residue was purified by flash chromatography (SiO₂, 2% 7 M NH3 in MeOH/dichloromethane). The desired Boc-protected intermediate was obtained after drying. This was taken up in a minimal amount of methanol and dichloromethane and treated with 4 M HCl in dioxane (4 mL, 16 mmol). The mixture was heated at 50° C. and stirred for 20 minutes, after which time the flask was removed from heat, allowed to cool to room temperature, and dioxane was added. The resulting white precipitate, (3S)-1-(3-isopropylpyrrolo[1,2-a]pyrazin-1-yl)pyrrolidin-3-amine dihydrochloride was collected by filtration and dried in vacuo; 925 mg, 52% yield.

e) 1-phenyl-1,2,4-triazole-3-carboxylic acid (54 mg 0.29 mmol), (3S)-1-(3-isopropylpyrrolo[1,2-a]pyrazin-1-yl)pyrrolidin-3-amine dihydrochloride (98 mg, 0.31 mmol) and triethylamine (0.16 mL, 1.2 mmol) were combined in 0.6 mL DMSO. HATU (110 mg, 0.29 mmol) was added and the mixture was stirred for 1 hour. DMSO was removed under reduced pressure and the residue was purified by reverse phase preparative HPLC (10-30% gradient of CH₃CN/H₂O with 0.1% TFA modifier) and dried (lyophilizer) to give the desired compound. ¹H NMR (400 MHz, CD₃OD) δ 9.14 (s, 1H), 7.89 (d, J=7.4 Hz, 2H), 7.73 (s, 1H), 7.60-7.46 (m, 5H), 6.90 (dd, J=2.7, 4.3 Hz, 1H), 5.00-4.80 (m, 1H), 4.60-3.85 (br, 4H), 3.05-2.95 (m, 1H), 2.60-2.38 (m, 2H), 1.35 (d, J=6.6 Hz, 6H). MS: (ES) 416.2 (M+H⁺).

Example 38: Synthesis of 1-(4-fluorophenyl)-N-[(3S)-1-(3-isopropylpyrrolo[1,2-a]pyrazin-1-yl)pyrrolidin-3-yl]-1,2,4-triazole-3-carboxamide.trifluoroacetate salt

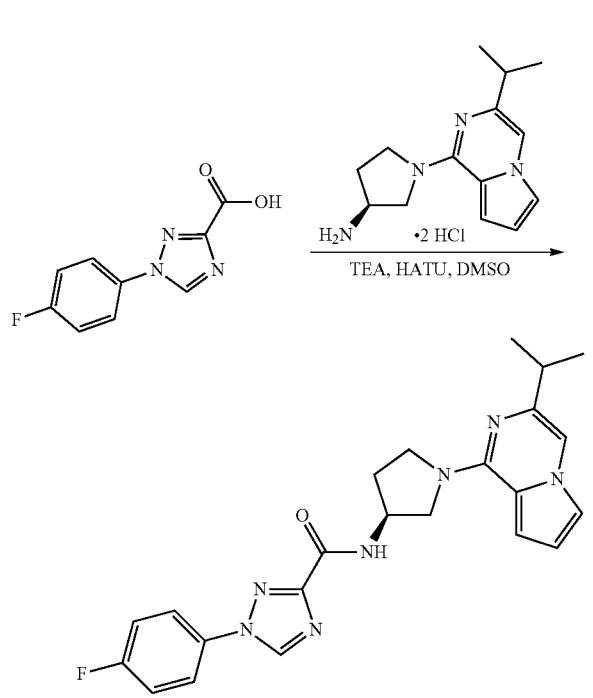

1-(4-Fluorophenyl)-1,2,4-triazole-3-carboxylic acid (53 mg 0.26 mmol), (3S)-1-(3-isopropylpyrrolo[1,2-a]pyrazin-1-yl)pyrrolidin-3-amine dihydrochloride (91 mg, 0.29 mmol) and triethylamine (0.16 mL, 1.15 mmol) were combined in 0.6 mL DMSO. HATU (104 mg, 0.27 mmol) was added and the mixture was stirred for 1 hour. DMSO was removed under reduced pressure and the residue was purified by reverse phase preparative HPLC (10-30% gradient of CH₃CN/H₂O with 0.1% TFA modifier) and dried (lyophilizer) to give the desired compound. ¹H NMR (400 MHz, CD₃OD) δ 9.10 (s, 1H), 7.92 (dd, J=4.7, 7.0 Hz, 2H), 7.73 (s, 1H), 7.57 (s, 1H), 7.54 (d, J=4.3 Hz, 1H), 7.35 (t, J=8.6 Hz, 2H), 6.91 (dd, J=2.7, 4.3 Hz, 1H), 5.00-4.85 (m, 1H), 4.60-3.65 (br, 4H), 3.05-2.95 (m, 1H), 2.60-2.38 (m, 2H), 1.35 (d, J=7.0 Hz, 6H). MS: (ES) 434.2 (M+H⁺).

Example 39: Synthesis of 2-(4-hydroxy-1-piperidyl)-N-[(3S)-1-(3-isopropylpyrrolo[1,2-a]pyrazin-1-yl)pyrrolidin-3-yl]thiazole-4-carboxamide.trifluoroacetate salt

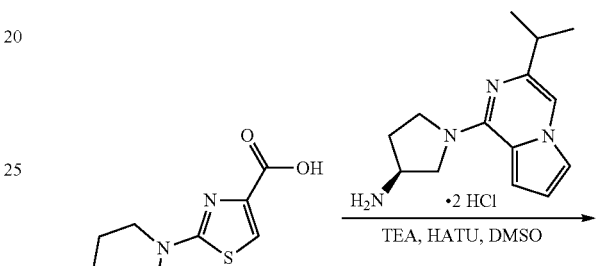

2-(4-hydroxy-1-piperidyl)thiazole-4-carboxylic acid (54 mg, 0.24 mmol), (3S)-1-(3-isopropylpyrrolo[1,2-a]pyrazin-1-yl)pyrrolidin-3-amine dihydrochloride (81 mg, 0.26 mmol) and triethylamine (0.14 mL, 1.0 mmol) were combined in 0.6 mL DMSO. HATU (104 mg, 0.27 mmol) was added and the mixture was stirred for 25 minutes. DMSO was removed under reduced pressure and the residue was purified by reverse phase preparative HPLC (10-30% gradient of CH₃CN/H₂O with 0.1% TFA modifier) and dried (lyophilizer) to give the desired compound. ¹H NMR (400 MHz, CD₃OD) δ 7.72 (d, J=2.4 Hz, 1H), 7.56 (s, 1H), 7.52 (d, J=4.3 Hz, 1H), 7.41 (s, 1H), 6.90-6.87 (m, 1H), 4.95-4.70 (m, 2H), 4.60-3.80 (br, 4H), 3.95-3.80 (m, 2H), 3.36-3.20 (m, 2H), 3.05-2.95 (m, 1H), 2.60-2.30 (m, 2H), 1.98-1.90 (m, 2H), 1.62-1.55 (m, 2H), 1.35 (d, J=6.6 Hz, 6H). MS: (ES) 455.2 (M+H⁺).

Example 40: Synthesis of 1-(2-fluorophenyl)-N-[(3S)-1-imidazo[1,2-a]pyrazin-8-ylpyrrolidin-3-yl]-1,2,4-triazole-3-carboxamide.trifluoroacetate salt

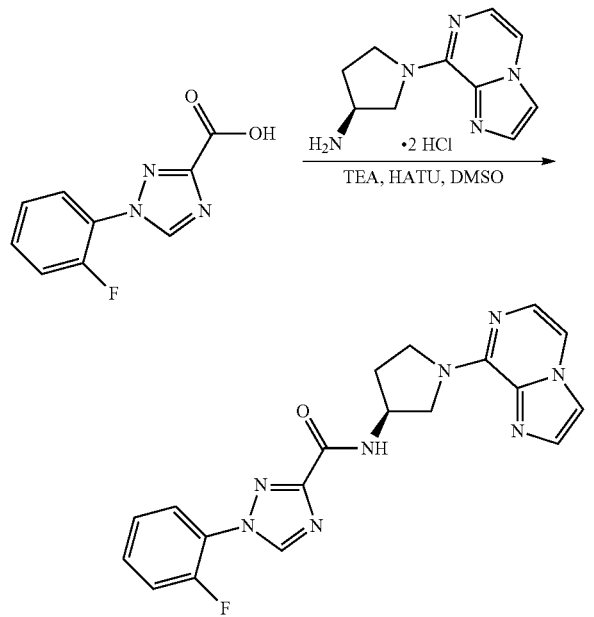

1-(2-Fluorophenyl)-1,2,4-triazole-3-carboxylic acid (41 mg 0.20 mmol), (3S)-1-imidazo[1,2-a]pyrazin-8-ylpyrrolidin-3-amine dihydrochloride (69 mg, 0.25 mmol), and triethylamine (0.11 mL, 0.80 mmol) were combined in 0.5 mL DMSO. HATU (80 mg, 0.21 mmol) was added and the mixture was stirred for 10 minutes. This was followed by the addition of acetic acid (0.1 mL), MeOH (0.4 mL) and water (1 mL), filtration, and purification by reverse phase preparative HPLC (10-30% gradient of $CH_3CN/H_2O$ with 0.1% TFA modifier) and dried (lyophilizer) to give 40 mg of the the desired compound (40% yield). $^1$H NMR (400 MHz, $CD_3OD$) δ 8.96 (d, J=2.7 Hz, 1H), 8.05 (s, 1H), 7.95-7.82 (m, 3H), 7.56-7.38 (m, 3H), 7.17 (d, J=5.5 Hz, 1H), 5.00-3.65 (br, 5H), 2.60-2.38 (m, 2H). MS: (ES) 393.2 ($M+H^+$).

Example 41: Synthesis of N-[(3S)-1-imidazo[1,2-a]pyrazin-8-ylpyrrolidin-3-yl]-1-(4-methylsulfonylphenyl)-1,2,4-triazole-3-carboxamide.trifluoroacetate salt

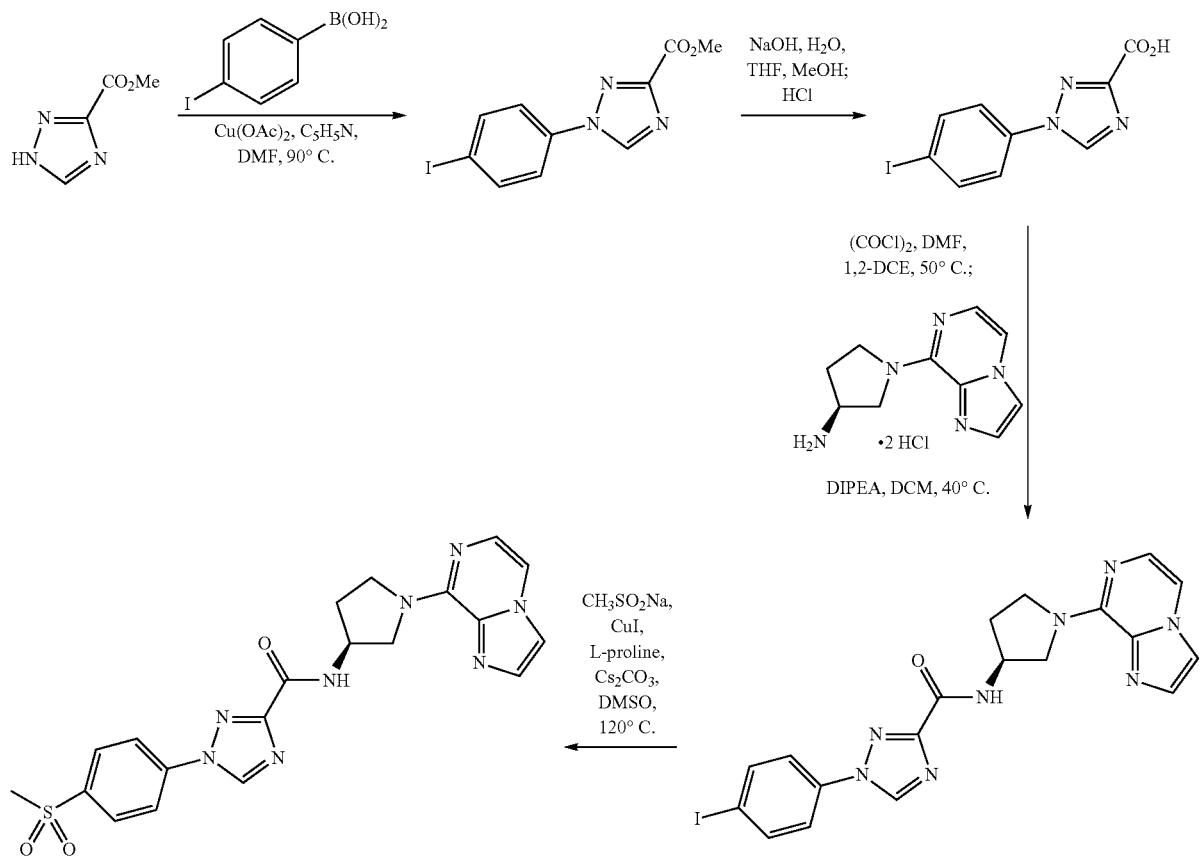

a) A 100 mL flask was charged with methyl 1H-1,2,4-triazole-3-carboxylate (2.8 g, 16 mmol), 4-iodopheynylboronic acid (4.0 g, 16 mmol), Cu(OAc)$_2$ (3.3 g, 18 mmol), pyridine (1.5 mL, 19 mmol), and DMF (30 mL). The mixture was stirred on a preheated oil bathe set to 90° C. for 30 minutes, during which time the solution changed color from a deep blue to a light green. The mixture was diluted in EtOAc (200 mL), filtered, and washed with 3:1 v/v saturated NH$_4$Cl-30% NH$_4$OH. The organic phase was concentrated in vacuo and the resulting residue was purified by flash chromatography (SiO$_2$, 20%-60% EtOAc/hexanes) to obtain a white powder of methyl 1-(4-iodophenyl)-1,2,4-triazole-3-carboxylate (830 mg, 16% yield).

b) Methyl 1-(4-iodophenyl)-1,2,4-triazole-3-carboxylate (830 mg, 2.5 mmol) was dissolved in MeOH (20 mL) and THF (10 mL). 1 M NaOH (2.5 mL, 2.5 mmol) was added and the mixture stirred at room temperature for 2 h. Additional 1 M NaOH was added (2.5 mL, 2.5 mmol) and the reaction was heated to 50° C. for 30 minutes. After cooling to room temperature, the pH was adjusted to 4 by the addition of 6 M HCl, MeOH and THF were removed under reduced pressure and the resulting white precipitate was collected by filtration and dried in vacuo to obtain 680 mg (86% yield) of 1-(4-iodophenyl)-1,2,4-triazole-3-carboxylic acid.

c) To a suspension of 1-(4-iodophenyl)-1,2,4-triazole-3-carboxylic acid (680 mg, 2.15 mmol) in 1,2-dichloroethane (8 mL) was added oxalyl chloride (0.30 mL, 3.4 mmol), followed by DMF (0.020 mL, 0.26 mmol). The mixture was stirred in a 50° C. oil bath for 5 minutes, and afterward was concentrated under reduced pressure and dried in vacuo. The residue obtained was suspended in DCM (10 mL) and to this was added (3S)-1-imidazo-[1,2-a]pyrazin-8-ylpyrrolidin-3-amine dihydrochloride (650 mg, 2.36 mmol), followed by DIPEA (1.5 mL, 8.6 mmol). The mixture was stirred, briefly brought to a boil, removed from the heat source and stirred for an additional 20 minutes. After concentrating under reduced pressure, the residue was purified by flash chromatography (SiO$_2$; 2% MeOH/dichoromethane) to obtain 886 mg of a white foam (82% yield).

d) N-[(3S)-1-Imidazo[1,2-a]pyrazin-8-ylpyrrolidin-3-yl]-1-(4-iodophenyl)-1,2,4-triazole-3-carboxamide from step c (73 mg, 0.15 mmol), sodium methanesulfinate (31 mg, 0.30 mmol), CuI (5.4 mg, 0.028 mmol), proline (6.8 mg, 0.059 mmol), Cs$_2$CO$_3$ (23 mg, 0.70 mmol) and DMSO (0.40 mL) were combined together in a 4 mL vial and stirred at 120° C. for 3 h. The reaction mixture was purified by reverse phase preparative HPLC (10-30% gradient of CH$_3$CN/H$_2$O with 0.1% TFA modifier) and dried (lyophilizer) to give the desired compound. $^1$H NMR (400 MHz, CD3OD) d 9.31 (s, 1H), 9.15 (d, J=7.0 Hz, 0.5H), 8.20-8.10 (m, 4H), 8.05 (s, 1H), 7.95 (d, J=5.4 Hz, 1H), 7.82 (s, 1H), 7.18 (d, =5.8 Hz, 1H), 5.00-3.65 (br, 5H), 3.18 (s, 3H), 2.60-2.38 (m, 2H). MS: (ES) 453.2 (M+H$^+$).

Example 42: Synthesis of N-[(3S)-1-imidazo[1,2-a]pyrazin-8-ylpyrrolidin-3-yl]-1-(p-tolyl)-1,2,4-triazole-3-carboxamide.trifluoroacetate salt

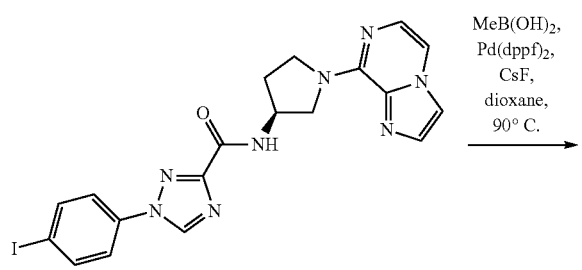

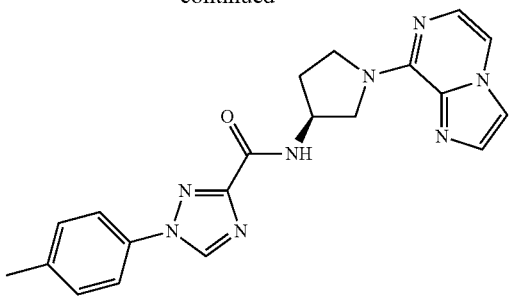

In a 4 mL vial were combined N-[(3S)-1-imidazo[1,2-a]pyrazin-8-ylpyrrolidin-3-yl]-1-(4-iodophenyl)-1,2,4-triazole-3-carboxamide (64 mg, 0.13 mmol), methylboronic acid (32 mg, 0.53 mmol), (1,1'-Bis(diphenylphosphino)ferrocene)palladium(II) dichloride (9.5 mg, 0.013 mmol), CsF (67 mg, 0.44 mmol), and degassed dioxane (0.80 mL). The vial was sealed and stirred at 90° C. for 2 hours. Dioxane was removed under reduced pressure and the residue was purified by reverse phase preparative HPLC (10-30% gradient of CH$_3$CN/H$_2$O with 0.1% TFA modifier) and dried (lyophilizer) to give the desired compound. $^1$H NMR (400 MHz, CD$_3$OD) δ 9.07 (s, 1H), 8.05 (s, 1H), 7.94 (d, J=5.9 Hz, 1H), 7.82 (s, 1H), 7.74 (d, J=8.6 Hz, 2H), 7.38 (d, J=8.6 Hz, 2H), 7.17 (d, J=5.4 Hz, 1H), 5.00-3.65 (br, 5H), 2.60-2.38 (m, 2H), 2.41 (s, 1H). MS: (ES) 389.2 (M+H$^+$).

Example 43: Synthesis of 1-(4-fluorophenyl)-N-[(3S)-1-pyrrolo[1,2-a]pyrazin-1-ylpyrrolidin-3-yl]-1,2,4-triazole-3-carboxamide.trifluoroacetate salt

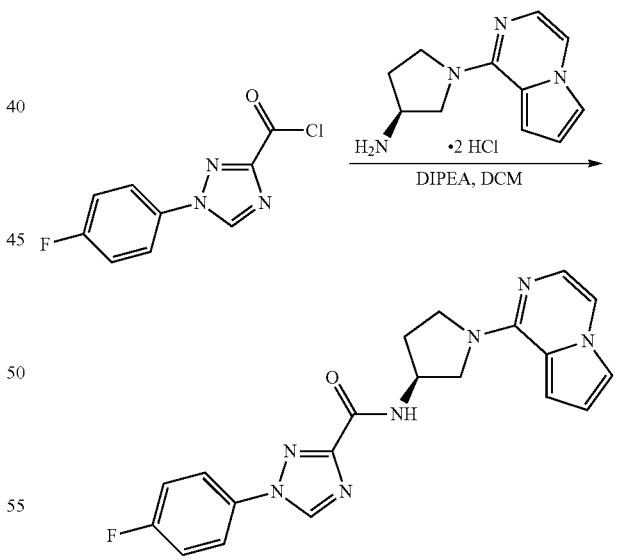

To a suspension of 1-(4-fluorophenyl)-1,2,4-triazole-3-carbonyl chloride (70 mg, 0.31 mmol) in DCM (10 mL) was added (3S)-1-pyrrolo[1,2-a]pyrazin-1-ylpyrrolidin-3-amine dihydrochloride (104 mg, 0.38 mmol), followed by DIPEA (0.70 mL, 4.0 mmol). The reaction mixture was stirred 10 minutes, concentrated under reduced pressure, and purified by reverse phase preparative HPLC (10-30% gradient of CH$_3$CN/H$_2$O with 0.1% TFA modifier) and dried (lyophilizer) to give the desired compound. $^1$H NMR (400

MHz, CD₃OD) δ 9.10 (s, 1H), 7.91-7.88 (m, 2H), 7.79 (dd, J=1.2, 2.8 Hz, 1H), 7.74 (d, J=5.9 Hz, 1H), 7.59 (d, J=4.3 Hz, 1H), 7.34 (t. J=8.6 Hz, 2H), 6.95 (dd, J=2.8, 4.7 Hz, 1H), 6.86 (d, J=5.5 Hz, 1H), 5.00-4.85 (m, 1H), 4.80-3.65 (br, 4H), 2.60-2.38 (m, 2H). MS: (ES) 392.2 (M+H⁺).

Example 44: Synthesis of 1-(4-cyanophenyl)-N-[(3S)-1-imidazo[1,2-a]pyrazin-8-ylpyrrolidin-3-yl]-1,2,4-triazole-3-carboxamide

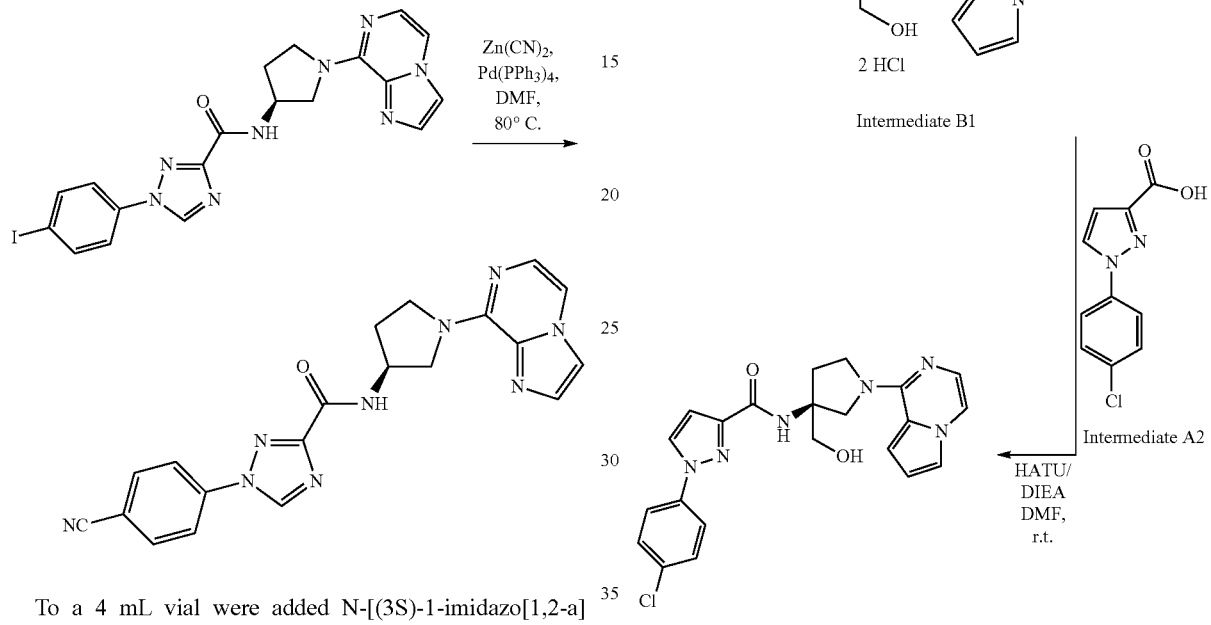

To a 4 mL vial were added N-[(3S)-1-imidazo[1,2-a]pyrazin-8-ylpyrrolidin-3-yl]-1-(4-iodophenyl)-1,2,4-triazole-3-carboxamide (82 mg, 0.16 mmol), Zn(CN)₂ (24 mg, 0.20 mmol), tetrakis(triphenylphospine)palladium(0) (23 mg, 0.020 mmol), and degassed DMF. The vial was sealed and the mixture stirred at 80° C. for 1 hour. DMF was removed under reduced pressure and the residue was purified by flash chromatography (SiO₂, 7 M NH₃ in MeOH/dichloromethane) to obtain 48 mg of white powder of the desired product (74% yield). ¹H NMR (400 MHz, CDCl₃) δ 8.64 (s, 1H), 7.94 (d, J=6.6 Hz, 2H), 7.85 (d, J=6.6 Hz, 2H), 7.55 (s, 1H), 7.50 (s, 1H), 7.44 (d, J=4.3 Hz, 1H), 7.40-7.30 (m, 2H), 5.00-4.85 (m, 1H), 4.50-4.35 (br, 1H), 4.30-4.15 (br, 3H), 2.50-2.38 (m, 1H), 2.25-2.15 (m, 1H). MS: (ES) 400.1 (M+H⁺).

Example 45: Synthesis of 1-(4-chlorophenyl)-N-[(3S)-3-(hydroxymethyl)-1-pyrrolo[1,2-a]pyrazin-1-yl-pyrrolidin-3-yl]pyrazole-3-carboxamide

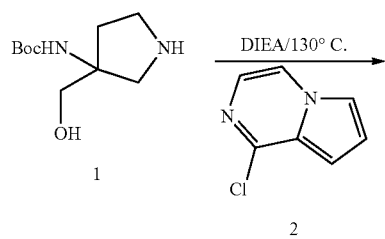

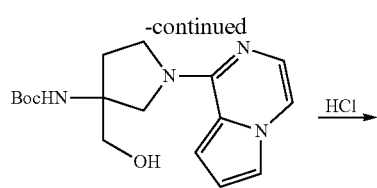

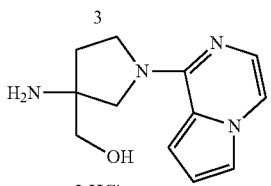

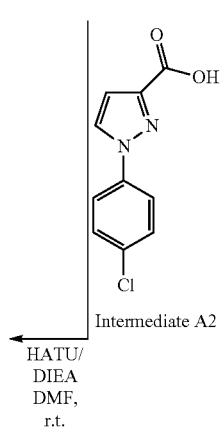

a) To a mixture of 1 (1.0 g, 4.6 mmol) and 580 mg of 2 (580 mg, 3.8 mmol) was added 1.7 ml of Hunig's base (9.5 mmol). The resulting mixture was stirred at 130° C. for 3 h. After the mixture was cooled down to room temperature, 200 ml of isopropanol/chloroform (1:2) was added, and the organics were washed with saturated aqueous NaHCO₃ (2×20 ml) and brine (2×50 ml). The organics were dried over MgSO₄ and concentrated under reduced pressure. The residue was purified via flash column chromatography on silica gel (0-10% MeOH in EtOAc) to get the desired product 3 as a brown powder (700 mg, 46%).

b) A mixture of 3 (332 mg, 1.0 mmol) and 3 mL of 4.0 M of HCl in dioxane (12 mmol) was stirred at 50° C. for 1 h. Then the mixture was concentrated under reduced pressure to give a brown powder (300 mg, 98%), which was used for next step without further purification.

c) A 10 mL vial was charged with intermediate A2 (92 mg, 0.417 mmol), intermediate B1 (122 mg, 0.40 mmol), HATU (166 mg, 0.437 mmol), Hunig's base (146 mg, 1.12 mmol) and 4 mL of DMF. The mixture was stirred at room temperature for 1 h and was then diluted with 100 ml of isopropanol/chloroform (1:2), followed by washing with water (2×20 ml) and brine (2×20 ml). The organics were dried over MgSO₄ and concentrated under reduced pressure. The residue was purified via preparative HPLC to get the desired product (105 mg, 60%). ¹H NMR (400 MHz, CD₃OD) δ 8.28 (d, J=2.5 Hz, 1H), 7.85 (dd, J=2.2, 6.9 Hz, 2H), 7.48 (dd, J=2.2, 6.9 Hz, 2H), 7.42 (d, J=5.2 Hz, 1H), 7.39 (dd, J=1.1, 2.6 Hz, 1H), 6.98 (d, J=4.4 Hz, 1H), 6.93 (d, J=2.6 Hz, 1H), 6.86 (d, J=5.1 Hz, 1H), 6.65 (dd, J=2.5, 4.1

Hz, 1H), 4.34 (d, J=11.4 Hz, 1H), 4.15 (d, J=11.4 Hz, 1H), 4.02-3.88 (m, 4H), 2.65-2.55 (m, 1H), 2.45-2.36 (m, 1H); MS: (ES) m/z calculated for $C_{22}H_{21}ClN_6O_2$ [M+H]$^+$ 437.2, found 437.

Example 46: Synthesis of 1-(4-fluorophenyl)-N-[(3S)-3-(hydroxymethyl)-1-pyrrolo[1,2-a]pyrazin-1-yl-pyrrolidin-3-yl]pyrazole-3-carboxamide

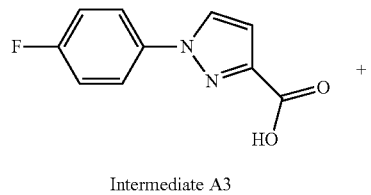

Intermediate A3

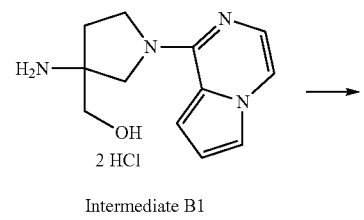

Intermediate B1

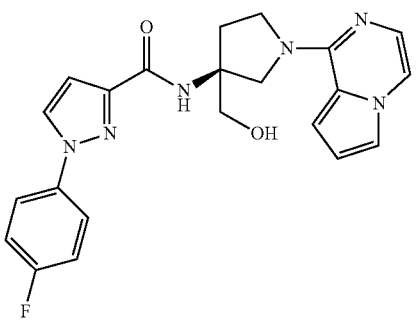

To a 10 mL vial was charged with intermediated A3 (83 mg, 0.417 mmol), intermediate B1 (122 mg, 0.40 mmol), HATU (166 mg, 0.437 mmol), Hunig's base (146 mg, 1.12 mmol) and 4 mL of DMF. The mixture was stirred at room temperature for 1 h and then was diluted with 100 ml of isopropanol/chloroform (1:2), followed by washing with water (2×20 ml) and brine (2×20 ml). The organics was dried over MgSO$_4$ and concentrated under reduced pressure. The residue was purified via HPLC to get the desired product (120 mg, 71%). $^1$H NMR (400 MHz, CD$_3$OD) δ 8.22 (d, J=2.6 Hz, 1H), 7.86-7.82 (m, 2H), 7.42 (d, J=4.7 Hz, 1H), 7.38 (t. J=1.5 Hz, 1H), 7.21 (dt, J=2.2, 8.4 Hz, 2H), 6.98 (d, J=4.4 Hz, 1H), 6.91 (d, J=2.5 Hz, 1H), 6.86 (d, J=4.7 Hz, 1H), 6.64 (dd, J=2.5, 4.0 Hz, 1H), 4.34 (d, J=11.4 Hz, 1H), 4.15 (d, J=11.4 Hz, 1H), 4.02-3.88 (m, 4H), 2.65-2.55 (m, 1H), 2.45-2.36 (m, 1H); MS: (ES) m/z calculated for $C_{22}H_{21}FN_6O_2$ [M+H]$^+$ 421.2, found 421.

Example 47: Synthesis of N-[(3S)-3-(hydroxymethyl)-1-pyrrolo[1,2-a]pyrazin-1-yl-pyrrolidin-3-yl]-2-(4-hydroxy-1-piperidyl)thiazole-4-carboxamide

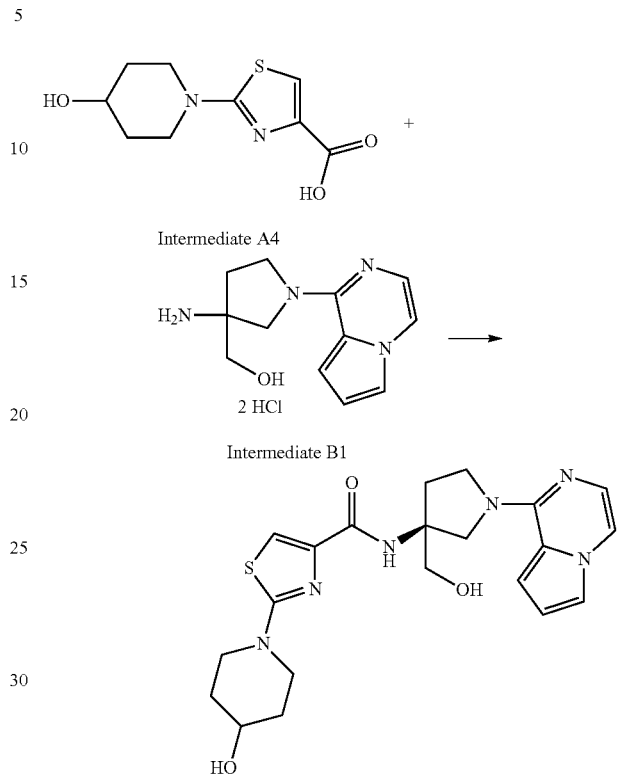

A 10 mL vial was charged with intermediated A4 (90 mg, 0.395 mmol), intermediate B1 (122 mg, 0.40 mmol), HATU (166 mg, 0.437 mmol), Hunig's base (146 mg, 1.12 mmol) and 4 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO$_4$ and concentrated under reduced pressure. The residue was purified via HPLC to get the desired product (85 mg, 49%). $^1$H NMR (400 MHz, CD$_3$OD) δ 8.07 (s, 1H), 7.80-7.76 (m, 1H), 7.72 (d, J=5.6 Hz, 1H), 7.56 (d, J=4.4 Hz, 1H), 7.37 (s, 1H), 6.94 (dd, J=2.4, 4.4 Hz, 1H), 6.85 (d, J=6.0 Hz, 1H), 4.80-4.60 (br, 1H), 4.50-4.20 (br, 2H), 4.02-3.80 (m, 4H), 3.35-3.25 (m, 4H), 2.78-2.66 (m, 1H), 2.56-2.45 (m, 1H), 1.98-1.88 (m, 2H), 1.64-1.52 (m, 2H); MS: (ES) m/z calculated for $C_{21}H_{26}N_6O_3S$ [M+H]$^+$ 443.2, found 443.

Example 48: Synthesis of N-[(3S)-3-(hydroxymethyl)-1-pyrrolo[1,2-a]pyrazin-1-yl-pyrrolidin-3-yl]-1-phenyl-1,2,4-triazole-3-carboxamide

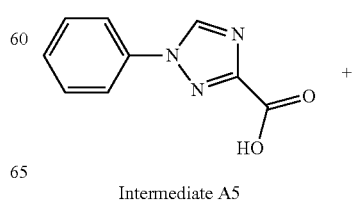

Intermediate A5

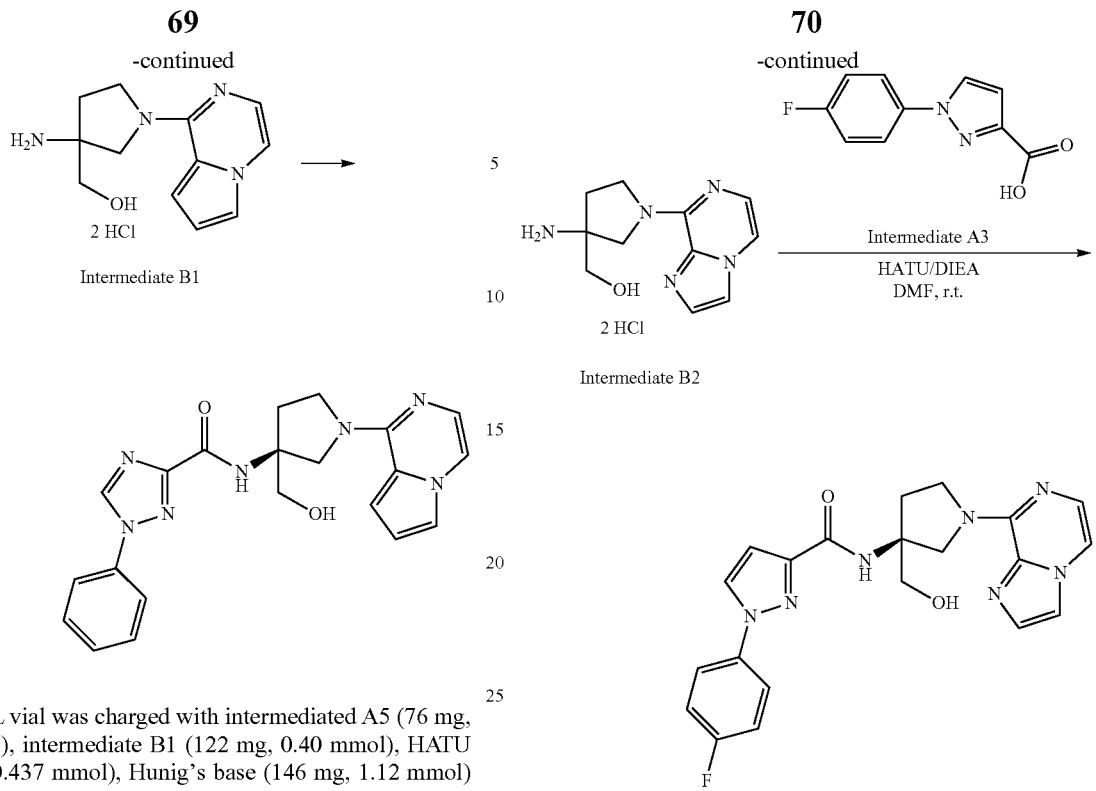

A 10 mL vial was charged with intermediated A5 (76 mg, 0.40 mmol), intermediate B1 (122 mg, 0.40 mmol), HATU (166 mg, 0.437 mmol), Hunig's base (146 mg, 1.12 mmol) and 4 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO$_4$ and concentrated under reduced pressure. The residue was purified via preperative HPLC to get the desired product (110 mg, 62%). $^1$H NMR (400 MHz, CD$_3$OD) δ 9.12 (s, 1H), 7.85 (td, J=1.5, 7.4 Hz, 2H), 7.76 (d, J=2.2 Hz, 1H), 7.70 (d, J=5.5 Hz, 2H), 7.55 (m, 2H), 7.46 (m, 1H), 6.92 (s, 1H), 6.83 (d, J=5.5 Hz, 1H), 4.60-3.80 (br, 4H), 4.02 (s, 2H), 2.82-2.70 (m, 1H), 2.58-2.48 (m, 1H); MS: (ES) m/z calculated for C$_{21}$H$_{21}$N$_7$O$_2$ [M+H]$^+$ 404.2, found 404.

Example 49: Synthesis of 1-(4-fluorophenyl)-N-[(3S)-3-(hydroxymethyl)-1-imidazo[1,2-a]pyrazin-8-yl-pyrrolidin-3-yl]pyrazole-3-carboxamide

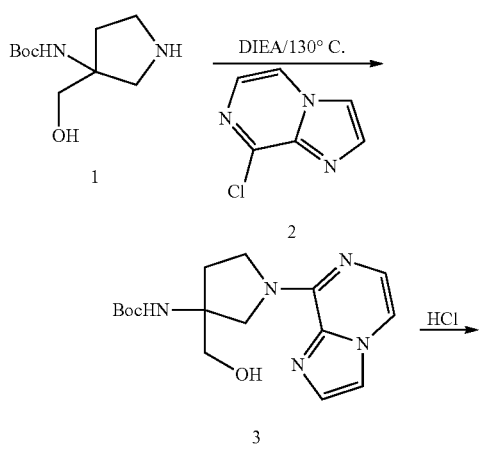

a) To a mixture of 1 (1.0 g, 4.6 mmol) and 580 mg of 2 (580 mg, 3.8 mmol) was added 1.7 ml of Hunig's base (9.5 mmol). The resulting mixture was stirred at 130° C. for 3 h. After the mixture was cooled down to room temperature 200 ml of isopropanol/chloroform (1:2) was added, and the organics were washed with saturated aqueous NaHCO$_3$ (2×20 ml) and brine (2×50 ml). The organics were dried over MgSO$_4$ and concentrated under reduced pressure. The residue was purified through flash column chromatography on silica gel (0-10% MeOH in EtOAc) to get the desired product 3 as a brown powder (900 mg, 58%).

b) A mixture of 3 (333 mg, 1 mmol) and 3 mL of 4.0 M HCl in dioxane (12 mmol) was stirred at 50° C. for 1 h. Then the mixture was concentrated under reduced pressure to give a brown powder (300 mg, 98%), which was used for next step without further purification.

c) A 10 mL vial was charged with intermediated A3 (86 mg, 0.417 mmol), intermediate B2 (120 mg, 0.40 mmol), HATU (166 mg, 0.437 mmol), Hunig's base (146 mg, 1.12 mmol) and 4 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO$_4$ and concentrated under reduced pressure. The residue was purified via HPLC to get the desired product (118 mg, 71%). $^1$H NMR (400 MHz, CD$_3$OD) δ 8.23 (d, J=2.5 Hz, 1H), 8.01 (d, J=1.1 Hz, 1H), 7.89 (d, J=5.7 Hz, 1H), 7.86-7.82 (m, 2H), 7.78 (s, 1H), 7.22 (t, J=8.8 Hz, 2H), 7.12 (d, J=5.5 Hz, 1H), 6.91 (d, J=2.6 Hz, 1H), ), 4.60-3.80 (br, 4H), 4.00 (s, 2H), 2.80-2.70 (m, 1H), 2.56-2.46 (m, 1H); MS: (ES) m/z calculated for C$_{21}$H$_{20}$FN$_7$O$_2$ [M+H]$^+$ 422.2, found 422.

Example 50: Synthesis of N-[(3S)-3-(hydroxymethyl)-1-imidazo[1,2-a]pyrazin-8-yl-pyrrolidin-3-yl]-2-(4-hydroxy-1-piperidyl)thiazole-4-carboxamide

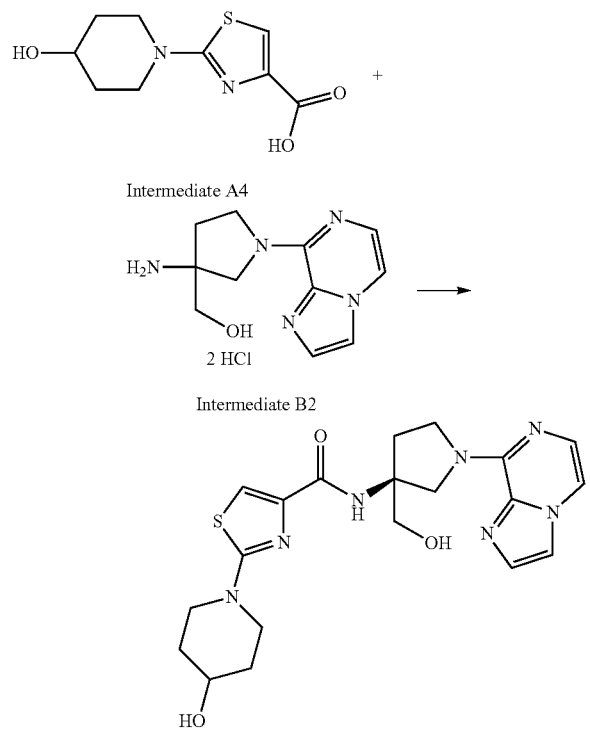

A 10 mL vial was charged with intermediated A4 (90 mg, 0.395 mmol), intermediate B2 (120 mg, 0.40 mmol), HATU (166 mg, 0.437 mmol), Hunig's base (146 mg, 1.12 mmol) and 4 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO4 and concentrated under reduced pressure. The residue was purified via preperative HPLC to get the desired product (81 mg, 49%). $^1$H NMR (400 MHz, CD$_3$OD) δ 8.02 (s, 1H), 7.90 (d, J=5.5 Hz, 1H), 7.79 (s, 1H), 7.35 (s, 2H), 7.14 (d, J=5.8 Hz, 1H), 4.60-3.80 (br, 4H), 3.94 (s, 2H), 3.90-3.80 (m, 3H), 3.32-3.20 (m, 2H), 2.75-2.65 (m, 1H), 2.52-2.45 (m, 1H), 1.97-1.87 (m, 2H), 1.64-1.50 (m, 2H); MS: (ES) m/z calculated for C$_{20}$H$_{25}$N$_7$O$_3$S[M+H]$^+$ 444.2. found 444.

Example 51: Synthesis of N-[(3S)-3-(hydroxymethyl)-1-imidazo[1,2-a]pyrazin-8-yl-pyrrolidin-3-yl]-1-phenyl-1,2,4-triazole-3-carboxamide

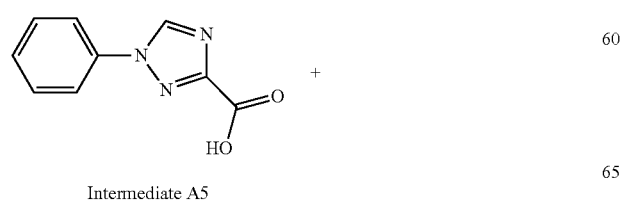

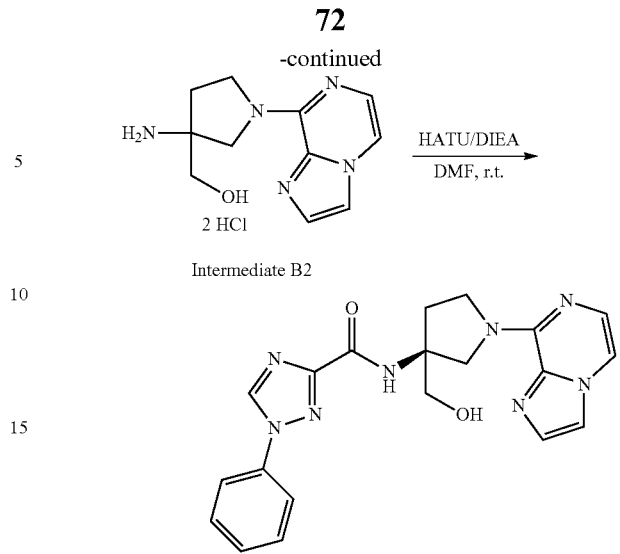

A 10 mL vial was charged with intermediated A5 (76 mg, 0.40 mmol), intermediate B2 (122 mg, 0.40 mmol), HATU (166 mg, 0.437 mmol), Hunig's base (146 mg, 1.12 mmol) and 4 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO$_4$ and concentrated under reduced pressure. The residue was purified vie preperative HPLC to get the desired product (110 mg, 62%). $^1$H NMR (400 MHz, CD$_3$OD) δ 9.12 (s, 1H), 8.02 (d, J=1.1 Hz, 1H), 7.90 (d, J=5.9 Hz, 1H), 7.84 (dd, J=1.5, 8.8 Hz, 2H), 7.79 (s, 1H), 7.55 (t, J=7.3 Hz, 2H), 7.46 (t, J=7.3 Hz, 1H), 7.13 (d, J=5.5 Hz, 1H), 4.02 (s, 2H), 4.60-3.80 (br, 4H), 2.80-2.70 (m, 1H), 2.58-2.48 (m, 1H); MS: (ES) m/z calculated for C$_{20}$H$_{20}$N$_8$O$_2$ [M+H]$^+$ 405.2, found 405.

Example 52: Synthesis of 1-(4-fluorophenyl)-N-[(3R,4S)-4-hydroxy-1-pyrrolo[1,2-a]pyrazin-1-yl-pyrrolidin-3-yl]pyrazole-3-carboxamide

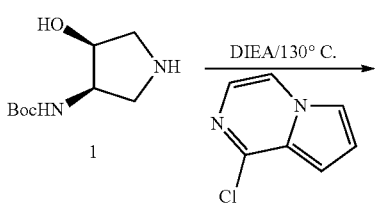

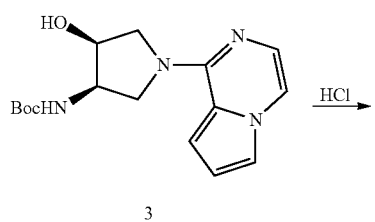

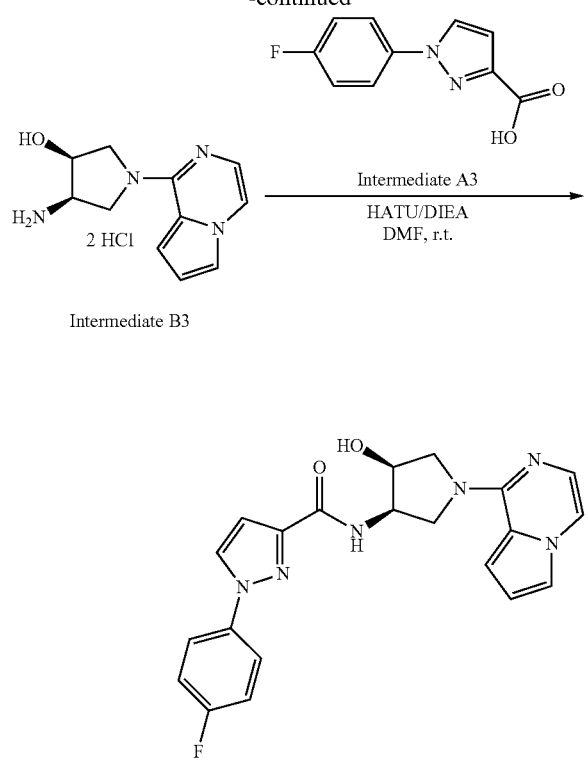

Intermediate B3

Example 53: Synthesis of Intermediate A1

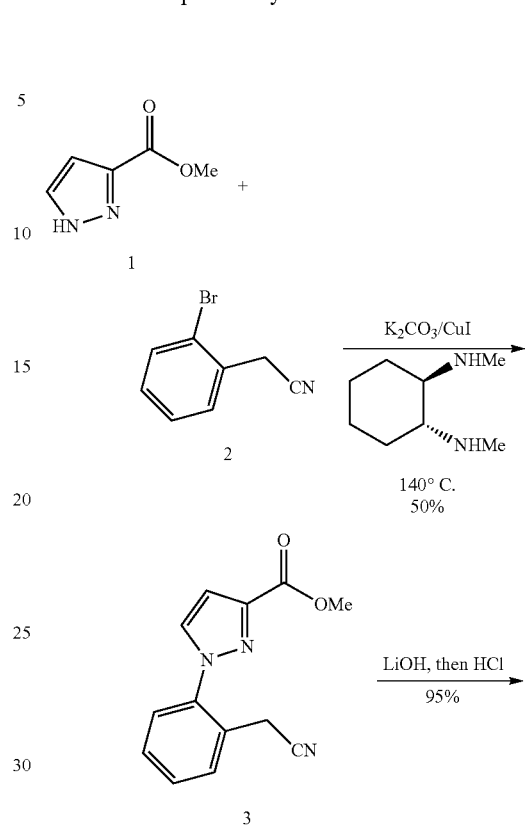

Intermediate A1 a) To a mixture of 1 (120 mg, 0.59 mmol) and 2 (90 mg, 0.59 mmol) was added 1.0 ml of Hunig's base (5.5 mmol). The resulting mixture was stirred at 130° C. for 3 h. After the mixture was cooled down to room temperature, 200 ml of isopropanol/chloroform (1:2) was added, and the organics were washed with saturated aqueous NaHCO$_3$ (2×20 ml) and brine (2×50 ml). The organics were dried over MgSO$_4$ and concentrated under reduced pressure. The residue was purified via flash column chromatography on silica gel (0-10% MeOH in EtOAc) to get the desired product 3 as a brown powder (150 mg, 79%).

b) A mixture of 3 (150 mg, 0.47 mmol) and 2 mL of 4.0 M HCl in dioxane (8.0 mmol) was stirred at 50° C. for 1 h. Then the mixture was concentrated under reduced pressure to give a brown powder (130 mg, 95%), which was used for the next step without further purification.

c) A 10 mL vial was charged with intermediated A3 (43 mg, 0.209 mmol), intermediate B2 (60 mg, 0.20 mmol), HATU (83 mg, 0.218 mmol), Hunig's base (73 mg, 0.56 mmol) and 2 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO$_4$ and concentrated under reduced pressure. The residue was purified via preperative HPLC to get the desired product (54 mg, 50%). $^1$H NMR (400 MHz, CD$_3$OD) δ 8.29 (d, J=2.6 Hz, 1H), 7.89-7.84 (m, 2H). 7.77 (d, J=1.5 Hz, 1H), 7.72 (d, J=5.9 Hz, 1H), 7.57 (d, J=4.4 Hz, 1H), 7.26 (t, J=8.8 Hz, 2H), 6.98 (d, J=2.2 Hz, 1H), 6.92 (t, J=3.0 Hz, 1H), 6.84 (d, J=5.8 Hz, 1H), 4.85 (m, 1H), 4.64 (m, 1H), 4.70-3.60 (br, 4H), MS: (ES) m/z calculated for C$_{21}$H$_{19}$FN$_6$O$_2$ [M+H]$^+$ 407.2, found 407.

a) A 50 mL flask was charged with 1.89 g of starting material 1 (15 mmol), 1.96 g of starting material 2 (10 mmol), 400 mg of CuI (2.0 mmol), 4.5 g of K$_2$CO$_3$ (3.3 mmol) and 0.9 mL of trans-N,N'-dimethylcyclohexayl-diamine (2.0 mmol). The resulting mixture was stirred at 140° C. for 3 h. After the mixture was cooled down to room temperature, 200 mL of EtOAc was added and the organics were washed with water (2×50 mL), brine (2×50 mL). The organics were dried over MgSO$_4$ and concentrated under reduced pressure. The residue was purified via flash chromatography on silica gel (0-25% EtOAc in hexanes) to get the desired product 3 (1.2 g, 50%).

b) To a solution of the ester 3 (240 mg, 1 mmol) in THF was added 3.0 mL of 1.0 M LiOH (3.0 mmol). The resulting mixture was stirred at room temperature for 3 h. 1.0 M HCl was added to adjust the pH to 1.0 and the organics were extracted with EtOAc (2×100 mL), followed by drying over MgSO$_4$. Concentration under reduced pressure gave the product as a white solid (217 mg, 96%), which was used for the next step without further purification.

Example 54: Synthesis of 1-[2-(cyanomethyl)phenyl]-N-[(3S)-1-pyrrolo[1,2-a]pyrazin-1-ylpyrrolidin-3-yl]pyrazole-3-carboxamide Example 55: Synthesis of 1-[2-(cyanomethyl)phenyl]-N-[(3S)-1-(8-methylpyrrolo[1,2-a]pyrazin-1-yl)pyrrolidin-3-yl]pyrazole-3-carboxamide

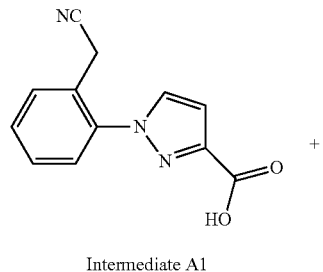

Intermediate A1

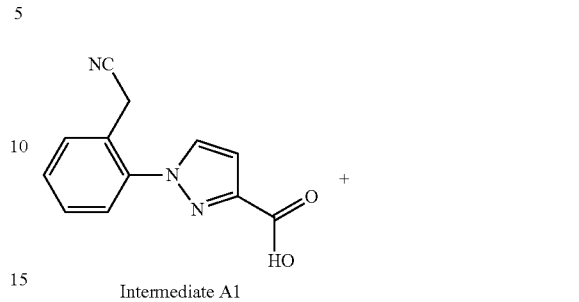

Intermediate A1

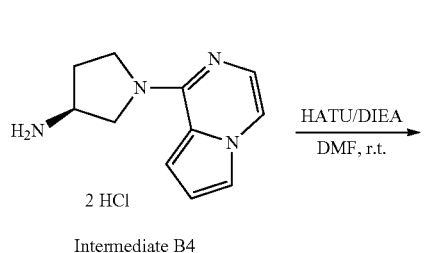

Intermediate B4

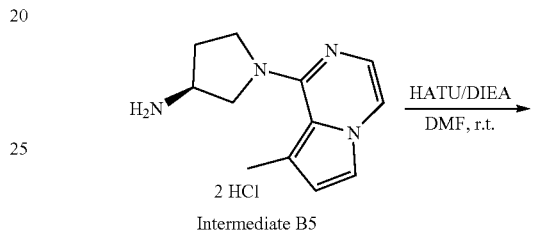

Intermediate B5

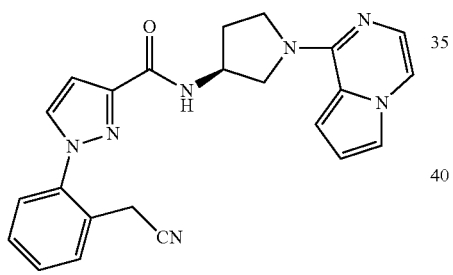

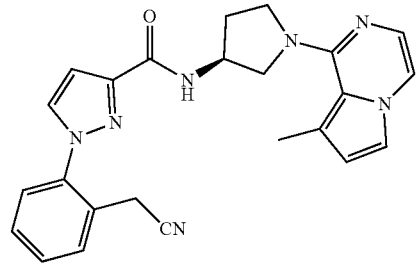

A 10 mL vial was charged with intermediate A1 (45 mg, 0.20 mmol), intermediate B4 (55 mg, 0.20 mmol), HATU (83 mg, 0.22 mmol), Hunig's base (73 mg, 0.6 mmol) and 2 mL of DMF. The mixture was stirred at room temperature for 1 h and was then diluted with 100 ml of isopropanol/chloroform (1:2), followed by washing with water (2×20 ml) and brine (2×20 ml). The organics were dried over $MgSO_4$ and concentrated under reduced pressure. The residue was purified via preperative HPLC to get the desired product (56 mg, 68%). $^1$H NMR (400 MHz, CD$_3$OD) δ 8.03 (d, J=2.2 Hz, 1H), 7.75 (s, 1H), 7.70 (d, J=5.5 Hz, 1H), 7.60-7.48 (m, 5H), 6.98 (d, J=2.5 Hz, 1H), 6.91 (dd, J=2.6, 4.4 Hz, 1H), 6.82 (d, J=5.8 Hz, 1H), 4.95-3.65 (br, 5H), 3.93 (s, 2H), 2.55-2.30 (m, 2H); MS: (ES) m/z calculated for $C_{23}H_{21}N_7O$ [M+H]$^+$ 412.2, found 412.

A 10 mL vial was charged with intermediated A1 (45 mg, 0.20 mmol), intermediate B5 (58 mg, 0.20 mmol), HATU (83 mg, 0.22 mmol), Hunig's base (78 mg, 0.6 mmol) and 2 mL of DMF. The mixture was stirred at room temperature for 1 h and then was diluted with 100 ml of isopropanol/chloroform (1:2), followed by washing with water (2×20 ml) and brine (2×20 ml). The organics were dried over $MgSO_4$ and concentrated under reduced pressure. The residue was purified via preperative HPLC to get the desired product (60 mg, 56%). $^1$H NMR (400 MHz, CD$_3$OD) δ 8.02 (d, J=2.2 Hz, 1H), 7.65-7.57 (m, 3H), 7.54-7.46 (m, 3H), 6.97 (d, J=2.2 Hz, 1H), 6.75-6.72 (m, 2H), 4.82-4.75 (m, 1H), 4.28-4.24 (m, 1H), 4.08-4.00 (m, 1H), 3.98-3.90 (m, 4H), 2.61 (s, 3H), 2.52-2.30 (m, 2H); MS: (ES) m/z calculated for $C_{24}H_{23}N_7O$ [M+H]$^+$ 426.2, found 426.

Example 56: Synthesis of 1-(4-chloro-3-fluoro-phenyl)-N-[(3S)-1-(8-methylpyrrolo[1,2-a]pyrazin-1-yl)pyrrolidin-3-yl]pyrazole-3-carboxamide and 1-(3-fluorophenyl)-N-[(3S)-1-(8-methylpyrrolo[1,2-a]pyrazin-1-yl)pyrrolidin-3-yl]pyrazole-3-carboxamide

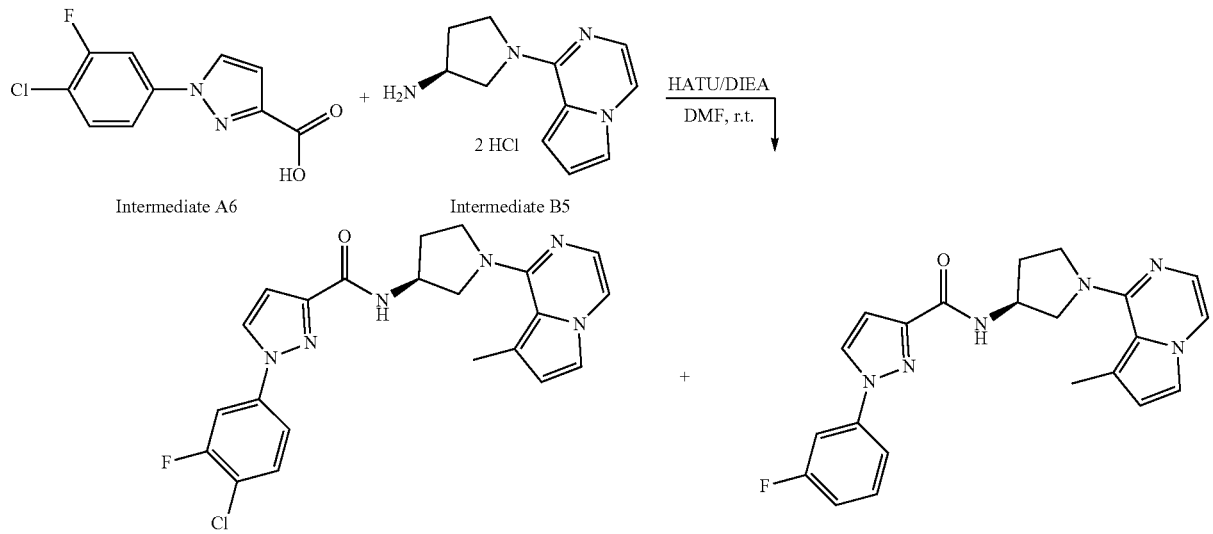

A 10 mL vial was charged with intermediate A6 (48 mg, 0.20 mmol), intermediate B5 (58 mg, 0.20 mmol), HATU (83 mg, 0.22 mmol), Hunig's base (78 mg, 0.6 mmol) and 2 mL of DMF. The mixture was stirred at room temperature for 1 h and then was diluted with 100 ml of isopropanol/chloroform (1:2), followed by washing with water (2×20 ml) and brine (2×20 mil). The organics were dried over $MgSO_4$ and concentrated under reduced pressure. The residue was purified via preperative HPLC to get the chlorofluoro (40 mg, 46%) and a fluoro (5 mg, 6%) products. 1-(4-chloro-3-fluoro-phenyl)-N-[(3S)-1-(8-methylpyrrolo[1,2-a]pyrazin-1-yl)pyrrolidin-3-yl]pyrazole-3-carboxamide: $^1H$ NMR (400 MHz, $CD_3OD$) δ 8.36 (d, J=2.6 Hz, 1H), 7.90 (dd, J=2.6, 10.3 Hz, 1H), 7.72-7.64 (m, 3H), 7.61 (t, J=8.0 Hz, 1H), 6.95 (d, J=2.6 Hz, 1H), 6.77-6.73 (m, 2H), 4.82-4.75 (m, 1H), 4.30-4.24 (m, 1H), 4.08-3.92 (m, 3H), 2.63 (s, 3H), 2.52-2.30 (m, 2H); MS: (ES) m/z calculated for $C_{22}H_{20}ClFN_6O[M+H]^+$ 439.2, found 439. 1-(3-fluorophenyl)-N-[(3S)-1-(8-methylpyrrolo[1,2-a]pyrazin-1-yl)pyrrolidin-3-yl]pyrazole-3-carboxamide: $^1H$ NMR (400 MHz, $CD_3OD$) δ 8.35 (d, J=2.6 Hz, 1H), 7.76-7.64 (m, 3H), 7.53 (dt, J=6.2, 8.4 Hz, 2H), 7.13 (dt, J=2.5, 8.4 Hz, 1H), 6.95 (d, J=2.6 Hz, 1H), 6.77-6.73 (m, 2H), 4.82-4.75 (m, 1H), 4.30-4.24 (m, 1H), 4.08-3.92 (m, 3H), 2.63 (s, 3H), 2.52-2.30 (m, 2H); MS: (ES) m/z calculated for $C_{22}H_{21}FN_6O$ $[M+H]^+$ 405.2, found 405.

Example 57: Synthesis of 2-(4-hydroxy-1-piperidyl)-N-[(3S)-1-(8-methylpyrrolo[1,2-a]pyrazin-1-yl)pyrrolidin-3-yl]thiazole-4-carboxamide

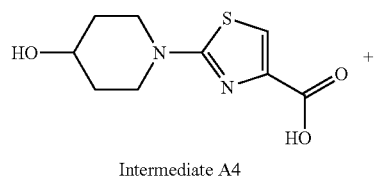

Intermediate A4

A 10 mL vial was charged with intermediated A4 (45 mg, 0.20 mmol), intermediate B5 (58 mg, 0.20 mmol), HATU (83 mg, 0.22 mmol), Hunig's base (78 mg, 0.6 mmol) and 2 mL of DMF. The mixture was stirred at room temperature for 1 h and then was diluted with 100 ml of isopropanol/chloroform (1:2), followed by washing with water (2×20 ml) and brine (2×20 ml). The organics were dried over $MgSO_4$ and concentrated under reduced pressure. The residue was purified via preperative HPLC to get the desired product (35 mg, 41%). $^1H$ NMR (400 MHz, $CD_3OD$) δ 7.68-7.65 (m, 2H), 7.38 (s, 1H), 6.76-6.74 (m, 2H), 4.75-4.65 (m, 1H), 4.25-4.15 (m, 1H), 4.06-3.80 (m, 5H), 3.35-3.20 (m, 3H), 2.62 (s, 1H), 2.50-2.30 (m, 2H), 1.98-1.90 (m, 2H), 1.65-1.52 (m, 2H); MS: (ES) m/z calculated for $C_{21}H_{26}N_6O_2S$ $[M+H]^+$ 427.2, found 427.

Example 58: Synthesis of 1-(4-chloro-3-fluoro-phenyl)-N-[(3S)-1-pyrrolo[1,2-a]pyrazin-1-ylpyrrolidin-3-yl]pyrazole-3-carboxamide and 1-(3-fluorophenyl)-N-[(3S)-1-pyrrolo[1,2-a]pyrazin-1-ylpyrrolidin-3-yl]pyrazole-3-carboxamide

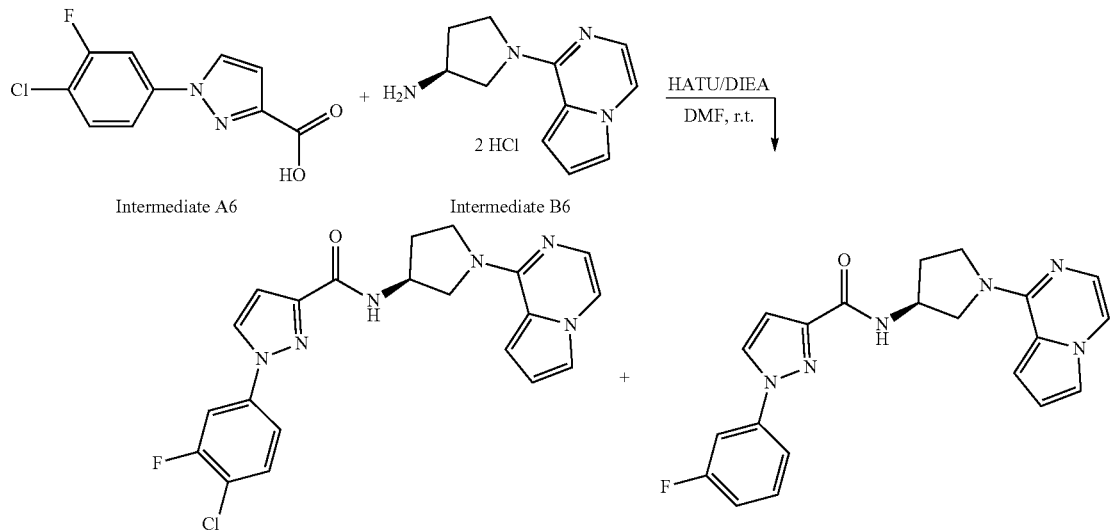

A 10 mL vial was charged with intermediated A6 (48 mg, 0.20 mmol), intermediate B6 (58 mg, 0.20 mmol), HATU (83 mg, 0.22 mmol), Hunig's base (78 mg, 0.6 mmol) and 2 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO$_4$ and concentrated under reduced pressure. The residue was purified via preperative HPLC to get the 4-chloro-3-fluoro product (38 mg, 45%) and and the 3-fluoro product (8 mg, 10%). Synthesis of 1-(4-chloro-3-fluoro-phenyl)-N-[(3S)-1-pyrrolo[1,2-a]pyrazin-1-ylpyrrolidin-3-yl]pyrazole-3-carboxamide: $^1$H NMR (400 MHz, CD$_3$OD) δ 8.37 (d, J=2.9 Hz, 1H), 7.91 (dd, J=2.6, 10.3 Hz, 1H), 7.77 (s, 1H), 7.71-7.68 (m, 2H), 7.61-7.55 (m 2H), 6.97 (d, J=2.6 Hz, 1H), 6.92 (dd, J=2.6, 4.4 Hz, 1H), 6.84 (d, J=5.9 Hz, 1H), 4.95-3.70 (br, 5H), 2.60-2.36 (m, 2H); MS: (ES) m/z calculated for C$_{21}$H$_{18}$ClFN$_6$O [M+H]$^+$ 425.2, found 425. 1-(3-fluorophenyl)-N-[(3S)-1-pyrrolo[1,2-a]pyrazin-1-ylpyrrolidin-3-yl]pyrazole-3-carboxamide: $^1$H NMR (400 MHz, CD$_3$OD) δ 8.80 (d, J=5.9 Hz, 1H), 8.38 (d, J=2.3 Hz, 1H), 7.79-7.68 (m, 4H), 7.59-7.48 (m, 2H), 7.14 (dt, J=2.8, 8.6 Hz, 1H), 6.98 (d, J=2.4 Hz, 1H), 6.95 (dd, J=2.6, 4.4 Hz, 1H), 6.86 (d, J=5.5 Hz, 1H), 4.95-3.70 (br, 5H), 2.60-2.36 (m, 2H); MS: (ES) m/z calculated for C$_{21}$H$_{19}$FN$_6$O [M+H]$^+$ 391.2, found 391.

Example 59: Synthesis of 2-(4-hydroxy-1-piperidyl)-N-[(3S)-1-pyrrolo[1,2-a]pyrazin-1-ylpyrrolidin-3-yl]thiazole-4-carboxamide

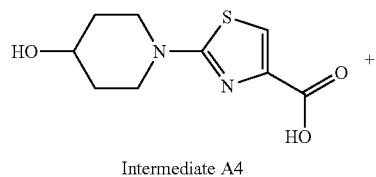

Intermediate A4

+

-continued

[Intermediate B6 structure with 2 HCl, HATU/DIEA, DMF, r.t.]

[Product structure]

A 10 mL vial was charged with intermediate A4 (45 mg, 0.20 mmol), intermediate B6 (55 mg, 0.20 mmol), HATU (83 mg, 0.22 mmol), Hunig's base (78 mg, 0.6 mmol) and 2 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO$_4$ and concentrated under reduced pressure. The residue was purified via preperative HPLC to get the desired product (65 mg, 79%). $^1$H NMR (400 MHz, CD$_3$OD) δ 7.76 (s, 1H), 7.70 (d, J=5.8 Hz, 1H), 7.54 (d, J=3.7 Hz, 1H), 7.39 (s, 1H), 7.53 (dd, J=2.5, 4.0 Hz, 1H), 6.84 (d, J=5.5 Hz, 1H), 4.82-4.75 (m, 1H), 4.70-3.60 (br, 4H), 3.90-3.80 (m, 2H), 3.40-3.20

(m, 3H), 2.52-2.30 (m, 2H), 1.96-1.90 (m, 2H), 1.65-1.52 (m, 2H); MS: (ES) m, calculated for $C_{20}H_{24}FN_6O_2S[M+H]^+$ 413.2, found 413.

Example 60: Synthesis of 1-(5-chloro-2-pyridyl)-N-[(3S)-1-pyrrolo[1,2-a]pyrazin-1-ylpyrrolidin-3-yl]pyrazole-3-carboxamide

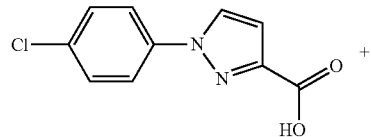

Intermediate A7

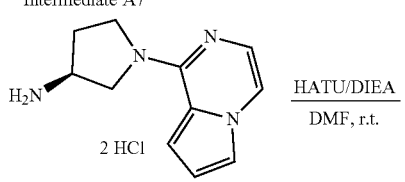

Intermediate B6

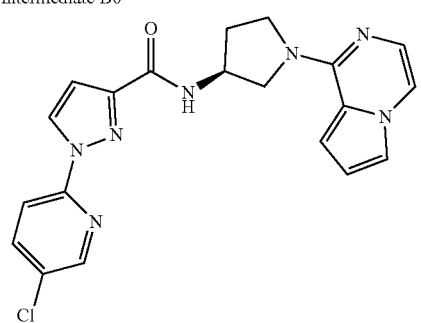

A 10 mL vial was charged with intermediated A7 (45 mg, 0.20 mmol), intermediate B6 (55 mg, 0.20 mmol), HATU (83 mg, 0.22 mmol), Hunig's base (78 mg, 0.6 mmol) and 2 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO₄ and concentrated under reduced pressure. The residue was purified via preperative HPLC to get the desired product (45 mg, 56%). ¹H NMR (400 MHz, CD₃OD) δ 8.61 (s, 1H), 8.44 (s, 1H), 8.07 (d, J=8.8 Hz, 1H), 7.99 (d, J=8.8 Hz, 1H), 7.77 (s, 1H), 7.72 (d, J=5.9 Hz, 1H), 7.57 (d, J=4.4 Hz, 1H), 6.96 (s, 1H), 6.94-6.91 (m, 1H), 6.85 (d, J=5.9 Hz, 1H), 5.00-3.65 (br, 5H), 2.60-2.30 (m, 2H); MS: (ES) m/z calculated for $C_{20}H_{18}ClN_7O[M+H]^+$ 408.2, found 408.

Example 61: Synthesis of 2-(4-hydroxy-1-piperidyl)-N-[(3S)-1-imidazo[1,2-a]pyrazin-8-ylpyrrolidin-3-yl]thiazole-4-carboxamide

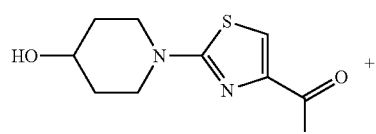

Intermediate A4

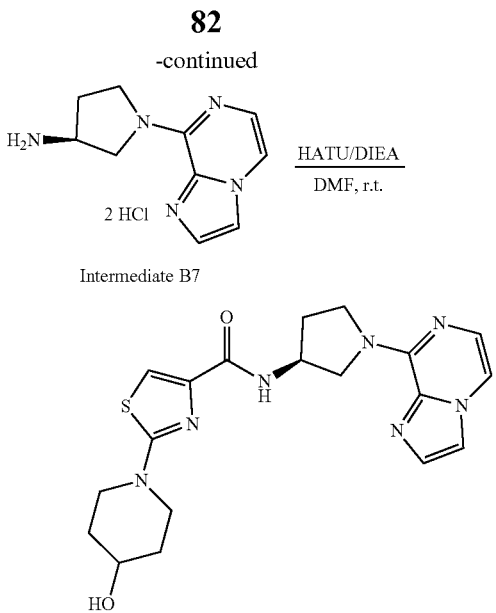

A 10 mL vial was charged with intermediated A4 (90 mg, 0.40 mmol), intermediate B7 (100 mg, 0.40 mmol), HATU (166 mg, 0.40 mmol), Hunig's base (156 mg, 1.2 mmol) and 4 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO₄ and concentrated under reduced pressure. The residue was purified via preperative HPLC to get the desired product (80 mg, 48%). ¹H NMR (400 MHz, CD₃OD) δ 7.74 (s, 1H), 7.66 (d, J=4.7 Hz, 1H), 7.50 (s, 1H), 7.36 (s, 1H), 7.22 (d, J=4.9 Hz, 1H), 4.76-4.65 (m, 1H), 4.40-4.30 (m, 1H), 4.20-3.75 (m, 4H), 3.40-3.20 (m, 4H), 2.42-2.10 (m, 2H), 1.95-1.85 (m, 2H), 1.65-1.50 (m, 2H); MS: (ES) m/z calculated for $C_{19}H_{23}N_7O_2S[M+H]^+$ 414.2. found 414.

Example 62: Synthesis of 1-(4-fluorophenyl)-N-[(3S)-1-imidazo[1,2-a]pyrazin-8-ylpyrrolidin-3-yl]-5-methyl-1,2,4-triazole-3-carboxamide

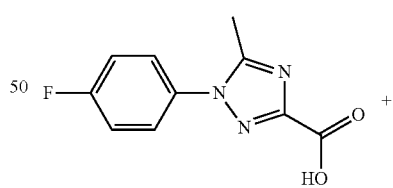

Intermediate A8

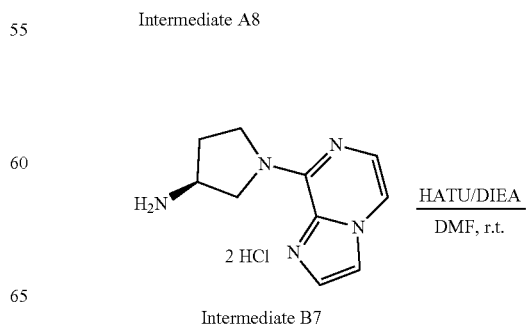

Intermediate B7

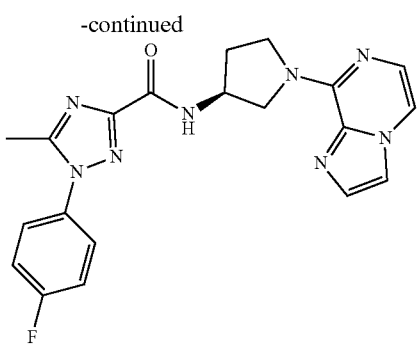

A 10 mL vial was charged with intermediated A8 (82 mg, 0.30 mmol), intermediate B7 (82 mg, 0.30 mmol), HATU (125 mg, 0.33 mmol), Hunig's base (160 mg, 1.23 mmol) and 4 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO$_4$ and concentrated under reduced pressure. The residue was purified via preperative HPLC to get the desired product (65 mg, 53%). $^1$H NMR (400 MHz, CD$_3$OD) δ 8.95 (d, J=6.3 Hz, 0.2H), 8.05 (s, 1H), 7.94 (d, J=5.5 Hz, 1H), 7.81 (s, 1H), 7.64-7.59 (m, 2H), 7.36-7.30 (m, 2H), 7.17 (d, J=5.4 Hz, 1H), 5.00-4.85 (m, 1H), 4.80-3.65 (br, 4H), 2.51 (s, 3H), 2.60-2.38 (m, 2H); MS: (ES) m/z calculated for C$_{20}$H$_{19}$FN$_8$O [M+H]$^+$ 407.2, found 407.

Example 63: Synthesis of 2-(4-hydroxy-1-piperidyl)-N-[(3S)-1-imidazo[1,2-a]pyrazin-8-ylpyrrolidin-3-yl]thiazole-4-carboxamide

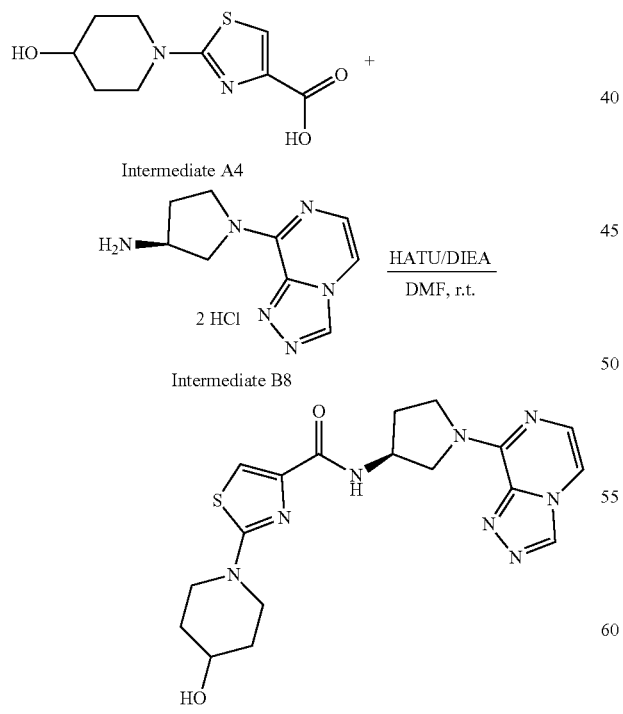

A 10 mL vial was charged with intermediated A4 (90 mg, 0.40 mmol), intermediate B8 (100 mg, 0.40 mmol), HATU (166 mg, 0.40 mmol), Hunig's base (156 mg, 1.2 mmol) and 4 mL of DMF. The mixture was stirred at room temperature for 1 h and then was diluted with 100 ml of isopropanol/chloroform (1:2), followed by washing with water (2×20 ml) and brine (2×20 ml). The organics were dried over MgSO$_4$ and concentrated under reduced pressure. The residue was purified via preperative HPLC to get the desired product (75 mg, 45%). $^1$H NMR (400 MHz, CD$_3$OD) δ 9.06 (s, 1H), 7.64 (d, J=4.8 Hz, 1H), 7.36 (s, 1H), 7.26 (d, J=4.8 Hz, 1H), 4.73-4.68 (m, 1H), 4.60-3.60 (br, 4H), 3.96-3.80 (m, 3H), 3.35-3.20 (m, 2H), 2.45-2.35 (m, 1H), 2.30-2.18 (m, 1H), 1.95-1.88 (m, 2H), 1.62-1.50 (m, 2H); MS: (ES) m/z calculated for C$_{18}$H$_{22}$N$_8$O$_2$S[M+H]$^+$ 415.2, found 415.

Example 64: Synthesis of 3-[[1-(4-fluorophenyl)pyrazole-3-carbonyl]amino]-1-pyrrolo[1,2-a]pyrazin-1-yl-pyrrolidine-3-carboxylic acid and N-3-carbamoyl-1-pyrrolo[1,2-a]pyrazin-1-yl-pyrrolidin-3-yl-1-(4-fluorophenyl)pyrazole-3-carboxamide

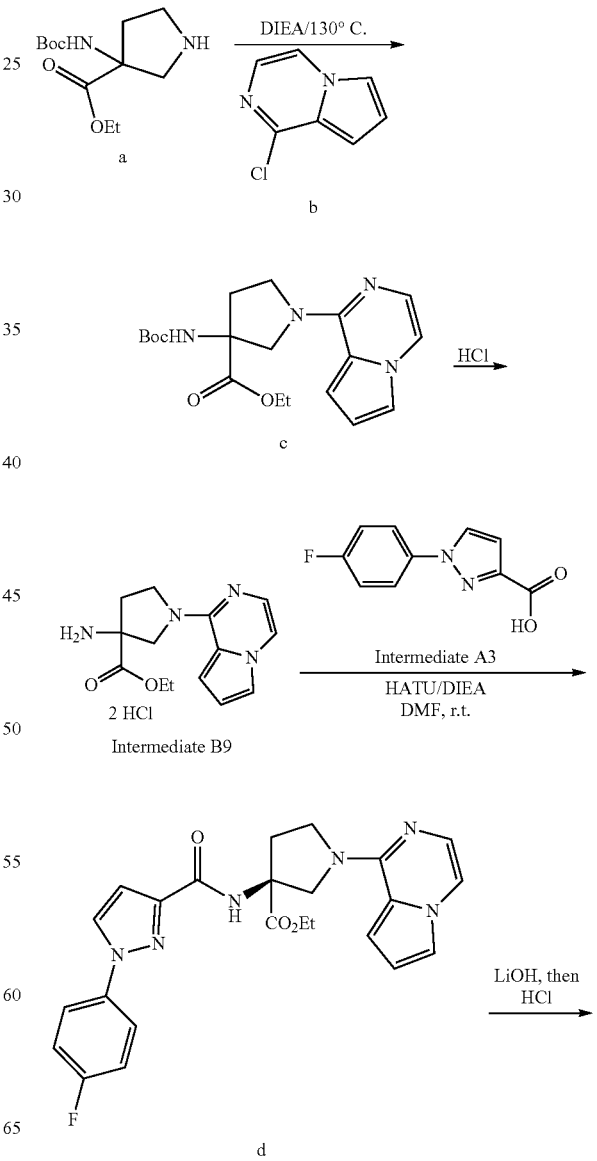

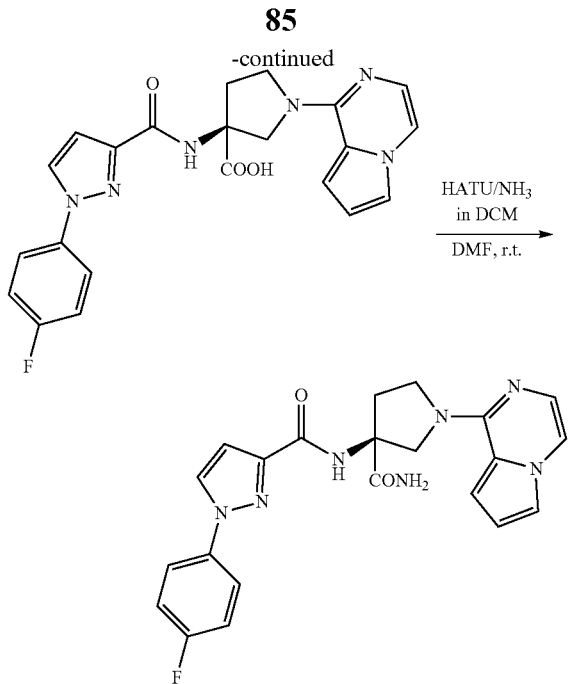

a) To a mixture of a (248 mg, 1.0 mmol) and b (152 mg, 1.0 mmol) was added 2.0 mL of Hunig's base (9.5 mmol). The resulting mixture was stirred at 130° C. for 3 h. After the mixture was cooled down to room temperature, 100 mL of isopropanol/chloroform (1:2) was added, and the mixture was then washed with saturated aqueous NaHCO$_3$ (2×20 mL) and brine (2×50 mL). The organics were dried over MgSO$_4$ and concentrated under reduced pressure. The residue was purified via flash chromatography on silica gel (0-10% MeOH in EtOAc) to get the desired product c as a brown powder (250 mg, 67%).

b) A mixture of c (250 mg, 0.67 mmol) and 2 mL of 4.0 M HCl in dioxane (8 mmol) was stirred at 50° C. for 1 h. The mixture was then concentrated under reduced pressure to give a brown powder (228 mg, 98%), which was used as intermediate B9 for next step without further purification.

c) A 10 mL vial was charged with intermediated A3 (136 mg, 0.66 mmol), intermediate B9 (228 mg, 0.66 mmol), HATU (274 mg, 0.72 mmol), Hunig's base (257 mg, 1.98 mmol) and 5 mL of DMF. The mixture was stirred at room temperature for 1 h and then was diluted with 100 ml of EtOAc, followed by washing with water (2×20 ml) and brine (2×20 ml). The organics were dried over MgSO$_4$ and concentrated under reduced pressure. The residue was purified via flash chromatography on sica gel (50-100% EtOAc in hexanes) to get the desired product d (220 mg, 72%).

d) A 10 mL vial was charged with d (230 mg, 0.50 mmol), 1 N LiOH (3 ml) and 3 mL of MeOH. The mixture was stirred at room temperature for 1 h and then was adjusted to pH 3.0. The mixture was then extracted with 100 mL of EtOAc, followed by washing with water (2×20 mL) and brine (2×20 mL). The organics were dried over MgSO$_4$ and concentrated under reduced pressure. The residue was purified via flash column chromatography on sica gel (100% EtOAc in hexanes) to get the desired product (205 mg, 95%). 3-[[1-(4-fluorophenyl)pyrazole-3-carbonyl]amino]-1-pyrrolo[1,2-a]pyrazin-1-yl-pyrrolidine-3-carboxylic acid: $^1$H NMR (400 MHz, CD$_3$OD) δ 8.29 (d, J=2.7 Hz, 1H), 7.89 (m, 2H), 7.78 (dd, J=1.2, 2.7 Hz, 1H), 7.73 (d, J=5.4 Hz, 1H), 7.55 (d, J=3.5 Hz, 1H), 7.30-7.22 (m, 2H), 6.97 (d, J=2.7 Hz, 1H), 6.94 (dd, J=2.8, 4.3 Hz, 1H), 6.84 (d, J=5.5 Hz, 1H), 4.60-3.80 (br, 4H), 2.90-2.82 (m, 1H), 2.80-2.70 (m, 1H); MS: (ES) m/z calculated for C$_{22}$H$_{19}$FN$_6$O$_3$[M+H]$^+$ 435.2, found 435.

e) A 10 mL vial was charged 3-[[1-(4-fluorophenyl)pyrazole-3-carbonyl]amino]-1-pyrrolo[1,2-a]pyrazin-1-yl-pyrrolidine-3-carboxylic acid (100 mg, 0.25 mmol), HATU (114 mg, 0.3 mmol), saturated NH$_3$ in DCM (2 mL) and 5 mL of DMF. The mixture was stirred at room temperature for 1 h and then was diluted with 100 ml of EtOAc, followed by washing with water (2×20 mL) and brine (2×20 mL). The organics were dried over MgSO$_4$ and concentrated under reduced pressure. The residue was purified via flash chromatography on sica gel (50-100% EtOAc in hexanes) to get the desired product (75 mg, 69%). N-3-carbamoyl-1-pyrrolo[1,2-a]pyrazin-1-yl-pyrrolidin-3-yl-1-(4-fluorophenyl)pyrazole-3-carboxamide: $^1$H NMR (400 MHz, CD$_3$OD) δ 8.30 (d, J=2.4 Hz, 1H), 7.88 (m, 2H), 7.78 (q, J=1.2 Hz, 1H), 7.72 (d, J=5.9 Hz, 1H), 7.55 (d, J=3.9 Hz, 1H), 7.30-7.22 (m, 2H), 6.99 (d, J=2.7 Hz, 1H), 6.93 (dd, J=2.7, 4.3 Hz, 1H), 6.83 (d, J=5.5 Hz, 1H), 4.60-3.80 (br, 4H), 2.90-2.80 (m, 1H), 2.78-2.68 (m, 1H); MS: (ES) m/z calculated for C$_{22}$H$_{20}$FN$_7$O$_2$ [M+H]$^+$ 434.2, found 434.

Example 65: Synthesis of ethyl 2-phenyl-2H-tetrazole-5-carboxylate

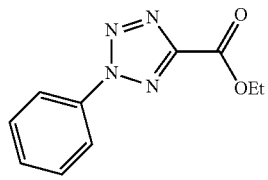 [SMILES: CCOC(=O)c1nnn(-c2ccccc2)n1]

To a solution of aniline (0.58 g, 6.2 mmol) in 9.2 mL of EtOH/H$_2$O (1:1) at 0° C. was added 2.3 mL of conc. HCl followed by NaNO$_2$ (0.47 g, 6.8 mmol, 1.1 eq). The mixture was stirred at 0° C. for 30 min. To a separate solution of ethylglyoxalate (1.74 g, 17 mmol, 3.1 eq) in 34 mL of EtOH was added p-toluenesulfonylhydrazide (1.0 g, 5.4 mmol, 1 eq). The mixture was stirred at room temperature for 30 min then concentrated. The residue was redissolved in 34 mL of pyridine and cooled to 0° C. To the cooled solution was added the preformed diazonium salt. The reaction mixture was stirred at room temperature for 3 h and then quenched with H$_2$O. The contents were extracted with ethyl acetate and the organic layer was dried with Na$_2$SO$_4$ and concentrated in vacuo. Purification by silica gel flash chromatography (hex: EtOAc 9:1) afforded ethyl 2-phenyl-2H-tetrazole-5-carboxylate (0.84 g, 3.9 mmol, 71%).

Example 66: Synthesis of 2-phenyl-2H-tetrazole-5-carboxylic acid

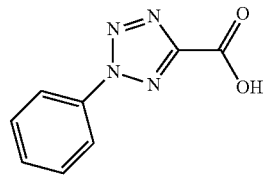 [SMILES: O=C(O)c1nnn(-c2ccccc2)n1]

To a solution of ethyl 2-phenyl-2H-tetrazole-5-carboxylate (0.84 g, 3.9 mmol, 1 eq) in 7.6 mL of EtOH/H$_2$O (1.5:1) was added NaOH (0.31 g, 7.8 mmol, 2 eq). The reaction mixture was heated at 60° C. for 30 min and was then quenched with 0.65 mL of conc. HCl. The contents were filtered and washed with MeOH and the filtrate was dried with Na$_2$SO$_4$ and concentrated in vacuo. Purification by silica gel flash chromatography (100% EtoAc) afforded 2-phenyl-2H-tetrazole-5-carboxylic acid (0.41 g, 2.2 mmol, 55%).

Example 67: Synthesis of (S)-tert-butyl (1-(imidazo[1,2-a]pyrazin-8-yl)pyrrolidin-3-yl)carbamate

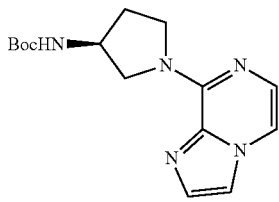 [SMILES: CC(C)(C)OC(=O)N[C@H]1CCN(c2nccn3ccnc23)C1]

To a solution of (S)-tert-butyl pyrrolidin-3-ylcarbamate (80.2 g, 0.43 mol, 1.1 eq) in 75 mL of diisopropylamine and 34 mL of NMP was added portionwise 8-chloroimidazo[1,2-a]pyrazine (60 g, 0.39 mol, 1 eq). The reaction mixture was heated at 100° C. for 4 h and was then diluted with 1.2 L of ethyl acetate. The organic layer was washed with H$_2$O and brine, dried with Na$_2$SO$_4$ and concentrated to give (S)-tert-butyl (1-(imidazo[1,2-a]pyrazin-8-yl)pyrrolidin-3-yl)carbamate (111.7 g, 0.37 mol, 94%).

Example 68: Synthesis of (S)-1-(imidazo[1,2-a]pyrazin-8-yl)pyrrolidin-3-amine

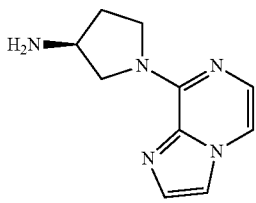 [SMILES: N[C@H]1CCN(c2nccn3ccnc23)C1]

To a solution of acetyl chloride (114 mL, 1.6 mol) in 290 mL of MeOH at 0° C. was added a solution of (S)-tert-butyl (1-(imidazo[1,2-a]pyrazin-8-yl)pyrrolidin-3-yl)carbamate (111.7 g, 0.37 mol) in 450 mL of MeOH. The reaction mixture was stirred at room temperature for 2 h then heated at 60° C. for 30 min. The product was filtered, washed with 200 mL of MeOH and dried in a vacuum oven to afforded (S)-1-(imidazo[1,2-a]pyrazin-8-yl)pyrrolidin-3-amine (101.2 g, 1.6 mol, 100%).

Example 69: Synthesis of (S)—N-(1-(imidazo[1,2-a]pyrazin-8-yl)pyrrolidin-3-yl)-2-phenyl-2H-tetrazole-5-carboxamide

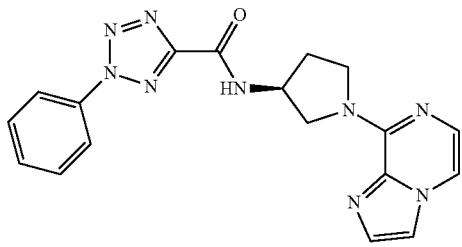 [SMILES: O=C(N[C@H]1CCN(c2nccn3ccnc23)C1)c1nnn(-c2ccccc2)n1]

To a solution of 2-phenyl-2H-tetrazole-5-carboxylic acid (0.10 g, 0.53 mmol, 1 eq) and (S)-1-(imidazo[1,2-a]pyrazin-8-yl)pyrrolidin-3-amine (0.15 g, 0.53 mmol, 1 eq) in 1 mL of DMSO was added triethylamine (0.22 mL, 0.58 mmol, 1.1 eq) and HATU (0.22 g, 0.58 mmol, 3 eq). The mixture was stirred at room temperature for 1 h and was then concentrated and purified by HPLC to afford (S)—N-(1-(imidazo[1,2-a]pyrazin-8-yl)pyrrolidin-3-yl)-2-phenyl-2H-tetrazole-5-carboxamide (0.10 g, 0.26 mmol, 49'). $^1$H NMR (400 MHz, CD$_3$OD) δ 8.19 (d, J=7.0 Hz, 2H), 8.06 (s, 1H), 7.95 (d, J=5.5 Hz, 1H), 7.82 (s, 1H), 7.70-7.58 (m, 3H), 7.19 (d, J=5.8 Hz, 1H), 5.00-4.90 (m, 1H), 4.80-3.80 (br, 4H), 2.62-2.38 (m, 2H); MS: (ES) m/z calculated for C18H17N9O [M+H]+ 376.2. found 376.

Example 70: Synthesis of methyl 6-(4-hydroxypiperidin-1-yl)pyridazine-3-carboxylate

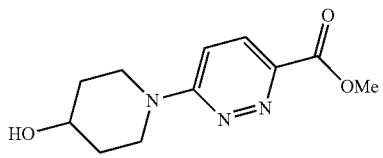 [SMILES: COC(=O)c1ccc(N2CCC(O)CC2)nn1]

A solution of 6-chloropyridazine-3-carboxylic acid (0.50 g, 3.2 mmol) in 11 mL of SOCl$_2$ was heated at 75° C. for 2 h and was then concentrated and redissolved in 5 mL of MeOH. To the solution was added a 25% solution of sodium methoxide (0.75 mL, 3.5 mmol, 1.1 eq) in MeOH. The reaction mixture was stirred at room temperature for 20 h and was then quenched with H$_2$O and extracted with dichloromethane. Silica gel flash chromatography (EtOAc/MeOH 90:10) of the residue afford a 2:1 mixture of the 6-chloropyridazine-3-carboxylic acid and 6-methoxypyridazine-3-carboxylic acid (0.160 g). To a solution of the mixture of ester and chloride in 1.9 mL of p-dioxane was added 4-hydroxy piperidine (0.094 g, 93 mmol) followed by diisopropylethylamine (0.49 mL, 2.8 mmol). The mixture was heated at 100° C. for 20 h then concentrated. Purification with silica gel flash chromatography afforded methyl 6-(4-hydroxypiperidin-1-yl)pyridazine-3-carboxylate (0.15 g, 63 mmol).

Example 71: Synthesis of 6-(4-hydroxypiperidin-1-yl)pyridazine-3-carboxylic acid

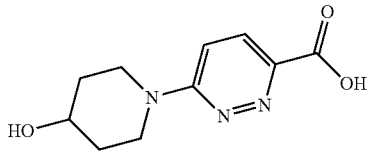 [SMILES: O=C(O)c1ccc(N2CCC(O)CC2)nn1]

To a solution of the ester (0.15 g, 0.63 mmol, 1 eq) in 2.5 mL of EtOH/H₂O (1.5:1) was added NaOH (0.08 g, 1.9 mmol, 3 eq). The reaction mixture was heated at 50° C. for 1 h then quenched with 0.16 mL of conc. HCl. The contents were filtered and washed with MeOH and the filtrate was dried with Na₂SO₄ and concentrated in the vacuo to afford 6-(4-hydroxypiperidin-1-yl)pyridazine-3-carboxylic acid.

Example 72: Synthesis of (S)-6-(4-hydroxypiperidin-1-yl)-N-(1-(imidazo[1,2-a]pyrazin-8-yl)pyrrolidin-3-yl)pyridazine-3-carboxamide

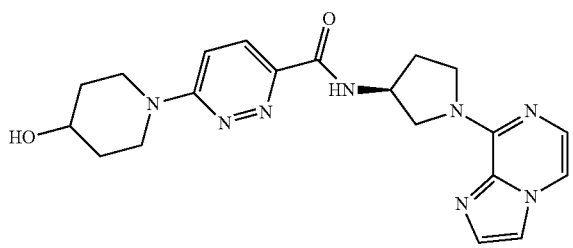 [SMILES: O=C(N[C@H]1CCN(c2nccn3ccnc23)C1)c1ccc(N2CCC(O)CC2)nn1]

To a solution of 6-(4-hydroxypiperidin-1-yl)pyridazine-3-carboxylic acid (0.10 g, 0.45 mmol, 1 eq) and (S)-1-(imidazo[1,2-a]pyrazin-8-yl)pyrrolidin-3-amine (0.12 g, 0.44 mmol, 1 eq) in 1 mL of DMSO was added triethylamine (0.19 mL, 0.49 mmol, 1.1 eq) and HATU (0.19 g, 0.49 mmol, 3 eq). The mixture was stirred at room temperature for 30 min then concentrated and purified by HPLC to afford (S)-6-(4-hydroxypiperidin-1-yl)-N-(1-(imidazo[1,2-a]pyrazin-8-yl)pyrrolidin-3-yl)pyridazine-3-carboxamide (0.12 g, 0.29 mmol, 66%). $^1$H NMR (400 MHz, CD₃OD) δ 8.05 (s, 1H), 8.02 (d, J=9.8 Hz, 1H), 7.94 (d, J=5.5 Hz, 1H), 7.81 (s, 1H), 7.5 (d, J=9.8 Hz, 1H), 7.18 (d, J=5.8 Hz, 1H), 4.98-4.80 (m, 1H), 4.80-3.80 (br, 4H), 4.20-4.10 (m, 2H), 4.00-3.90 (m, 1H), 3.55-3.45 (m, 2H), 2.60-2.35 (m, 2H), 2.05-1.95 (m, 2H), 1.68-1.55 (m, 2H); MS: (ES) m/z calculated for C₂₀H₂₄N₈O₂ [M+H]+ 409.2, found 409.

Example 73: Synthesis of ethyl 1-(3,4-difluorophenyl)-1H-1,2,4-triazole-3-carboxylate

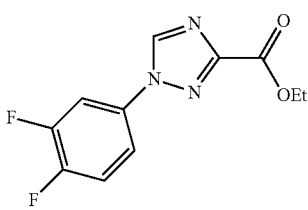 [SMILES: CCOC(=O)c1ncn(-c2ccc(F)c(F)c2)n1]

To a solution of 3,4-difluoroaniline (1 mL, 10 mmol) in 5.4 mL of H₂O at 0° C. was added 2.8 mL of conc. HCl followed by NaNO₂ (1.0 g, 15 mmol, 1.5 eq). The mixture was stirred at 0° C. for 30 min. An additional amount of NaNO₂ (0.35 g, 5 mmol, 0.5 eq) was added and the mixture was stirred for 1 h at 0° C. To a separate solution of NaOAc (8.9 g, 108 mmol, 11 eq) in 13 mL EtOH/H₂O (12:1) was added ethyl-2-isocyanoacetate (1.1 mL, 10 mmol, 1 eq). The mixture was cooled to 0° C. and the diazonium salt mixture was added dropwise. After stirring for 1 h, the reaction was quenched with H₂O and extracted with EtOAc. The organic layer was dried with Na₂SO₄ and concentrated in vacuo. Purification by silica gel flash chromatography (hex: EtoAc 1:1) afforded ethyl 1-(3,4-difluorophenyl)-1H-1,2,4-triazole-3-carboxylate (0.30 g, 1.3 mmol, 13%).

Example 74: Synthesis of 1-(3,4-difluorophenyl)-1H-1,2,4-triazole-3-carboxylic acid

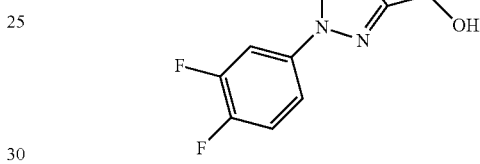

To a solution of ethyl 1-(3,4-difluorophenyl)-1H-1,2,4-triazole-3-carboxylate (0.30 g, 1.2 mmol, 1 eq) in 5 mL of EtOH/H₂O (1.5:1) was added NaOH (0.095 g, 2.4 mmol, 2 eq). The reaction mixture was heated at 50° C. for 1 h then quenched with 0.20 mL of conc. HCl. The contents were filtered and washed with EtOAc then with MeOH and the MeOH filtrate was dried with Na₂SO₄ and concentrated in vacuo to afford 1-(3,4-difluorophenyl)-1H-1,2,4-triazole-3-carboxylic acid (0.22 g, 0.98 mmol, 84%).

Example 75: Synthesis of (S)-1-(3,4-difluorophenyl)-N-(1-(imidazo[1,2-a]pyrazin-8-yl)pyrrolidin-3-yl)-1H-1,2,4-triazole-3-carboxamide

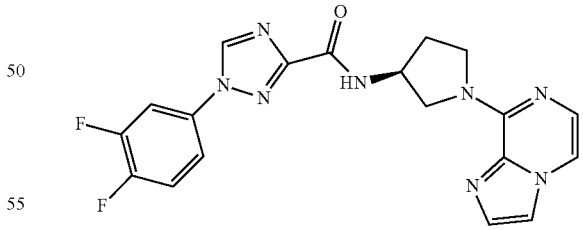

To a solution of 1-(3,4-difluorophenyl)-1H-1,2,4-triazole-3-carboxylic acid (0.10 g, 0.44 mmol, 1 eq) and (S)-1-(imidazo[1,2-a]pyrazin-8-yl)pyrrolidin-3-amine (0.12 g, 0.44 mmol, 1 eq) in 1 mL of DMSO was added triethylamine (0.19 mL, 0.49 mmol, 1.1 eq) and HATU (0.19 g, 1.3 mmol, 3 eq). After stirring for 1 h at room temperature, the mixture was concentrated and purified by HPLC to afford (S)-1-(3,4-difluorophenyl)-N-(1-(imidazo[1,2-a]pyrazin-8-yl)pyrrolidin-3-yl)-1H-1,2,4-triazole-3-carboxamide (0.046 g, 0.11 mmol, 25%). $^1$H NMR (400 MHz, CD₃OD) δ 9.14 (s, 1H), 8.05 (s, 1H), 7.96-7.88 (m, 2H), 7.81 (s, 1H), 7.75-7.71 (m, 1H), 7.52 (q, J=8.6 Hz, 1H), 7.19 (d, J=5.5 Hz, 1H), 4.98-4.80 (m, 1H), 4.80-3.80 (br, 4H), 2.62-2.40 (m, 2H); MS: (ES) m/z calculated for $C_{19}H_6F_2N_8O$ [M+H]+ 411.2, found 411.

Example 76: Synthesis of (S)-tert-butyl (1-(pyrazolo[1,5-a]pyrazin-4-yl)pyrrolidin-3-yl)carbamate

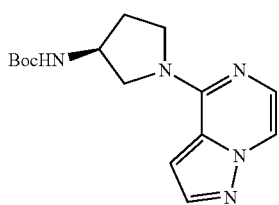 [SMILES: CC(C)(C)OC(=O)N[C@H]1CCN(c2nccn3nccc23)C1]

To a solution of (S)-tert-butyl pyrrolidin-3-ylcarbamate (0.50 g, 2.7 mmol, 1 eq) and diisopropylamine (0.66 mL, 3.8 mmol, 1.4 eq) in 0.2 mL of NMP was added 4-chloropyrazolo[1,5-a]pyrazine (0.47 mL, 3.1 mmol, 1.1 eq). After stirring for 1 h at room temperature, the mixture was concentrated and purified by silica gel column chromatography (100% EtOAc) to afford (S)-tert-butyl (1-(pyrazolo[1,5-a]pyrazin-4-yl)pyrrolidin-3-yl)carbamate (0.740 g, 2.4 mmol, 91%).

Example 77: Synthesis of(S)-1-(pyrazolo[1,5-a]pyrazin-4-yl)pyrrolidin-3-amine

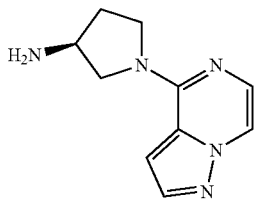 [SMILES: N[C@H]1CCN(c2nccn3nccc23)C1]

To a solution of (S)-tert-butyl (1-(pyrazolo[1,5-a]pyrazin-4-yl)pyrrolidin-3-yl)carbamate (0.74 g, 2.4 mmol, 1 eq) in 3 mL of dioxane was added a solution of 4.0 M HCl in dioxane (3 mL, 20 mmol, 4 eq). After heating for 3 h at 60° C., the mixture was concentrated to afford (S)-1-(pyrazolo[1,5-a]pyrazin-4-yl)pyrrolidin-3-amine (0.670 g, 2.4 mmol, 100%).

Example 78: Synthesis of (S)-1-phenyl-N-(1-(pyrazolo[1,5-a]pyrazin-4-yl)pyrrolidin-3-yl)-1H-1,2,4-triazole-3-carboxamide

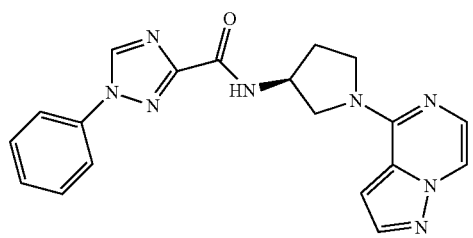 [SMILES: O=C(N[C@H]1CCN(c2nccn3nccc23)C1)c1ncn(-c2ccccc2)n1]

To a solution of 1-phenyl-1H-1,2,4-triazole-3-carboxylic acid (0.093 g, 0.49 mmol, 1.4 eq) and (S)-1-(pyrazolo[1,5-a]pyrazin-4-yl)pyrrolidin-3-amine (0.10 g, 0.36 mmol, 1 eq) in 1 mL of DMSO was added triethylamine (0.20 mL, 1.4 mmol, 2.6 eq) and HATU (0.21 g, 0.55 mmol, 1.5 eq). After stirring for 1 h at room temperature, the mixture was concentrated and purified by HPLC to afford (S)-1-phenyl-N-(1-(pyrazolo[1,5-a]pyrazin-4-yl)pyrrolidin-3-yl)-1H-1,2,4-triazole-3-carboxamide (0.095 g, 0.25 mmol, 52%). $^1$H NMR (400 MHz, CD$_3$OD) δ 9.13 (s, 1H), 8.16 (d, J=2.4 Hz, 1H), 8.09 (d, J=5.8 Hz, 1H), 7.86 (d, J=7.8 Hz, 2H), 7.60-7.46 (m, 4H), 7.19 (d, J=5.5 Hz, 1H), 4.95-4.80 (m, 1H), 4.78-3.80 (br, 4H), 2.62-2.40 (m, 2H); MS: (ES) m/z calculated for $C_{19}H_{18}N_8O$ [M+H]+ 375.2, found 375.

Example 79: Synthesis of (S)-tert-butyl N-(1-(pyrrolo[1,2-a]pyrazin-1-yl)pyrrolidin-3-yl)carbamate

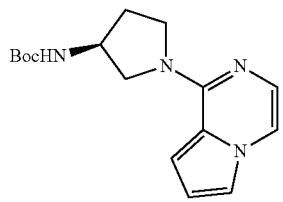 [SMILES: CC(C)(C)OC(=O)N[C@H]1CCN(c2nccn3cccc23)C1]

To a solution of (S)-tert-butyl pyrrolidin-3-ylcarbamate (0.91 g, 4.9 mmol, 1 eq) in 2.6 mL of DIPEA was added 1-chloropyrrolo[1,2-a]pyrazine (0.75 g, 4.9 mmol, 1 eq) and 1 drop of 1-butyl-3-methylimidazolium tetrafluorborate. After heating for 3 h at 110° C., the mixture was concentrated and purified by silica gel flash chromatography (100% EtOAc) to afford (S)-tert-butyl N-(1-(pyrrolo[1,2-a]pyrazin-1-yl)pyrrolidin-3-yl)carbamate (0.88 g, 2.9 mmol, 59%).

Example 80: Synthesis of (S)-1-(pyrrolo[1,2-a]pyrazin-1-yl)pyrrolidin-3-amine

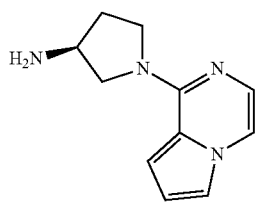 [SMILES: N[C@H]1CCN(c2nccn3cccc23)C1]

To a solution of (S)-tert-butyl N-(1-(pyrrolo[1,2-a]pyrazin-1-yl)pyrrolidin-3-yl)carbamate (0.88 g, 2.9 mmol, 1 eq) in 3.6 mL of dioxane was added a solution of 4.0 M HCl in dioxane (3.6 mL, 14.5 mmol, 5 eq). After heating for 1 h at 60° C., the mixture was concentrated to afford (S)-1-(pyrrolo[1,2-a]pyrazin-1-yl)pyrrolidin-3-amine (0.79 g, 2.9 mmol, 100%).

Example 81: Synthesis of (S)-5-bromo-N-(1-(pyrrolo[1,2-a]pyrazin-1-yl)pyrrolidin-3-yl)pyrimidine-2-carboxamide

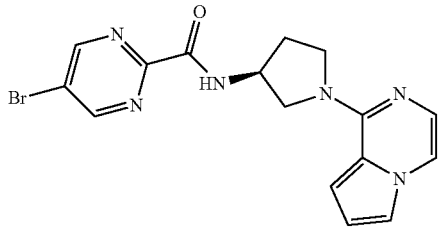 [SMILES: O=C(N[C@H]1CCN(c2nccn3cccc23)C1)c1ncc(Br)cn1]

To a solution of 5-bromopyrimidine-2-carboxylic acid (2.0 g, 9.9 mmol, 1 eq) and (S)-1-(pyrrolo[1,2-a]pyrazin-1-yl)pyrrolidin-3-amine (2.7 g, 9.9 mmol, 1 eq) in 20 mL of DMSO was added triethylamine (5.4 mL, 39 mmol, 3.9 eq) and HATU (4.1 g, 11 mmol, 1.1 eq). After stirring for 1 h at room temperature, the mixture was concentrated and purified by silica gel flash chromatography (EtoAc:MeOH 2:3) to produce (S)-5-bromo-N-(1-(pyrrolo[1,2-a]pyrazin-1-yl)pyrrolidin-3-yl)pyrimidine-2-carboxamide (5.0 g, 1.3 mmol, 13%).

Example 82: Synthesis of (S)-5-(cyclopent-1-en-1-yl)-N-(1-(pyrrolo[1,2-a]pyrazin-1-yl)pyrrolidin-3-yl)pyrimidine-2-carboxamide

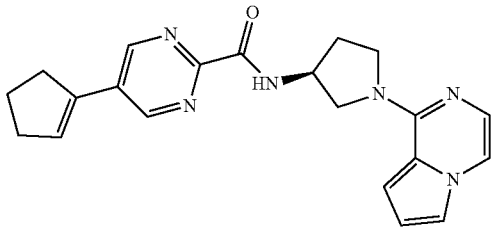 [SMILES: O=C(N[C@H]1CCN(c2nccn3cccc23)C1)c1ncc(C2=CCCC2)cn1]

To a solution of (S)-5-bromo-N-(1-(pyrrolo[1,2-a]pyrazin-1-yl)pyrrolidin-3-yl)pyrimidine-2-carboxamide (0.10 g, 0.27 mmol, 1 eq) in 1.8 mL of DMF was added 2-(cyclopent-1-en-1-yl)-4,4,5,5-tetramethyl-1,3,2-dioxaborolane (0.15 g, 0.77 mmol, 2.8 eq), followed by $K_2CO_3$ (0.18 g, 1.3 mmol, 4.8 eq) in 0.2 mL of $H_2O$ and Pd(dppf)$Cl_2$ (0.02 g, 0.03 mmol, 0.09 eq). After heating for 1 h at 120° C. the mixture was concentrated and purified by silica gel flash chromatography (EtoAc:MeOH 1:1) followed by HPLC to afford (S)-5-(cyclopent-1-en-1-yl)-N-(1-(pyrrolo[1,2-a]pyrazin-1-yl)pyrrolidin-3-yl)pyrimidine-2-carboxamide (0.070 g, 0.19 mmol, 69%).

Example 83: Synthesis of (S)-5-cyclopentyl-N-(1-(pyrrolo[1,2-a]pyrazin-1-yl)pyrrolidin-3-yl)pyrimidine-2-carboxamide

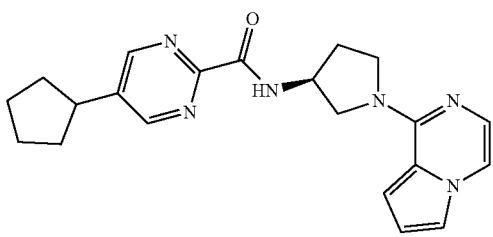 [SMILES: O=C(N[C@H]1CCN(c2nccn3cccc23)C1)c1ncc(C2CCCC2)cn1]

To a solution of (S)-5-(cyclopent-1-en-1-yl)-N-(1-(pyrrolo[1,2-a]pyrazin-1-yl)pyrrolidin-3-yl)pyrimidine-2-carboxamide (0.07 g, 0.19 mmol, 1 eq) in 1 mL of MeOH was added 10% Pd/C (0.02 g, 0.02 mmol, 0.1 eq). The reaction mixture was equipped with a $H_2$ balloon and stirred for 3 hr at room temperature. The contents were filtered and the purified by HPLC to afford (S)-5-cyclopentyl-N-(1-(pyrrolo[1,2-a]pyrazin-1-yl)pyrrolidin-3-yl)pyrimidine-2-carboxamide (0.005 g, 0.013 mmol, 7%). $^1$H NMR (400 MHz, $CD_3OD$) δ 8.83 (s, 2H), 7.78 (q, J=1.1 Hz, 1H), 7.73 (d, J=5.8 Hz, 1H), 7.57 (d, J=3.9 Hz, 1H), 6.94 (dd, J=2.7, 4.7 Hz, 1H), 6.86 (d, J=5.9 Hz, 1H), 5.00-4.80 (m, 1H), 4.50-3.50 (br, 4H), 3.20-3.10 (m, 1H), 2.60-2.48 (m, 1H), 2.48-2.38 (br, 1H), 2.22-2.12 (m, 2H), 1.95-1.60 (m, 6H); MS: (ES) m/z calculated for $C_{21}H_{24}N_6O$ [M+H]+ 377.2, found 377.

Example 84: Synthesis of (S)—N-(1-([1,2,4]triazolo[4,3-a]pyrazin-8-yl)pyrrolidin-3-yl)-6-methylquinazoline-2-carboxamide

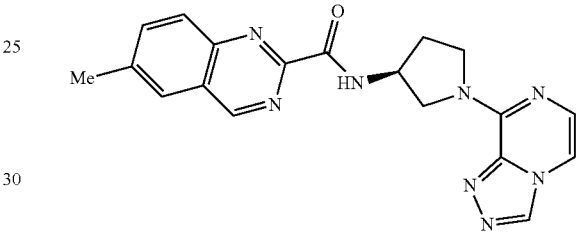

To a solution of 6-methylquinazoline-2-carboxylic acid (0.040 g, 0.21 mmol, 1.2 eq) and (S)-1-([1,2,4]triazolo[4,3-a]pyrazin-8-yl)pyrrolidin-3-amine (0.49 g, 0.18 mmol, 1 eq) in 1 mL of DMSO was added triethylamine (0.10 mL, 0.7 mmol, 4 eq) and HATU (0.075 g, 0.20 mmol, 1.1 eq). After stirring for 1 h at room temperature, the mixture was concentrated and purified by HPLC to afford (S)—N-(1-([1,2,4]triazolo[4,3-a]pyrazin-8-yl)pyrrolidin-3-yl)-6-methylquinazoline-2-carboxamide (0.028 g, 0.07 mmol, 42%). $^1$H NMR (400 MHz, DMSO) δ 9.62 (s, 1H), 9.31 (t, J=3.9 Hz, 1H), 8.08-8.00 (m, 2H), 8.00-7.92 (m, 1H), 7.85 (d, J=5.1 Hz, 1H), 7.29 (d, J=5.0 Hz, 1H), 4.82-4.70 (m, 1H), 4.70-3.60 (br, 4H), 2.56 (s, 3H), 2.40-2.20 (br, 2H); MS: (ES) m/z calculated for $C_{19}H_{18}N_8O$ [M+H]+375.2, found 375.

Example 85: Synthesis of (S)—N-(1-(imidazo[1,2-a]pyrazin-8-yl)pyrrolidin-3-yl)-6-methylquinazoline-2-carboxamide

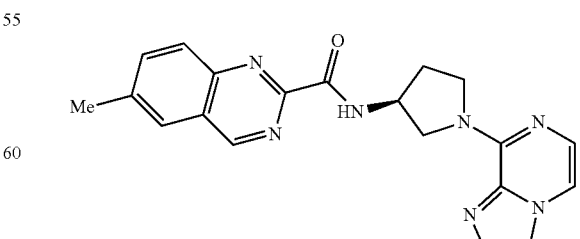

To a solution of 6-methylquinazoline-2-carboxylic acid (0.040 g, 0.21 mmol, 1.2 eq) and (S)-1-(imidazo[1,2-a]

pyrazin-8-yl)pyrrolidin-3-amine (0.49 g, 0.18 mmol, 1 eq) in 1 mL of DMSO was added triethylamine (0.10 mL, 0.7 mmol, 4 eq) and HATU (0.075 g, 0.20 mmol, 1.1 eq). After stirring for 1 h at room temperature, the mixture was concentrated and purified by HPLC to afford (S)—N-(1-(imidazo[1,2-a]pyrazin-8-yl)pyrrolidin-3-yl)-6-methylquinazoline-2-carboxamide (0.057 g, 0.15 mmol, 86%). $^1$H NMR (400 MHz, CD$_3$OD) δ 9.48 (s, 1H), 8.02 (d, J=1.6 Hz, 2H), 7.98-7.88 (m, 3H), 7.78 (s, 1H), 7.17 (d, J=5.8 Hz, 1H), 5.00-3.80 (br, 4H), 2.60 (s, 3H), 2.65-2.40 (br, 2H); MS: (ES) m/z calculated for C$_{20}$H$_9$N$_7$O [M+H]+ 374.2, found 374.

Example 86: Synthesis of ethyl 2-(4-chloro-2-formyl-anilino)-2-oxo-acetate

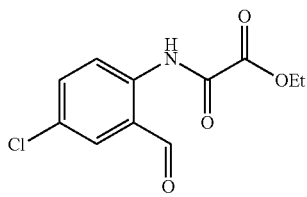 [SMILES: CCOC(=O)C(=O)Nc1ccc(Cl)cc1C=O]

To a solution of 2-amino-5-chloro-benzaldehyde (0.10 g, 0.65 mmol, 1 eq) in 1.6 mL of DCM at 0° C. was added ethylchloroacetate (0.09 mL, 0.85 mmol, 1.3 eq) and pyridine (0.16 mL, 2.0 mmol, 3 eq). After stirring at room temperature for 1 h, the reaction was quenched with H$_2$O and extracted with ethyl acetate. The organic layer was washed with 10% citric acid followed by saturated NaHCO$_3$ then dried with Na$_2$SO$_4$ and concentrated. The residue was purified on silica gel column chromatography (hex:EtoAc 3:2) to provide ethyl 2-(4-chloro-2-formyl-anilino)-2-oxo-acetate (0.14 g, 0.55 mmol, 84%).

Example 87: Synthesis of ethyl 6-chloroquinazoline-2-carboxylate

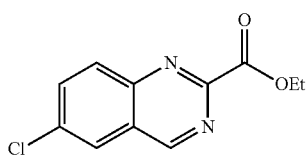 [SMILES: CCOC(=O)c1ncc2cc(Cl)ccc2n1]

To a solution of ethyl 2-(4-chloro-2-formyl-anilino)-2-oxo-acetate (0.14 g, 0.55 mmol, 1 eq) in 5.5 mL of acetic acid was added ammonium acetate (0.42 g, 5.4 mmol, 10 eq). After heating at 115° C. for 1 h, the mixture was concentrated then diluted with H$_2$O and extracted with ethyl acetate. The organic layer was concentrated and the residue was purified on silica gel column chromatography (hex:EtoAc 3:2) to give ethyl 6-chloroquinazoline-2-carboxylate (0.11 g, 0.48 mmol, 88%).

Example 88: Synthesis of (S)-tert-butyl 3-(6-chloro-quinazoline-2-carboxamido)pyrrolidine-1-carboxylate

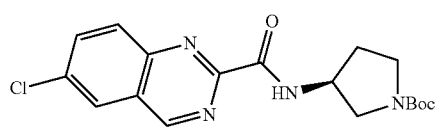 [SMILES: CC(C)(C)OC(=O)N1CC[C@H](NC(=O)c2ncc3cc(Cl)ccc3n2)C1]

To a solution of ethyl 6-chloroquinazoline-2-carboxylate (0.200 g, 0.85 mmol, 1 eq) in 0.42 mL of NMP was added (S)-tert-butyl 3-aminopyrrolidine-1-carboxylate (0.16 g, 0.86 mmol, 1 eq) and diisopropylethylamine (0.6 mL, 3.4 mmol, 4 eq). After stirring at 150° C. for 20 h, the mixture was concentrated and purified via silica gel flash chromatography to provide (S)-tert-butyl 3-(6-chloroquinazoline-2-carboxamido)pyrrolidine-1-carboxylate (0.08 g, 0.21 mmol, 25%).

Example 89: Synthesis of (S)-6-chloro-N-(1-(pyrrolo[1,2-a]pyrazin-1-yl)pyrrolidin-3-yl)quinazoline-2-carboxamide

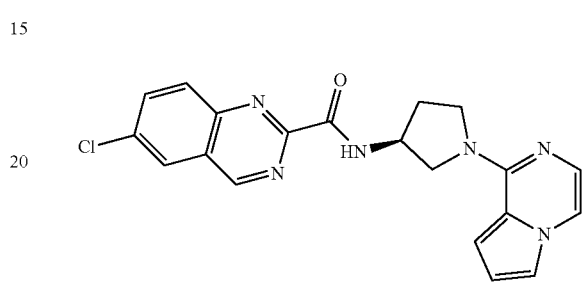

To a solution of (S)-tert-butyl 3-(6-chloroquinazoline-2-carboxamido)pyrrolidine-1-carboxylate (0.086 g, 0.23 mmol, 1 eq) in 1 mL of p-dioxane was added a solution of 4.0 M HCl in dioxane (0.29 mL, 1.2 mmol, 5 eq). After stirring at 60° C. for 1 h, the mixture was concentrated to provide (S)-6-chloro-N-(pyrrolidin-3-yl)quinazoline-2-carboxamide which was carried on without further purification.

To a solution of the crude amine in 0.16 mL of diisopropylethylamine was added 1-chloropyrrolo[1,2-a]pyrazine (0.047 g, 0.31 mmol) followed by 1 drop of 1-butyl-3-methylimidazolium tetrafluoroborate. The reaction was heated at 90° C. for 20 h. Purification of the residue by HPLC afforded (S)-6-chloro-N-(1-(pyrrolo[1,2-a]pyrazin-1-yl)pyrrolidin-3-yl)quinazoline-2-carboxamide (0.05 g, 0.013 mmol, 6%). $^1$H NMR (400 MHz, CD$_3$OD) δ 9.60 (s, 1H), 8.26 (s, 1H), 8.17 (d, J=9.1 Hz, 1H), 8.07 (dd, J=1.8, 9.1 Hz, 1H), 7.76 (d, J=1.5 Hz, 1H), 7.72 (d, J=5.8 Hz, 1H), 7.57 (s, 1H), 6.93 (m, 1H), 6.85 (d, J=5.8 Hz, 1H), 5.06-4.84 (m, 1H), 4.82-3.60 (br, 4H), 2.65-2.40 (br, 2H); MS: (ES) m/z calculated for C$_{20}$H$_{17}$ClN$_6$O [M+H]+ 393.2, found 393.

Example 90: Synthesis of (S)-5-methyl-N-(1-(pyrrolo[1,2-a]pyrazin-1-yl)pyrrolidin-3-yl)pyrimidine-2-carboxamide

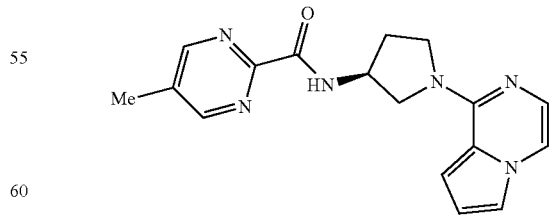

To a solution of 5-methylpyrimidine-2-carboxylic acid (0.03 g, 0.22 mmol, 1 eq) and (S)-1-(pyrrolo[1,2-a]pyrazin-1-yl)pyrrolidin-3-amine (0.060 g, 0.22 mmol, 1 eq) in 1 mL of DMSO was added triethylamine (0.12 mL, 0.86 mmol, 4 eq) and HATU (0.09 g, 0.24 mmol, 1.1 eq). After stirring for 1 h at room temperature, the mixture was concentrated and purified by HPLC to afford (S)-5-methyl-N-(1-(pyrrolo[1,2-a]pyrazin-1-yl)pyrrolidin-3-yl)pyrimidine-2-carboxamide (0.029 g, 0.09 mmol, 41%). $^1$H NMR (400 MHz, CD$_3$OD) δ 8.75 (s, 2H), 7.76 (s, 1H), 7.71 (d, J=5.5 Hz, 1H), 7.54 (s, 1H), 6.91 (s, 1H), 6.85 (d, J=5.8 Hz, 1H), 5.00-3.60 (br, 5H), 2.65-2.30 (br, 2H), 2.40 (s, 3H); MS: (ES) m/z calculated for C$_{17}$H$_{18}$N$_6$O [M+H]+ 323.2, found 323.

Example 91: Synthesis of (S)—N-(1-(pyrrolo[1,2-a]pyrazin-1-yl)pyrrolidin-3-yl)-5-vinylpyrimidine-2-carboxamide

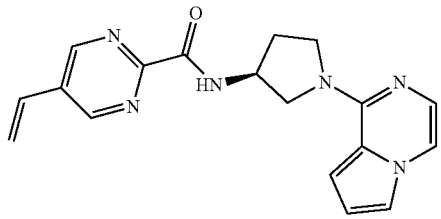 [SMILES: C=Cc1cnc(C(=O)N[C@H]2CCN(c3nccn4cccc34)C2)nc1]

To a solution of (S)-5-bromo-N-(1-(pyrrolo[1,2-a]pyrazin-1-yl)pyrrolidin-3-yl)pyrimidine-2-carboxamide (0.10 g, 0.26 mmol, 1 eq) in 1 mL of DMF was added 4,4,5,5-tetramethyl-2-vinyl-1,3,2-dioxaborolane (0.13 g, 0.84 mmol, 3.2 eq), followed by K$_2$CO$_3$ (0.18 g, 1.3 mmol, 5 eq) in 0.2 mL of H$_2$O and Pd(dppf)Cl$_2$ (0.02 g, 0.02 mmol, 0.1 eq). After heating for 1 h at 120° C. the mixture was concentrated and purified by silica gel column chromatography (EtoAc:MeOH 1:1) followed by HPLC to afford (S)—N-(1-(pyrrolo[1,2-a]pyrazin-1-yl)pyrrolidin-3-yl)-5-vinylpyrimidine-2-carboxamide (0.040 g, 0.12 mmol, 46%).

Example 92: Synthesis of (S)-5-ethyl-N-(1-(pyrrolo[1,2-a]pyrazin-1-yl)pyrrolidin-3-yl)pyrimidine-2-carboxamide

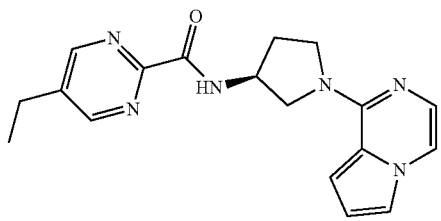 [SMILES: CCc1cnc(C(=O)N[C@H]2CCN(c3nccn4cccc34)C2)nc1]

To a solution of (S)—N-(1-(pyrrolo[1,2-a]pyrazin-1-yl)pyrrolidin-3-yl)-5-vinylpyrimidine-2-carboxamide (0.04 g, 0.12 mmol, 1 eq) in 1 mL of MeOH was added 10% Pd/C (0.013 g, 0.01 mmol, 0.1 eq). The reaction mixture was equipped with a H$_2$ balloon and stirred for 1 hr at room temperature. The contents were filtered and the purified by HPLC to afford (S)-5-ethyl-N-(1-(pyrrolo[1,2-a]pyrazin-1-yl)pyrrolidin-3-yl)pyrimidine-2-carboxamide (0.009 g, 0.25 mmol, 22%). $^1$H NMR (400 MHz, CD$_3$OD) δ 8.80 (s, 2H), 7.76 (m, 1H), 7.71 (d, J=5.8 Hz, 1H), 7.54 (s, 1H), 6.92 (dd, J=2.6, 4.4 Hz, 1H), 6.84 (d, J=5.5 Hz, 1H), 5.00-3.60 (br, 5H), 2.81 (q, J=7.4 Hz, 2H), 2.65-2.30 (br, 2H), 1.33 (t, J=7.4 Hz, 3H); MS: (ES) m/z calculated for C$_{17}$H$_{18}$N$_6$O [M+H]+ 337.2, found 337.

Example 93: Synthesis of (S)-5-cyclopropyl-N-(1-(pyrrolo[1,2-a]pyrazin-1-yl)pyrrolidin-3-yl)pyrimidine-2-carboxamide

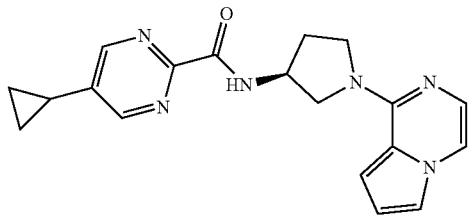 [SMILES: O=C(N[C@H]1CCN(c2nccn3cccc23)C1)c1ncc(C2CC2)cn1]

To a solution of (S)-5-bromo-N-(1-(pyrrolo[1,2-a]pyrazin-1-yl)pyrrolidin-3-yl)pyrimidine-2-carboxamide (0.25 g, 0.65 mmol, 1 eq) in 2 mL of toluene was added 2-cyclopropyl-4,4,5,5-tetramethyl-1,3,2-dioxaborolane (0.16 g, 1.86 mmol, 2.8 eq), followed by PCy$_3$ (0.033 g, 0.11 mmol, 0.2 eq), K$_3$PO$_4$ (0.48 g, 2.3 mmol, 3.5 eq) in 0.1 mL of H$_2$O and Pd(OAc)$_2$ (0.013 g, 0.06 mmol, 0.1 eq). After heating for 1 h at 120° C. the mixture was filtered and purified by HPLC to afford (S)-5-cyclopropyl-N-(1-(pyrrolo[1,2-a]pyrazin-1-yl)pyrrolidin-3-yl)pyrimidine-2-carboxamide (0.009 g, 0.026 mmol, 4%). $^1$H NMR (400 MHz, CD$_3$OD) δ 8.64 (s, 2H), 7.76 (m, 1H), 7.71 (d, J=5.4 Hz, 1H), 7.54 (s, 1H), 6.92 (dd, J=2.6, 4.4 Hz, 1H), 6.84 (d, J=5.5 Hz, 1H), 5.00-3.60 (br, 5H), 2.65-2.30 (br, 2H), 2.07-2.02 (m, 1H), 1.23-1.18 (m, 2H), 0.96-0.91 (m, 2H); MS: (ES) m/z calculated for C$_{19}$H$_{20}$N$_6$O [M+H]+ 349.2, found 349.

Example 94: Synthesis of (S)-5-(4-fluorophenyl)-N-(1-(pyrrolo[1,2-a]pyrazin-1-yl)pyrrolidin-3-yl)pyrimidine-2-carboxamide

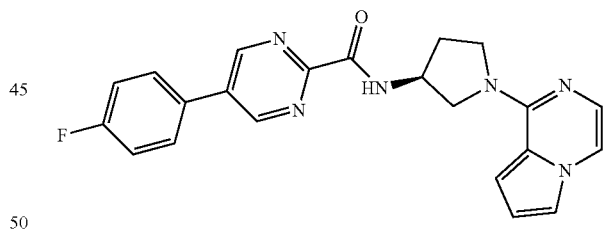

To a solution of (S)-5-bromo-N-(1-(pyrrolo[1,2-a]pyrazin-1-yl)pyrrolidin-3-yl)pyrimidine-2-carboxamide (0.036 g, 0.093 mmol, 1 eq) in 1.8 mL of DMF was added (4-fluorophenyl)boronic acid (0.10 g, 0.71 mmol, 7.7 eq), followed by K$_2$CO$_3$ (0.18 g, 1.3 mmol, 14 eq) in 0.2 mL of H$_2$O and Pd(dppf)Cl$_2$ (0.02 g, 0.03 mmol, 0.3 eq). After heating for 1 h at 120° C. the mixture was filtered and purified by HPLC to afford (S)-5-(4-fluorophenyl)-N-(1-(pyrrolo[1,2-a]pyrazin-1-yl)pyrrolidin-3-yl) pyrimidine-2-carboxamide (0.014 g, 0.035 mmol, 37%). $^1$H NMR (400 MHz, CD$_3$OD) δ 9.17 (s, 2H), 7.83 (m, 3H), 7.71 (d, J=5.4 Hz, 1H), 7.56 (s, 1H), 7.31 (t, J=8.5 Hz, 2H), 6.92 (s, 1H), 6.85 (d, J=5.9 Hz, 1H), 5.00-3.60 (br, 5H), 2.65-2.30 (br, 2H); MS: (ES) m/z calculated for C$_{22}$H$_{19}$FN$_6$O [M+H]+ 403.2, found 403.

Example 95: Synthesis of (S)-5-(prop-1-en-2-yl)-N-(1-(pyrrolo[1,2-a]pyrazin-1-yl)pyrrolidin-3-yl)pyrimidine-2-carboxamide

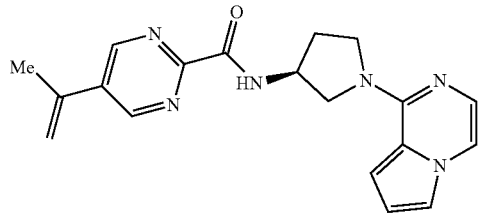 [SMILES: C=C(C)c1cnc(C(=O)N[C@H]2CCN(c3nccn4cccc34)C2)nc1]

To a solution of (S)-5-bromo-N-(1-(pyrrolo[1,2-a]pyrazin-1-yl)pyrrolidin-3-yl)pyrimidine-2-carboxamide (0.075 g, 0.19 mmol, 1 eq) in 1.8 mL of DMF was added 4,4,5,5-tetramethyl-2-(prop-1-en-2-yl)-1,3,2-dioxaborolane (0.10 g, 0.6 mmol, 3 eq), followed by K$_2$CO$_3$ (0.14 g, 0.99 mmol, 5 eq) in 0.2 mL of H$_2$O and Pd(dppf)Cl$_2$ (0.02 g, 0.02 mmol, 0.1 eq). After heating for 2 h at 120° C. the mixture was filtered, concentrated and carried forward to the next step.

Example 96: Synthesis of (S)-5-isopropyl-N-(1-(pyrrolo[1,2-a]pyrazin-1-yl)pyrrolidin-3-yl)pyrimidine-2-carboxamide

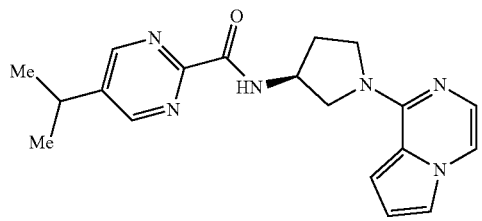 [SMILES: CC(C)c1cnc(C(=O)N[C@H]2CCN(c3nccn4cccc34)C2)nc1]

To a solution of (S)-5-(prop-1-en-2-yl)-N-(1-(pyrrolo[1,2-a]pyrazin-1-yl)pyrrolidin-3-yl)pyrimidine-2-carboxamide (0.090 g, 0.26 mmol, 1 eq) in 1 mL of MeOH was added 10% Pd/C (0.027 g, 0.03 mmol, 0.1 eq). The reaction mixture was equipped with a H$_2$ balloon and stirred for 1 hr at room temperature. The contents were filtered and the purified by HPLC to afford (S)-5-isopropyl-N-(1-(pyrrolo[1,2-a]pyrazin-1-yl)pyrrolidin-3-yl)pyrimidine-2-carboxamide (0.048 g, 0.14 mmol, 53%). $^1$H NMR (400 MHz, CD$_3$OD) δ 8.81 (s, 2H), 7.76 (s, 1H), 7.71 (d, J=5.8 Hz, 1H), 7.55 (s, 1H), 6.92 (s, 1H), 6.84 (d, J=5.9 Hz, 1H), 5.00-3.60 (br, 5H), 3.18-3.00 (m, 1H), 2.65-2.30 (br, 2H), 1.36 (d, J=7.0 Hz, 6H); MS: (ES) m/z calculated for C$_{19}$H$_{22}$N$_6$O [M+H]+ 351.2, found 351.

Example 97: Synthesis of ethyl 1-(4-fluorophenyl)pyrazole-3-carboxylate

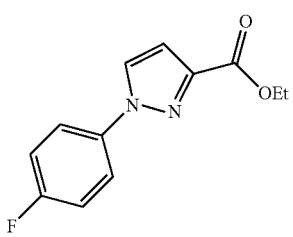 [SMILES: CCOC(=O)c1ccn(-c2ccc(F)cc2)n1]

To a solution of 1-fluoro-4-iodo-benzene (1.47 g, 6.6 mmol, 1.3 eq) and ethyl 1H-pyrazole-3-carboxylate (0.71 g, 5.1 mmol, 1 eq) in 15 mL of toluene was added CuI (0.19 g, 1.0 mmol, 0.2 eq), trans-N,-N-dimethylcyclohexane 1,2-diamine (0.4 mL, 2.5 mmol, 0.2 eq), and potassium carbonate (1.4 g, 10 mmol, 2 eq). The reaction mixture was heated at 110° C. for 2 d then filtered and concentrated. The residue was purified by silica gel column chromatography (hex:EtoAc 4:1) to afford ethyl 1-(4-fluorophenyl)pyrazole-3-carboxylate (0.92 g, 3.9 mmol, 77%).

Example 98: Synthesis of 1-(4-fluorophenyl)pyrazole-3-carboxylic acid

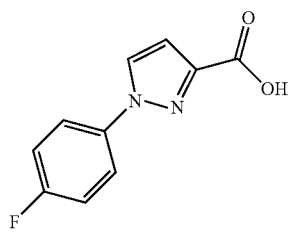 [SMILES: O=C(O)c1ccn(-c2ccc(F)cc2)n1]

To a solution of ethyl 1-(4-fluorophenyl)pyrazole-3-carboxylate (0.92 g, 3.9 mmol, 1 eq) in 18 mL of EtOH/H$_2$O (1.5:1) was added NaOH (0.47 g, 11.8 mmol, 3 eq). The reaction mixture was heated at 50° C. for 1 h then quenched with H$_2$O and extracted with ethyl acetate. The combined organic layers were concentrated and purified by silica gel column chromatography (EtoAc:MeOH 3:1) to provide 1-(4-fluorophenyl)pyrazole-3-carboxylic acid (0.42 g, 2.0 mmol, 52%).

Example 99: Synthesis of (S)-1-(4-fluorophenyl)-N-(1-(8-methylpyrrolo[1,2-a]pyrazin-1-yl)pyrrolidin-3-yl)-1H-pyrazole-3-carboxamide

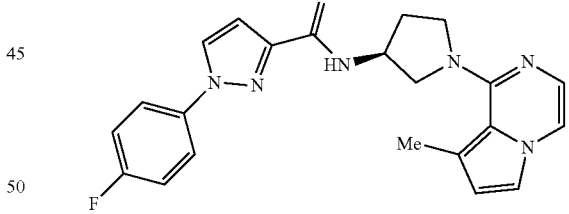

To a solution of 1-(4-fluorophenyl)-1H-pyrazole-3-carboxylic acid (0.04 g, 0.19 mmol, 1.5 eq) in 1 mL of DCM was added (S)-1-(8-methylpyrrolo[1,2-a]pyrazin-1-yl)pyrrolidin-3-amine (0.036 g, 0.13 mmol, 1 eq), propylphosphonic anhydride (0.3 mL, 0.47 mmol, 2.5 eq), and N-methylmorpholine (0.15 mL, 1.36 mmol, 10.5 eq). The reaction mixture was stirred at room temperature for 1 h then quenched with H$_2$O and extracted with ethyl acetate. The combined organic layers were concentrated and purified by HPLC to afford (S)-1-(4-fluorophenyl)-N-(1-(8-methylpyrrolo[1,2-a]pyrazin-1-yl)pyrrolidin-3-yl)-1H-pyrazole-3-carboxamide (0.030 g, 0.074 mmol, 57%). $^1$H NMR (400 MHz, CDCl$_3$) δ 7.91 (d, J=7.3 Hz, 1H), 7.82 (s, 1H), 7.68 (dd, J=4.4, 8.8 Hz, 2H), 7.33 (d, J=4.8 Hz, 1H), 7.19 (t, J=8.8 Hz, 3H), 7.00 (m, 2H), 6.50 (s, 1H), 4.75 (s, 1H), 3.90-3.56 (m, 4H), 2.57 (s, 3H), 2.42-2.38 (m, 1H), 2.02-1.80 (m, 1H); MS: (ES) m/z calculated for $C_{22}H_{21}FN_6O[M+H]+$ 405.2, found 405.

Example 100: Synthesis of (S)—N-(1-([1,2,4]triazolo[4,3-a]pyrazin-8-yl)pyrrolidin-3-yl)-1-phenyl-1H-1,2,4-triazole-3-carboxamide

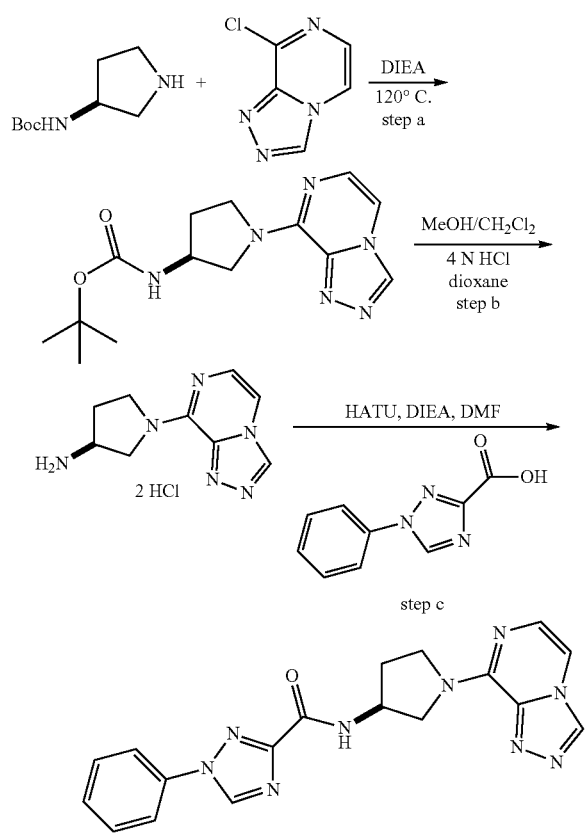

a) A mixture of 8-chloro-[1,2,4]triazolo[4,3-a]pyrazine (620 mg, 4.0 mmol) and (S)-tert-butyl pyrrolidin-3-yl carbamate (1.2 g, 6.5 mmol) in diethylisopropyl amine (3 mL) was heated to 120° C. for 2 h. After cooling to room temperature, the mixture was diluted with 10% MeOH in EtOAc and washed with saturated aqueous solutions of $KH_2PO_4$ and $NaHCO_3$, followed by brine. The organic layer was concentrated in vacuo and the residue purified by flash chromatography ($SiO_2$, 2 to 5% MeOH in $CH_2Cl_2$ as eluent) to give the desired compound as a foam (1.15 g, 95% yield, which was used directly for the next step). MS: (ES) m/z 305.2 (M+H$^+$).

b) The above Boc-amine was dissolved in $CH_2Cl_2$ (4 mL) and MeOH (3 mL) at room temperature, followed by addition of 4 N HCl in dioxane (9 mL, 36 mmol). The mixture was stirred at room temperature for 2 h. The resulting suspension was diluted with EtOAc. Filtration and air-drying gave the desired compound as an off-white solid (1.05 g, quantitative, which was used directly for the next step). MS: (ES) m/z 205.1 (M+H$^+$).

c) To a suspension of the above (S)-1-([1,2,4]triazolo[4,3-a]pyrazin-8-yl)pyrrolidin-3-amine hydrochloride salt (90 mg, 0.32 mmol), 1-phenyl-1H-1,2,4-triazole-3-carboxylic acid (58 mg, 0.30 mmol) in DMF (5 mL) was added diethylisopropyl amine (650 mg, 5 mmol), followed by HATU (120 mg, 0.31 mmol). The resulting solution was stirred at room temperature for 1 h. The reaction mixture was diluted with ethyl acetate and washed with saturated aqueous solutions of $KH_2PO_4$ and $NaHCO_3$, followed by brine. The organic layer was concentrated in vacuo and the residue purified by reverse phase HPLC (acetonitrile-$H_2O$ with 0.1% TFA as eluent) to give 23 mg of the title compound (20% yield) as white solid. $^1$H NMR (400 MHz, d6-DMSO) δ 2.10-2.38 (two sets of m, 2H), 3.50-4.60 (br, 4H), 4.65 (m, 1H), 7.29 (d, J=4.4 Hz, 1H), 7.46 (t, J=7.3 Hz, 1H), 7.59 (t, J=7.3 Hz, 2H), 7.75 (d, J=4.7 Hz, 1H), 7.90 (d, J=8.0 Hz, 2H), 9.00 (d, J=7.0H, 1H), 9.20 (s, 1H), 9.40 (s, 1H). MS: (ES) m/z calculated for $C_{18}H_{17}N_9O$ [M+H]$^+$ 376.2, found 376.2.

Example 101: Synthesis of (S)—N-(1-([1,2,4]triazolo[4,3-a]pyrazin-8-yl)pyrrolidin-3-yl)-1-(4-fluorophenyl)-1H-1,2,4-triazole-3-carboxamide

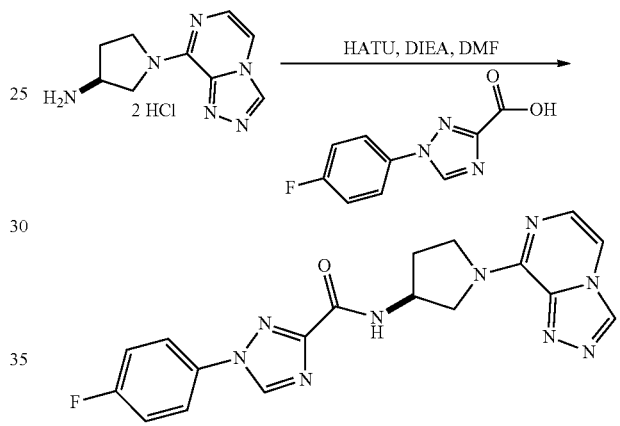

To a suspension of(S)-1-([1,2,4]triazolo[4,3-a]pyrazin-8-yl)pyrrolidin-3-amine hydrochloride salt (63 mg, 0.23 mmol), 1-(4-fluorophenyl)-1H-1,2,4-triazole-3-carboxylic acid (42 mg, 0.2 mmol) in DMF (5 mL) was added diethylisopropyl amine (650 mg, 5 mmol), followed by HATU (76 mg, 0.2 mmol). The resulting solution was stirred at room temperature for 1 h. The reaction mixture was diluted with ethyl acetate and washed with saturated aqueous solutions of $KH_2PO_4$ and $NaHCO_3$, followed by brine. The organic layer was concentrated in vacuo and the residue purified by reverse phase HPLC (acetonitrile-$H_2O$ with 0.1% TFA as eluent) to give 32 mg of the title compound (40% yield) as white solid. MS: (ES) m/z found 394.2.

Example 102: Synthesis of (S)—N-(1-([1,2,4]triazolo[4,3-a]pyrazin-8-yl)pyrrolidin-3-yl)-1-(4-fluorophenyl)-1H-pyrazole-3-carboxamide

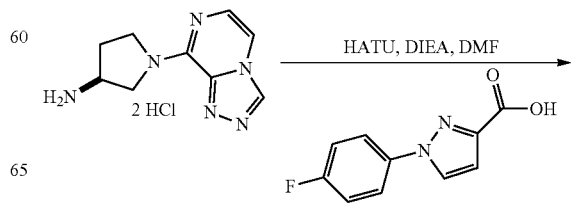

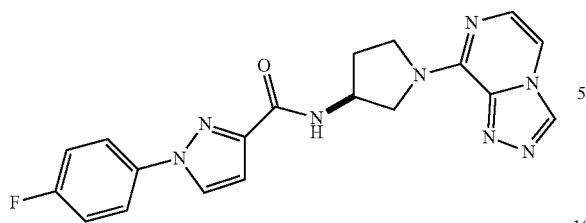

To a suspension of (S)-1-([1,2,4]triazolo[4,3-a]pyrazin-8-yl)pyrrolidin-3-amine hydrochloride salt (94 mg, 0.34 mmol), 1-(4-fluorophenyl)-1H-pyrazole-3-carboxylic acid (63 mg, 0.3 mmol) in DMF (5 mL) was added diethylisopropyl amine (650 mg, 5 mmol), followed by HATU (120 mg, 0.31 mmol). The resulting solution was stirred at room temperature for 1 h. The reaction mixture was diluted with ethyl acetate and washed with saturated aqueous solutions of KH$_2$PO$_4$ and NaHCO$_3$, followed by brine. The organic layer was concentrated in vacuo and the residue purified by reverse phase HPLC (acetonitrile-H$_2$O with 0.1% TFA as eluent) to give 50 mg of the title compound (42% yield) as a white solid. MS: (ES) m/z found 393.2.

Example 103: Synthesis of (S)—N-(1-([1,2,4]triazolo[4,3-a]pyrazin-8-yl)pyrrolidin-3-yl)-1-phenyl-1H-imidazole-4-carboxamide

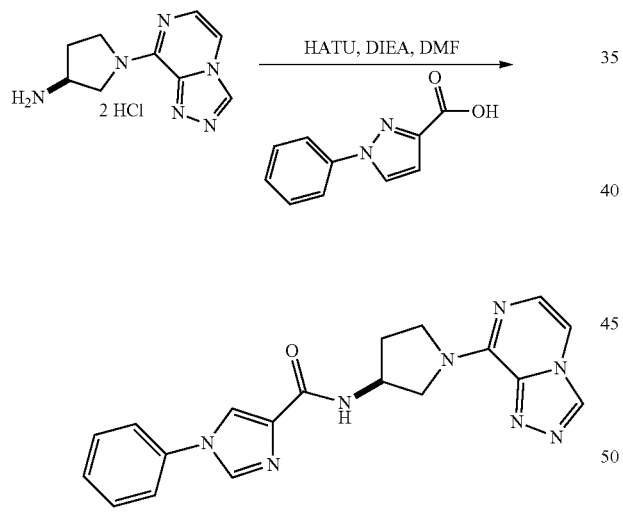

To a suspension of (S)-1-([1,2,4]triazolo[4,3-a]pyrazin-8-yl)pyrrolidin-3-amine hydrochloride salt (109 mg, 0.4 mmol) and 1-phenyl-1H-imidazole-4-carboxylic acid (76 mg, 04 mmol) in DMF (5 mL) was added diethylisopropyl amine (650 mg, 5 mmol), followed by HATU (160 mg, 0.41 mmol). The resulting solution was stirred at room temperature for 1 h. The reaction mixture was diluted with ethyl acetate and washed with saturated aqueous solutions of KH$_2$PO$_4$ and NaHCO$_3$, followed by brine. The organic layer was concentrated in vacuo and the residue purified by reverse phase HPLC (acetonitrile-H$_2$O with 0.1% TFA as eluent) to give 100 mg of the title compound (67% yield) as a white solid. MS: (ES) m/z found 375.1.

Example 104: Synthesis of (S)—N-(1-([1,2,4]triazolo[4,3-a]pyrazin-8-yl)pyrrolidin-3-yl)-5-isopropylpyrimidine-2-carboxamide

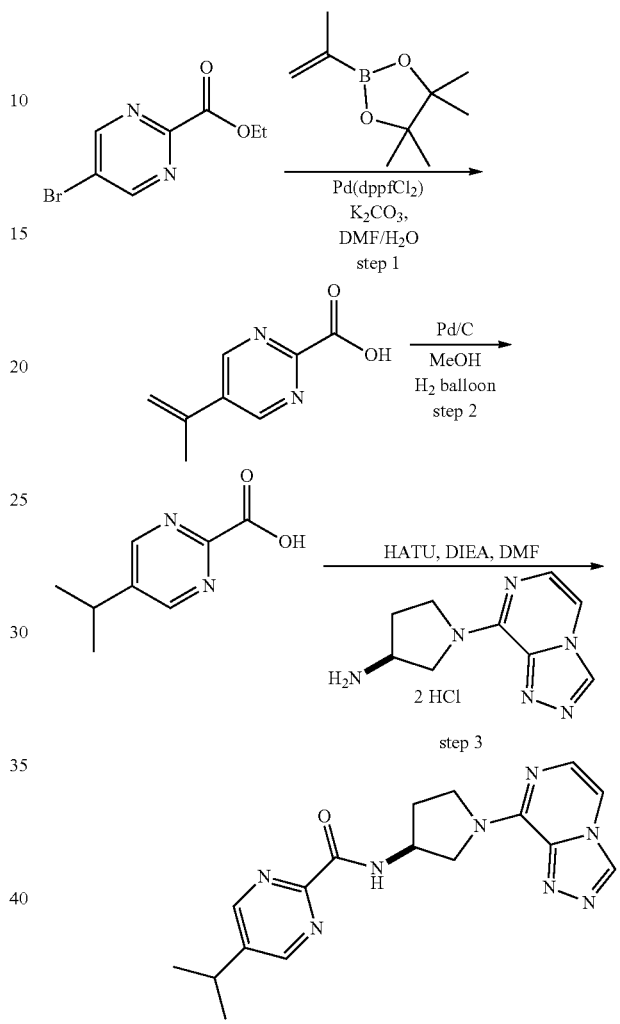

a) To a suspension of the ethyl 5-bromopyrimidine-2-carboxylate (700 mg, 3 mmol), 4,4,5,5-tetramethyl-2-(prop-1-en-2-yl)-1,3,2-dioxaborolane (1.5 g, 9 mmol), and K$_2$CO$_3$ (2.1 g, 15 mmol) in DMF (5 mL) and water (1 mL), was added Pd(dppfCl2) (250 mg, 0.3 mmol). The resulting mixture was degassed (N$_2$) for 2 min and then heated to heated to 120° C. for 1 h. After cooling to room temperature, the reaction mixture was diluted with MeOH and filtered through celite. The filtrate was used directly for next step. MS: (ES) m/z 165.2 (M+H$^+$).

b) To the above filtrate was added 10% Pd/C (wet, 300 mg) and the mixture stirred under a H$_2$-balloon overnight. Solid was filtered off. The filtrate was diluted with CH$_2$Cl$_2$ and washed with 1N HCl and brine. The organic layer was concentrated in vacuo to give 300 mg of the title compound (60% yield) as light brown solid. MS: (ES) m/z 167.2 (M+H$^+$).

c) To a suspension of =(S)-1-([1,2,4]triazolo[4,3-a]pyrazin-8-yl)pyrrolidin-3-amine hydrochloride salt (84 mg, 0.3 mmol), 5-isopropylpyrimidine-2-carboxylic acid (51 mg, 0.3 mmol) in DMF (5 mL) was added diethylisopropyl amine (650 mg, 5 mmol), followed by HATU (120 mg, 0.31 mmol). The resulting solution was stirred at room temperature for 1 h. The reaction mixture was diluted with ethyl acetate and washed with saturated aqueous solutions of $KH_2PO_4$ and $NaHCO_3$, followed by brine. The organic layer was concentrated in vacuo and the residue purified by reverse phase HPLC (acetonitrile-$H_2O$ with 0.1% TFA as eluent) to give 6 mg of the title compound (5% yield) as a white solid. MS: (ES) m/z found 353.1.

Example 105: Synthesis of (S)—N-(1-(imidazo[1,2-a]pyrazin-8-yl)pyrrolidin-3-yl)-5-isopropylpyrimidine-2-carboxamide

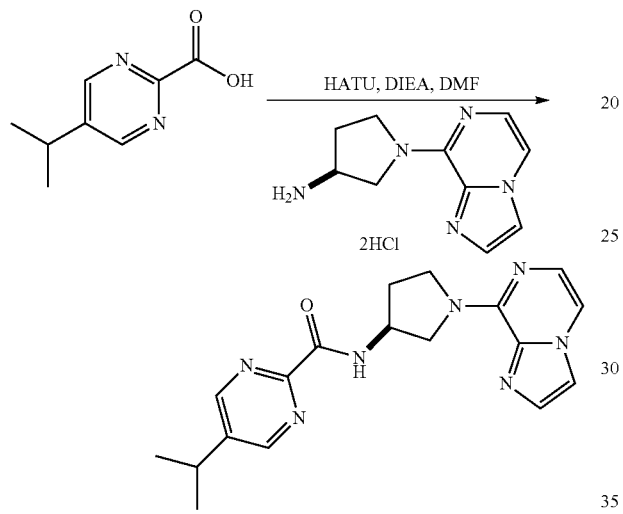

To a suspension of (S)-1-(imidazo[1,2-a]pyrazin-8-yl)pyrrolidin-3-amine hydrochloride salt (84 mg, 0.3 mmol) and 5-isopropylpyrimidine-2-carboxylic acid (85 mg, 0.5 mmol) in DMF (5 mL) was added diethylisopropyl amine (650 mg, 5 mmol), followed by HATU (190 mg, 0.5 mmol). The resulting solution was stirred at room temperature for 1 h. The reaction mixture was diluted with ethyl acetate and washed with saturated aqueous solutions of $KH_2PO_4$ and $NaHCO_3$, followed by brine. The organic layer was concentrated in vacuo and the residue purified by reverse phase HPLC (acetonitrile-$H_2O$ with 0.1% TFA as eluent) to give 35 mg of the title compound (32% yield) as a white solid. MS: (ES) m/z found 352.1.

Example 106: Synthesis of (±)-N-(3-(hydroxymethyl)-1-(pyrrolo[1,2-a]pyrazin-1-yl)pyrrolidin-3-yl)-5-isopropylpyrimidine-2-carboxamide

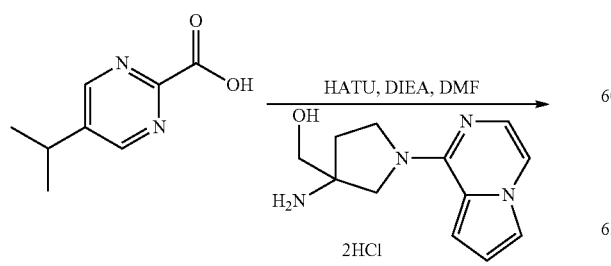

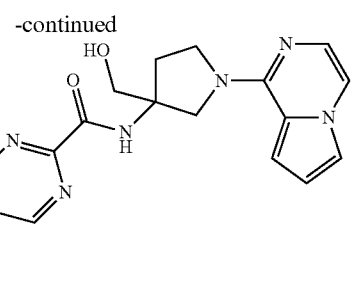

To a suspension of (±)-(3-amino-1-(pyrrolo[1,2-a]pyrazin-1-yl)pyrrolidin-3-yl)methanol hydrochloride salt (62 mg, 0.2 mmol) and 5-isopropylpyrimidine-2-carboxylic acid (40 mg, 0.22 mmol) in DMF (5 mL) was added diethylisopropyl amine (650 mg, 5 mmol), followed by HATU (76 mg, 0.2 mmol). The resulting solution was stirred at room temperature for 1 h. The reaction mixture was diluted with ethyl acetate and washed with saturated aqueous solutions of $KH_2PO_4$ and $NaHCO_3$, followed by brine. The organic layer was concentrated in vacuo and the residue purified by reverse phase HPLC (acetonitrile-$H_2O$ with 0.1% TFA as eluent) to give 25 mg of the title compound (32% yield) as a white solid. MS: (ES) m/z found 381.1.

Example 107: Synthesis of (S)—N-(1-([1,2,4]triazolo[1,5-a]pyrazin-8-yl)pyrrolidin-3-yl)-1-(4-fluorophenyl)-1H-pyrazole-3-carboxamide

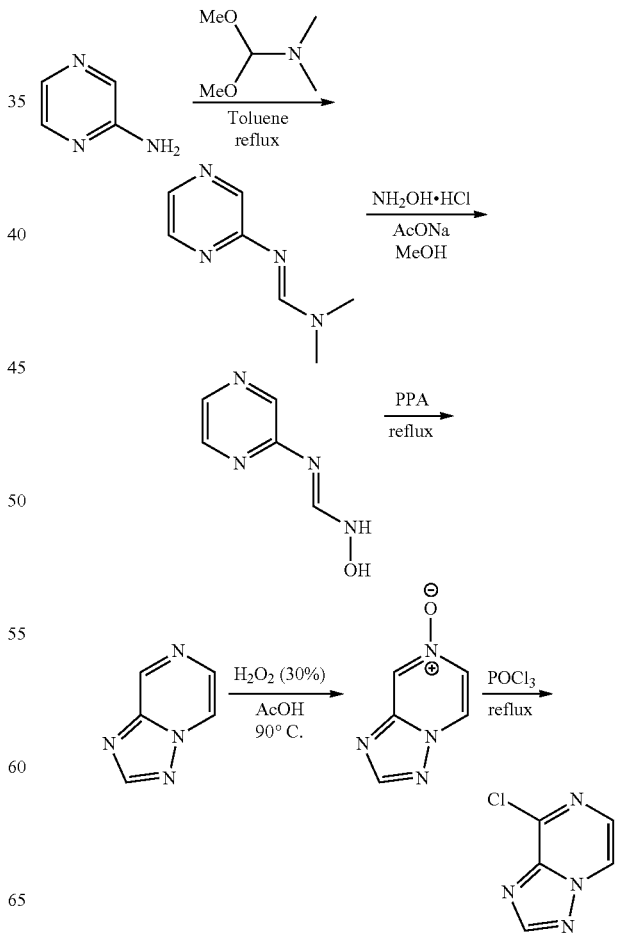

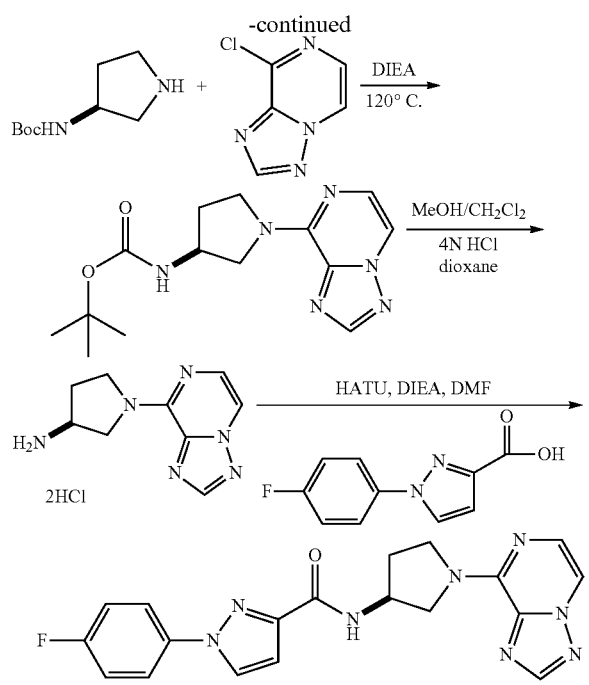

a) A mixture of 2-aminopyrazine (1.9 g, 20 mmol) and N,N-dimethylformamide dimethyl acetal (2.62 g, 22 mmol) in toluene was heated to reflux for 6 h. The solvent was evaporated and residue was used directly for the next step.

b) To a solution of the above in MeOH (30 mL) cooled in an ice-bath, was added NaOAc trihydrate (3.65 g, 25 mmol) followed by slowly addition of $NH_2OH \cdot HCl$ (1.74 g, 25 mmol). The mixture was allowed slowly warm up to room temperature over 6 h and was then diluted with DCM and with 20% 7 N ammonia solution in MeOH. Solid was filtered off and the filtrate was concentrated in vacuo and the residue was triturated with EtOH. Filtration and air-drying gave the desired compound as an off-white solid (1.9 g, 69% yield, which was used directly for the next step). MS: (ES) m/z 139.1 (M+H+).

c) A mixture of the above solid (1.9 g, 13.8 mmol) and PPA (15 mL) was heated to 90° C. for 6 h and was then diluted with ice-water and the pH was adjusted to 8 with aqueous ammonia solution and $NaHCO_3$. The mixture was then extracted with 10% MeOH in $CH_2Cl_2$. The organic layer was dried ($Na_2SO_4$), filtered and concentrated in vacuo to give the desired compound as off-white solid (1.2 g, 75% yield, which was used directly for the next step). MS: (ES) m/z 121.1 (M+H+).

d) To a mixture of the above solid (600 mg, 5 mmol) in AcOH was added slowly a 30% aqueous $H_2O_2$ solution (1.8 mL, 19 mmol) at room temperature. The resulting mixture was heated to 90° C. for 6 h and then was poured into ice-water and the pH was adjusted to 8 with 1 N NaOH. The mixture was extracted with 10% MeOH in $CH_2Cl_2$. The organic layer was dried ($Na_2SO_4$), filtered and concentrated in vacuo to give the desired compound as a foam (120 mg, 17% yield, which was used directly for the next step). MS: (ES) m/z 137.2.1 (M+H+).

e) A mixture of the above foam (120 mg, 0.9 mmol) and $POCl_3$ (5 mL) was heated to 120° C. for 6 h and then concentrated in vacuo. The residue was diluted with EtOAc and washed with saturated aqueous $NaHCO_3$. The organic layer was dried ($Na_2SO_4$), filtered and concentrated in vacuo to give the desired compound as tan solid (50 mg, 36% yield, which was used directly for the next step). MS: (ES) m/z 155.0 (M+H+).

f) A mixture of the above 8-chloro-[1,2,4]triazolo[1,5-a]pyrazine (50 mg, 0.32 mmol) and (S)-tert-butyl pyrrolidin-3-yl carbamate (100 mg, 0.53 mmol) in diethylisopropyl amine (2 mL) was heated to 120° C. for 2 h. After cooling to room temperature, the mixture was diluted with 10% MeOH in EtOAc and washed with saturated aqueous solutions of $KH_2PO_4$ and $NaHCO_3$, followed by brine. The organic layer was concentrated in vacuo and the residue purified by flash chromatography ($SiO_2$, 2 to 5% MeOH in $CH_2Cl_2$ as eluent) to give the desired compound as a foam (80 mg, 82% yield, which was used directly for the next step). MS: (ES) m/z 305.2 (M+H+).

g) The above Boc-amine was dissolved in $CH_2Cl_2$ (3 mL) and MeOH (1 mL) at room temperature, followed by addition of 4 N HCl in dioxane (4 mL, 16 mmol). The mixture was stirred at room temperature for 2 h and then was concentrated in vacuo to give the desired compound as a light yellow solid (72 mg, quantitative, which was used directly for the next step). MS: (ES) m/z 205.1 (M+H+).

h) To a suspension of the above amine hydrochloride salt (60 mg, 0.22 mmol) and 1-(4-fluorophenyl)-1H-pyrazole-3-carboxylic acid (46 mg, 0.22 mmol) in DMF (5 mL) was added diethylisopropyl amine (650 mg, 5 mmol), followed by HATU (86 mg, 0.22 mmol). The resulting solution was stirred at room temperature for 1 h. The reaction mixture was diluted with ethyl acetate and washed with saturated aqueous solutions of $KH_2PO_4$ and $NaHCO_3$, followed by brine. The organic layer was concentrated in vacuo and the residue purified by silica gel flash chromatography (2 to 5% MeOH in $CH_2Cl_2$ as eluent) followed by reverse phase HPLC (acetonitrile-$H_2O$ with 0.1% TFA as eluent) to give 28 mg of the title compound (32% yield) as a white solid. $^1$H NMR (400 MHz, d6-DMSO) δ 2.05-2.38 (two sets of m, 2H), 3.60-4.58 (br, 4H), 4.63 (m, 1H), 6.89 (d, J=2.2 Hz, 1H), 7.36 (t, J=6.6 Hz, 2H), 7.29 (d, J=4.4 Hz, 1H), 7.46 (t, J=7.3 Hz, 1H), 7.57 (d, J=4.4 Hz, 1H), 7.97-7.92 (m, 2H) (check F-coupling), 8.13 (d, J=4.4 Hz, 1H), 8.46 (s, 1H), 8.52 (d, J=2.6 Hz, 1H), δ 8.55 (d, J=7.0 Hz, 1H). MS: (ES) m/z calculated for $C_{19}H_{17}FN_8O$ [M+H]+ 393.2, found 393.

Example 108: Synthesis of (S)—N-(1-(imidazo[1,2-a]pyrazin-8-yl)pyrrolidin-3-yl)-1-phenyl-1H-1,2,4-triazole-3-carboxamide

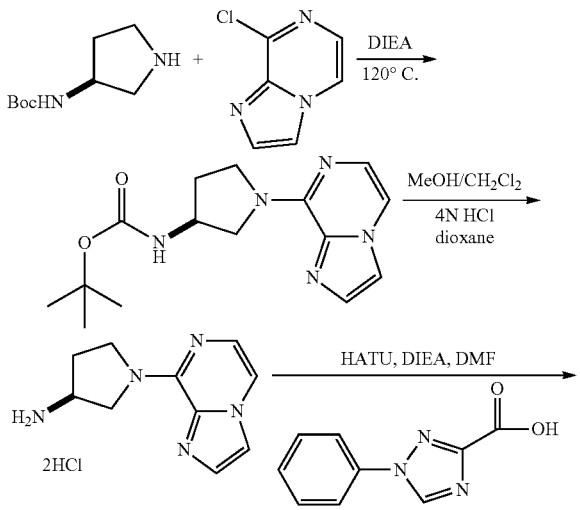

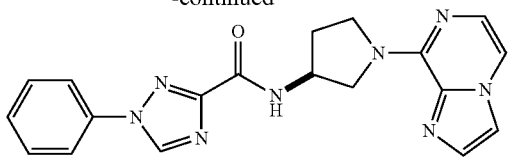

a) A mixture of 8-chloroimidazo[1,2-a]pyrazine (500 mg, 3.25 mmol) and (S)-tert-butyl pyrrolidin-3-yl carbamate (1.0 g, 5.38 mmol) in diethylisopropyl amine (3 mL) was heated to 120° C. for 3 h. After cooling to room temperature, the mixture was diluted with 10% MeOH in EtOAc and washed with saturated aqueous solutions of $KH_2PO_4$ and $NaHCO_3$, followed by brine. The organic layer was concentrated in vacuo and the residue purified by flash chromatography ($SiO_2$, 2 to 5% MeOH in $CH_2Cl_2$ as eluent) to give the desired compound as a foam (985 mg, quantitative, which was used directly for the next step). MS: (ES) m/z 304.1 $(M+H^+)$.

b) The above Boc-amine was dissolved in $CH_2C_2$ (5 mL) and MeOH (3 mL) at room temperature, followed by addition of 4 N HCl in dioxane (9 mL, 16 mmol). The mixture was stirred at room temperature for 2 h. The resulting suspension was diluted with EtOAc. Filtration and air-drying gave the desired compound as an off-white solid (895 mg, quantitative, which was used directly for the next step). MS: (ES) m/z 204.1 $(M+H^+)$.

c) To a suspension of the above (S)-1-(imidazo[1,2-a]pyrazin-8-yl)pyrrolidin-3-amine hydrochloride salt (84 mg, 0.3 mmol) and 1-phenyl-1H-1,2,4-triazole-3-carboxylic acid (57 mg, 0.3 mmol) in DMF (5 mL) was added diethylisopropyl amine (650 mg, 5 mmol), followed by HATU (120 mg, 0.31 mmol). The resulting solution was stirred at room temperature for 1 h. The reaction mixture was diluted with ethyl acetate and washed with saturated aqueous solutions of $KH_2PO_4$ and $NaHCO_3$, followed by brine. The organic layer was concentrated in vacuo and the residue purified by silica gel flash chromatography (2 to 5% MeOH in $CH_2Cl_2$ as eluent) followed by reverse phase HPLC (acetonitrile-$H_2O$ with 0.1% TFA as eluent) to give 60 mg of the title compound (54% yield) as white solid. MS: (ES) m/z calculated for $C_{19}H_{18}N_8O$ $[M+H]^+$ 375.2, found 375.2.

Example 109: Synthesis of (S)-1-(4-fluorophenyl)-N-(1-(imidazo[1,2-a]pyrazin-8-yl)pyrrolidin-3-yl)-1H-1,2,4-triazole-3-carboxamide

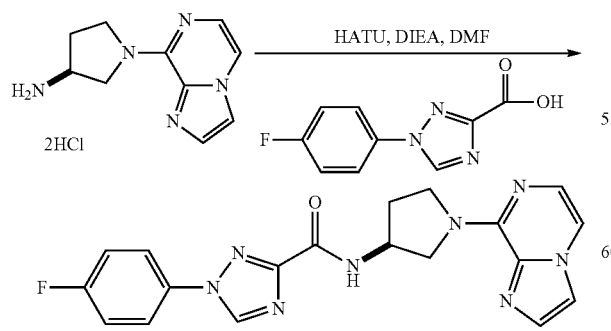

To a suspension of (S)-1-(imidazo[1,2-a]pyrazin-8-yl)pyrrolidin-3-amine hydrochloride salt (55 mg, 0.2 mmol) and 1-(4-fluorophenyl)-1H-1,2,4-triazole-3-carboxylic acid (42 mg, 0.2 mmol) in DMF (5 mL) was added diethylisopropyl amine (650 mg, 5 mmol), followed by HATU (76 mg, 0.2 mmol). The resulting solution was stirred at room temperature for 1 h. The reaction mixture was diluted with ethyl acetate and washed with saturated aqueous solutions of $KH_2PO_4$ and $NaHCO_3$, followed by brine. The organic layer was concentrated in vacuo and the residue purified by reverse phase HPLC (acetonitrile-$H_2O$ with 0.1% TFA as eluent) to give 45 mg of the title compound (57% yield) as white solid. MS: (ES) m/z found 393.1.

Example 110: Synthesis of (S)-1-(3-fluorophenyl)-N-(1-(imidazo[1,2-a]pyrazin-8-yl)pyrrolidin-3-yl)-1H-1,2,4-triazole-3-carboxamide

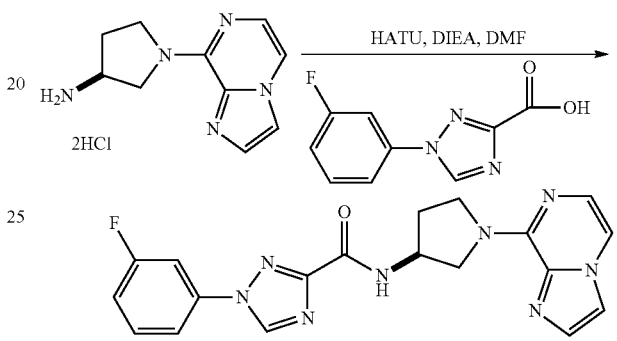

To a suspension of (S)-1-(imidazo[1,2-a]pyrazin-8-yl)pyrrolidin-3-amine hydrochloride salt (84 mg, 0.3 mmol) and 1-(3-fluorophenyl)-1H-1,2,4-triazole-3-carboxylic acid (63 mg, 0.3 mmol) in DMF (5 mL) was added diethylisopropyl amine (650 mg, 5 mmol), followed by HATU (120 mg, 0.31 mmol). The resulting solution was stirred at room temperature for 1 h. The reaction mixture was diluted with ethyl acetate and washed with saturated aqueous solutions of $KH_2PO_4$ and $NaHCO_3$, followed by brine. The organic layer was concentrated in vacuo and the residue purified by reverse phase HPLC (acetonitrile-$H_2O$ with 0.1% TFA as eluent) to give 88 mg of the title compound (75% yield) as a white solid. MS: (ES) m/z found 393.1.

Example 111: Synthesis of (S)—N-(1-(imidazo[1,2-a]pyrazin-8-yl)pyrrolidin-3-yl)-5-phenyl-1,2,4-oxadiazole-3-carboxamide

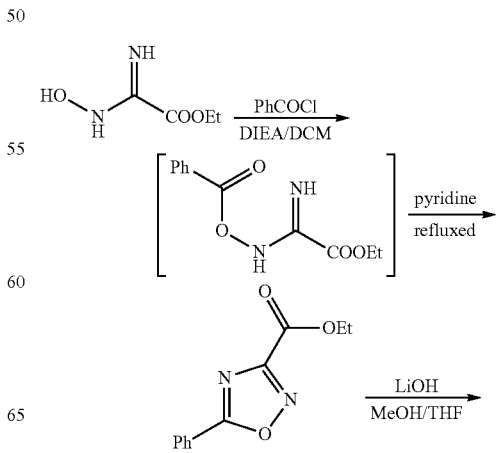

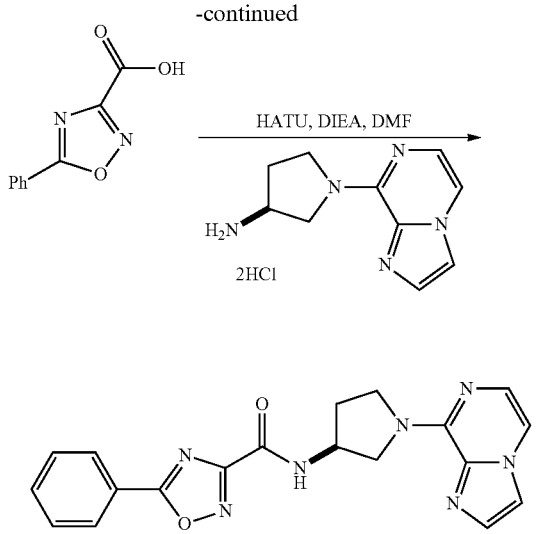

a) To a mixture of ethyl 2-oximinoxamate (1.32 g, 10 mmol) and diethylisopropyl amine (4 mL, 23 mmol) in CH$_2$Cl$_2$ (30 mL) at −15° C. was added slowly benzoyl chloride (1.41 g, 10 mmol), over 2 h. The mixture was allowed slowly warm up to room temperature over 5 h and then poured into ice-water and extracted with CH$_2$Cl$_2$. The organic layer was dried (Na$_2$SO$_4$), filtered and was concentrated to give the desired compound as a white solid (2.36 g, quantitative, which was used directly for the next step).

b) A mixture of the above solid (1.2 g, 5 mmol) and pyridine (6 mL) was heated to at 120° C. for 10 h. After evaporation of the solvent, the residue was purified by silica gel flash chromatography (10 to 25% EtOAc in hexane as eluent) to give the desired compound as an off-white solid (900 mg, 83% yield, which was used directly for the next step). MS: (ES) m/z 219.1 (M+H$^+$).

c) To a mixture of the above ester (900 mg, 4.1 mmol), MeOH (5 mL), THF (5 mL) and DI H$_2$O (5 mL) was added LiOH monohydrate (420 mg, 10 mmol). The resulting mixture was stirred at room temperature for 3 h. The mixture was then diluted with ice-water, pH adjusted to 3 with 1 N HCl, and mixture was then extracted with 10% MeOH in CH$_2$Cl$_2$. The organic layer was dried (Na$_2$SO$_4$), filtered and concentrated in vacuo give the desired compound as an off-white solid (900 mg, 83% yield, which was used directly for the next step). MS: (ES) m/z 219.1 (M+H$^+$).

d) To a suspension of the above 5-phenyl-1,2,4-oxadiazole-3-carboxylic acid (58 mg, 0.3 mmol), (S)-1-([1,2,4]triazolo[1,5-a]pyrazin-5-yl)pyrrolidin-3-amine hydrochloride salt (90 mg, 0.32 mmol) in DMF (5 mL) was added diethylisopropyl amine (650 mg, 5 mmol), followed by HATU (120 mg, 0.31 mmol). The resulting solution was stirred at room temperature for 1 h. The reaction mixture was then diluted with ethyl acetate and washed with saturated aqueous solutions of KH$_2$PO$_4$ and NaHCO$_3$, followed by brine. The organic layer was concentrated in vacuo and the residue was purified by reverse phase HPLC (acetonitrile-H$_2$O with 0.1% TFA as eluent) to give 26 mg of the title compound (23% yield) as a white solid. MS: (ES) m/z found 376.2.

Example 112: Synthesis of (S)-1-(4-chlorophenyl)-N-(1-(pyrrolo[1,2-a]pyrazin-1-yl)pyrrolidin-3-yl)-1H-1,2,4-triazole-3-carboxamide

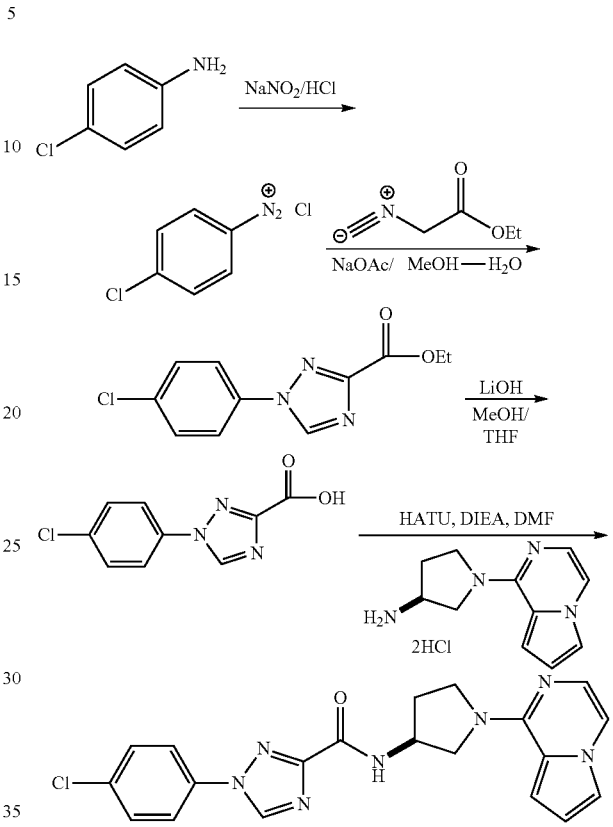

a) To a mixture of 4-chloroaniline (2.56 g, 20 mmol) and con HCl (15 mL) in H$_2$O (30 mL) at −5° C. was added dropwisely a solution of NaNO$_2$ (1.38 g, 20 mmol) in H$_2$O (5 mL) which was then stirred at 0° C. for 10 min to form the diazonium salt.

b) The above mixture was added slowly to a solution of ethyl isocyanoacetate (2.26 g, 20 mmol) in MeOH (100 mL) and H$_2$O (10 mL) under ice-bath. The mixture was allowed to slowly warm up to room temperature over 5 h and solvent was evaporated. The residue was diluted with 10% MeOH in CH$_2$Cl$_2$ and washed with saturated aqueous solution of NaHCO$_3$, followed by brine. The organic layer was dried (Na$_2$SO$_4$), filtered and was concentrated under reduced pressure to give the desired compound as a yellow solid (1.5 g, 29% yield, which was used directly for the next step). MS: (ES) m/z 252.2 (M+H$^+$).

c) To a mixture of the above ester (1.5 g, 6 mmol), MeOH (30 mL), THF (50 mL) and DI H$_2$O (15 mL) was added LiOH monohydrate (2.5 g, 60 mmol). The resulting mixture was stirred at room temperature for 3 h. The mixture was diluted with ice-water, pH was adjusted to 3 with 1 N HCl, and the mixture was then extracted with 15% iPrOH in CH$_2$Cl$_2$. The organic layer was dried (Na$_2$SO$_4$), filtered and concentrated in vacuo to give the desired compound as an off-white solid (900 mg, 83% yield, which was used directly for the next step). MS: (ES) m/z 219.1 (M+H$^+$).

d) To a suspension of the above 5-phenyl-1,2,4-oxadiazole-3-carboxylic acid (58 mg, 0.3 mmol), (S)-1-([1,2,4]triazolo[1,5-a]pyrazin-5-yl)pyrrolidin-3-amine hydrochloride salt (90 mg, 0.32 mmol) in DMF (5 mL) was added diethylisopropyl amine (650 mg, 5 mmol), followed by HATU (120 mg, 0.31 mmol). The resulting solution was stirred at room temperature for 1 h. The reaction mixture was diluted with ethyl acetate and washed with saturated aqueous solutions of $KH_2PO_4$ and $NaHCO_3$, followed by brine. The organic layer was concentrated in vacuo and the residue purified by reverse phase HPLC (acetonitrile-$H_2O$ with 0.1% TFA as eluent) to give 26 mg of the title compound (23% yield) as white solid. MS: (ES) m/z found 376.2.

Example 113: Synthesis of (S)-5-phenyl-N-(1-(pyrrolo[1,2-a]pyrazin-1-yl)pyrrolidin-3-yl)-1,2,4-oxadiazole-3-carboxamide

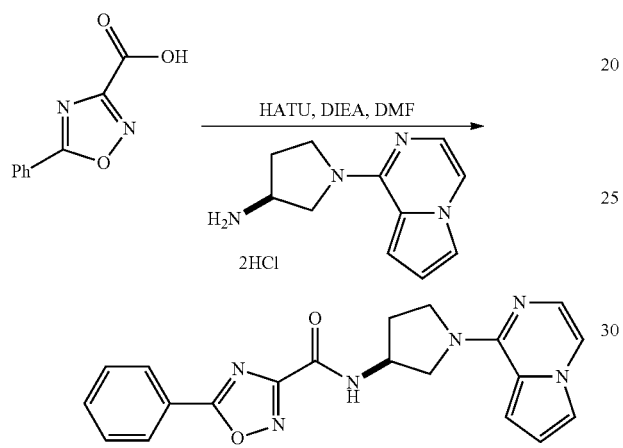

To a suspension of (S)-1-(pyrrolo[1,2-a]pyrazin-1-yl)pyrrolidin-3-amine hydrochloride salt (90 mg, 0.32 mmol) and 5-phenyl-1,2,4-oxadiazole-3-carboxylic acid (58 mg, 0.3 mmol) in DMF (5 mL) was added diethylisopropyl amine (650 mg, 5 mmol), followed by HATU (120 mg, 0.31 mmol). The resulting solution was stirred at room temperature for 1 h. The reaction mixture was diluted with ethyl acetate and washed with saturated aqueous solutions of $KH_2PO_4$ and $NaHCO_3$, followed by brine. The organic layer was concentrated in vacuo and the residue was purified by silica gel flash chromatography (2 to 5% MeOH in $CH_2Cl_2$ as eluent) followed by reverse phase HPLC (acetonitrile-$H_2O$ with 0.1% TFA as eluent) to give 15 mg of the title compound (18% yield) as white solid. MS: (ES) m/z found 374.1.

Example 114: Synthesis of (S)-1-phenyl-N-(1-(pyrrolo[1,2-a]pyrazin-1-yl)pyrrolidin-3-yl)-1H-1,2,4-triazole-3-carboxamide

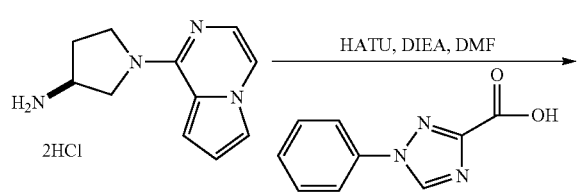

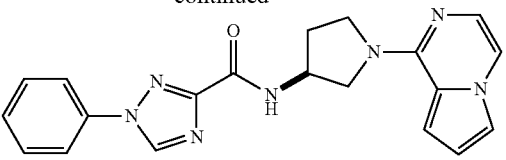

To a suspension of(S)-1-(pyrrolo[1,2-a]pyrazin-1-yl)pyrrolidin-3-amine hydrochloride salt (60 mg, 0.21 mmol) and 1-phenyl-1H-1,2,4-triazole-3-carboxylic acid (40 mg, 0.21 mmol) in DMF (5 mL) was added diethylisopropyl amine (650 mg, 5 mmol), followed by HATU (80 mg, 0.21 mmol). The resulting solution was stirred at room temperature for 1 h. The reaction mixture was then diluted with ethyl acetate and washed with saturated aqueous solutions of $KH_2PO_4$ and $NaHCO_3$, followed by brine. The organic layer was concentrated in vacuo and the residue purified by reverse phase HPLC (acetonitrile-$H_2O$ with 0.1% TFA as eluent) to give 15 mg of the title compound (18% yield) as white solid. MS: (ES) m/z found 374.1

Example 115: Synthesis of 1-(4-fluoro-phenyl)-1H-pyrazole-3-carboxylic acid (1-pyrrolo 1,2-al pyrazin-1-yl-pyrrolidin-3-yl)-amide

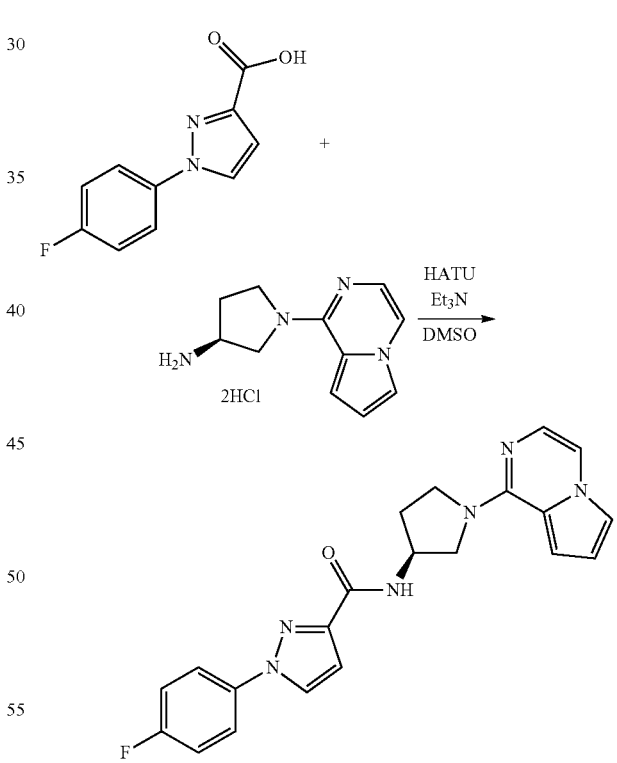

DMSO (0.5 mL) was added to a mixture of 1-(4-fluoro-phenyl)-1H-pyrazole-3-carboxylic acid (41 mg, 0.20 mmol) and 1-pyrrolo[1,2-a]pyrazin-1-yl-pyrrolidin-3-ylamine dihydrochloride salt (55 mg, 0.20 mmol). To this was added triethylamine (0.112 mL, 0.80 mmol) followed by HATU (84 mg, 0.22 mmol). The mixture was allowed to stir for 30 min, diluted with dichloromethane (1.0 mL), then washed with water (3×1.0 mL), dried over sodium sulfate, filtered and concentrated. The crude material was purified by reverse phase HPLC (10:90-95:5 MeCN/H$_2$O+0.1% TFA). The combined product fractions were lyophilized to give the TFA salt of the product as a white solid (9.5 mg, 0.02 mmol, 9% yield). $^1$H NMR (400 MHz, CD3OD) δ 8.26 (s, 1H), 7.87 (dd, J=4.8, 9.2 Hz, 2H), 7.77 (d, J=2.6 Hz, 1H), 7.71 (d, J=5.5 Hz, 1H), 7.56 (d, J=4.4 Hz, 1H), 7.25 (t, J=9.2 Hz, 2H), 6.95 (d, J=2.5 Hz, 1H), 6.92 (dd, J=2.6, 4.4 Hz, 1H), 6.84 (d, J=5.5 Hz, 1H), 4.95-3.65 (br, 5H), 2.58-2.30 (m, 2H); MS: (ES) m/z calculated for C$_{21}$H$_{19}$FN$_6$O [M+H]$^+$ 391.2, found 391.

Example 116: Synthesis of 2-phenyl-oxazole-4-carboxylic acid

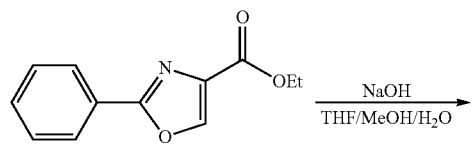

2-Phenyl-oxazole-4-carboxylic acid ethyl ester (500 mg, 2.30 mmol) was dissolved in a mixture of THF (2.3 mL) and MeOH (2.3 mL). To this was added NaOH (10% aqueous, 2.3 mL). The reaction mixture was stirred for 2 h, and was then diluted with EtOAc and washed with 1N HCl The aqueous layer was extracted with EtOAc and the combined organics were dried over Na$_2$SO$_4$, filtered and concentrated to give the product as a white solid (366 mg, 84%).

Example 117: Synthesis of 2-phenyl-oxazole-4-carboxylic acid (1-pyrrolo[1,2-a]pyrazin-1-yl-pyrrolidin-3-yl)-amide

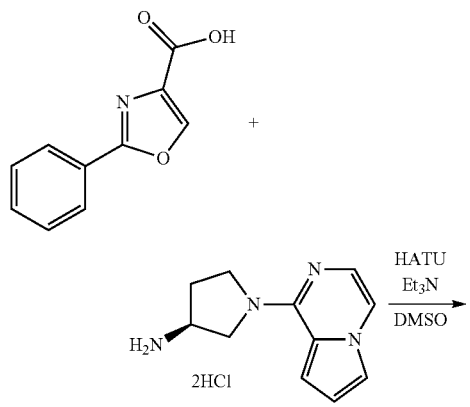

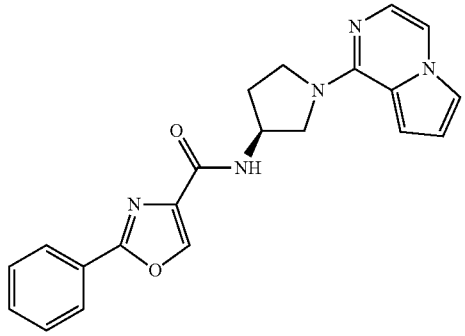

DMSO (0.5 mL) was added to a mixture of 2-phenyl-oxazole-4-carboxylic acid (38 mg, 0.20 mmol) and 1-pyrrolo[1,2-a]pyrazin-1-yl-pyrrolidin-3-ylamine dihydrochloride salt (55 mg, 0.20 mmol). To this was added triethylamine (0.112 mL, 0.80 mmol) followed by HATU (84 mg, 0.22 mmol). The mixture was allowed to stir for 30 min, and was then diluted with dichloromethane (1.0 mL), washed with water (3×1.0 mL), dried over sodium sulfate, filtered and concentrated to give the crude material. The crude material was purified by reverse phase HPLC (10:90-95:5 MeCN/H$_2$O+0.1% TFA). The combined product fractions were lyophilized to give the TFA salt of the product as a white solid (27 mg, 0.06 mmol, 28% yield). $^1$H NMR (400 MHz, CD3OD) δ 8.76 (d, J=6.6 Hz, 1H), 8.49 (s, 1H), 8.10-8.06 (m, 2H), 7.79 (dd, J=1.2, 2.4 Hz, 1H), 7.74 (d, J=5.5 Hz, 1H), 7.59-7.50 (m, 4H), 6.95 (dd, J=2.7, 4.2 Hz, 1H), 6.87 (d, J=5.4 Hz, 1H), 4.95-3.65 (br, 5H), 2.60-2.30 (m, 2H); MS: (ES) m/z calculated for C$_{21}$H$_{19}$N$_5$O$_2$ [M+H]$^+$ 374.2, found 374.

Example 118: Synthesis of 2-phenyl-thiazole-4-carboxylic acid (1-pyrrolo[1,2-a]pyrazin-1-yl-pyrrolidin-3-yl)-amide

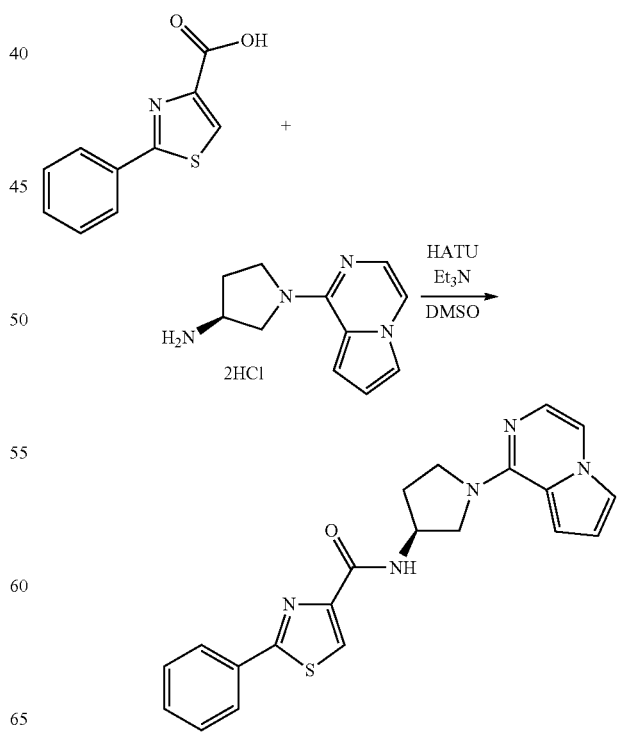

DMSO (0.5 mL) was added to a mixture of 2-phenyl-thiazole-4-carboxylic acid (41 mg, 0.20 mmol) and 1-pyrrolo[1,2-a]pyrazin-1-yl-pyrrolidin-3-ylamine dihydrochloride salt (55 mg, 0.20 mmol). To this mixture was added triethylamine (0.112 mL, 0.80 mmol) followed by HATU (84 mg, 0.22 mmol). The mixture was allowed to stir for 30 min and was then diluted with dichloromethane (1.0 mL) and washed with water (3×1.0 mL). The organics were dried over sodium sulfate, filtered, and concentrated under reduced pressure to give the crude product. The crude product was purified by reverse phase HPLC (10:90-95:5 MeCN/H$_2$O+0.1% TFA). The combined product fractions were lyophilized to give the TFA salt of the product as a white solid (34 mg, 0.07 mmol, 34% yield). $^1$H NMR (400 MHz, CD3OD) δ 8.87 (d, J=6.7 Hz, 1H), 8.26 (s, 1H), 8.07-8.01 (m, 2H), 7.79 (dd, J=1.2, 2.7 Hz, 1H), 7.74 (d, J=5.5 Hz, 1H), 7.59 (d, J=4.3 Hz, 1H), 7.51-7.46 (m, 3H), 6.95 (dd, J=2.3, 4.4 Hz, 1H), 6.87 (d, J=5.5 Hz, 1H), 4.95-3.65 (br, 5H), 2.60-2.38 (m, 2H), MS: (ES) m/z calculated for C$_{21}$H$_{19}$N$_5$OS [M+H]$^+$ 390.2, found 390.

Example 119: Synthesis of 1-o-tolyl-1H-pyrazole-3-carboxylic acid (1-pyrrolo[1,2-a]pyrazin-1-yl-pyrrolidin-3-yl)-amide DMSO (0.4 mL) was added to a mixture of 1-o-tolyl-1H-pyrazole-3-carboxylic acid (15 mg, 0.07 mmol) and 1-pyrrolo[1,2-a]pyrazin-1-yl-pyrrolidin-3-ylamine dihydrochloride salt (19 mg, 0.07 mmol). To this was added triethylamine (0.039 mL, 0.28 mmol) followed by HATU (30 mg, 0.08 mmol). The mixture was allowed to stir for 30 min and was then diluted with dichloromethane (1.0 mL) and washed with water (3×1.0 mL). The organics were dried over sodium sulfate, filtered and concentrated under reduced pressure to give the crude product. The crude material was purified by reverse phase HPLC (10:90-95:5 MeCN/H$_2$O+ 0.1% TFA). The combined product fractions were lyophilized to give the TFA salt of the product as a white solid (12 mg, 0.02 mmol, 34% yield). $^1$H NMR (400 MHz, CD3OD) δ 8.62 (d, J=5.9 Hz, 1H), 7.88 (d, J=2.5 Hz, 1H), 7.75 (s, 1H), 7.70 (d, J=5.9 Hz, 1H), 7.54 (d, J=3.6 Hz, 1H), 7.40-7.25 (m, 4H), 6.94 (d, J=2.2 Hz, 1H), 6.91 (dd, J=2.6, 4.4 Hz, 1H), 6.82 (d, J=5.5 Hz, 1H), 4.95-3.65 (br, 5H), 2.58-2.30 (m, 2H), 2.20 (s, 3H); MS: (ES) m/z calculated for C$_{22}$H$_{22}$N$_6$O[M+H]$^+$ 387.2, found 387.

Example 120: Synthesis of 2-(4-fluoro-phenyl)-thiazole-4-carboxylic acid [1-(8-methyl-pyrrolo[1,2-a]pyrazin-1-yl)-pyrrolidin-3-yl]-amide

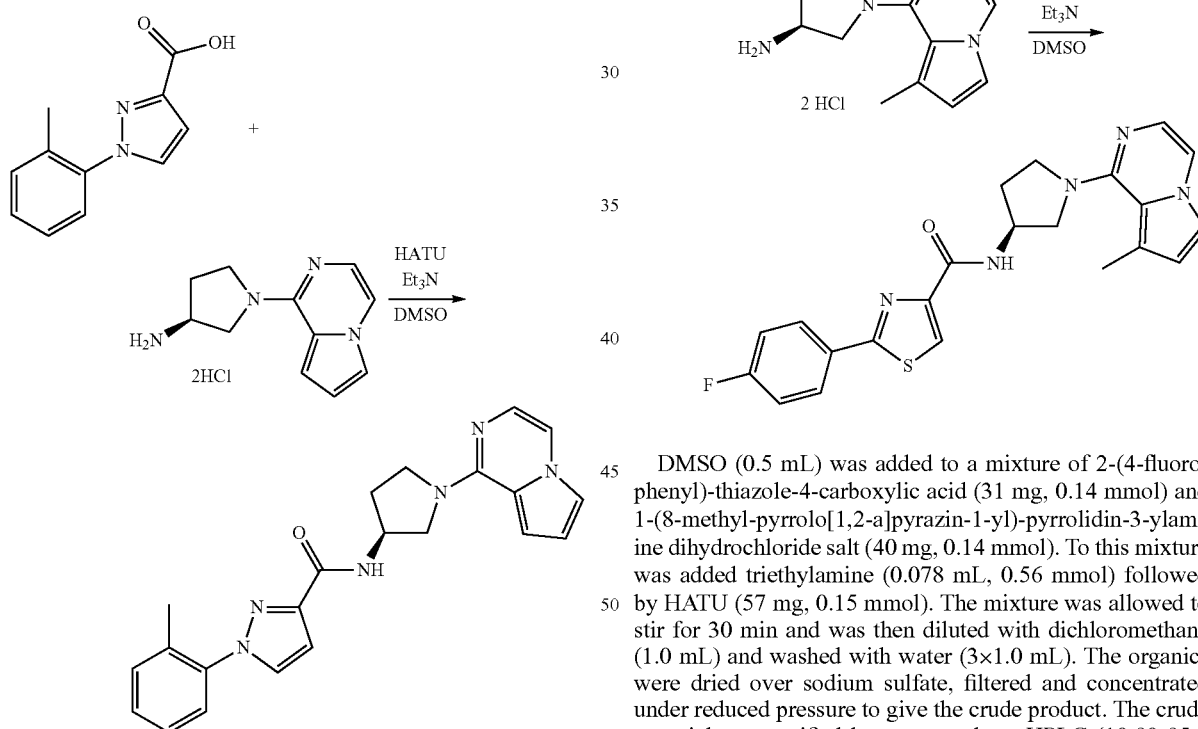

DMSO (0.5 mL) was added to a mixture of 2-(4-fluorophenyl)-thiazole-4-carboxylic acid (31 mg, 0.14 mmol) and 1-(8-methyl-pyrrolo[1,2-a]pyrazin-1-yl)-pyrrolidin-3-ylamine dihydrochloride salt (40 mg, 0.14 mmol). To this mixture was added triethylamine (0.078 mL, 0.56 mmol) followed by HATU (57 mg, 0.15 mmol). The mixture was allowed to stir for 30 min and was then diluted with dichloromethane (1.0 mL) and washed with water (3×1.0 mL). The organics were dried over sodium sulfate, filtered and concentrated under reduced pressure to give the crude product. The crude material was purified by reverse phase HPLC (10:90-95:5 MeCN:H$_2$O+0.1% TFA). The combined fractions were concentrated, taken up in CH$_2$Cl$_2$, washed with NaHCO$_3$, dried over Na$_2$SO$_4$, filtered and concentrated under reduced pressure. The resulting oil was then purified via flash chromatography on silica gel (CH$_2$Cl$_2$:MeOH gradient 99:1 to 90:10). The combined product fractions were concentrated and then lyophilized from a mixture of MeCN and 1M HCl to give the HCl salt of the product as a white solid (32 mg, 0.06 mmol, 43% yield). $^1$H NMR (400 MHz, CD3OD) δ 8.22 (s, 1H), 8.09 (dd, J=5.1, 8.8 Hz, 2H), 7.67 (d, J=5.5 Hz, 2H), 7.24 (t, J=8.8 Hz, 2H), 6.75 (d, J=5.5 Hz, 2H), 4.85-4.75 (m, 1H), 4.30-4.22 (m, 1H), 4.10-3.90 (m, 3H), 2.64 (s, 3H), 2.55-2.35 (m, 2H); MS: (ES) m z calculated for C$_{22}$H$_{20}$FN$_5$OS[M+H]$^+$ 422.2, found 422.

Example 121: Synthesis of 2-(4-fluorophenyl)-thiazole-4-carboxylic acid (1-pyrrolo[1,2-a]pyrazin-1-yl-pyrrolidin-3-yl)-amide

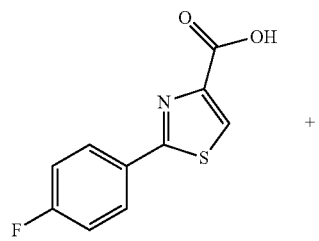

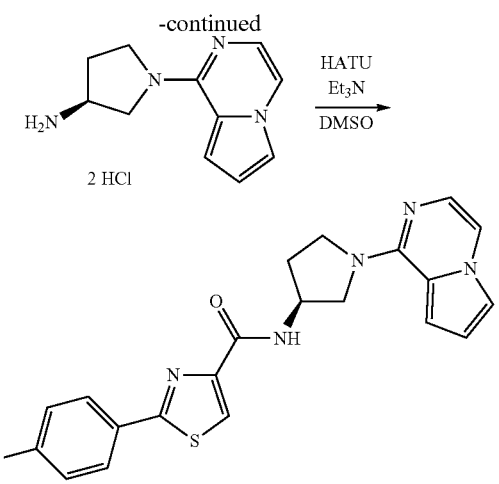

DMSO (0.5 mL) was added to a mixture of 2-(4-fluorophenyl)-thiazole-4-carboxylic acid (56 mg, 0.25 mmol) and 1-pyrrolo[1,2-a]pyrazin-1-yl-pyrrolidin-3-ylamine dihydrochloride salt (70 mg, 0.25 mmol). To this was added triethylamine (0.139 mL, 1.0 mmol) followed by HATU (106 mg, 0.28 mmol). The mixture was allowed to stir for 30 min, diluted with dichloromethane (1.0 mL), then washed with water (3×1.0 mL), dried over sodium sulfate, filtered and concentrated to give the crude product. The crude material was purified by reverse phase HPLC (10:90-95:5 MeCN/H$_2$O+0.1% TFA). The combined product fractions were lyophilized to give the TFA salt of the product as a yellow solid (67 mg, 0.13 mmol, 51% yield). $^1$H NMR (400 MHz, CD3OD) δ 8.85 (d, J=6.6 Hz, 1H), 8.23 (s, 1H), 8.09-8.05 (m, 2H), 7.76 (s, 1H), 7.72 (d, J=5.9 Hz, 1H), 7.56 (s, 1H), 7.23 (t, J=8.8 Hz, 1H), 6.93 (dd, J=2.5, 4.4 Hz, 1H), 6.85 (d, J=5.9 Hz, 1H), 5.00-3.60 (m, 5H), 2.60-2.35 (m, 2H); MS: (ES) m/z calculated for C$_{21}$H$_{18}$FN$_5$OS[M+H]$^+$ 408.2, found 408.

Example 122: Synthesis of 1-(tetrahydro-pyran-4-yl)-1H-pyrazole-3-carboxylic acid

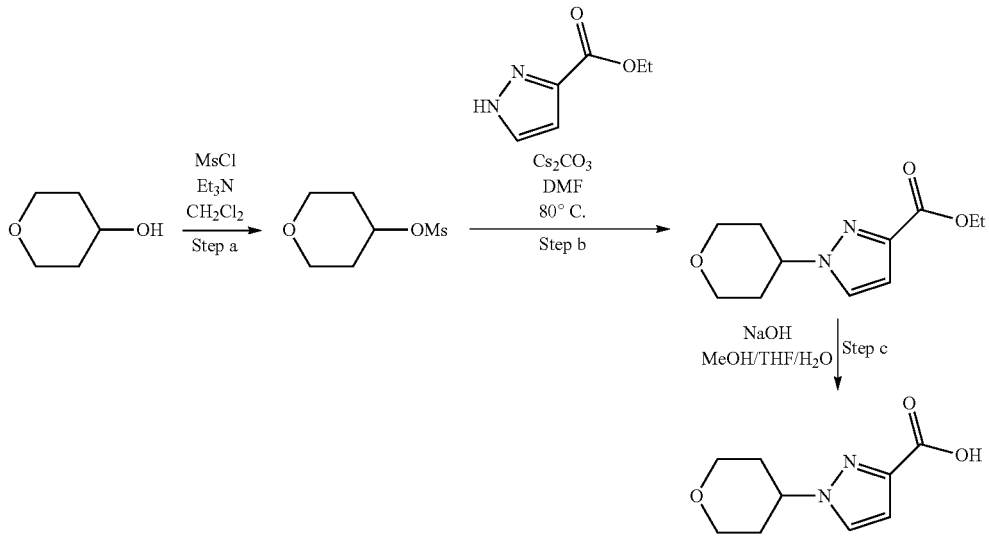

a) A flask was charged with 4-hydroxytetrahydropyran (3.00 g, 29.4 mmol), Methanesulfonyl chloride (2.39 mL, 30.9 mmol), triethylamine (8.20 mL, 58.8 mmol), and CH$_2$Cl$_2$. The resulting mixture was stirred overnight at room temperature. The reaction mixture was then washed with saturated aqueous NaHCO$_3$ (100 mL) and water (100 mL), dried over Na$_2$SO$_4$, filtered and concentrated under reduced pressure. The crude product thus obtained was used without further purification.

b) A vial was charged with ethyl-1H-pyrazole-3-carboxylate (3.74 g, 26.7 mmol), the crude methanesulfonic acid tetrahydro-pyran-4-yl ester (29.4 mmol), Cs$_2$CO$_3$ (17.4 g, 53.4 mmol), and DMF (100 mL). The reaction mixture was heated to 80° C. and stirred overnight. The reaction was then partitioned between CH$_2$Cl$_2$ (250 mL) and water (250 mL), and the organic layer was washed with water (5×250 mL), dried over Na$_2$SO$_4$, filtered, and concentrated under reduced pressure. The crude product containing 2 regioisomers was purified via flash chromatography on silica gel (95:5-50:50 hexanes:EtOAc) and the later eluting isomer was isolated. This was purified on silica gel a second time (85:15-60:40 hexanes:EtOAc) to give the pure desired product (1.14 g, 19%).

c) 1-(Tetrahydro-pyran-4-yl)-1H-pyrazole-3-carboxylic acid ethyl ester (1.14 g, 5.09 mmol) was dissolved in a mixture of THF (5.0 mL) and MeOH (5.0 mL). To this was added NaOH (20% aqueous, 5.0 mL). The reaction mixture was stirred overnight and was then diluted with EtOAc and washed with 1 M NaHSO$_4$. The aqueous layer was extracted with EtOAc and the combined organics were dried over Na$_2$SO$_4$, filtered and concentrated under reduced pressure to give the product as a white solid (802 mg, 80%).

Example 123: Synthesis of 1-(tetrahydro-pyran-4-yl)-1H-pyrazole-3-carboxylic acid (1-pyrrolo[1,2-a]pyrazin-1-yl-pyrrolidin-3-yl)-amide

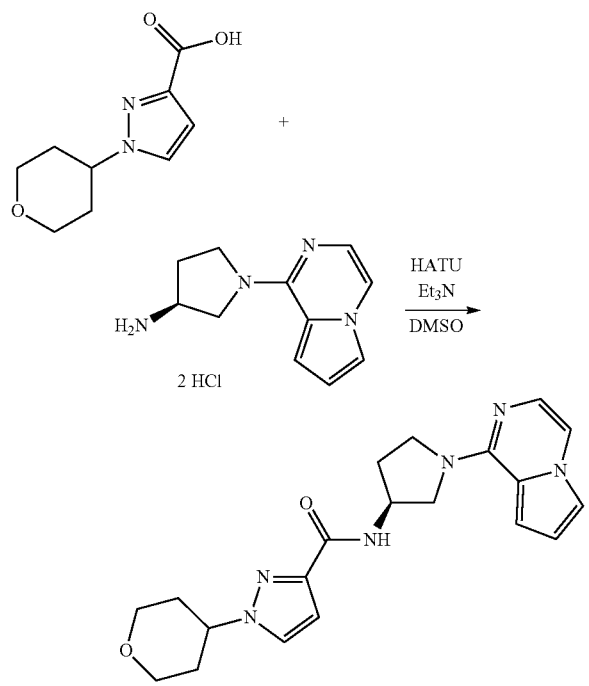

DMSO (0.5 mL) was added to a mixture of 1-(tetrahydropyran-4-yl)-1H-pyrazole-3-carboxylic acid (31 mg, 0.16 mmol) and 1-pyrrolo[1,2-a]pyrazin-1-yl-pyrrolidin-3-ylamine dihydrochloride salt (45 mg, 0.16 mmol). To this was added triethylamine (0.089 mL, 0.64 mmol) followed by HATU (68 mg, 0.18 mmol). The mixture was allowed to stir for 30 min, and was then diluted with dichloromethane (1.0 mL), washed with water (3×1.0 mL), dried over sodium sulfate, filtered and concentrated under reduced pressure. The crude material was purified by reverse phase HPLC (10:90-95:5 MeCN/H$_2$O+0.1% TFA). The combined product fractions were lyophilized to give the TFA salt of the product as a pale yellow solid (29 mg, 0.06 mmol, 37% yield). $^1$H NMR (400 MHz, CD3OD) δ 8.48 (d, J=6.2 Hz, 1H), 7.78-7.70 (m, 3H), 7.55 (s, 1H), 6.91 (dd, J=2.5, 4.4 Hz, 1H), 6.83 (d, J=5.5 Hz, 1H), 6.73 (d, J=2.2 Hz, 1H), 5.00-3.60 (m, 8H), 3.55 (dt, J=2.2, 11.7 Hz, 2H), 2.60-2.39 (m, 2H), 2.20-1.95 (m, 4H); MS: (ES) m/z calculated for C$_{20}$H$_{24}$N$_6$O$_2$ [M+H]$^+$ 381.2, found 381.

Example 124: Synthesis of 1-(tetrahydro-pyran-4-yl)-1H-pyrazole-3-carboxylic acid (1-[1,2,4]triazolo[4,3-a]pyrazin-8-yl-pyrrolidin-3-yl)-amide

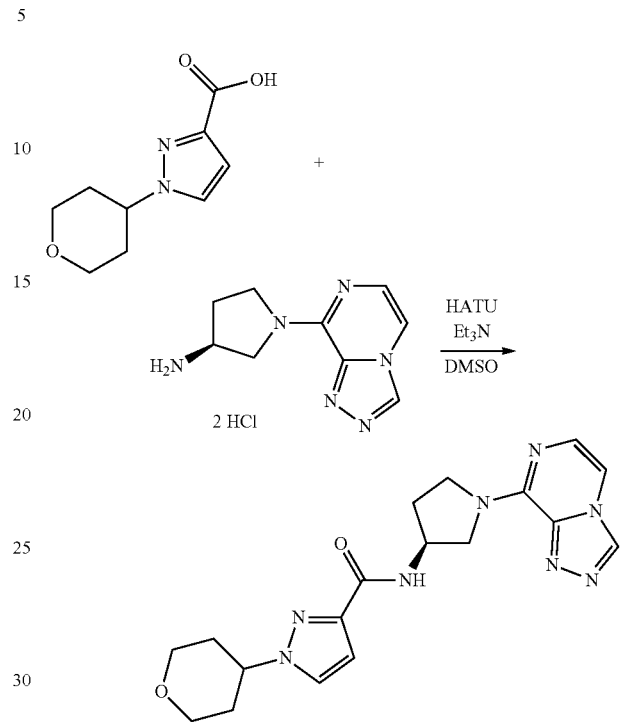

DMSO (0.5 mL) was added to a mixture of 1-(tetrahydropyran-4-yl)-1H-pyrazole-3-carboxylic acid (35 mg, 0.18 mmol) and 1-[1,2,4]triazolo[4,3-a]pyrazin-8-yl-pyrrolidin-3-ylamine (50 mg, 0.18 mmol). To this was added triethylamine (0.100 mL, 0.72 mmol) followed by HATU (76 mg, 0.20 mmol). The mixture was allowed to stir for 30 min and was then diluted with dichloromethane (1.0 mL), washed with water (3×1.0 mL), dried over sodium sulfate, filtered, and concentrated under reduced pressure. The crude was purified by reverse phase HPLC (10:90-95:5 MeCN/H$_2$O+0.1% TFA). The combined product fractions were lyophilized to give the TFA salt of the product as a white solid (16 mg, 0.03 mmol, 18% yield). $^1$H NMR (400 MHz, CD3OD) δ 9.25 (s, 1H), 7.85 (d, J=5.1 Hz, 1H), 7.73 (d, J=2.6 Hz, 1H), 7.20 (d, J=5.5 Hz, 1H), 6.73 (d, J=2.5 Hz, 1H), 5.00-3.60 (m, 8H), 3.55 (dt, J=2.2, 11.7 Hz, 2H), 2.60-2.39 (m, 2H), 2.20-1.95 (m, 4H); MS: (ES) m/z calculated for C$_{18}$H$_{22}$N$_8$O$_2$ [M+H]$^+$ 383.2, found 383.

Example 125: Synthesis of 1-(tetrahydro-pyran-4-yl)-1H-pyrazole-3-carboxylic acid (1-imidazo[1,2-a]pyrazin-8-yl-pyrrolidin-3-yl)-amide

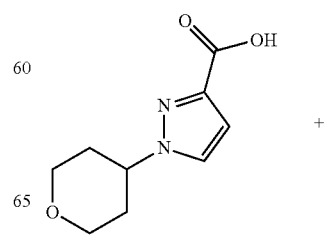

-continued

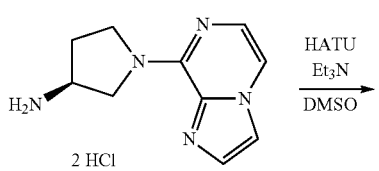

sulfate, filtered, and concentrated under reduced pressure. The crude material was purified by reverse phase HPLC (10:90-95:5 MeCN/H$_2$O+0.1% TFA). The combined product fractions were lyophilized to give the TFA salt of the product as a pale yellow oil (35 mg, 0.07 mmol, 39% yield). $^1$H NMR (400 MHz, CD3OD) δ 8.02 (s, 1H), 7.90 (d, J=5.9 Hz, 1H), 7.79 (s, 1H), 7.73 (d, J=2.5 Hz, 1H), 7.14 (d, J=5.5 Hz, 1H), 6.72 (d, J=2.6 Hz, 1H), 5.00-3.70 (m, 8H), 3.55 (dt, J=2.2, 11.7 Hz, 2H), 2.60-2.30 (m, 2H), 2.20-1.95 (m, 4H); MS: (ES) m z calculated for C$_{19}$H$_{23}$N$_7$O$_2$ [M+H]$^{30}$ 382.2. found 382.

Example 126: Synthesis of 2-o-tolyloxazole-4-carboxylic acid (1-pyrrolo[1,2-a]pyrazin-1-yl-pyrrolidin-3-yl)-amide

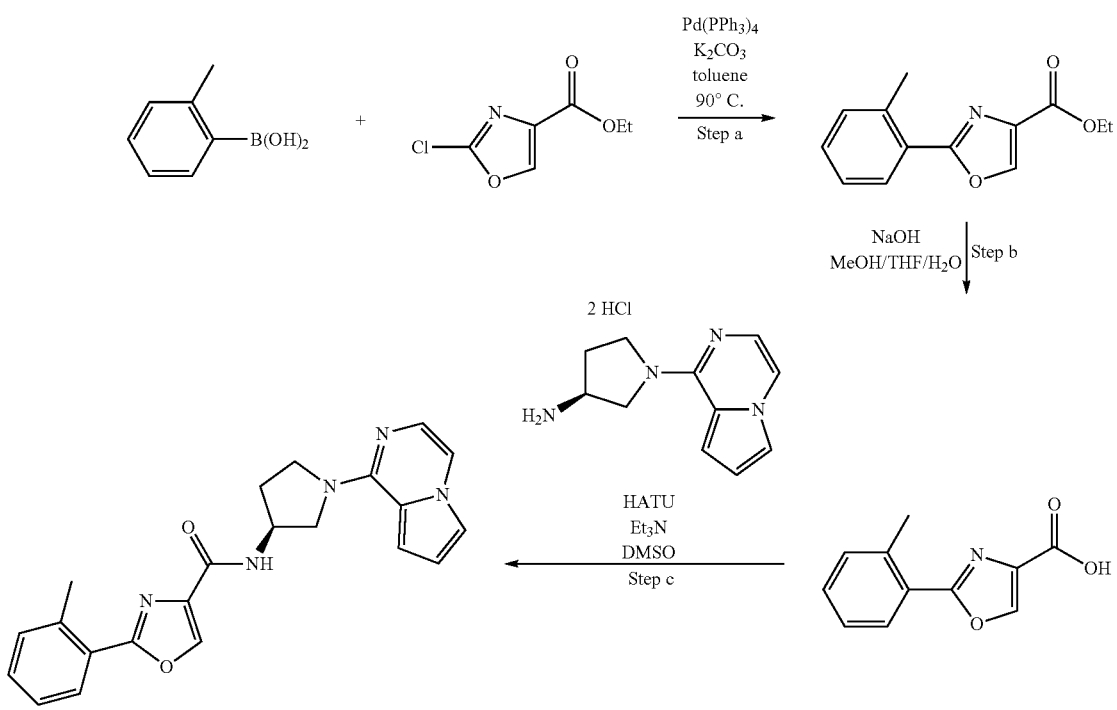

a) A flask was charged with ethyl 2-chlorooxazole-4-carboxylate (500 mg, 2.85 mmol), 2-methylbenzeneboronic acid (387 mg, 2.85 mmol), Pd(PPh$_3$)$_4$ (132 mg, 0.114 mmol), K$_2$CO$_3$ (787 mg, 5.7 mmol), and toluene (29 mL). The reaction mixture was degassed under a stream of N$_2$, and was then heated to 90° C. for 1 h. The reaction was then diluted with EtOAc and washed with 1M aqueous NaOH. The organic layer was dried over Na$_2$SO$_4$, filtered, and concentrated under reduced pressure. The crude material was purified on via flash chromatography on silica gel (hexanes:EtOAc) to give a 2:1 mixture of product to ethyl 2-chlorooxazole-4-carboxylate (360 mg) that was carried on without further purification.

b) The 2:1 mixture of 2-o-Tolyl-oxazole-4-carboxylic acid ethyl ester:ethyl 2-chlorooxazole-4-carboxylate (360 mg) was dissolved in a mixture of THF (1.0 mL) and MeOH (1.0 mL). To this was added NaOH (20% aqueous, 1.0 mL). The reaction mixture was stirred overnight and was then diluted with EtOAc (50 mL) and washed with 1M NaHSO$_4$ (50 mL). The aqueous layer was extracted with EtOAc (2×50 mL) and the combined organics were dried over -continued

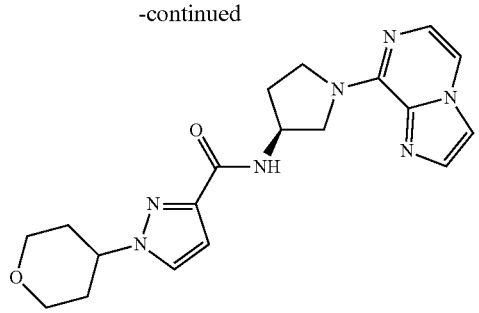

DMSO (0.5 mL) was added to a mixture of 1-(tetrahydropyran-4-yl)-1H-pyrazole-3-carboxylic acid (35 mg, 0.18 mmol) and 1-imidazo[1,2-a]pyrazin-8-yl-pyrrolidin-3-ylamine dihydrochloride salt (50 mg, 0.18 mmol). To this was added triethylamine (0.100 mL, 0.72 mmol) followed by HATU (76 mg, 0.20 mmol). The mixture was allowed to stir for 30 min and was then diluted with dichloromethane (1.0 mL), washed with water (3×1.0 mL), dried over sodium $Na_2SO_4$, filtered and concentrated to give a 2:1 mixture of product: 2-Chloro-oxazole-4-carboxylic acid (360 mg).

c) The 2:1 mixture of acids from step b (37 mg) was dissolved in DMSO (0.5 mL) and 1-pyrrolo[1,2-a]pyrazin-1-yl-pyrrolidin-3-ylamine dihydrochloride salt (50 mg, 0.18 mmol) was added. To this was added triethylamine (0.100 mL, 0.72 mmol) followed by HATU (76 mg, 0.20 mmol). The mixture was allowed to stir for 30 min and was then diluted with dichloromethane (1.0 mL), washed with water (3×1.0 mL), dried over sodium sulfate, filtered and concentrated under reduced pressure to give the crude. The crude was purified by reverse phase HPLC (10:90-95:5 MeCN/$H_2O$+0.1% TFA). The combined product fractions were lyophilized to give the TFA salt of the product as a yellow solid (26 mg, 0.05 mmol, 29% yield). $^1$H NMR (400 MHz, CD3OD) δ 8.61 (d, J=6.2 Hz, 1H), 8.49 (s, 1H), 7.94 (d, J=7.7 Hz, 1H), 7.76 (d, J=1.1 Hz, 1H), 7.71 (d, J=5.4 Hz, 1H), 7.56 (d, J=2.9 Hz, 1H), 7.40-7.26 (m, 3H), 6.92 (dt, J=1.8, 2.6 Hz, 1H), 6.83 (d, J=5.5 Hz, 1H), 5.00-3.60 (m, 5H), 2.66 (s, 3H), 2.60-2.38 (m, 2H); MS: (ES) m/z calculated for $C_{22}H_{21}N_5O_2$ [M+H]$^+$ 388.2, found 388.

Example 127: Synthesis of 2-phenyloxazole-4-carboxylic acid (1-imidazo[1,2-a]pyrazin-8-yl-pyrrolidin-3-yl)-amide

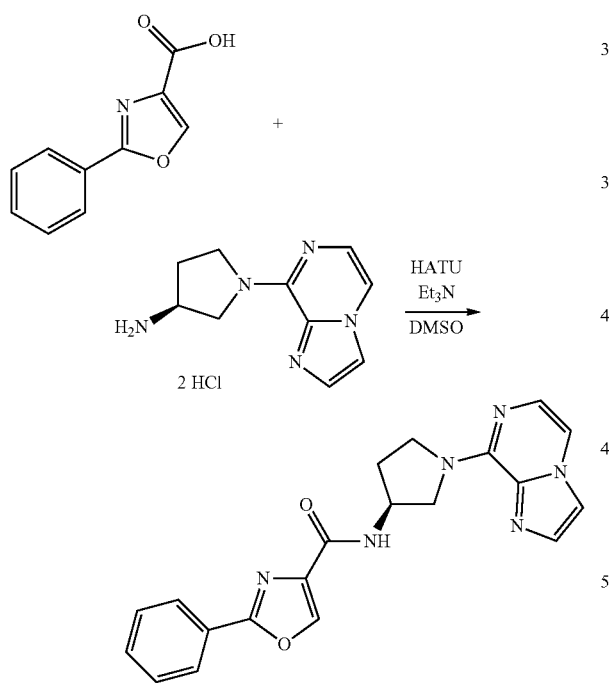

DMSO (0.5 mL) was added to a mixture of 2-phenyloxazole-4-carboxylic acid (42 mg, 0.22 mmol) and 1-imidazo[1,2-a]pyrazin-8-yl-pyrrolidin-3-ylamine dihydrochloride salt (60 mg, 0.22 mmol). To this was added triethylamine (0.123 mL, 0.88 mmol) followed by HATU (91 mg, 0.24 mmol). The mixture was allowed to stir for 30 min and was then diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN/$H_2O$+0.1% TFA). The combined product fractions were lyophilized to give the TFA salt of the product as a white solid (62 mg, 0.13 mmol, 58% yield). $^1$H NMR (400 MHz, CD3OD) δ 8.71 (d, J=6.3 Hz, 1H), 8.46 (s, 1H), 8.06-8.02 (m, 3H), 7.91 (d, J=5.5 Hz, 1H), 7.80 (s, 1H), 7.49 (m, 3H), 7.15 (d, J=5.9 Hz, 1H), 5.00-3.80 (m, 5H), 2.60-2.38 (m, 2H); MS: (ES) m/z calculated for $C_{20}H_{18}N_6O_2$[M+H]$^+$ 375.2, found 375.

Example 128: Synthesis of 2-phenyloxazole-4-carboxylic acid (1-[1,2,4]triazolo[4,3-a]pyrazin-8-yl-pyrrolidin-3-yl)-amide

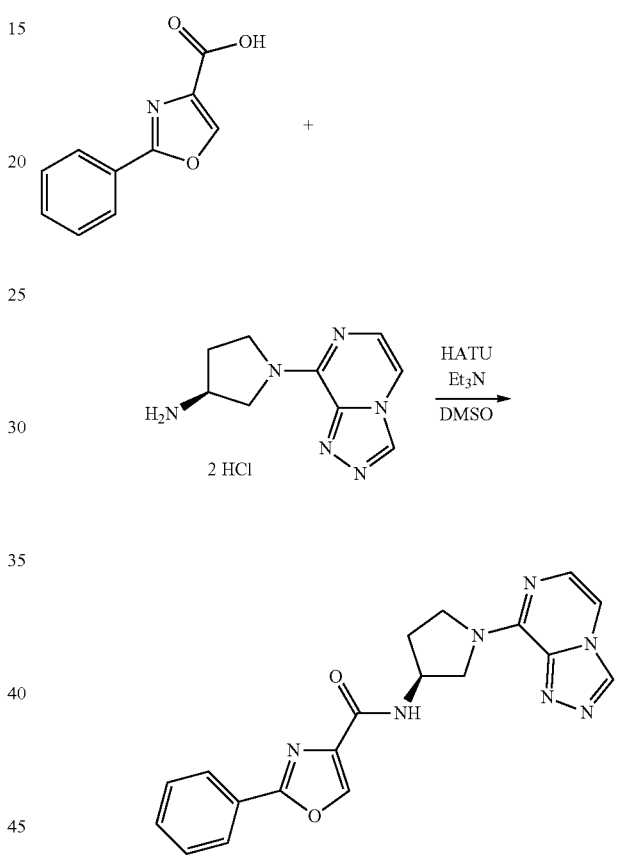

DMSO (0.5 mL) was added to a mixture of 2-phenyloxazole-4-carboxylic acid (42 mg, 0.22 mmol) and 1-[1,2,4]triazolo[4,3-a]pyrazin-8-yl-pyrrolidin-3-ylamine (60 mg, 0.22 mmol). To this was added triethylamine (0.123 mL, 0.88 mmol) followed by HATU (91 mg, 0.24 mmol). The mixture was allowed to stir for 30 min and was then diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN:$H_2O$+0.1% TFA). The combined product fractions were lyophilized to give the TFA salt of the product as a white solid (58 mg, 0.12 mmol, 54% yield). $^1$H NMR (400 MHz, CD3OD) δ 9.26 (s, 1H), 8.70 (d, J=5.9 Hz, 0.5H), 8.45 (s, 1H), 8.04 (d, J=5.5 Hz, 2H), 7.86 (d, J=5.5 Hz, 1H), 7.49 (m, 3H), 7.21 (d, J=5.5 Hz, 1H), 5.00-3.80 (m, 5H), 2.60-2.38 (m, 2H); MS: (ES) m/z calculated for $C_{19}H_{17}N_7O_2$ [M+H]$^+$ 376.2, found 376.

Example 129: Synthesis of 2-phenylthiazole-4-carboxylic acid (1-imidazo[1,2-a]pyrazin-8-yl-pyrrolidin-3-yl)-amide

Example 130: Synthesis of 2-phenylthiazole-4-carboxylic acid (1-[1,2,4]triazolo[4,3-a]pyrazin-8-yl-pyrrolidin-3-yl)-amide

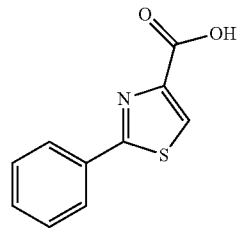
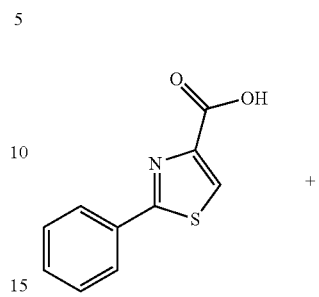
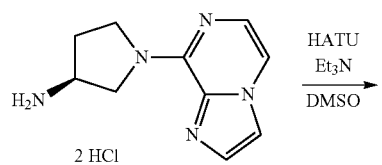
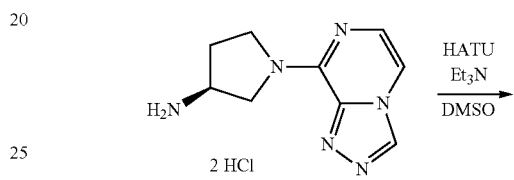
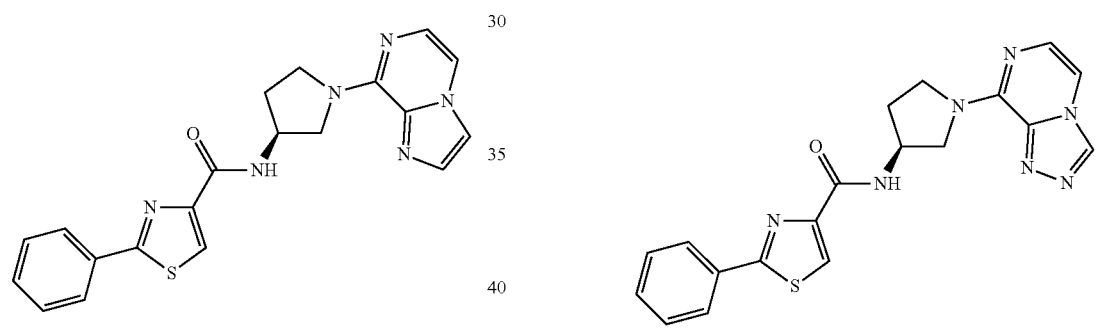

DMSO (0.5 mL) was added to a mixture of 2-phenylthiazole-4-carboxylic acid (45 mg, 0.22 mmol) and 1-imidazo[1,2-a]pyrazin-8-yl-pyrrolidin-3-ylamine dihydrochloride salt (60 mg, 0.22 mmol). To this was added triethylamine (0.123 mL, 0.88 mmol) followed by HATU (91 mg, 0.24 mmol). The mixture was allowed to stir for 30 min and was then diluted with dichloromethane (1.0 mL), washed with water (3×1.0 mL), dried over sodium sulfate, filtered, and concentrated under reduced pressure. The crude material was purified by reverse phase chromatography (10:90-95:5 MeCN/H$_2$O+0.1% TFA). The combined product fractions were lyophilized to give the TFA salt of the product as a pale yellow solid (74 mg, 0.15 mmol, 67% yield). $^1$H NMR (400 MHz, CD3OD) δ 8.82 (d, J=6.3 Hz, 1H), 8.23 (s, 1H), 8.03-8.01 (m, 3H), 7.92-7.90 (m, 1H), 7.88 (s, 1H), 7.48-7.45 (m, 3H), 7.15 (d, J=5.8 Hz, 1H), 4.98-3.80 (m, 5H), 2.60-2.40 (m, 2H); MS: (ES) m/z calculated for C$_{20}$H$_{18}$N$_6$OS [M+H]$^+$ 391.2, found 391.

DMSO (0.5 mL) was added to a mixture of 2-phenylthiazole-4-carboxylic acid (45 mg, 0.22 mmol) and 1-[1,2,4]triazolo[4,3-a]pyrazin-8-yl-pyrrolidin-3-ylamine dihydrochloride salt (60 mg, 0.22 mmol). To this was added triethylamine (0.123 mL, 0.88 mmol) followed by HATU (91 mg, 0.24 mmol). The mixture was allowed to stir for 30 min and was then diluted with dichloromethane, washed with water (3×), dried over sodium sulfate, filtered, and concentrated under reduced pressure. The crude material was triturated with MeCN, filtered, and the solid was washed with MeCN. The resulting solid was taken up in MeCN and 1 M HCl, then lyophilized to give the HCl salt of the product as a white solid (17 mg, 0.04 mmol, 18% yield). $^1$H NMR (400 MHz, CD3OD) δ 9.31 (s, 1H), 8.85 (d, J=3.6 Hz, 1H), 8.24 (s, 1H), 8.02 (d, J=3.6 Hz, 2H), 7.92 (d, J=5.4 Hz, 1H), 7.47 (s, 3H), 7.19 (d, J=5.4 Hz, 1H), 5.00-3.80 (m, 5H), 2.60-2.40 (m, 2H); MS: (ES) m/z calculated for C$_{19}$H$_{17}$N$_7$OS [M+H]$^+$ 392.2, found 392.

Example 131: Synthesis of 1-o-tolyl-1H-pyrazole-3-carboxylic acid

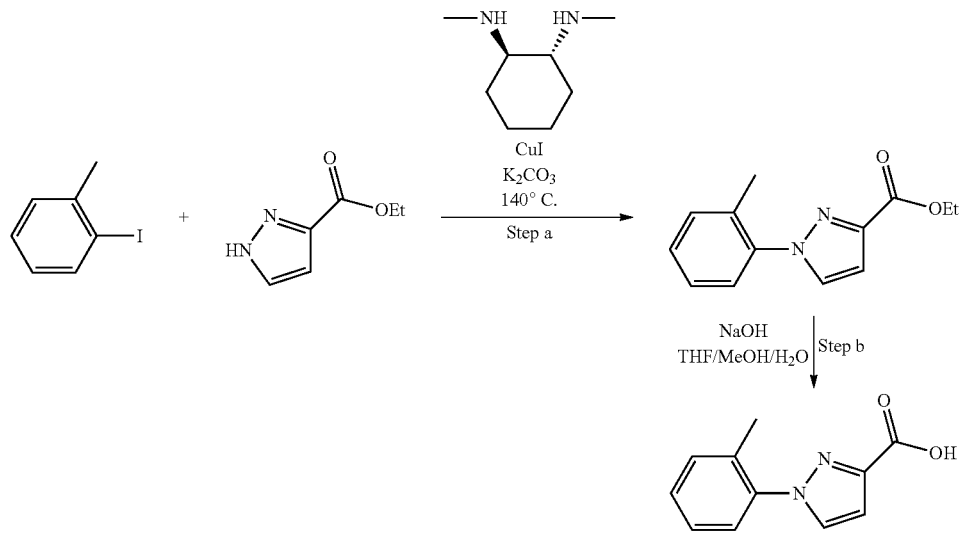

a) A flask was charged with 2-iodotoluene (0.964 mL, 7.57 mmol), ethyl-1H-pyrazole-3-carboxylate (1.00 g, 7.14 mmol), CuI (272 mg, 1.43 mmol), trans-N,N'-dimethylcyclohexane-1,2-diamine (0.451 mL, 2.86 mmol), and $K_2CO_3$ (3.15 g, 22.8 mmol). The reaction mixture was then heated to 140° C. for 3 h. The reaction was then partitioned between $CH_2Cl_2$ and saturated aqueous $NH_4Cl$ and separated. The organic layer was washed with water, dried over $Na_2SO_4$, filtered and concentrated. The crude was purified via flash chromatography on silica gel (90:10-70:30 hexanes:methyl tert-butyl ether) to give the product (238 mg, 1.03 mmol, 14%) as a colorless oil.

b) 1-o-Tolyl-1H-pyrazole-3-carboxylic acid ethyl ester (238 mg, 1.03 mmol) was dissolved in a mixture of THF (2.0 mL) and MeOH (2.0 mL). To this was added NaOH (20% aqueous, 1.0 mL). The reaction mixture was stirred for 2 h, and was then diluted with EtOAc and washed with 1M HCl. The aqueous layer was extracted with EtOAc and the combined organics were dried over $Na_2SO_4$, filtered and concentrated to give the product as a white solid (164 mg, 0.81 mmol, 79%).

Example 132: Synthesis of 1-o-tolyl-1H-pyrazole-3-carboxylic acid (1-imidazo[1,2-a]pyrazin-8-yl-pyrrolidin-3-yl)-amide

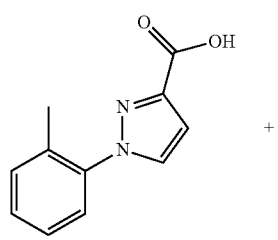

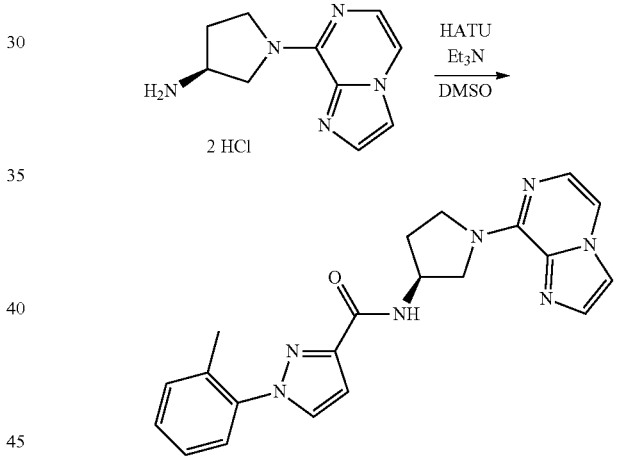

DMSO (0.5 mL) was added to a mixture of 1-o-tolyl-1H-pyrazole-3-carboxylic acid (44 mg, 0.22 mmol) and 1-imidazo[1,2-a]pyrazin-8-yl-pyrrolidin-3-ylamine dihydrochloride salt (60 mg, 0.22 mmol). To this was added triethylamine (0.123 mL, 0.88 mmol) followed by HATU (91 mg, 0.24 mmol). The mixture was allowed to stir for 30 min and was then diluted with dichloromethane (1.0 mL), washed with water (3×1.0 mL), dried over sodium sulfate, filtered, and concentrated under reduced pressure. The crude product was purified by reverse phase chromatography (10:90-95:5 $MeCN/H_2O$+0.1% TFA). The combined product fractions were lyophilized to give the TFA salt of the product as a yellow solid (29 mg, 0.06 mmol, 26% yield). $^1$H NMR (400 MHz, CD3OD) δ 8.58 (d, J=7.3 Hz, 1H), 8.01 (d, J=0.7 Hz, 1H), 7.92-7.87 (m, 2H), 7.78 (d, J=1.1 Hz, 1H), 7.40-7.28 (m, 4H), 7.12 (d, J=5.8 Hz, 1H), 6.93 (d, J=2.2 Hz, 1H), 4.94-3.80 (m, 5H), 2.56-2.32 (m, 2H), 2.20 (s, 3H); MS: (ES) m/z calculated for $C_{21}H_{21}N_7O$ [M+H]$^+$ 388.2, found 388.

Example 133: Synthesis of 1-o-tolyl-1H-pyrazole-3-carboxylic acid (1-[1,2,4]triazolo[4,3-a]pyrazin-8-yl-pyrrolidin-3-yl)-amide

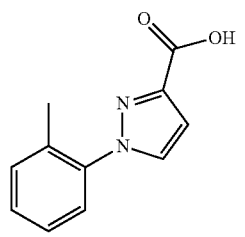

concentrated under reduced pressure. The crude material was triturated with MeCN, filtered, and the solid was washed with MeCN. The resulting solid was taken up in MeCN and 1M HCl and lyophilized to give the HCl salt of the product as a white solid (13 mg, 0.03 mmol, 12% yield). $^1$H NMR (400 MHz, CD3OD) δ 9.30 (s, 1H), 7.91 (d, J=5.8 Hz, 1H), 7.88 (s, 1H), 7.40-7.28 (m, 4H), 7.17 (m, 1H), 6.95 (s, 1H), 4.94-4.70 (m, 4H), 4.24-3.84 (m, 3H), 2.62-2.38 (m, 2H), 2.20 (s, 3H); MS: (ES) m/z calculated for $C_{20}H_{20}N_8O$ [M+H]$^+$ 389.2, found 389.

Example 134: Synthesis of 2-o-tolyl-thiazole-4-carboxylic acid

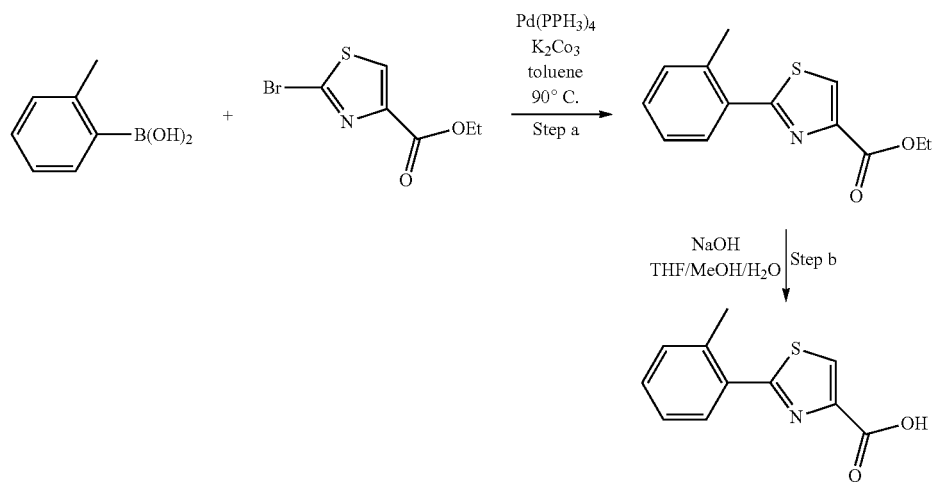

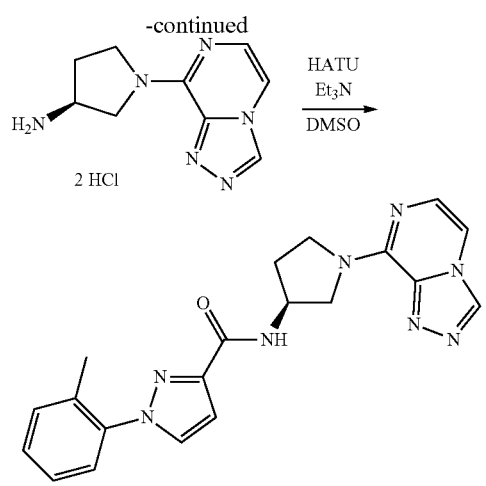

DMSO (0.5 mL) was added to a mixture of 1-o-tolyl-1H-pyrazole-3-carboxylic acid (44 mg, 0.22 mmol) and 1-[1,2,4]triazolo[4,3-a]pyrazin-8-yl-pyrrolidin-3-ylamine dihydrochloride salt (60 mg, 0.22 mmol). To this was added triethylamine (0.123 mL, 0.88 mmol) followed by HATU (91 mg, 0.24 mmol). The mixture was allowed to stir for 30 min and was then diluted with dichloromethane, washed with water (3×), dried over sodium sulfate, filtered, and a) A flask was charged 2-methylbenzeneboronic acid (500 mg, 3.68 mmol), ethyl 2-bromothiazole-4-carboxylate (869 mg, 3.68 mmol), Pd(PPh$_3$)$_4$ (173 mg, 0.150 mmol), K$_2$CO$_3$ (2 M aqueous, 3.68 mL, 7.36 mmol), and toluene (37 mL). The reaction mixture was degassed under a stream of N$_2$, then heated to 90° C. and stirred overnight. The reaction was then diluted with EtOAc and washed with 1M aqueous NaOH. The aqueous layer was extracted with EtOAc (2×100 mL), and the combined organic layer was dried over Na$_2$SO$_4$, filtered, and concentrated under reduced pressure. The crude was purified via flash chromatography on silica gel (95:5-70:30 hexanes:EtOAc) to give the product (550 mg, 2.22 mmol, 60%) as a pale yellow oil.

b) 2-o-Tolyl-thiazole-4-carboxylic acid ethyl ester (550 mg, 2.22 mmol) was dissolved in a mixture of THF (1.0 mL) and MeOH (1.0 mL). To this was added NaOH (20% aqueous, 0.444 mL). The reaction mixture was stirred overnight and was then diluted with CH$_2$Cl$_2$ (30 mL) and washed with 1M NaHSO$_4$ (30 mL). The aqueous layer was extracted with CH$_2$Cl$_2$ (2×30 mL), then the combined organic layers were washed with water (1×30 mL), dried over Na$_2$SO$_4$, filtered and concentrated under reduced pressure to give the product (434 mg, 1.98 mmol, 89%) as a white solid.

Example 135: Synthesis of 2-o-tolylthiazole-4-carboxylic acid (1-pyrrolo[1,2-a]pyrazin-1-yl-pyrrolidin-3-yl)-amide Example 136: Synthesis of 2-o-tolylthiazole-4-carboxylic acid (1-imidazo[1,2-a]pyrazin-8-yl-pyrrolidin-3-yl)-amide

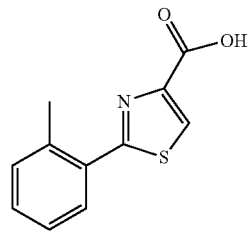

+

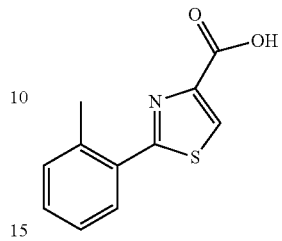

+

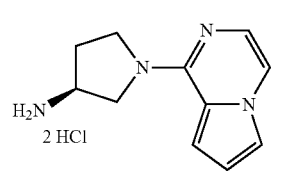

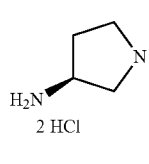

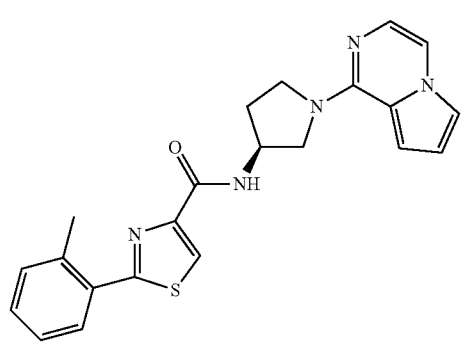

DMSO (0.5 mL) was added to a mixture of 2-o-tolylthiazole-4-carboxylic acid (48 mg, 0.22 mmol) and 1-pyrrolo[1,2-a]pyrazin-1-yl-pyrrolidin-3-ylamine dihydrochloride salt (60 mg, 0.22 mmol). To this was added triethylamine (0.123 mL, 0.88 mmol) followed by HATU (91 mg, 0.24 mmol). The mixture was allowed to stir for 30 min, diluted with dichloromethane (1.0 mL), then washed with water (3×1.0 mL), dried over sodium sulfate, filtered and concentrated under reduced pressure. The crude material was purified by reverse phase HPLC (10:90-95:5 MeCN:H$_2$O+ 0.1% TFA). The combined product fractions were lyophilized to give the TFA salt of the product as a yellow solid (10 mg, 0.02 mmol, 9% yield). $^1$H NMR (400 MHz, CD3OD) δ 8.74 (d, J=6.7 Hz, 1H), 8.34 (s, 1H), 7.78 (dd, J=1.2, 2.7 Hz, 1H), 7.76-7.70 (m, 2H), 7.57 (d, J=4.3 Hz, 1H), 7.42-7.26 (m, 3H), 6.93 (dd, J=2.8, 4.7 Hz, 1H), 6.84 (d, J=5.9 Hz, 1H), 5.00-4.80 (m, 1H), 4.60-3.60 (br, 4H), 2.60-2.36 (m, 2H), 2.55 (s, 3H); MS: (ES) m/z calculated for C$_{22}$H$_{21}$N$_5$OS [M+H]$^+$ 404.2, found 404.

DMSO (0.5 mL) was added to a mixture of 2-o-tolylthiazole-4-carboxylic acid (48 mg, 0.22 mmol) and 1-imidazo[1,2-a]pyrazin-8-yl-pyrrolidin-3-ylamine dihydrochloride salt (60 mg, 0.22 mmol). To this was added triethylamine (0.123 mL, 0.88 mmol) followed by HATU (91 mg, 0.24 mmol). The mixture was allowed to stir for 30 min after which time it was diluted with dichloromethane (1.0 mL), washed with water (3×1.0 mL), dried over sodium sulfate, filtered, and concentrated under reduced pressure. The crude product containing material was purified by reverse phase HPLC (10:90-95:5 MeCN/H$_2$O+0.1% TFA). The combined product fractions were lyophilized to give the TFA salt of the product as a yellow solid (58 mg, 0.11 mmol, 51% yield). $^1$H NMR (400 MHz, CD3OD) δ 8.33 (s, 1H), 8.04 (d, J=1.2 Hz, 1H), 7.92 (d, J=5.5 Hz, 1H), 7.81 (d, J=1.2 Hz, 1H), 7.73 (dd, J=1.5, 7.8 Hz, 1H), 7.42-7.26 (m, 3H), 7.16 (d, J=5.5 Hz, 1H), 5.00-4.80 (m, 1H), 4.60-3.60 (br, 4H), 2.60-2.38 (m, 2H), 2.55 (s, 3H); MS: (ES) m/z calculated for C$_{21}$H$_{20}$N$_6$OS [M+H]$^+$ 405.2, found 405.

Example 137: Synthesis of 1-(3-methyl-pyrrolo[1,2-a]pyrazin-1-yl)-pyrrolidin-3-ylamine dihydrochloride salt

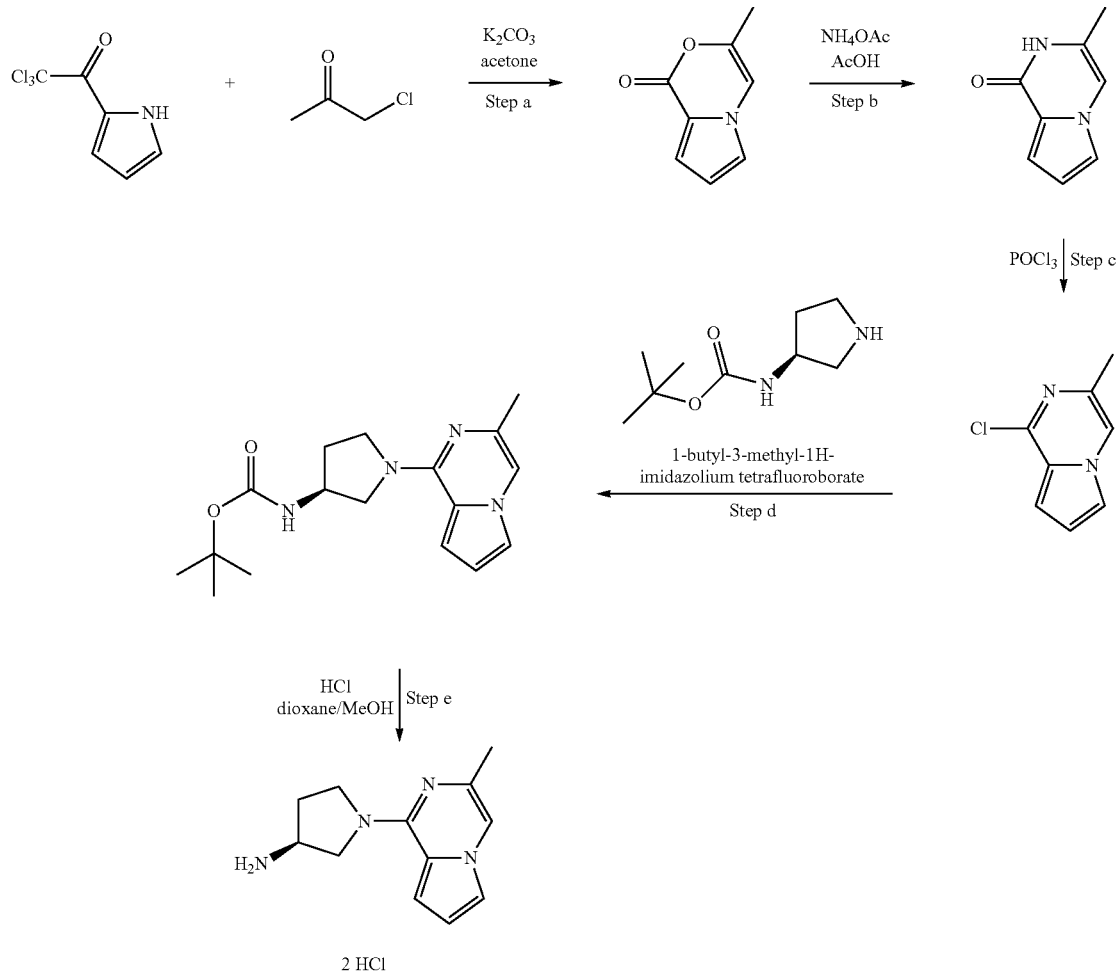

a) A solution of chloroacetone (2.81 mL, 35.3 mmol) in acetone (50 mL) was added dropwise to a slurry of 2-(trichloroacetyl)pyrrole (5.00 g, 23.5 mmol), acetone (70 mL) and $K_2CO_3$ (9.74 g, 70.5 mmol). The mixture was stirred overnight at room temperature. The reaction mixture was then filtered and the solids were washed with acetone. The filtrate was concentrated and the residue was partitioned between water (100 mL) and ethyl acetate (100 mL). The layers were separated and the aqueous layer was extracted with ethyl acetate (100 mL). The combined organic layers were washed with water (3×100 mL), dried over $Na_2SO_4$, filtered and concentrated under reduced pressure. The crude material was purified via flash chromatography on silica gel using hexanes:ethyl acetate to give the product (2.35 g, 15.8 mmol, 67%).

b) A mixture of 3-methyl-pyrrolo[2,1-c][1,4]oxazin-1-one (2.35 g, 15.8 mmol), $NH_4OAc$ (5.32 g, 69.0 mmol) and AcOH (13.8 mL) was heated to 160° C. in a sealed vial for 48 h. The solvent was removed in vacuo, and the crude was taken up in $CH_2Cl_2$. This was washed with saturated $NaHCO_3$, dried over $Na_2SO_4$, filtered and concentrated under reduced pressure. Purification via flash chromatography (silica gel using hexanes:EtOAc) gave the product (710 mg, 4.79 mmol, 35%).

c) $POCl_3$ (2 mL) was added to 3-methyl-2H-pyrrolo[1,2-a]pyrazin-1-one (710 mg, 4.79 mmol) and the solution was heated to 105° C. for 3 h. The reaction mixture was concentrated in vacuo. The resulting oil was taken up in $CH_2Cl_2$ and washed with saturated aqueous $NaHCO_3$ then water. The organic layer was dried over $Na_2SO_4$, filtered and concentrated under reduced pressure. Purification via flash chromatography on silica gel (95:5-70:30 hexanes: EtOAc) gave the product (798 mg, 4.79 mmol, quantitative yield) as a yellow solid.

d) A vial was charged with 1-chloro-3-methylpyrrolo[1,2-a]pyrazine (798 mg, 4.79 mmol), (S)-3-(Boc-amino)pyrrolidine (901 mg, 4.84 mmol), $iPr_2NEt$ (2.52 mL, 14.52 mmol), and 1-butyl-3-methyl-1H-imidazolium tetrafluoroborate (catalytic) and heated to 110° C. for 15 h. The reaction mixture was concentrated in vacuo and purified via flash chromatography on silica gel (99:1-90:10 $CH_2Cl_2$: MeOH) to give the product (965 mg, 3.05 mmol, 64%).

e) HCl (4 M in dioxane, 3.80 mL, 15.2 mmol) was added to [1-(3-methyl-pyrrolo[1,2-a]pyrazin-1-yl)-pyrrolidin-3- yl]-carbamic acid tert-butyl ester (965 mg, 3.04 mmol) in MeOH (10 mL). This was stirred overnight then concentrated to give the product (860 mg, 2.97 mmol, 98%) as a white solid.

Example 138: Synthesis of 1-(4-fluorophenyl)-H-pyrazole-3-carboxylic acid [1-(3-methyl-pyrrolo[1,2-a]pyrazin-1-yl-pyrrolidin-3-yl]-amide

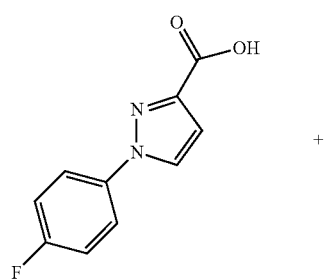

+

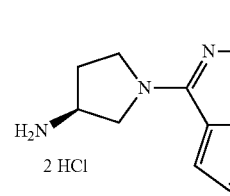

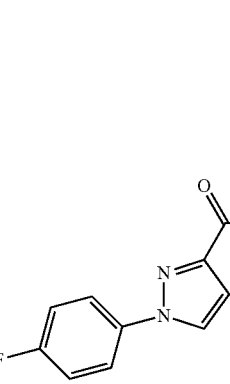

DMSO (0.5 mL) was added to a mixture of 1-(4-fluorophenyl)-1H-pyrazole-3-carboxylic acid (50 mg, 0.24 mmol) and 1-(3-methylpyrrolo[1,2-a]pyrazin-1-yl)-pyrrolidin-3-ylamine dihydrochloride salt (69 mg, 0.29 mmol). To this was added triethylamine (0.134 mL, 0.96 mmol) followed by HATU (99 mg, 0.26 mmol). The mixture was allowed to stir for 30 min, and was then diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN:H$_2$O+0.1% TFA). The combined product fractions were lyophilized to give the TFA salt of the product as a white solid (31 mg, 0.06 mmol, 25% yield). $^1$H NMR (400 MHz, CD3OD) δ 8.75 (d, J=7.0 Hz, 1H), 8.28 (d, J=2.7 Hz, 1H), 7.88 (m, 2H), 7.68 (q, J=1.2 Hz, 1H), 7.52 (d, J=4.3 Hz, 1H), 7.49 (s, 1H), 7.27-7.22 (m, 2H), 6.96 (d, J=2.4 Hz, 1H), 6.87 (dd, J=2.7, 4.3 Hz, 1H), 5.00-4.80 (m, 1H), 4.60-3.60 (br, 4H), 2.60-2.38 (m, 2H), 2.30 (d, J=1.1 Hz, 3H); MS: (ES) m z calculated for C$_{22}$H$_{21}$FN$_6$O [M+H]$^+$ 405.2, found 405.

Example 139: Synthesis of 1-phenyl-1H-[1,2,4]triazole-3-carboxylic acid [1-(3-methylpyrrolo[1,2-a]pyrazin-1-yl)-pyrrolidin-3-yl]-amide

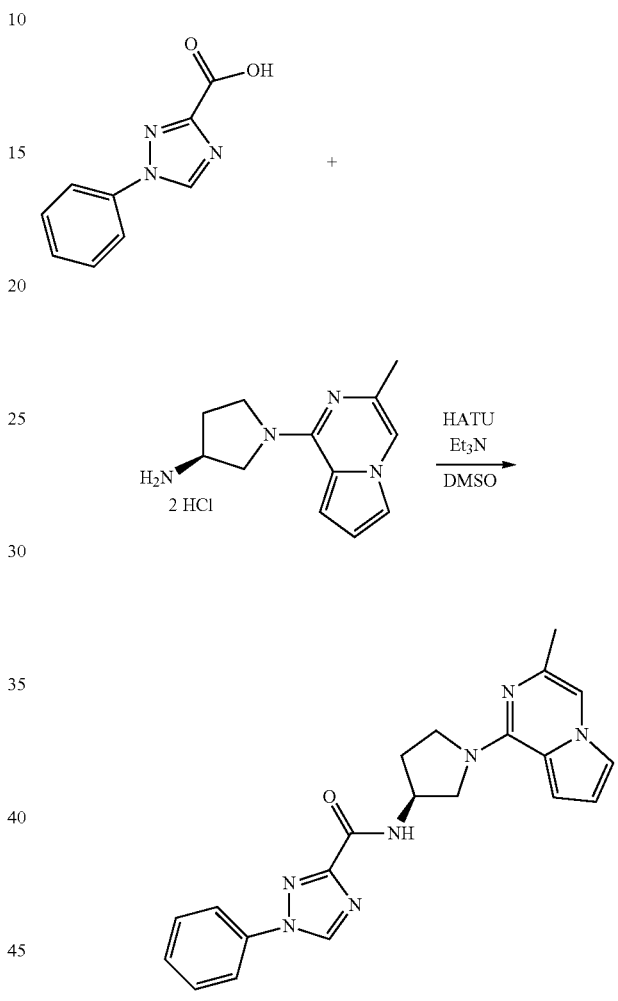

DMSO (0.5 mL) was added to a mixture of 1-phenyl-1H-1,2,4-triazole-3-carboxylic acid (50 mg, 0.26 mmol) and 1-(3-methylpyrrolo[1,2-a]pyrazin-1-yl)-pyrrolidin-3-ylamine dihydrochloride salt (74 mg, 0.26 mmol). To this was added triethylamine (0.145 mL, 1.04 mmol) followed by HATU (110 mg, 0.29 mmol). The mixture was allowed to stir for 30 min after which time it was diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN/H$_2$O+0.1% TFA). The combined product fractions were lyophilized to give the TFA salt of the product as a brown solid (66 mg, 0.13 mmol, 51% yield). $^1$H NMR (400 MHz, CD3OD) δ 9.14 (s, 1H), 7.88 (td, J=1.2, 6.2 Hz, 2H), 7.68 (q, J=1.2 Hz, 1H), 7.62-7.44 (m, 6H), 6.88 (dd, J=2.3, 4.3 Hz, 1H), 5.00-4.80 (m, 1H), 4.60-3.60 (br, 4H), 2.60-2.38 (m, 2H), 2.30 (d, J=1.1 Hz, 3H); MS: (ES) m/z calculated for C$_{21}$H$_{21}$N$_7$O [M+H]$^+$388.2, found 388.

Example 140: Synthesis of 1-phenyl-1H-imidazole-4-carboxylic acid (1-pyrrolo[1,2-a]pyrazin-1-yl-pyrrolidin-3-yl)-amide

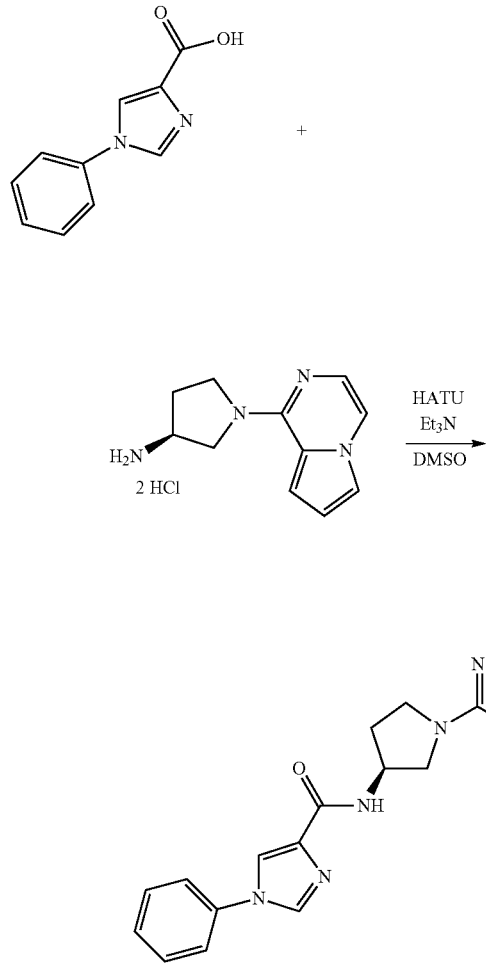

DMSO (0.5 mL) was added to a mixture of 1-phenyl-1H-imidazole-4-carboxylic acid (34 mg, 0.18 mmol) and 1-pyrrolo[1,2-a]pyrazin-1-yl-pyrrolidin-3-ylamine dihydrochloride salt (50 mg, 0.18 mmol). To this was added triethylamine (0.100 mL, 0.72 mmol) followed by HATU (76 mg, 0.20 mmol). The mixture was allowed to stir for 30 min after which time it was diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN/H$_2$O+0.1% TFA). The combined product fractions were lyophilized to give the TFA salt of the product as a pale yellow solid (49 mg, 0.10 mmol, 56% yield). $^1$H NMR (400 MHz, CD3OD) δ 8.23 (d, J=1.1 Hz, 1H), 8.15 (d, J=1.6 Hz, 1H), 7.79 (dd, J=1.2, 2.8 Hz, 1H), 7.73 (d, J=5.5 Hz, 1H), 7.64-7.52 (m, 5H), 7.50-7.42 (m, 1H), 6.94 (dd, J=2.3, 4.3 Hz, 1H), 6.86 (d, J=5.5 Hz, 1H), 5.00-4.80 (m, 1H), 4.50-3.50 (br, 4H), 2.58-2.48 (m, 1H), 2.48-2.35 (br, 1H); MS: (ES) m/z calculated for C$_{21}$H$_{20}$N$_6$O [M+H]$^+$ 373.2, found 373.

Example 141: Synthesis of 2-(4-hydroxypiperidin-1-yl)-thiazole-4-carboxylic acid [1-(3-methyl-pyrrolo[1,2-a]pyrazin-1-yl)-pyrrolidin-3-yl]-amide

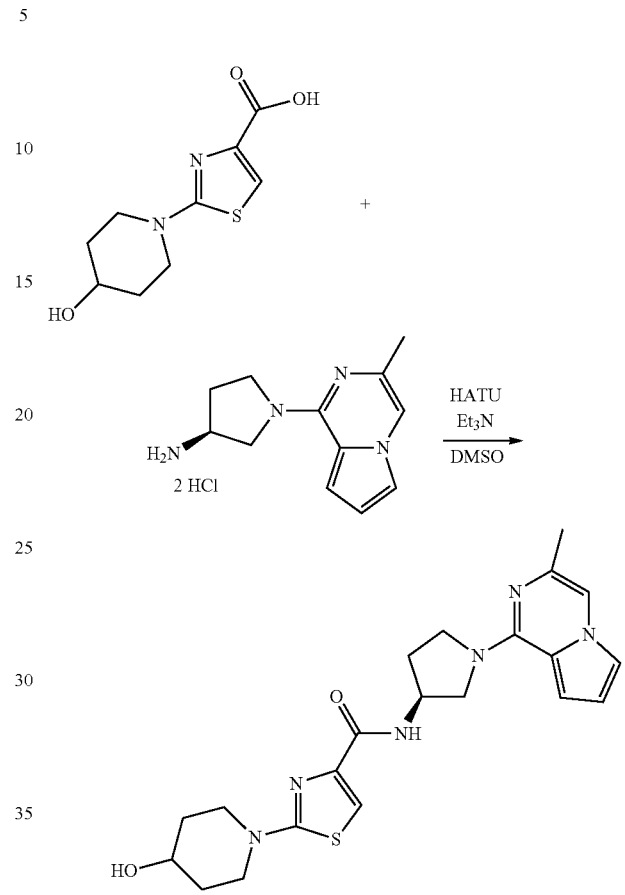

DMSO (0.5 mL) was added to a mixture of 2-(4-hydroxypiperidin-1-yl)-thiazole-4-carboxylic acid (48 mg, 0.21 mmol) and 1-(3-methylpyrrolo[1,2-a]pyrazin-1-yl)-pyrrolidin-3-ylamine dihydrochloride salt (60 mg, 0.21 mmol). To this was added triethylamine (0.117 mL, 0.84 mmol) followed by HATU (87 mg, 0.23 mmol). The mixture was allowed to stir for 30 min after which time it was diluted with dichloromethane (1.0 mL), washed with water (3×1.0 mL), dried over sodium sulfate, filtered, and concentrated under reduced pressure.

The crude material was purified by reverse phase HPLC (10:90-95:5 MeCN:H$_2$O+0.1% TFA). The combined fractions were concentrated, taken up in CH$_2$Cl$_2$, washed with NaHCO$_3$, dried over Na$_2$SO$_4$, filtered and concentrated. The resulting oil was then purified via flash chromatography on silica gel (CH$_2$Cl$_2$:MeOH gradient 99:1 to 90:10). The combined product fractions were concentrated and then lyophilized from a mixture of MeCN and 1 M HCl to give the HCl salt of the product as a yellow solid (22 mg, 0.04 mmol, 19% yield). $^1$H NMR (400 MHz, CD3OD) δ 7.37 (s, 1H), 7.28 (q, J=1.2 Hz, 1H), 7.25 (s, 1H), 6.86 (d, J=4.3 Hz, 1H), 6.57 (dd, J=2.7, 4.3 Hz, 1H), 5.48 (s, 2H), 4.70-4.60 (m, 1H), 4.22-3.78 (m, 8H), 3.28-3.10 (m, 1H), 2.40-2.28 (m, 1H), 2.22-2.12 (m, 4H), 1.96-1.88 (m, 2H); 1.62-1.52 (m, 2H); MS: (ES) nm/z calculated for C$_{21}$H$_{26}$N$_6$O$_2$S [M+H]$^+$ 427.2, found 427.

Example 142: Synthesis of 1-phenyl-1H-imidazole-4-carboxylic acid [1-(3-methyl-pyrrolo[1,2-a]pyrazin-1-yl)-pyrrolidin-3-yl]-amide

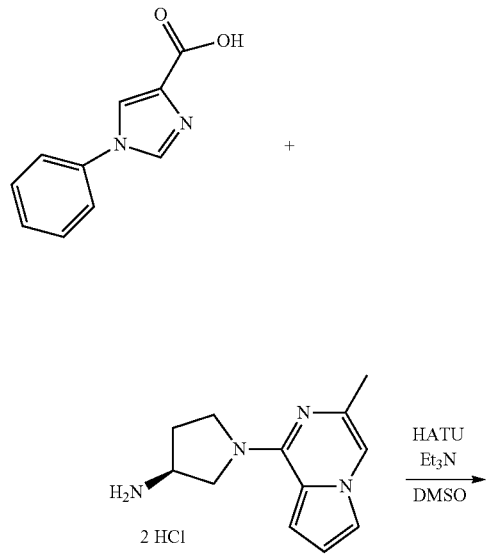

Example 143: Synthesis of 1-(4-chlorophenyl)-1H-pyrazole-3-carboxylic acid [1-(3-methyl-pyrrolo[1,2-a]pyrazin-1-yl)-pyrrolidin-3-yl]-amide

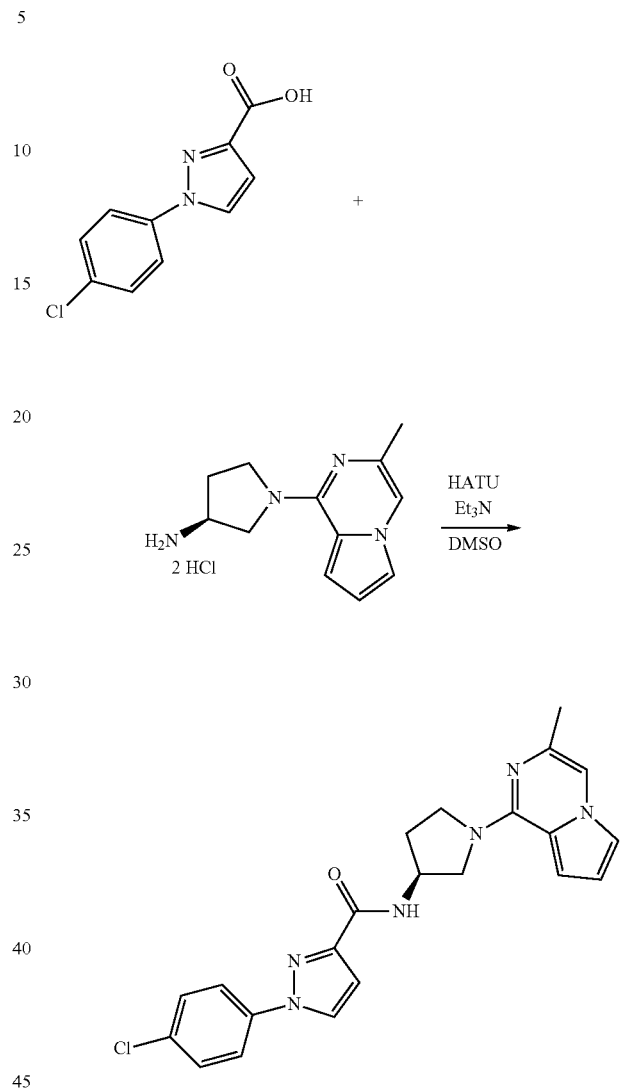

DMSO (0.5 mL) was added to a mixture of I-phenyl-1H-imidazole-4-carboxylic acid (32 mg, 0.17 mmol) and 1-(3-methylpyrrolo[1,2-a]pyrazin-1-yl)-pyrrolidin-3-ylamine dihydrochloride salt (50 mg, 0.17 mmol). To this was added triethylamine (0.095 mL, 0.68 mmol) followed by HATU (72 mg, 0.19 mmol). The mixture was allowed to stir for 30 min after which time it was diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN/H$_2$O+0.1% TFA). The combined product fractions were lyophilized to give the TFA salt of the product as a light brown solid (33 mg, 0.07 mmol, 39% yield). $^1$H NMR (400 MHz, CD$_3$OD) δ 8.23 (d, J=1.6 Hz, 1H), 8.15 (d, J=1.6 Hz, 1H), 7.67 (q, J=1.2 Hz, 1H), 7.62-7.45 (m, 6H), 6.88 (q, J=2.3 Hz, 1H), 5.00-4.80 (m, 1H), 4.60-3.60 (br, 4H), 2.58-2.48 (m, 1H), 2.48-2.38 (br, 1H), 2.30 (d, J=1.1 Hz, 3H); MS: (ES) m/z calculated for C$_{22}$H$_{22}$N$_6$O [M+H]$^+$ 387.2, found 387.

DMSO (0.5 mL) was added to a mixture of 1-(4-chlorophenyl)-1H-pyrazole-3-carboxylic acid (38 mg, 0.17 mmol) and 1-(3-methylpyrrolo[1,2-a]pyrazin-1-yl)-pyrrolidin-3-ylamine dihydrochloride salt (50 mg, 0.17 mmol). To this was added triethylamine (0.095 mL, 0.68 mmol) followed by HATU (72 mg, 0.19 mmol). The mixture was allowed to stir for 30 min after which time it was diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN:H$_2$O+0.1% TFA). The combined product fractions were lyophilized to give the TFA salt of the product as a white solid (50 mg, 0.09 mmol, 55% yield). $^1$H NMR (400 MHz, CD3OD) δ 8.78 (d, J=7.0 Hz, 0.5H), 8.33 (d, J=2.7 Hz, 1H), 7.87 (td, J=2.4, 9.0 Hz, 2H), 7.67 (q, J=1.2 Hz, 1H), 7.51 (td, J=3.1, 9.0 Hz, 4H), 6.98 (d, J=2.8 Hz, 1H), 6.87 (q, J=2.8, 1.9 Hz, 1H), 4.50-3.50 (br, 5H), 2.58-2.48 (min, 1H), 2.48-2.38 (br, 1H), 2.30 (d, J=0.7 Hz, 3H); MS: (ES) m z calculated for C$_{22}$H21ClN$_6$O [M+H]$^+$ 421.2, found 421.

Example 144: Synthesis of 2-pyrrolidin-1-yl-thiazole-4-carboxylic acid [1-(3-methyl-pyrrolo[1,2-a]pyrazin-1-yl)-pyrrolidin-3-yl]-amide

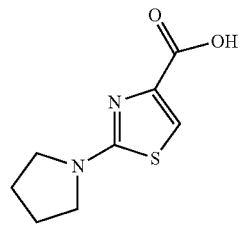

+

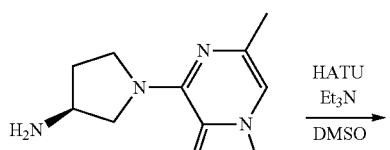

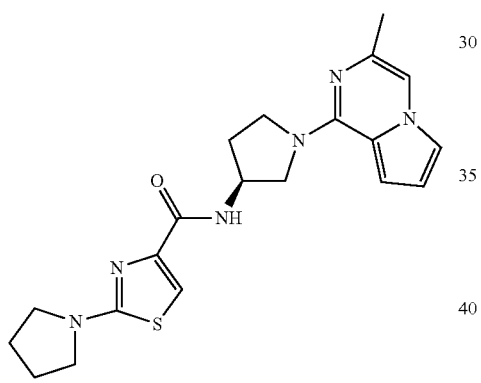

DMSO (0.5 mL) was added to a mixture of 2-pyrrolidin-1-yl-thiazole-4-carboxylic acid (34 mg, 0.17 mmol) and 1-(3-methylpyrrolo[1,2-a]pyrazin-1-yl)-pyrrolidin-3-ylamine dihydrochloride salt (50 mg, 0.17 mmol). To this was added triethylamine (0.095 mL, 0.68 mmol) followed by HATU (72 mg, 0.19 mmol). The mixture was allowed to stir for 30 min after which time it was diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN/H$_2$O+0.1% TFA). The combined product fractions were lyophilized to give the TFA salt of the product as a reddish solid (20 mg, 0.04 mmol, 23% yield). $^1$H NMR (400 MHz, CD3OD) δ 7.67 (dd, J=1.2, 2.3 Hz, 1H), 7.52 (d, J=4.6 Hz, 1H), 7.49 (s, 1H), 7.36 (s, 1H), 6.87 (dd, J=2.7, 4.7 Hz, 1H), 5.00-4.80 (m, 1H), 4.50-3.50 (br, 4H), 3.50-3.40 (m, 3H), 2.58-2.48 (m, 1H), 2.48-2.38 (br, 1H), 2.30 (d, J=0.7 Hz, 3H), 2.10-2.00 (m, 4H); MS: (ES) m/z calculated for C$_{20}$H$_{24}$N$_6$OS [M+H]$^+$ 397.2, found 397.

Example 145: Synthesis of 2-phenyloxazole-4-carboxylic acid [1-(3-methyl-pyrrolo[1,2-a]pyrazin-1-yl)-pyrrolidin-3-yl]-amide

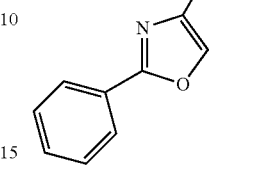

+

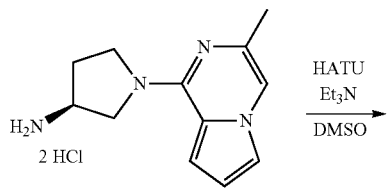

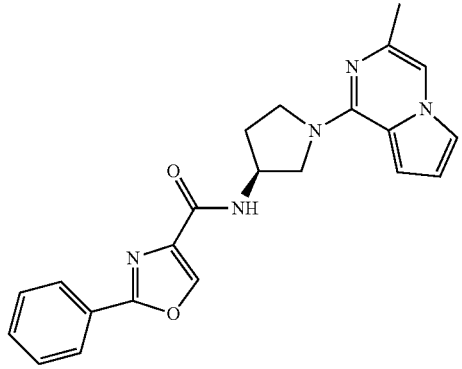

DMSO (0.5 mL) was added to a mixture of 2-phenyloxazole-4-carboxylic acid (32 mg, 0.17 mmol) and 1-(3-methyl-pyrrolo[1,2-a]pyrazin-1-yl)-pyrrolidin-3-ylamine dihydrochloride salt (50 mg, 0.17 mmol). To this was added triethylamine (0.095 mL, 0.68 mmol) followed by HATU (72 mg, 0.19 mmol). The mixture was allowed to stir for 30 min after which time it was diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN/H$_2$O+0.1% TFA). The combined product fractions were lyophilized to give the TFA salt of the product as a light brown solid (42 mg, 0.08 mmol, 49% yield). $^1$H NMR (400 MHz, CD3OD) d 8.74 (d, J=6.7 Hz, 1H), 8.49 (s, 1H), 8.10-8.06 (m, 2H), 7.68 (dd, J=1.2, 2.7 Hz, 1H), 7.57-7.50 (m, 4H), 6.88 (dd, J=2.7, 4.7 Hz, 1H), 5.00-4.80 (m, 1H), 4.50-3.50 (br, 4H), 2.58-2.48 (m, 1H), 2.48-2.38 (br, 1H), 2.31 (d, J=1.1 Hz, 3H); MS: (ES) m/z calculated for C$_{22}$H$_{21}$N$_5$O$_2$ [M+H]$^+$ 388.2, found 388.

Example 146: Synthesis of 2-phenylthiazole-4-carboxylic acid [1-(3-methyl-pyrrolo[1,2-a]pyrazin-1-yl)-pyrrolidin-3-yl]-amide

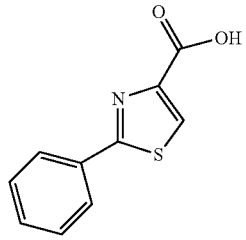

+

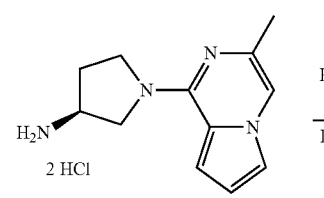

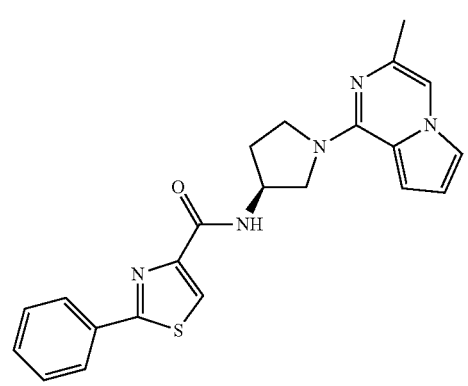

DMSO (0.5 mL) was added to a mixture of 2-phenylthiazole-4-carboxylic acid (43 mg, 0.21 mmol) and 1-(3-methylpyrrolo[1,2-a]pyrazin-1-yl)-pyrrolidin-3-ylamine dihydrochloride salt (60 mg, 0.21 mmol). To this was added triethylamine (0.117 mL, 0.84 mmol) followed by HATU (87 mg, 0.23 mmol). The mixture was allowed to stir for 30 min after which time it was diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN:H$_2$O+0.1% TFA). The combined product fractions were lyophilized to give the TFA salt of the product as a gray solid (30 mg, 0.06 mmol, 28% yield). $^1$H NMR (400 MHz, CD3OD) δ 8.87 (d, J=6.6 Hz, 1H), 8.26 (s, 1H), 8.06-8.03 (m, 2H), 7.68 (dd, J=1.2, 2.7 Hz, 1H), 7.54-7.45 (m, 5H), 6.88 (dd, J=2.4, 6.7 Hz, 1H), 5.00-4.80 (m, 1H), 4.50-3.50 (br, 4H), 2.60-2.40 (m, 2H), 2.31 (d, J=1.1 Hz, 3H); MS: (ES) m/z calculated for C$_{22}$H$_{21}$N$_5$OS [M+H]$^+$ 404.2, found 404.

Example 147: Synthesis of 1-(4-fluorophenyl)-1H-[1,2,4]triazole-3-carboxylic acid [1-(3-methyl-pyrrolo[1,2-a]pyrazin-1-yl)-pyrrolidin-3-yl]-amide

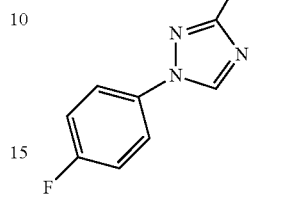

+

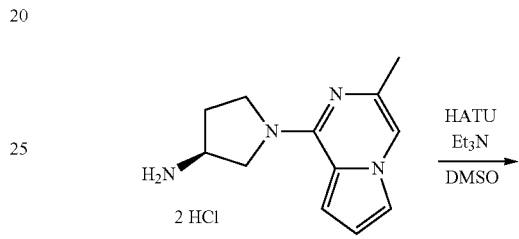

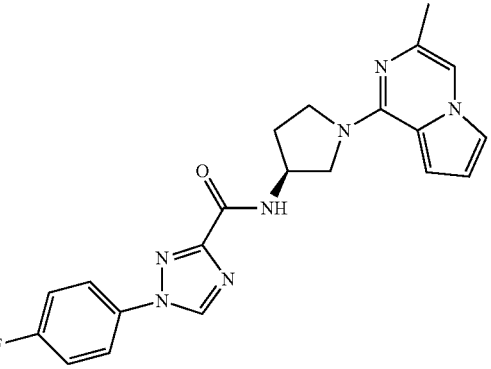

DMSO (0.5 mL) was added to a mixture of 1-(4-fluorophenyl)-1H-[1,2,4]triazole-3-carboxylic acid and 1-(3-methyl-pyrrolo[1,2-a]pyrazin-1-yl)-pyrrolidin-3-ylamine dihydrochloride salt (60 mg, 0.21 mmol). To this was added triethylamine (0.150 mL, 1.05 mmol) followed by HATU (87 mg, 0.23 mmol). The mixture was allowed to stir for 30 min after which time it was diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN/H$_2$O+0.1% TFA). The combined product fractions were lyophilized to give the TFA salt of the product as a yellow solid (11 mg, 0.02 mmol, 10% yield). $^1$H NMR (400 MHz, CD3OD) δ 9.10 (s, 1H), 9.07 (d, J=6.2 Hz, 1H), 7.92-7.88 (m, 2H), 7.68 (dd, J=1.2, 2.6 Hz, 1H), 7.53 (d, J=4.4 Hz, 1H), 7.50 (s, 1H), 7.34 (t, J=8.6 Hz, 2H), 6.89 (dd, J=2.4, 4.4 Hz, 1H), 5.00-4.80 (m, 1H), 4.50-3.50 (br, 4H), 2.60-2.40 (m, 2H), 2.31 (d, J=1.1 Hz, 3H); MS: (ES) m/z calculated for C$_{21}$H$_{20}$FN$_7$O [M+H]$^+$ 406.2, found 406.

Example 148: Synthesis of 6-methylquinazoline-2-carboxylic acid (1-pyrrolo[1,2-a]pyrazin-1-yl-pyrrolidin-3-yl)-amide

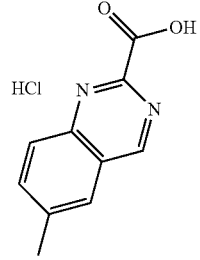

+

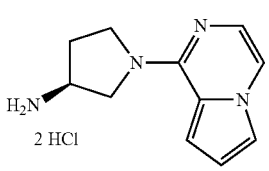

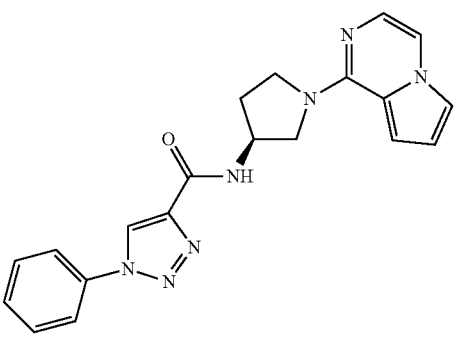

DMSO (0.5 mL) was added to a mixture of 6-methylquinazoline-2-carboxylic acid.HCl (27 mg, 0.12 mmol) and 1-pyrrolo[1,2-a]pyrazin-1-yl-pyrrolidin-3-ylamine dihydrochloride salt (33 mg, 0.12 mmol). To this was added triethylamine (0.084 mL, 0.60 mmol) followed by HATU (49 mg, 0.13 mmol). The mixture was allowed to stir for 30 min after which time it was diluted with dichloromethane (1.0 mL), washed with water (3×1.0 mL), dried over sodium sulfate, filtered, and concentrated under reduced pressure. The crude material was purified by reverse phase chromatography (10:90-95:5 MeCN:H$_2$O+0.1% TFA). The combined product fractions were lyophilized to give the TFA salt of the product as a reddish solid (13 mg, 0.03 mmol, 22% yield). $^1$H NMR (400 MHz, CD3OD) δ 9.55 (s, 1H), 8.11 (d, J=9.4 Hz, 1H), 7.98 (d, J=9.4 Hz, 2H), 7.53 (dd, J=1.2, 2.4 Hz, 1H), 7.55 (d, J=4.8 Hz, 1H), 7.50 (s, 1H), 6.89 (dd, J=2.3, 4.8 Hz, 1H), 5.00-4.80 (m, 1H), 4.50-3.50 (br, 4H), 2.63 (s, 3H), 2.60-2.40 (m, 2H), 2.31 (d, J=1.1 Hz, 3H); MS: (ES) m/z calculated for C$_{22}$H$_{22}$N$_6$O [M+H]$^+$ 387.2, found 387.

Example 149: Synthesis of 1-phenyl-1H-[1,2,3]triazole-4-carboxylic acid (1-pyrrolo[1,2-a]pyrazin-1-yl-pyrrolidin-3-yl)-amide

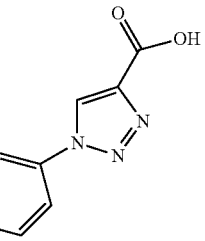

+

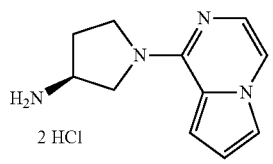

DMSO (0.5 mL) was added to a mixture of 1-phenyl-1H-[1,2,3]triazole-4-carboxylic acid (42 mg, 0.22 mmol) and 1-pyrrolo[1,2-a]pyrazin-1-yl-pyrrolidin-3-ylamine dihydrochloride salt (60 mg, 0.22 mmol). To this was added triethylamine (0.123 mL, 0.88 mmol) followed by HATU (91 mg, 0.24 mmol). The mixture was allowed to stir for 30 min after which time it was diluted with dichloromethane (1.0 mL), washed with water (3×1.0 mL), dried over sodium sulfate, filtered, and concentrated under reduced pressure. The crude material was purified by reverse phase HPLC (10:90-95:5 MeCN/H$_2$O+0.1% TFA). The combined product fractions were lyophilized to give the TFA salt of the product as a pale yellow solid (68 mg, 0.14 mmol, 63% yield). $^1$H NMR (400 MHz, CD3OD) δ 9.03 (d, J=6.7 Hz, 1H), 8.97 (s, 1H), 7.89 (d, J=8.2 Hz, 2H), 7.79 (dd, J=1.2, 2.7 Hz, 1H), 7.74 (d, J=5.9 Hz, 1H), 7.65-7.50 (m, 4H), 6.95 (dd, J=2.8, 4.7 Hz, 1H), 6.87 (d, J=5.9 Hz, 1H), 5.00-4.80 (m, 1H), 4.70-3.70 (br, 4H), 2.60-2.38 (m, 2H); MS: (ES) m/z calculated for C$_{20}$H$_{19}$N$_7$O [M+H]$^+$ 374.2. found 374.

Example 150

The compounds in the Table below were prepared as described above. Characterization data (NMR) is provided for each.

TABLE 1

Specific Examples

| Structure | Avg Bind IC50 (nM) | Avg Ser IC50 (nM) | NMR and MS Data |
|---|---|---|---|
| | | +++ | Compound 1.001: $^1$H NMR (400 MHz, CD$_3$OD) δ 8.95 (d, J = 6.3 Hz, 0.2 H), 8.05 (s, 1 H), 7.94 (d, J = 5.5 Hz, 1 H), 7.81 (s, 1 H), 7.64-7.59 (m, 2 H), 7.36-7.30 (m, 2 H), 7.17 (d, J = 5.4 Hz, 1 H), 5.00-4.85 (m, 1H), 4.80-3.65 (br, 4 H), 2.51 (s, 3 H), 2.60-2.38 (m, 2 H); MS: (ES) m/z calculated for C$_{20}$H$_{19}$FN$_8$O [M + H]$^+$ 407.2, found 407. |
| | | + | Compound 1.002: $^1$H NMR (400 MHz, CDCl$_3$) δ 8.64 (s, 1 H), 7.94 (d, J = 6.6 Hz, 2 H), 7.85 (d, J = 6.6 Hz, 2 H), 7.55 (s, 1 H), 7.50 (s, 1 H), 7.44 (d, J = 4.3 Hz, 1 H), 7.40-7.30 (m, 2 H), 5.00-4.85 (m, 1H), 4.50-4.35 (br, 1 H), 4.30-4.15 (br, 3 H), 2.50-2.38 (m, 1 H), 2.25-2.15 (m, 1 H); MS: (ES) m/z calculated for C$_{20}$H$_{17}$N$_9$O [M + H]$^+$ 400.2, found 400. |
| | | +++ | Compound 1.003: $^1$H NMR (400 MHz, CD$_3$OD) δ 9.10 (s, 1 H), 7.91-7.88 (m, 2 H), 7.79 (dd, J = 1.2, 2.8 Hz, 1 H), 7.74 (d, J = 5.9 Hz, 1 H), 7.59 (d, J = 4.3 Hz, 1 H), 7.34 (t, J = 8.6 Hz, 2 H), 6.95 (dd, J = 2.8, 4.7 Hz, 1 H), 6.86 (d, J = 5.5 Hz, 1 H), 5.00-4.85 (m, 1H), 4.80-3.65 (br, 4 H), 2.60-2.38 (m, 2 H); MS: (ES) m/z calculated for C$_{20}$H$_{18}$FN$_7$O [M + H]$^+$ 392.2, found 392. |
| | | ++ | Compound 1.004: $^1$H NMR (400 MHz, CD$_3$OD) δ 9.07 (s, 1 H), 8.05 (s, 1 H), 7.94 (d, J = 5.9 Hz, 1 H), 7.82 (s, 1 H), 7.74 (d, J = 8.6 Hz, 2 H), 7.38 (d, J = 8.6 Hz, 2 H), 7.17 (d, J = 5.4 Hz, 1 H), 5.00-3.65 (br, 5 H), 2.60-2.38 (m, 2 H), 2.41 (s, 1 H); MS: (ES) m/z calculated for C$_{20}$H$_{20}$N$_8$O [M + H]$^+$ 389.2, found 389. |

TABLE 1-continued

Specific Examples

| Structure | Avg Bind IC50 (nM) | Avg Ser IC50 (nM) | NMR and MS Data |
|---|---|---|---|
| 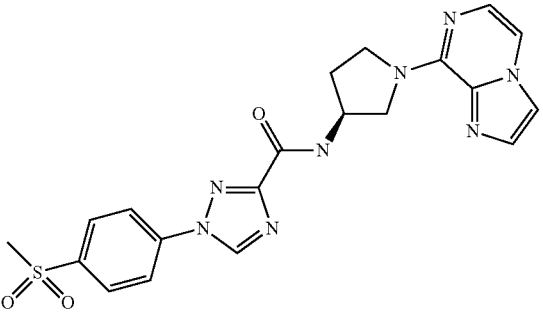 [SMILES: CS(=O)(=O)c1ccc(-n2cnc(C(=O)N[C@H]3CCN(c4nccn5ccnc45)C3)n2)cc1] | | + | Compound 1.005: $^1$H NMR (400 MHz, CD$^3$OD) δ 9.31 (s, 1 H), 9.15 (d, J = 7.0 Hz, 0.5 H), 8.20-8.10 (m, 4 H), 8.05 (s, 1 H), 7.95 (d, J = 5.4 Hz, 1 H), 7.82 (s, 1 H), 7.18 (d, J = 5.8 Hz, 1 H), 5.00-3.65 (br, 5 H), 3.18 (s, 3 H), 2.60-2.38 (m, 2 H); MS: (ES) m/z calculated for C$_{20}$H$_{20}$N$_8$O$_3$S [M + H]$^+$ 453.2, found 453. |
| 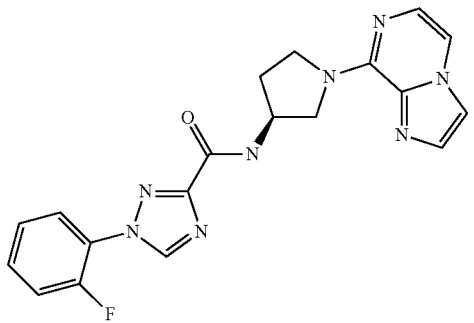 [SMILES: O=C(N[C@H]1CCN(c2nccn3ccnc23)C1)c1ncn(-c2ccccc2F)n1] | | +++ | Compound 1.006: $^1$H NMR (400 MHz, CD$_3$OD) δ 8.96 (d, J = 2.7 Hz, 1 H), 8.05 (s, 1 H), 7.95-7.82 (m, 3 H), 7.56-7.38 (m, 3 H), 7.17 (d, J = 5.5 Hz, 1 H), 5.00-3.65 (br, 5 H), 2.60-2.38 (m, 2 H); MS: (ES) m/z calculaled for C$_{19}$H$_{17}$FN$_8$O [M + H]$^+$ 393.2, found 393. |
| 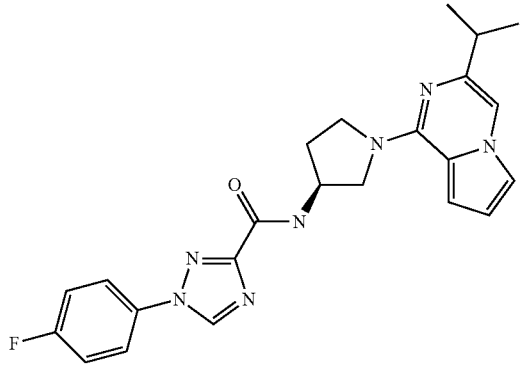 [SMILES: CC(C)c1cn2cccc2c(N2CC[C@H](NC(=O)c3ncn(-c4ccc(F)cc4)n3)C2)n1] | | ++ | Compound 1.007: $^1$H NMR (400 MHz, CD$_3$OD) δ 9.10 (s, 1 H), 7.92 (dd, J = 4.7, 7.0 Hz, 2 H), 7.73 (s, 1 H), 7.57 (s, 1 H), 7.54 (d, J = 4.3 Hz, 1 H), 7.35 (t, J = 8.6 Hz, 2 H), 6.91 (dd, J = 2.7, 4.3 Hz, 1 H), 5.00-4.85 (m, 1H), 4.60-3.65 (br, 4 H), 3.05-2.95 (m, 1 H), 2.60-2.38 (m, 2 H), 1.35 (d, J = 7.0 Hz, 6 H); MS: (ES) m/z calculated for C$_{23}$H$_{24}$FN$_7$O [M + H]$^+$ 434.2, found 434. |
| 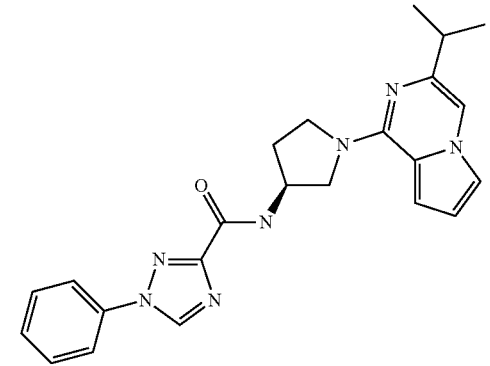 [SMILES: CC(C)c1cn2cccc2c(N2CC[C@H](NC(=O)c3ncn(-c4ccccc4)n3)C2)n1] | | ++ | Compound 1.008: $^1$H NMR (400 MHz, CD$_3$OD) δ 9.14 (s, 1 H), 7.89 (d, J = 7.4 Hz, 2 H), 7.73 (s, 1 H), 7.60-7.46 (m, 5 H), 6.90 (dd, J = 2.7, 4.3 Hz, 1 H), 5.00-4.80 (m, 1H), 4.60-3.85 (br, 4 H), 3.05-2.95 (m, 1 H), 2.60-2.38 (m, 2 H), 1.35 (d, J = 6.6 Hz, 6 H); MS; (ES) m/z calculated for C$_{23}$H$_{25}$N$_7$O [M + H]$^+$ 416.2, found 416. |

TABLE 1-continued

| Structure | Avg Bind IC50 (nM) | Avg Ser IC50 (nM) | NMR and MS Data |
|---|---|---|---|
| | | +++ | Compound 1.009: ¹H NMR (400 MHz, CD³OD) δ 7.72 (d, J = 2.4 Hz, 1 H), 7.56 (s, 1 H), 7.52 (d, J = 4.3 Hz, 1 H), 7.41 (s, 1 H), 6.90-6.87 (m, 1 H), 4.95-4.70 (m, 2 H), 4.60-3.80 (br, 4 H), 3.95-3.80 (m, 2 H), 3.36-3.20 (m, 2 H), 3.05-2.95 (m, 1 H), 2.60-2.30 (m, 2 H), 1.98-1.90 (m, 2H), 1.62-1.55 (m, 2H), 1.35 (d, J = 6.6 Hz, 6H); MS: (ES) m/z calculated for $C_{23}H_{30}N_6O_2S$ [M + H]⁺ 455.2, found 455. |
| | | ++ | Compound 1.010: ¹H NMR (400 MHz, DMSO) δ 9.31 (s, 1 H), 8.92 (d, J = 5.9 Hz, 1 H), 7.92-7.85 (m, 3 H), 7.76 (s, 1 H), 7.53 (s, 1 H), 7.41 (t, J = 9.0 Hz, 2 H), 7.21 (d, J = 4.7 Hz, 1 H), 4.65-4.50 (m, 1 H), 4.48-3.65 (br, 4 H), 2.30-2.05 (m, 2 H); MS: (ES) m/z calculated for $C_{19}H_{17}FN_8O$ [M + H]⁺ 393.2, found 393. |
| | | + | Compound 1.011: ¹H NMR (400 MHz, CD₃OD) δ 8.05 (s, 1 H), 8.02 (d, J = 9.8 Hz, 1 H), 7.94 (d, J = 5.5 Hz, 1 H), 7.81 (s, 1 H), 7.5 (d, J = 9.8 Hz, 1 H), 7.18 (d, J = 5.8 Hz, 1 H), 4.98-4.80 (m, 1 H), 4.80-3.80 (br, 4 H), 4.20-4.10 (m, 2 H), 4.00-3.90 (m, 1 H), 3.55-3.45 (m, 2 H), 2.60-2.35 (m, 2 H), 2.05-1.95 (m, 2 H), 1.68-1.55 (m, 2 H); MS: (ES) m/z calculated for $C_{20}H_{24}N_8O_2$ [M + H]⁺ 409.2, found 409. |
| | | +++ | Compound 1.012: ¹H NMR (400 MHz, CD₃OD) δ 7.70 (d, J = 2.4 Hz, 1 H), 7.52-7.50 (m, 2 H), 7.41 (s, 1 H), 6.89 (dd, J = 2.4, 4.3 Hz, 1 H), 4.95-4.78 (m, 2 H), 4.60-3.70 (br, 4 H), 3.95-3.80 (m, 2 H), 3.36-3.20 (m, 2 H), 2.68 (q, J = 7.4 Hz, 2 H), 2.60-2.30 (m, 2 H), 1.98-1.90 (m, 2 H), 1.62-1.55 (m, 2 H), 1.33 (t, J = 7.4 Hz, 3 H); MS: (ES) m/z calculated for $C_{22}H_{28}N_6O_2S$ [M + H]⁺ 441.2, found 441. |

TABLE 1-continued

Specific Examples

| Structure | Avg Bind IC50 (nM) | Avg Ser IC50 (nM) | NMR and MS Data |
|---|---|---|---|
| | | +++ | Compound 1.013: ¹H NMR (400 MHz, CD₃OD) δ 9.10 (s, 1 H), 7.92-7.88 (m, 2 H), 7.71 (s, 1 H), 7.53 (s, 2 H), 7.35 (t, J = 8.8 Hz, 2 H), 6.89 (dd, J = 2.4, 4.7 Hz, 1 H), 4.95-4.80 (m, 1 H), 4.78-3.80 (br, 4 H), 2.68 (q, J = 7.4 Hz, 2 H), 2.60-2.35 (m, 2 H), 1.33 (t, J = 7.4 Hz, 3 H); MS: (ES) m/z calculated for $C_{22}H_{22}FN_7O$ [M + H]⁺ 420.2, found 420. |
| | | +++ | Compound 1.014: ¹H NMR (400 MHz, CD₃OD) δ 9.14 (s, 1 H), 8.05 (s, 1 H), 7.96-7.88 (m, 2 H), 7.81 (s, 1 H), 7.75-7.71 (m, 1 H), 7.52 (q, J = 8.6 Hz, 1 H), 7.19 (d, J = 5.5 Hz, 1 H), 4.98-4.80 (m, 1 H), 4.80-3.80 (br, 4 H), 2.62-2.40 (m, 2 H); MS: (ES) m/z calculated for $C_{19}H_{16}F_2N_8O$ [M + H]⁺ 411.2, found 411. |
| | | +++ | Compound 1.015: ¹H NMR (400 MHz, CD₃OD) δ 9.14 (s, 1 H), 9.05 (d, J = 6.7 Hz, 1 H), 7.88 (d, J = 7.4 Hz, 2 H), 7.71 (s, 1 H), 7.60-7.46 (m, 5 H), 6.89 (dd, J = 2.8, 4.7 Hz, 1 H), 4.95-4.80 (m, 1 H), 4.78-3.80 (br, 4 H), 2.68 (q, J = 7.4 Hz, 2 H), 2.60-2.40 (m, 2 H), 1.33 (t, J = 7.4 Hz, 3 H); MS: (ES) m/z calculated for $C_{22}H_{23}N_7O$ [M + H]⁺ 402.2, found 402. |
| | | +++ | Compound 1.016: ¹H NMR (400 MHz, DMSO) δ 9.45 (s, 1 H), 8.95 (d, J = 7.0 Hz, 1 H), 7.87-7.75 (m, 4 H), 7.65 (q, J = 6.2 Hz, 1 H), 7.50 (s, 1 H), 7.31 (t, J = 2.4 Hz, 1 H), 7.26 (d, J = 4.3 Hz, 1 H), 4.65-4.55 (m, 1 H), 4.40-3.75 (br, 4 H), 2.30-2.04 (m, 2 H); MS: (ES) m/z calculated for $C_{19}H_{17}FN_8O$ [M + H]⁺ 393.2, found 393. |

TABLE 1-continued

Specific Examples

| Structure | Avg Bind IC50 (nM) | Avg Ser IC50 (nM) | NMR and MS Data |
|---|---|---|---|
| | | +++ | Compound 1.017: ¹H NMR (400 MHz, CD₃OD) δ 9.03 (d, J = 6.7 Hz, 1 H), 8.97 (s, 1 H), 7.89 (d, J = 8.2 Hz, 2 H), 7.79 (dd, J = 1.2, 2.7 Hz, 1 H), 7.74 (d, J = 5.9 Hz, 1 H), 7.65-7.50 (m, 4 H), 6.95 (dd, J = 2.8, 4.7 Hz, 1 H), 6.87 (d, J = 5.9 Hz, 1 H), 5.00-4.80 (m, 1H), 4.70-3.70 (br, 4 H), 2.60-2.38 (m, 2 H); MS: (ES) m/z calculated for $C_{20}H_{19}N_7O$ [M + H]⁺ 374.2, found 374. |
| | | + | Compound 1.018: ¹H NMR (400 MHz, CD₃OD) δ 9.13 (s, 1 H), 8.16 (d, J = 2.4 Hz, 1 H), 8.09 (d, J = 5.8 Hz, 1 H), 7.86 (d, J = 7.8 Hz, 2 H), 7.60-7.46 (m, 4 H), 7.19 (d, J = 5.5 Hz, 1 H), 4.95-4.80 (m, 1 H), 4.78-3.80 (br, 4 H), 2.62-2.40 (m, 2 H); MS: (ES) m/z calculated for $C_{19}H_{18}N_8O$ [M + H]⁺ 375.2, found 375. |
| | | +++ | Compound 1.019: ¹H NMR (400 MHz, CD₃OD) δ 9.55 (s, 1 H), 8.11 (d, J = 9.4 Hz, 1 H), 7.98 (d, J = 9.4 Hz, 2 H), 7.53 (dd, J = 1.2, 2.4 Hz, 1 H), 7.55 (d, J = 4.8 Hz, 1 H), 7.50 (s, 1 H), 6.89 (dd, J = 2.3, 4.8 Hz, 1 H), 5.00-4.80 (m, 1H), 4.50-3.50 (br, 4 H), 2.63 (s, 3 H), 2.60-2.40 (m, 2 H), 2.31 (d, J = 1.1 Hz, 3 H); MS: (ES) m/z calculated for $C_{22}H_{22}N_6O$ [M + H]⁺ 387.2, found 387. |
| | | +++ | Compound 1.020: ¹H NMR (400 MHz, CD₃OD) δ 9.10 (s, 1 H), 9.07 (d, J = 6.2 Hz, 1 H), 7.92-7.88 (m, 2 H), 7.68 (dd, J = 1.2, 2.6 Hz, 1 H), 7.53 (d, J = 4.4 Hz, 1 H), 7.50 (s, 1 H), 7.34 (t, J = 8.6 Hz, 2 H), 6.89 (dd, J = 2.4, 4.4 Hz, 1 H), 5.00-4.80 (m, 1H), 4.50-3.50 (br, 4 H), 2.60-2.40 (m, 2 H), 2.31 (d, J = 1.1 Hz, 3 H); MS: (ES) m/z calculated for $C_{21}H_{30}FN_7O$ [M + H]⁺ 406.2, found 406. |
| | | +++ | Compound 1.021: ¹H NMR (400 MHz, DMSO) δ 9.39 (d, J = 7.0 Hz, 1 H), 8.16 (d, J = 7.0 Hz, 2 H), 7.73 (t, J = 7.4 Hz, 1 H), 7.66 (t, J = 7.9 Hz, 2 H), 7.41 (s, 1 H), 7.37 (s, 1 H), 6.77 (d, J = 4.3 Hz, 1 H), 6.56 (dd, J = 2.8, 4.3 Hz, 1 H), 4.63-4.50 (m, 1 H), 4.10-3.75 (br, 4 H), 2.30-2.04 (m, 2 H), 2.07 (s, 3 H); MS: (ES) m/z calculated for $C_{21}H_{20}N_6O_2$ [M + H]⁺ 389.2, found 389. |

TABLE 1-continued

Specific Examples

| Structure | Avg Bind IC50 (nM) | Avg Ser IC50 (nM) | NMR and MS Data |
|---|---|---|---|
| | | +++ | Compound 1.022: $^1$H NMR (400 MHz, DMSO) δ 9.42 (s, 1 H), 8.91 (d, J = 6.6 Hz, 1 H), 7.95 (d, J = 7.0 Hz, 2 H), 7.67 (d, J = 7.0 Hz, 2 H), 7.40 (m, 2 H), 6.76 (d, J = 4.3 Hz, 1 H), 6.55 (dd, J = 2.2, 4.3 Hz, 1 H), 4.63-4.50 (m, 1 H), 4.10-3.75 (m, 4 H), 2.30-2.04 (m, 2 H), 2.07 (s, 3 H); MS: (ES) m/z calculated for $C_{21}H_{20}ClN_7O$ [M + H]$^+$ 422.2, found 422. |
| | | +++ | Compound 1.023: $^1$H NMR (400 MHz, CD$_3$OD) δ 8.87 (d, J = 6.6 Hz, 1 H), 8.26 (s, 1 H), 8.06-8.03 (m, 2 H), 7.68 (dd, J = 1.2, 2.7 Hz, 1 H), 7.54-7.45 (m, 5 H), 6.88 (dd, J = 2.4, 6.7 Hz, 1 H), 5.00-4.80 (m, 1H), 4.50-3.50 (br, 4 H), 2.60-2.40 (m, 2 H), 2.31 (d, J = 1.1 Hz, 3 H); MS: (ES) m/z calculated for $C_{22}H_{21}N_5OS$ [M + H]$^+$ 404.2, found 404. |
| | | +++ | Compound 1.024: $^1$H NMR (400 MHz, CD$_3$OD) δ 8.74 (d, J = 6.7 Hz, 1 H), 8.49 (s, 1 H), 8.10-8.06 (m, 2 H), 7.68 (dd, J = 1.2, 2.7 Hz, 1 H), 7.57-7.50 (m, 4 H), 6.88 (dd, J = 2.7, 4.7 Hz, 1 H), 5.00-4.80 (m, 1H), 4.50-3.50 (br, 4 H), 2.58-2.48 (m, 1 H), 2.48-2.38 (br, 1 H), 2.31 (d, J = 1.1 Hz, 3 H); MS: (ES) m/z calculated for $C_{22}H_{21}N_5O_2$ [M + H]$^+$ 388.2, found 388. |
| | | +++ | Compound 1.025: $^1$H NMR (400 MHz, CD$_3$OD) δ 7.67 (dd, J = 1.2, 2.3 Hz, 1 H), 7.52 (d, J = 4.6 Hz, 1 H), 7.49 (s, 1 H), 7.36 (s, 1 H), 6.87 (dd, J = 2.7, 4.7 Hz, 1 H), 5.00-4.80 (m, 1H), 4.50-3.50 (br, 4 H), 3.50-3.40 (m, 3H), 2.58-2.48 (m, 1 H), 2.48-2.38 (br, 1 H), 2.30 (d, J = 0.7 Hz, 3 H), 2.10-2.00 (m, 4H); MS: (ES) m/z calculated for $C_{20}H_{24}N_6OS$ [M + H]$^+$ 397.2, found 397. |
| | | +++ | Compound 1.026: $^1$H NMR (400 MHz, DMSO) δ 8.03 (d, J = 7.1 Hz, 1 H), 7.85 (d, J = 1.2 Hz, 1 H), 7.74 (d, J = 4.7 Hz, 1 H), 7.48 (d, J = 0.8 Hz, 1 H), 7.41 (s, 1 H), 7.23 (d, J = 4.3 Hz, 1 H), 4.53-4.40 (m, 2 H), 4.40-3.80 (br, 7 H), 2.40-2.30 (m, 2 H), 2.25-2.10 (m, 1 H), 2.10-2.00 (m, 1 H); MS: (ES) m/z calculated for $C_{17}H_{19}N_7OS$ [M + H]$^+$ 370.2, found 370. |

TABLE 1-continued

Specific Examples

| Structure | Avg Bind IC50 (nM) | Avg Ser IC50 (nM) | NMR and MS Data |
|---|---|---|---|
| | | ++ | Compound 1.027: $^1$H NMR (400 MHz, CDCl$_3$) δ 8.54 (s, 1 H), 7.74 (td, J = 1.1, 7.5 Hz, 2 H), 7.56-7.48 (m, 4 H), 7.47-7.40 (m, 2H), 7.37 (d, J = 8.2 Hz, 1 H), 7.33 (d, J = 4.3 Hz, 1 H), 5.00-4.80 (m, 1H), 4.50-4.35 (br, 1 H), 4.30-4.15 (br, 3 H), 3.45-3.30 (m, 1H), 2.90-2.75 (m, 1 H), 2.50-2.38 (m, 1 H), 2.25-2.15 (m, 1 H); MS: (ES) m/z calculated for C$_{19}$H$_{18}$N$_8$O [M + H]$^+$ 375.2, found 375. |
| | | +++ | Compound 1.028: $^1$H NMR (400 MHz, CD$_3$OD) δ 8.83 (s, 2 H), 7.78 (q, J = 1.1 Hz, 1 H), 7.73 (d, J = 5.8 Hz, 1 H), 7.57 (d, J = 3.9 Hz, 1 H), 6.94 (dd, J = 2.7, 4.7 Hz, 1 H), 6.86 (d, J = 5.9 Hz, 1 H), 5.00-4.80 (m, 1H), 4.50-3.50 (br, 4 H), 3.20-3.10 (m, 1H), 2.60-2.48 (m, 1 H), 2.48-2.38 (br, 1 H), 2 22-2.12 (m, 2 H), 1.95-1.60 (m, 6 H); MS: (ES) m/z calculated for C$_{21}$H$_{24}$N$_6$O [M + H]$^+$ 377.2, found 377. |
| | | +++ | Compound 1.029: $^1$H NMR (400 MHz, CD$_3$OD) δ 8.78 (d, J = 7.0 Hz, 0.5 H), 8.33 (d, J = 2.7 Hz, 1 H), 7.87 (td, J = 2.4, 9.0 Hz, 2 H), 7.67 (q, J = 1.2 Hz, 1 H), 7.51 (td, J = 3.1, 9.0 Hz, 4 H), 6.98 (d, J = 2.8 Hz, 1 H), 6.87 (q, J = 2.8, 1.9 Hz, 1 H), 4.50-3.50 (br, 5 H), 2.58-2.48 (m, 1 H), 2.48-2.38 (br, 1 H), 2.30 (d, J = 0.7 Hz, 3 H); MS: (ES) m/z calculated for C$_{22}$H$_{21}$ClN$_6$O [M + H]$^+$ 421.2, found 421. |
| | | +++ | Compound 1.030: $^1$H NMR (400 MHz, CD$_3$OD) δ 8.23 (d, J = 1.6 Hz, 1 H), 8.15 (d, J = 1.6 Hz, 1 H), 7.67 (q, J = 1.2 Hz, 1 H), 7.62-7.45 (m, 6 H), 6.88 (q; J = 2.3 Hz, 1 H), 5.00-4.80 (m, 1H), 4.60-3.60 (br, 4 H), 2.58-2.48 (m, 1 H), 2.48-2.38 (br, 1 H), 2.30 (d, J = 1.1 Hz, 3 H); MS: (ES) m/z calculated for C$_{22}$H$_{22}$N$_6$O [M + H]$^+$ 387.2, found 387. |
| | | +++ | Compound 1.031: $^1$H NMR (400 MHz, DMSO) δ 8.35 (d, J = 1.2 Hz, 1 H), 8.27 (d, 1.6 Hz, 1 H), 8.24 (d, J = 7.4 Hz, 1 H), 7.77 (d, J = 0.8 Hz, 1 H), 7.73 (t, J = 1.2 Hz, 1 H), 7.71 (s, 1 H), 7.57 (s, 1 H), 7.52 (t, J = 12.8 Hz, 2 H), 7.44 (d, J = 0.8 Hz, 1 H), 7.38 (t, J = 7.4 Hz, 1 H), 4.60-4.50 (m, 1 H), 4.40-3.80 (br, 4 H), 2.22-2.00 (m, 5 H); MS: (ES) m/z calculated for C$_{21}$H$_{21}$N$_7$O [M + H]$^+$ 388.2, found 388. |

TABLE 1-continued

Specific Examples

| Structure | Avg Bind IC50 (nM) | Avg Ser IC50 (nM) | NMR and MS Data |
|---|---|---|---|
| | | +++ | Compound 1.032: $^1$H NMR (400 MHz, DMSO) δ 8.90 (d, J = 7.1 Hz, 1 H), 7.90 (d, J = 8.2 Hz, 2 H), 7.77 (d, J = 1.2 Hz, 1 H), 7 58 (t, J = 5 8 Hz, 3 H), 7.44 (t, J = 8.2 Hz, 2 H), 4.63-4.50 (m, 1 H), 4.40-3.80 (br, 4 H), 2.30-2.05 (m, 5 H); MS: (ES) m/z calculated for $C_{20}H_{20}N_8O$ [M + H]$^+$ 389.2, found 389. |
| | | ++ | Compound 1.033: $^1$H NMR (400 MHz, CD$_3$OD) δ 8.93 (s, 2 H), 7.79 (dd, J = 1.2, 2.7 Hz, 1 H), 7 74 (d, J = 5.9 Hz, 1 H), 7.58 (d, J = 3.5 Hz, 1 H), 6.94 (dd, J = 2.7, 5.7 Hz, 1 H), 6.87 (d, J = 5.9 Hz, 1 H), 5.02-4.95 (q, J = 6.6 Hz, 1 H), 4.80-3.60 (br, 5 H), 2.62-2.38 (m, 2 H), 1.53 (d, J = 6.6 Hz, 3 H); MS: (ES) m/z calculated for $C_{18}H_{20}N_6O_2$ [M + H]$^+$ 353.2, found 353. |
| | | +++ | Compound 1.034: $^1$H NMR (400 MHz, DMSO) δ 8.23 (d, J = 7.0 Hz, 1 H), 8.17 (s, 1 H), 8.00 (d, J = 5.5 Hz, 1 H), 7.81 (s, 1 H), 7.33 (s, 1 H), 7.27 (d, J = 5.5 Hz, 1 H), 4.70-4.58 (m, 1 H), 4.57-3.60 (br, 8 H), 2.40-2.05 (m, 2 H), 2.00-1.80 (m, 4 H); MS: (ES) m/z calculated for $C_{18}H_{21}N_7OS$ [M + H]$^+$ 384.2, found 384. |
| | | +++ | Compound 1.035: $^1$H NMR (400 MHz, DMSO) δ 9.20 (s, 1 H), 8.38 (d, J = 7.4 Hz, 1 H), 8.35 (d, J = 1.2 Hz, 1 H), 8.28 (d, J = 1.2 Hz, 1 H), 7.74 (m, 3H), 7.52 (t, J = 7.9 Hz, 2 H), 7.38 (t, J = 2.4 Hz, 1 H), 7.28 (d, J = 4.3 Hz, 1 H), 4.70-4.50 (m, 1 H), 4.40-3.80 (br, 4 H), 2.30-2.05 (m, 2 H); MS: (ES) m/z calculated for $C_{19}H_{18}N_8O$ [M + H]$^+$ 375.2, found 375. |
| | | +++ | Compound 1.036: $^1$H NMR (400 MHz, DMSO) δ 8.35 (d, J = 1.2 Hz, 1 H), 8.27 (d, J = 1.2 Hz, 1 H), 8.26 (d, J = 7.4 Hz, 1 H), 7.87 (d, J = 0.8 Hz, 1 H), 7.76-7.70 (m, 3 H), 7.56-7.48 (m, 3 H), 7.38 (t, J = 7.8 Hz, 1 H), 7.25 (d, J = 4.7 Hz, 1 H), 4.70-4.50 (m, 1 H), 4.40-3.80 (br, 4 H), 2.30-2.05 (m, 2 H); MS: (ES) m/z calculated for $C_{20}H_{19}N_7O$ [M + H]$^+$ 374.2, found 374. |

| Structure | Avg Bind IC50 (nM) | Avg Ser IC50 (nM) | NMR and MS Data |
|---|---|---|---|
| | | +++ | Compound 1.037: ¹H NMR (400 MHz, CD₃OD) δ 7.37 (s, 1 H), 7.28 (q, J = 1.2 Hz, 1 H), 7.25 (s, 1 H), 6.86 (d, J = 4.3 Hz, 1 H), 6.57 (dd, J = 2.7, 4.3 Hz, 1 H), 5.48 (s, 2 H), 4.70-4.60 (m, 1 H), 4.22-3.78 (m, 8 H), 3.28-3.10 (m, 1 H), 2.40-2.28 (m, 1 H), 2.22-2.12 (m, 4 H), 1.96-1.88 (m, 2 H); 1.62-1.52 (m, 2 H); MS: (ES) m/z calculated for $C_{21}H_{26}N_6O_2S$ [M + H]⁺ 427.2, found 427. |
| | | +++ | Compound 1.038: ¹H NMR (400 MHz, DMSO) δ 7.96 (d, J = 7.4 Hz, 1 H), 7.53 (d, J = 4.7 Hz, 1 H), 7.50 (q, J = 1.2 Hz, 1 H), 7.31 (s, 1 H), 6.94 (d, J = 4.7 Hz, 1 H), 6.82 (d, J = 4.3 Hz, 1 H), 6.61 (q, J = 2.3 Hz, 1 H), 4.60-4.46 (m, 1 H), 4.10-4.00 (m, 1 H), 3.98-3.84 (m, 1 H), 3.84-3.70 (m, 2 H), 3.38 (t, J = 6.6 Hz, 4 H), 2.30-2.00 (m, 2 H), 2.00-1.92 (m, 4 H); MS: (ES) m/z calculated for $C_{19}H_{22}N_6OS$ [M + H]⁺ 383.2, found 383. |
| | | +++ | Compound 1.039; ¹H NMR (400 MHz, CD₃OD) δ 8.23 (d, J = 1.1 Hz, 1 H), 8.15 (d, J = 1.6 Hz, 1 H), 7.79 (dd, J + 1.2, 2.8 Hz, 1 H), 7.73 (d, J = 5.5 Hz, 1 H), 7.64-7.52 (m, 5 H), 7.50-7.42 (m, 1 H), 6.94 (dd, J = 2.3, 4.3 Hz, 1 H), 6.86 (d, J = 5.5 Hz, 1 H), 5.00-4.80 (m, 1H), 4.50-3.50 (br, 4 H), 2.58-2.48 (m, 1 H), 2.48-2.35 (br, 1 H); MS: (ES) m/z calculated for $C_{21}H_{20}N_6O$ [M + H]⁺ 373.2, found 373. |
| | | +++ | Compound 1.040: ¹H NMR (400 MHz, CD₃OD) δ 9.14 (s, 1 H), 7.88 (td, J = 1.2, 6.2 Hz, 2 H), 7.68 (q, J = 1.2 Hz, 1 H), 7.62-7.44 (m, 6 H), 6.88 (dd, J = 2.3, 4.3 Hz, 1 H), 5.00-4.80 (m, 1H), 4.60-3.60 (br, 4 H), 2.60-2.38 (m, 2 H), 2.30 (d, J = 1.1 Hz, 3 H); MS: (ES) m/z calculated for $C_{21}H_{21}N_7O$ [M + H]⁺ 388.2, found 388. |
| | | +++ | Compound 1.041: ¹H NMR (400 MHz, CD₃OD) δ 8.75 (d, J = 7.0 Hz, 1 H), 8.28 (d, J = 2.7 Hz, 1 H), 7.88 (m, 2 H), 7.68 (q, J = 1.2 Hz, 1 H), 7.52 (d, J = 4.3 Hz, 1 H), 7.49 (s, 1 H), 7.27-7.22 (m, 2 H), 6.96 (d, J = 2.4 Hz, 1 H), 6.87 (dd, J = 2.7, 4.3 Hz, 1 H), 5.00-4.80 (m, 1H), 4.60-3.60 (br, 4 H), 2.60-2.38 (m, 2 H), 2.30 (d, J = 1.1 Hz, 3 H); MS: (ES) m/z calculated for $C_{22}H_{21}FN_6O$ [M + H]⁺ 405.2, found 405. |

TABLE 1-continued

Specific Examples

| Structure | Avg Bind IC50 (nM) | Avg Ser IC50 (nM) | NMR and MS Data |
|---|---|---|---|
| | | +++ | Compound 1.042: ¹H NMR (400 MHz, CD₃OD) δ 8.30 (d, J = 2.4 Hz, 1 H), 7.88 (m, 2 H), 7.78 (q, J = 1.2 Hz, 1 H), 7.72 (d, J = 5.9 Hz, 1 H), 7.55 (d, J = 3.9 Hz, 1 H), 7.30-7.22 (m, 2 H), 6.99 (d, J = 2.7 Hz, 1 H), 6.93 (dd, J = 2.7, 4.3 Hz, 1 H), 6.83 (d, J = 5.5 Hz, 1 H), 4.60-3.80 (br, 4 H), 2.90-2.80 (m, 1 H), 2.78-2.68 (m, 1 H); MS: (ES) m/z calculaled for $C_{22}H_{20}FN_7O_2$ [M + H]⁺ 434.2, found 434. |
| | | + | Compound 1.043: ¹H NMR (400 MHz, CD₃OD) δ 8.29 (d, J = 2.7 Hz, 1 H), 7.89 (m, 2H), 7.78 (dd, J = 1.2, 2.7 Hz, 1 H), 7.73 (d, J = 5.4 Hz, 1 H), 7.55 (d, J = 3.5 Hz, 1 H), 7.30-7.22 (m, 2 H), 6.97 (d, J = 2.7 Hz, 1 H), 6.94 (dd, J = 2.8, 4.3 Hz, 1 H), 6.84 (d, J = 5.5 Hz, 1 H), 4.60-3.80 (br, 4 H), 2.90-2.82 (m, 1 H), 2.80-2.70 (m, 1 H); MS: (ES) m/z calculated for $C_{22}H_{19}FN_6O_3$ [M + H]⁺ 435.2, found 435. |
| | | +++ | Compound 1.044: ¹H NMR (400 MHz, DMSO) δ 9.62 (s, 1 H), 9.31 (t, J = 3.9 Hz, 1 H), 8.08-8.00 (m, 2 H), 8.00-7.92 (m, 1 H), 7.85 (d, J = 5.1 Hz, 1 H), 7.29 (d, J = 5.0 Hz, 1 H), 4.82-4.70 (m, 1H), 4.70-3.60 (br, 4 H), 2.56 (s, 3H), 2.40-2.20 (br, 2 H); MS: (ES) m/z calculated for $C_{19}H_{18}N_8O$ [M + H]⁺ 375.2, found 375. |
| | | +++ | Compound 1.045: ¹H NMR (400 MHz, CD₃OD) δ 8.33 (s, 1 H), 8.04 (d, J = 1.2 Hz, 1 H), 7.92 (d, J = 5.5 Hz, 1 H), 7.81 (d, J = 1.2 Hz, 1 H), 7.73 (dd, J = 1.5, 7.8 Hz, 1 H), 7.42-7.26 (m, 3 H), 7.16 (d, J = 5.5 Hz, 1 H), 5.00-4.80 (m, 1H), 4.60-3.60 (br, 4 H), 2.60-2.38 (m, 2 H), 2.55 (s, 3 H); MS: (ES) m/z calculated for $C_{21}H_{20}N_6OS$ [M + H]⁺ 405.2, found 405. |

TABLE 1-continued

Specific Examples

| Structure | Avg Bind IC50 (nM) | Avg Ser IC50 (nM) | NMR and MS Data |
|---|---|---|---|
| 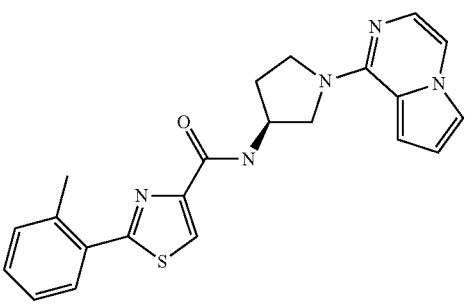 [SMILES: Cc1ccccc1-c1nc(C(=O)N[C@H]2CCN(c3nccn4cccc34)C2)cs1] | | +++ | Compound 1.046: $^1$H NMR (400 MHz, CD$_3$OD) δ 8.74 (d, J = 6.7 Hz, 1 H), 8.34 (s, 1 H), 7.78 (dd, J = 1.2, 2.7 Hz, 1 H), 7.76-7.70 (m, 2 H), 7.57 (d, J = 4.3 Hz, 1 H), 7.42-7.26 (m, 3 H), 6.93 (dd, J = 2.8, 4.7 Hz, 1 H), 6.84 (d, J = 5.9 Hz, 1 H), 5.00-4.80 (m, 1H), 4.60-3.60 (br, 4 H), 2.60-2.36 (m, 2 H), 2.55 (s, 3 H); MS: (ES) m/z calculated for C$_{22}$H$_{21}$N$_5$OS [M + H]$^+$ 404.2, found 404. |
| 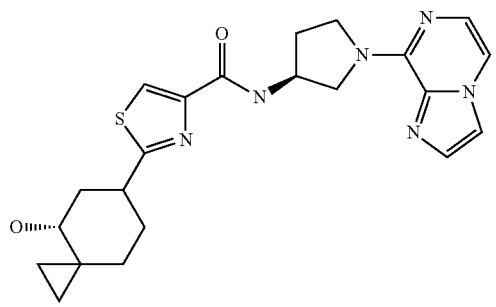 [SMILES: O=C(N[C@H]1CCN(c2nccn3ccnc23)C1)c1csc(C2CCC3(CC3)[C@H](O)C2)n1] | | + | Compound 1.047: $^1$H NMR (400 MHz, DMSO) δ 7.88 (d, J = 7.4 Hz, 1 H), 7.66 (s, 1 H), 7.54 (d, J = 4.3 Hz, 1 H), 7.29 (s, 1 H), 7.14 (s, 1 H), 7.04 (d, J = 4.3 Hz, 1 H), 4.65 (s, 1 H), 4.32-4.26 (m, 1 H), 4.20-3.56 (br, 4 H), 3.40-3.18 (m, 3 H), 3.08-3.00 (m, 2 H), 2.04-1.94 (m, 1 H), 1.90-1.80 (m, 1 H), 1.52-1.42 (m, 1 H), 1.16-0.98 (m, 1 H), 0.31 (d, J = 4.3 Hz, 2 H), 0.02 (d, J = 5.1 Hz, 2 H); MS: (ES) m/z calculated for C$_{21}$H$_{25}$N$_7$O$_2$S [M + H]$^+$ 440.2, found 440. |
| 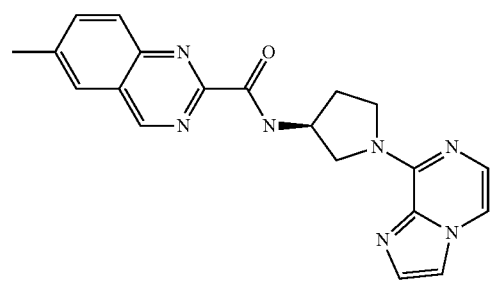 [SMILES: Cc1ccc2nc(C(=O)N[C@H]3CCN(c4nccn5ccnc45)C3)ncc2c1] | | +++ | Compound 1.048: $^1$H NMR (400 MHz, CD$_3$OD) δ 9.48 (s, 1 H), 8.02 (d, J = 1.6 Hz, 2 H), 7.98-7.88 (m, 3 H), 7.78 (s, 1 H), 7.17 (d, J = 5.8 Hz, 1 H), 5.00-3.80 (br, 4 H), 2.60 (s, 3H), 2.65-2.40 (br, 2 H); MS: (ES) m/z calculated for C$_{20}$H$_{19}$N$_7$O [M + H]$^+$ 374.2, found 374. |
| 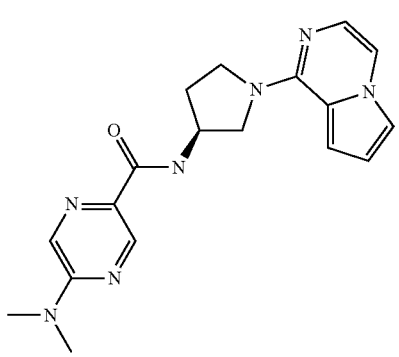 [SMILES: CN(C)c1cnc(C(=O)N[C@H]2CCN(c3nccn4cccc34)C2)cn1] | | +++ | Compound 1.049: $^1$H NMR (400 MHz, CD$_3$OD) δ 8.27 (s, 2 H), 7.75 (t, J = 1.1, 1 H), 7.70 ((d, J = 5.5, 1 H), 7.55 (s, 1 H), 6 91 (dt, J = 1.8, 2.6 Hz, 1 H), 6.83 (d, J = 5.5 Hz, 1 H), 5.00-4.80 (m, 1H), 4.65-3.70 (br, 4 H), 3.10 (s, 6 H), 2.60-2.30 (m, 2 H); MS: (ES) m/z calculated for C$_{18}$H$_{21}$N$_7$O [M + H]$^+$ 352.2, found 352. |

TABLE 1-continued

Specific Examples

| Structure | Avg Bind IC50 (nM) | Avg Ser IC50 (nM) | NMR and MS Data |
|---|---|---|---|
| | | +++ | Compound 1.050: ¹H NMR (400 MHz, CD$_3$OD) δ 9.12 (s, 1 H), 8.02 (d, J = 1.1 Hz, 1 H), 7.90 (d, J = 5.9 Hz, 1 H), 7.84 (dd, J = 1.5, 8.8 Hz, 2 H), 7.79 (s, 1 H), 7.55 (t, J = 7.3 Hz, 2 H), 7.46 (t, J = 7.3 Hz, 1 H), 7.13 (d, J = 5.5 Hz, 1 H), 4.02 (s, 2 H), 4.60-3.80 (br, 4 H), 2.80-2.70 (m, 1 H), 2.58-2.48 (m, 1 H); MS: (ES) m/z calculated for C$_{20}$H$_{20}$N$_8$O$_2$ [M + H]$^+$ 405.2, found 405. |
| | | +++ | Compound 1.051: ¹H NMR (400 MHz, CD$_3$OD) δ 9.12 (s, 1 H), 7.85 (td, 1.5, 7.4 Hz, 2 H), 7.76 (d, J = 2.2 Hz, 1 H), 7.70 (d, J = 5.5 Hz, 2 H), 7.55 (m, 2 H), 7 46 (m, 1 H), 6.92 (s, 1 H), 6.83 (d, J = 5.5 Hz, 1 H), 4.60-3.80 (br, 4 H), 4.02 (s, 2 H), 2.82-2.70 (m, 1 H), 2.58-2.48 (m, 1 H); MS: (ES) m/z calculated for C$_{21}$H$_{21}$N$_7$O$_2$ [M + H]$^+$ 404.2, found 404. |
| | | +++ | Compound 1.052: ¹H NMR (400 MHz, DMSO) δ 8.96 (d, J = 7.3 Hz, 1.5 Hz, 1 H), 8.64 (d, J = 1.5 Hz, 1 H), 7.52 (d, J = 4.8 Hz, 1 H), 7.48 (s, 1 H), 6.93 (d, J = 4.7 Hz, 1 H), 6.81 (d,. J = 4.3 Hz, 1 H), 6.60 (dd, J = 2.6, 4.1 Hz, 1 H), 4.65-4.55 (m, 1 H), 4.10-4.01 (m, 1 H), 3.95-3.88 (m, 1 H), 3.85-3.78 (m, 1 H), 2.48-2.08 (m, 3 H), 1.14-1.10 (m, 2 H), 1.05-1.01 (m, 2 H); MS: (ES) m/z calculated for C$_{21}$H$_{25}$N$_7$O$_2$S [M + H]$^+$ 349.2, found 349. |
| | | +++ | Compound 1.053: ¹H NMR (400 MHz, CD$_3$OD) δ 9.60 (s, 1 H), 8.26 (s, 1 H), 8.17 (d, J = 9.1 Hz, 1 H), 8.07 (dd, J = 1.8, 9.1 Hz, 1 H), 7.76 (d, J = 1.5 Hz, 1 H), 7.72 (d, J = 5.8 Hz, 1 H), 7.57 (s, 1 H), 6.93 (m, 1 H), 6.85 (d, J = 5.8 Hz, 1 H), 5.06-4.84 (m, 1 H), 4.82-3.60 (br, 4 H), 2.65-2.40 (br, 2 H); MS: (ES) m/z calculated for C$_{20}$H$_{21}$ClN$_6$O [M + H]$^+$ 393.2, found 393. |
| | | +++ | Compound 1.054: ¹H NMR (400 MHz, CD$_3$OD) δ 9.30 (s, 1 H), 7.91 (d, J = 5.8 Hz, 1 H), 7.88 (s, 1 H), 7 40-7.28 (m, 4 H), 7.17 (m, 1 H), 6.95 (s, 1 H), 4.94-4.70 (m, 4 H), 4.24-3.84 (m, 3 H), 2.62-2.38 (m, 2 H), 2.20 (s, 3 H); MS: (ES) m/z calculated for C$_{20}$H$_{20}$N$_8$O [M + H]$^+$ 389.2, found 389. |

TABLE 1-continued

Specific Examples

| Structure | Avg Bind IC50 (nM) | Avg Ser IC50 (nM) | NMR and MS Data |
|---|---|---|---|
| | | +++ | Compound 1.055: ¹H NMR (400 MHz, DMSO) δ 8.07 (d, J = 7.3 Hz, 1 H), 7.51 (d, J = 4.8 Hz, 1 H), 7.48 (dd, J = 1.4, 2.5 Hz, 1 H), 7.35 (d, J = 1.1 Hz, 1 H), 6.93 (d, J = 4.8 Hz, 1 H), 6.82 (d, J = 4.1 Hz, 1 H), 6.60 (dd, J = 2.6, 4.4 Hz, 1 H), 5.73 (d, J = 1.1 Hz, 1 H), 4.58-4.45 (m, 1 H), 4.43 (s, 1 H), ), 4.08-4.00 (m, 1 H), 3.95-3.85 (m, 1 H), 3.82-3.72 (m, 2 H), 3.68-3.58 (m, 2 H), 3.40-3.28 (m, 2 H), 2.25-2.05 (m, 2 H), 1.60-1.50 (m, 4 H), 1.24 (s, 3 H); MS: (ES) m/z calculated for $C_{21}H_{26}N_6O_2S$ [M + H]⁺ 427.2, found 427. |
| | | ++ | Compound 1.056: ¹H NMR (400 MHz, DMSO) δ 8.08 (d, J = 7.3 Hz, 1.4 H), 7.86 (d, J = 1.1 Hz, 1 H), 7.74 (d, J = 4.4 Hz, 1 H), 7.49 (d, J = 1.1 Hz, 1 H), 7.36 (s, 1 H), 7.24 (d, J = 4.8 Hz, 1 H), 5.74 (s, 1 H), 4.58-4.48 (m, 1 H), 4.43 (s, 1 H), 4.38-3.80 (br, 4 H), 3.64-3.54 (m, 2 H), 3.40-3.30 (m, 2 H), 2.25-2.05 (m, 2 H), 1.55-1.51 (m, 4 H), 1.15 (s, 3 H); MS: (ES) m/z calculated for $C_{20}H_{25}N_7O_2S$ [M + H]⁺ 427.2, found 427. |
| | | +++ | Compound 1.057: ¹H NMR (400 MHz, CD₃OD) δ 8.58 (d, J = 7.3 Hz, 1H), 8.01 (d, J = 0.7 Hz, 1 H), 7.92-7.87 (m, 2 H), 7.78 (d, J = 1.1 Hz, 1 H), 7.40-7.28 (m, 4 H), 7.12 (d, J = 5.8 Hz, 1 H), 6.93 (d, J = 2.2 Hz, 1 H), 4.94-3.80 (m, 5 H), 2.56-2.32 (m, 2 H), 2.20 (s, 3 H); MS: (ES) m/z calculated for $C_{21}H_{21}N_7O$ [M + H]⁺ 388.2, found 388. |
| | | +++ | Compound 1.058: ¹H NMR (400 MHz, CD₃OD) δ 8.02 (s, 1 H), 7.90 (d, J = 5.5 Hz, 1 H), 7.79 (s, 1 H), 7.35 (s, 2 H), 7.14 (d, J = 5.8 Hz, 1 H), 4.60-3.80 (br, 4 H), 3.94 (s, 2 H), 3.90-3.80 (m, 3 H), 3.32-3.20 (m, 2 H), 2.75-2.65 (m, 1 H), 2.52-2.45 (m, 1 H), 1.97-1.87 (m, 2 H), 1.64-1.50 (m, 2 H); MS: (ES) m/z calculated for $C_{20}H_{25}N_7O_3S$ [M + H]⁺ 444.2, found 444. |

TABLE 1-continued

Specific Examples

| Structure | Avg Bind IC50 (nM) | Avg Ser IC50 (nM) | NMR and MS Data |
|---|---|---|---|
| | | +++ | Compound 1.059: ¹H NMR (400 MHz, CD$_3$OD) δ 8.23 (d, J = 2.5 Hz, 1 H), 8.01 (d, J = 1.1 Hz, 1 H), 7.89 (d, J = 5.7 Hz, 1 H), 7.86-7.82 (m, 2 H), 7.78 (s, 1 H), 7.22 (t, J = 8.8 Hz, 2 H), 7.12 (d, J = 5.5 Hz, 1 H), 6.91 (d, J = 2.6 Hz, 1 H), ), 4.60-3.80 (br, 4 H), 4.00 (s, 2 H), 2.80-2.70 (m, 1 H), 2.56-2.46 (m, 1 H); MS: (ES) m/z calculated for C$_{21}$H$_{20}$FN$_7$O$_3$ [M + H]$^+$ 422.2, found 422. |
| | | +++ | Compound 1.060: ¹H NMR (400 MHz, DMSO) δ 8.82 (s, 1 H), 8.51 (s, 1 H), 7.56 (s, 2 H), 6.92 (d, J = 5.1 Hz, 1 H), 6.66 (s, 1 H), 5.17 (t, J = 5.9 Hz, 1 H), 4.26 (d, J = 1.7 Hz, 1 H), 4.00-3.80 (m, 2 H), 3.75 (d, J = 5.5 Hz, 1 H), 3.31 (s, 2 H), 3.10-2.98 (m, 1 H), 2 60-2.48 (m, 1 H), 2.28-2.18 (m, 1 H), 1.26 (d, J = 6.9 Hz, 6 H); MS: (ES) m/z calculated for C$_{20}$H$_{24}$N$_6$O$_2$ [M + H]$^+$ 381.2, found 381. |
| | | ++ | Compound 1.061: ¹H NMR (400 MHz, CD$_3$OD) δ 9.07 (s, 1 H), 8.80 (s, 2 H), 7.66 (d, J = 4.7 Hz, 1 H), 7.28 (d, J = 4.7 Hz, 1 H), 5.00-3.80 (br, 5 H), 3.18-3.00 (m, 1 H), 2.50-2.20 (m, 2 H), 1.34 (d, J = 7.0 Hz, 6 H); MS (ES) m/z calculated for C$_{17}$H$_{20}$N$_8$O [M + H]$^+$ 353.2, found 353. |
| | | +++ | Compound 1.062: ¹H NMR (400 MHz, CD$_3$OD) δ 8.29 (d, J = 2.6 Hz, 1 H), 7.89-7.84 (m, 2 H), 7.77 (d, J = 1.5 Hz, 1 H), 7.72 (d, J = 5.9 Hz, 1 H), 7.57 (d, J = 4.4 Hz, 1 H), 7.26 (t, J = 8.8 Hz, 2 H), 6.98 (d, J = 2.2 Hz, 1 H), 6.92 (t, J = 3.0 Hz, 1 H), 6.84 (d, J = 5.8 Hz, 1 H), 4.85 (m, 1 H), 4.64 (m, 1 H), 4.70-3.60 (br, 4 H); MS: (ES) m/z calculated for C$_{21}$H$_{19}$FN$_6$O$_2$ [M + H]$^+$ 407.2, found 407. |
| | | ++ | Compound 1.063: ¹H NMR (400 MHz, CD$_3$OD) δ 8.75 (s, 2 H), 7.76 (s, 1 H), 7.71 (d, J = 5.5 Hz, 1 H), 7.54 (s, 1 H), 6.91 (s, 1 H), 6.85 (d, J = 5.8 Hz, 1 H), 5.00-3.60 (br, 5 H), 2.65-2.30 (br, 2 H), 2.40 (s, 3 H); MS: (ES) m/z calculated for C$_{17}$H$_{18}$N$_6$O [M + H]$^+$ 323.2, found 323. |
| | | +++ | Compound 1.064: ¹H NMR (400 MHz, DMSO) δ 8.97 (d, J = 7.3 Hz, 1 H), 8.82 (s, 2 H), 7.86 (s, 1 H), 7.74 (d, J = 4.8 Hz, 1 H), 7.49 (s, 1 H), 7.24 (d, J = 4.4 Hz, 1 H), 4.58 (m, 1 H), 4.40-3.80 (br, 4 H), 3.03 (m, 1 H), 2.30-2.05 (m, 2 H), 1.26 (d, J = 7.0 Hz, 6 H); MS: (ES) m/z calculated for C$_{18}$H$_{21}$N$_7$O [M + H]$^+$ 352.2, found 352. |

TABLE 1-continued

Specific Examples

| Structure | Avg Bind IC50 (nM) | Avg Ser IC50 (nM) | NMR and MS Data |
|---|---|---|---|
| | | +++ | Compound 1.065: ¹H NMR (400 MHz, CD₃OD) δ 8.80 (s, 2 H), 7.76 (m, 1 H), 7.71 (d, J = 5.8 Hz, 1 H), 7.54 (s, 1 H), 6.92 (dd, J = 2.6, 4.4 Hz, 1 H), 6.84 (d, J = 5.5 Hz, 1 H), 5.00-3 60 (br, 5 H), 2.81 (q, J = 7.4 Hz, 2 H), 2.65-2.30 (br, 2 H), 1.33 (t, J = 7.4 Hz, 3 H); MS: (ES) m/z calculated for C₁₇H₁₈N₆O [M + H]⁺ 337.2, found 337. |
| | | +++ | Compound 1.066: ¹H NMR (400 MHz, CD₃OD) δ 9.31 (s, 1 H), 8.85 (d, J = 3.6 Hz, 1 H), 8.24 (s, 1 H), 8 02 (d, J = 3.6 Hz, 2 H), 7.92 (d, J = 5.4 Hz, 1 H), 7.47 (s, 3 H), 7.19 (d, J = 5.4 Hz, 1 H), 5.00-3.80 (m, 5 H), 2.60-2.40 (m, 2 H); MS: (ES) m/z calculated for C₁₉H₁₇N₇OS [M + H]⁺ 392.2, found 392. |
| | | +++ | Compound 1.067: ¹H NMR (400 MHz, DMSO) δ 8.55 (d, J = 7.0 Hz, 1 H), 8.52 (d, J = 2.6 Hz, 1 H), 8.46 (s, 1 H), 8.13 (d, J = 4.4 Hz, 1 H), 7.97-7.92 (m, 2 H), 7.57 (d, J = 4.4 Hz, 1 H), 7.36 (t, J = 6.6 Hz, 2 H), 6.89 (d, J = 2.2 Hz, 1 H), 4.66-4.58 (m, 1 H), 4,58-3.60 (br, 4 H), 2.38-2.05 (m, 2 H); MS: (ES) m/z calculated for C₁₉H₁₇FN₈O [M + H]⁺ 393.2, found 393. |
| | | +++ | Compound 1.068: ¹H NMR (400 MHz, CD₃OD) δ 8.82 (d, J = 6.3 Hz, 1 H), 8 23 (s, 1 H), 8.03-8.01 (m, 3 H), 7.92-7.90 (m, 1 H), 7.88 (s, 1 H), 7.48-7.45 (m, 3 H), 7.15 (d, J = 5.8 Hz, 1 H), 4.98-3.80 (m, 5 H), 2.60-2.40 (m, 2 H); MS: (ES) m/z calculated for C₂₀H₁₈N₆OS [M + H]⁺ 391.2, found 391. |
| | | +++ | Compound 1.069: ¹H NMR (400 MHz, CD₃OD) δ 9.26 (s, 1 H), 8.70 (d, J = 5.9 Hz, 0.5 H), 8.45 (s, 1 H), 8.04 (d, J = 5.5 Hz, 2 H), 7.86 (d, J = 5.5 Hz, 1 H), 7.49 (m, 3 H), 7.21 (d, J = 5.5 Hz, 1 H), 5.00-3.80 (m, 5 H), 2.60-2.38 (m, 2 H); MS: (ES) m/z calculated for C₁₉H₁₇N₇O₂ [M + H]⁺ 376.2, found 376. |

TABLE 1-continued

Specific Examples

| Structure | Avg Bind IC50 (nM) | Avg Ser IC50 (nM) | NMR and MS Data |
|---|---|---|---|
| 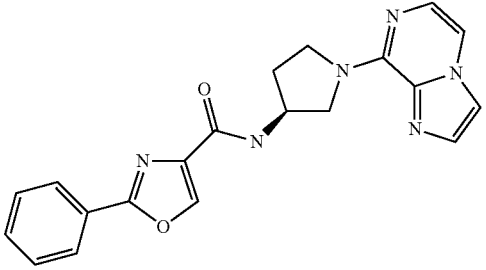 [SMILES: O=C(N[C@H]1CCN(c2nccn3ccnc23)C1)c1coc(-c2ccccc2)n1] | | +++ | Compound 1.070: $^1$H NMR (400 MHz, CD$_3$OD) δ 8.71 (d, J = 6.3 Hz, 1 H), 8.46 (s, 1 H), 8.06-8.02 (m, 3 H), 7.91 (d, J = 5.5 Hz, 1 H), 7.80 (s, 1 H), 7.49 (m, 3 H), 7.15 (d, J = 5.9 Hz, 1 H), 5.00-3.80 (m, 5 H), 2.60-2.38 (m, 2 H); MS: (ES) m/z calculated for C$_{20}$H$_{18}$N$_6$O$_2$ [M + H]$^+$ 375.2, found 375. |
| 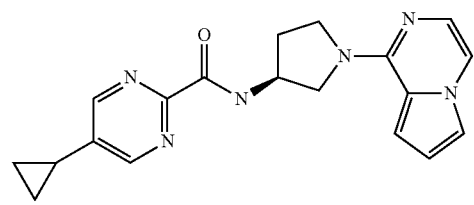 [SMILES: O=C(N[C@H]1CCN(c2nccn3cccc23)C1)c1ncc(C2CC2)cn1] | | +++ | Compound 1.071: $^1$H NMR (400 MHz, CD$_3$OD) δ 8.64 (s, 2 H), 7.76 (m, 1 H), 7.71 (d, J = 5.4 Hz, 1 H), 7.54 (s, 1 H), 6.92 (dd, J = 2.6, 4.4 Hz, 1 H), 6.84 (d, J = 5.5 Hz, 1 H), 5.00-3 60 (br, 5 H), 2.65-2.30 (br, 2 H), 2.07-2.02 (m, 1 H), 1.23-1.18 (m, 2 H), 0.96-0.91 (m, 2 H); MS: (ES) m/z calculated for C$_{19}$H$_{20}$N$_6$O [M + H]$^+$ 349.2, found 349. |
| 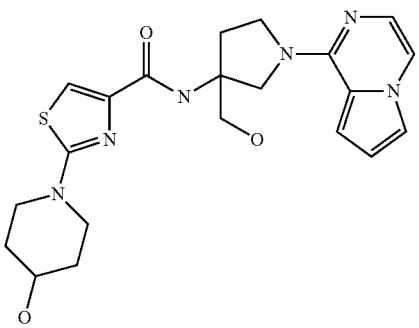 [SMILES: O=C(NC1(CO)CCN(c2nccn3cccc23)C1)c1csc(N2CCC(O)CC2)n1] | | +++ | Compound 1.072: $^1$H NMR (400 MHz, CD$_3$OD) δ 8.07 (s, 1 H), 7.80-7.76 (m, 1 H), 7.72 (d, J = 5.6 Hz, 1 H), 7.56 (d, J = 4.4 Hz, 1 H), 7.37 (s, 1 H), 6.94 (dd, J = 2.4, 4.4 Hz, 1 H), 6.85 (d, J = 6.0 Hz, 1 H), 4.80-4.60 (br, 1 H), 4.50-4.20 (br, 2 H), 4.02-3.80 (m, 4 H), 3.35-3.25 (m, 4 H), 2.78-2.66 (m, 1 H), 2.56-2.45 (m, 1 H), 1.98-1.88 (m, 2 H), 1.64-1.52 (m, 2 H); MS: (ES) m/z calculated for C$_{21}$H$_{26}$N$_6$O$_3$S [M + H]$^+$ 443.2, found 443. |
| 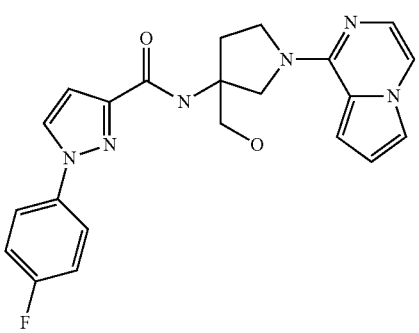 [SMILES: O=C(NC1(CO)CCN(c2nccn3cccc23)C1)c1ccn(-c2ccc(F)cc2)n1] | | +++ | Compound 1.073: $^1$H NMR (400 MHz, CD$_3$OD) δ 8.22 (d, J = 2.6 Hz, 1 H), 7.86-7.82 (m, 2 H), 7.42 (d, J = 4.7 Hz, 1 H), 7.38 (t, J = 1.5 Hz, 1 H), 7.21 (dt, J = 2.2, 8.4 Hz, 2 H), 6.98 (d, J = 4.4 Hz, 1 H), 6.91 (d, J = 2.5 Hz, 1 H), 6.86 (d, J = 4.7 Hz, 1 H), 6.64 (dd, J = 2.5, 4.0 Hz, 1 H), 4.34 (d, J = 11.4 Hz, 1 H), 4.15 (d, J = 11.4 Hz, 1 H), 4.02-3.88 (m, 4 H), 2.65-2.55 (m, 1 H), 2.45-2.36 (m, 1 H); MS: (ES) m/z calculated for C$_{22}$H$_{21}$FN$_6$O$_2$ [M + H]$^+$ 421.2, found 421. |
| 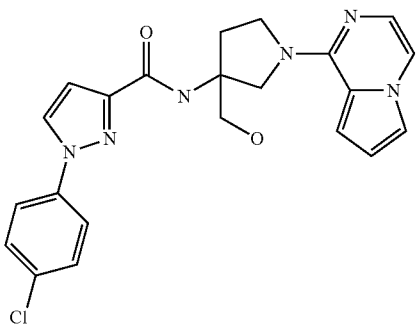 [SMILES: O=C(NC1(CO)CCN(c2nccn3cccc23)C1)c1ccn(-c2ccc(Cl)cc2)n1] | | +++ | Compound 1.074: $^1$H NMR (400 MHz, CD$_3$OD) δ 8.28 (d, J = 2.5 Hz, 1 H), 7.85 (dd, J = 2.2, 6.9 Hz, 2 H), 7.48 (dd, J = 2.2, 6.9 Hz, 2 H), 7.42 (d, J = 5.2 Hz, 1 H), 7.39 (dd, J = 1.1, 2.6 Hz, 1 H), 6.98 (d, J = 4.4 Hz, 1 H), 6.93 (d, J = 2.6 Hz, 1 H), 6.86 (d, J = 5.1 Hz, 1 H), 6.65 (dd, J = 2.5, 4.1 Hz, 1 H), 4.34 (d, J = 11.4 Hz, 1 H), 4.15 (d, J = 11.4 Hz, 1 H), 4.02-3.88 (m, 4 H), 2.65-2.55 (m, 1 H), 2.45-2.36 (m, 1 H); MS: (ES) m/z calculated for C$_{22}$H$_{21}$ClN$_6$O$_2$ [M + H]$^+$ 437.2, found 437. |

TABLE 1-continued

Specific Examples

| Structure | Avg Bind IC50 (nM) | Avg Ser IC50 (nM) | NMR and MS Data |
|---|---|---|---|
| 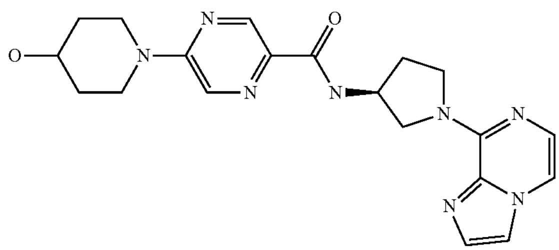 [SMILES: O=C(N[C@H]1CCN(c2nccn3ccnc23)C1)c1cnc(N2CCC(O)CC2)cn1] | ++ | + | Compound 1.075: $^1$H NMR (400 MHz, CD$_3$OD) δ 8.64 (s, 1 H), 8.17 (s 1 H), 7.75 (s, 1 H), 7.66 (d, J = 4.8 Hz, 1 H), 7.51 (s, 1 H), 7.22 (d, J = 4.4 Hz, 1 H), 4.75-4.68 (m, 1 H), 4.40-4.32 (m, 1 H), 4.30-3.80 (m, 4 H), 3.40-3.20 (m, 4 H), 2.42-2.32 (m, 1 H), 2.26-2.16 (m, 1 H), 1.98-1.90 (m, 2 H), 1.58-1.50 (m, 2 H); MS: (ES) m/z calculated for C$_{20}$H$_{24}$N$_8$O$_2$ [M + H]$^+$ 409.2, found 409. |
| | +++ | +++ | Compound 1.076: $^1$H NMR (400 MHz, CD$_3$OD) δ 9.17 (s, 2 H), 7.83 (m, 3 H), 7.71 (d, J = 5.4 Hz, 1H), 7.56 (s, 1 H), 7.31 (t, J = 8.5 Hz, 2 H), 6.92 (s, 1 H), 6.85 (d, J = 5.9 Hz, 1 H), 5.00-3.60 (br, 5 H), 2.65-2 30 (br, 2H); MS: (ES) m/z calculated for C$_{22}$H$_{19}$FN$_6$O [M + H]$^+$ 403.2, found 403. |
| | +++ | +++ | Compound 1.077: $^1$H NMR (400 MHz, CD$_3$OD) δ 8.81 (s, 2 H), 7.76 (s, 1 H), 7.71 (d, J = 5.8 Hz, 1 H), 7.55 (s, 1 H), 6.92 (s, 1 H), 6.84 (d, J = 5.9 Hz, 1 H), 5.00-3.60 (br, 5 H), 3.18-3.00 (m, 1 H), 2.65-2.30 (br, 2 H), 1.36 (d, J = 7.0 Hz, 6 H); MS: (ES) m/z calculated for C$_{19}$H$_{22}$N$_6$O [M + H]$^+$ 351.2, found 351. |
| | +++ | +++ | Compound 1.078: $^1$H NMR (400 MHz, CD$_3$OD) δ 9.06 (s, 1 H), 7.64 (d, J = 4.8 Hz, 1 H), 7.36 (s, 1 H), 7.26 (d, J = 4.8 Hz, 1 H), 4.73-4.68 (m, 1 H), 4.60-3.60 (br, 4 H), 3.96-3.80 (m, 3 H), 3.35-3.20 (m, 2 H), 2.45-2.35 (m, 1 H), 2.30-2.18 (m, 1 H), 1.95-1.88 (m, 2 H), 1.62-1.50 (m, 2 H); MS: (ES) m/z calculated for C$_{18}$H$_{22}$N$_8$O$_2$S [M + H]$^+$ 415.2, found 415. |
| | +++ | +++ | Compound 1.079: $^1$H NMR (400 MHz, CD$_3$OD) δ 7.74 (s, 1 H), 7.66 (d, J = 4.7 Hz, 1 H), 7.50 (s, 1 H), 7.36 (s, 1 H), 7.22 (d, J = 4.9 Hz, 1 H), 4.76-4.65 (m, 1 H), 4.40-4.30 (m, 1 H), 4.20-3.75 (m, 4 H), 3.40-3.20 (m, 4 H), 2.42-2.10 (m, 2 H), 1.95-1.85 (m, 2 H), 1.65-1.50 (m, 2 H); MS: (ES) m/z calculated for C$_{19}$H$_{23}$N$_7$O$_2$S [M + H]$^+$ 414.2, found 414. |

TABLE 1-continued

Specific Examples

| Structure | Avg Bind IC50 (nM) | Avg Ser IC50 (nM) | NMR and MS Data |
|---|---|---|---|
| | +++ | ++ | Compound 1.080: ¹H NMR (400 MHz, CD₃OD) δ 8.61 (d, J = 6.2 Hz, 1 H), 8.49 (s, 1 H), 7.94 (d, J = 7.7 Hz, 1 H), 7.76 (d, J = 1.1 Hz, 1 H), 7.71 (d, J = 5.4 Hz, 1 H), 7.56 (d, J = 2.9 Hz, 1 H), 7.40-7.26 (m, 3 H), 6.92 (d, J = 1.8, 2.6 Hz, 1 H), 6.83 (d, J = 5.5 Hz, 1 H), 5.00-3.60 (m, 5 H), 2.66 (s, 3 H), 2.60-2.38 (m, 2 H); MS: (ES) m/z calculated for C₂₂H₂₁N₅O₂ [M + H]⁺ 388.2, found 388. |
| | +++ | ++ | Compound 1.081: ¹H NMR (400 MHz, CD₃OD) δ 8.61 (s, 1 H), 8.44 (s, 1 H), 8.07 (d, J = 8.8 Hz, 1 H), 7.99 (d, J = 8.8 Hz, 1 H), 7.77 (s, 1 H), 7.72 (d, J = 5.9 Hz, 1 H), 7.57 (d, J = 4.4 Hz, 1 H), 6.96 (s, 1 H), 6.94-6.91 (m, 1 H), 6.85 (d, J = 5.9 Hz, 1 H), 5.00-3.65 (br, 5 H), 2.60-2.30 (m, 2 H); MS (ES) m/z calculated for C₂₀H₁₈ClN₇O [M + H]⁺ 408.2, found 408. |
| | +++ | ++ | Compound 1.082: ¹H NMR (400 MHz, CD₃OD) δ 9.28 (d, J = 5.5 Hz, 1 H), 7.77 (s, 1 H), 7.72 (d, J = 5.9 Hz, 1 H), 7.55 (s, 1 H), 6.92 (s, 1 H), 6.85 (d, J = 5.5 Hz, 1 H), 4.80-3.65 (m, 5 H), 3.99 (d, J = 7.0 Hz, 2 H), 3.59 (t, J = 11.0 Hz, 2H), 3.41-3.29 (m, 1 H), 2.60-2.30 (m, 2 H), 2.10-1.85 (m, 4 H); MS: (ES) m/z calculated for C₁₉H₂₂N₆O₃ [M + H]⁺ 383.2, found 383. |
| | +++ | ++ | Compound 1.083: ¹H NMR (400 MHz, DMSO) δ 11.40 (s, 1 H), 8.05 (d, J = 7.0 Hz, 2 H), 7.91 (s, 1 H), 7.84 (d, J = 4.4 Hz, 1 H), 7.60-7.40 (m, 4 H), 7.00-6.90 (m, 2 H), 4.85-3.50 (br, 5 H), 2.45-2.20 (m, 2 H); MS: (ES) m/z calculated for C₂₀H₁₉N₇O [M + H]⁺ 374.2, found 374. |
| | +++ | +++ | Compound 1.084: ¹H NMR (400 MHz, DMSO) δ 9.20 (s, 1 H), 8.57 (d, J = 7.0 Hz, 1 H), 8.52 (d, J = 2.2 Hz, 1 H), 7.97-7.93 (m, 2 H), 7.74 (d, J = 4.4 Hz, 1 H), 7.38 (t, J = 8.8 Hz, 2 H), 7.28 (d, J = 4.4 Hz, 1 H), 6.90 ( d, J = 2.5 Hz, 1 H), 4.70-3.50 (m, 5 H), 2.40-2.10 (m, 2 H); MS: (ES) m/z calculated for C₁₉H₁₇FN₈O [M + H]⁺ 393.2, found 393. |

TABLE 1-continued

Specific Examples

| Structure | Avg Bind IC50 (nM) | Avg Ser IC50 (nM) | NMR and MS Data |
|---|---|---|---|
| | +++ | +++ | Compound 1.085: $^1$H NMR (400 MHz, CD$_3$OD) δ 9.49 (s, 1 H), 8.04 (d, J = 9.1 Hz, 1 H), 7.93 (d, J = 6.9 Hz, 2 H), 7.75 (d, J = 1.5 Hz, 1 H), 7.70 (d, J = 5.9 Hz, 1 H), 7.55 (s, 1 H), 6.92 (s, 1 H), 6.85 (d, J = 5.5 Hz, 1 H), 5.00-3.70 (m, 5 H), 3.30 (s, 3 H), 2.60-2.30 (m, 2 H); MS: (ES) m/z calculated for C$_{21}$H$_{20}$N$_6$O [M + H]$^+$ 373.2, found 373. |
| 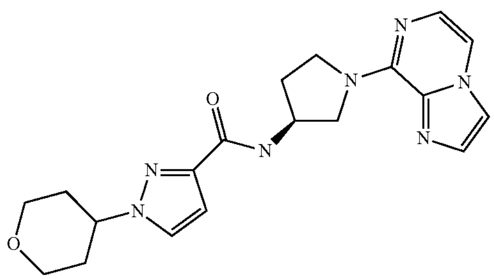 [SMILES: O=C(N[C@H]1CCN(c2nccn3ccnc23)C1)c1ccn(C2CCOCC2)n1] | ++ | ++ | Compound 1.086: $^1$H NMR (400 MHz, CD$_3$OD) δ 8.02 (s, 1 H), 7.90 (d, J = 5.9 Hz, 1 H), 7.79 (s, 1 H), 7.73 (d, J = 2.5 Hz, 1 H), 7.14 (d, J = 5.5 Hz, 1 H), 6.72 (d, J = 2.6 Hz, 1 H), 5.00-3.70 (m, 8 H), 3.55 (dt, J = 2.2, 11.7 Hz, 2 H), 2.60-2.30 (m, 2 H), 2.20-1.95 (m, 4 H); MS: (ES) m/z calculated for C$_{19}$H$_{23}$N$_7$O$_2$ [M + H]$^+$ 382.2, found 382. |
| 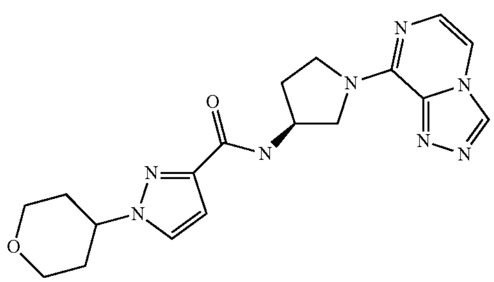 [SMILES: O=C(N[C@H]1CCN(c2nccn3cnnc23)C1)c1ccn(C2CCOCC2)n1] | + | ++ | Compound 1.087: $^1$H NMR (400 MHz, CD$_3$OD) δ 9.25 (s, 1 H), 7.85 (d, J = 5.1 Hz, 1 H), 7.73 (d, J = 2.6 Hz, 1 H), 7.20 (d, J = 5.5 Hz, 1 H), 6.73 (d, J = 2.5 Hz, 1 H), 5.00-3.60 (m, 8 H), 3.55 (dt, J = 2.2, 11.7 Hz, 2 H), 2.60-2.39 (m, 2 H), 2.20-1.95 (m, 4 H); MS: (ES) m/z calculated for C$_{18}$H$_{22}$N$_8$O$_2$ [M + H]$^+$ 383.2, found 383. |
| | +++ | +++ | Compound 1.088: $^1$H NMR (400 MHz, CD$_3$OD) δ 8.48 (d, J = 6.2 Hz, 1 H), 7.78-7.70 (m, 3 H), 7.55 (s, 1 H), 6.91 (dd, J = 2.5, 4.4 Hz, 1 H), 6.83 (d, J = 5.5 Hz, 1 H), 6.73 (d, J = 2.2 Hz, 1 H), 5.00-3.60 (m, 8 H), 3.55 (dt, J = 2.2, 11.7 Hz, 2 H), 2.60-2.39 (m, 2 H), 2.20-1.95 (m, 4 H); MS (ES) m/z calculated for C$_{20}$H$_{24}$N$_6$O$_2$ [M + H]$^+$ 381.2, found 381. |

TABLE 1-continued

Specific Examples

| Structure | Avg Bind IC50 (nM) | Avg Ser IC50 (nM) | NMR and MS Data |
|---|---|---|---|
| | +++ | +++ | Compound 1.089: ¹H NMR (400 MHz, DMSO) δ 9.35 (s, 1 H), 9.20 (s, 1 H), 8.99 (d, J = 7.0 Hz, 1.5 H), 7.95-7.91 (m, 2 H), 7.75 (d, J = 4.4 Hz, 1 H), 7.45 (t, J = 8.5 Hz, 2 H), 7.28 (d, J = 4.4 Hz, 1 H), 4.80-3.50 (m, 5 H), 2.40-2.10 (m, 2 H); MS: (ES) m/z calculated for $C_{18}H_{16}FN_9O$ $[M + H]^+$ 394.2, found 394. |
| | +++ | +++ | Compound 1.090: ¹H NMR (400 MHz, DMSO) δ 9.34 (s, 1 H), 8.91 (d, J = 8.0 Hz, 1 H), 7.95-7.91 (m, 2 H), 7.86 (s, 1 H), 7.75 (d, J = 4.8 Hz, 1 H), 7.50 (s, 1 H), 7.45 (t, J = 7.0 Hz, 2 H), 7.25 (d, J = 4.8 Hz, 1 H), 4.65-4.56 (m, 1 H), 4.50-3.70 (m, 4 H), 2.30-2.10 (m, 2 H); MS: (ES) m/z calculated for $C_{19}H_{17}FN_8O$ $[M + H]^+$ 393.2, found 393. |
| | +++ | +++ | Compound 1.091: ¹H NMR (400 MHz, DMSO) δ 9.39 (s, 1 H), 8.92 (d, J = 7.0 Hz, 1 H), 7.90-7.86 (m, 2 H), 7.75 (d, J = 4.4 Hz, 1 H), 7.58 (t, J = 7.4 Hz, 2 H), 7.50 (s, 1 H), 7.46 (t, J = 7.4 Hz, 1 H), 7.25 (d, J = 4.4 Hz, 1 H), 4.62-4.50 (m, 1 H), 4.50-3.70 (m, 4 H), 2.30-2.00 (m, 2 H); MS: (ES) m/z calculated for $C_{19}H_{18}N_8O$ $[M + H]^+$ 375.2, found 375. |
| | +++ | +++ | Compound 1.092: ¹H NMR (400 MHz, DMSO) δ 8.52 (d, J = 7.7 Hz, 2 H), 7.97 (m, 2H), 7.86 (s, 1 H), 7.75 (d, J = 4.1 Hz, 1 H), 7.50 (s, 1 H), 7.37 (t, J = 7.0 Hz, 2 H), 7.25 (d, J = 4.4 Hz, 1 H), 6.89 (s, 1 H), 4.62-4.50 (m, 1 H), 4.50-3.70 (m, 4 H), 2.30-2.00 (m, 2 H); MS: (ES) m/z calculated for $C_{20}H_{18}FN_7O$ $[M + H]^+$ 392.2, found 392. |
| | +++ | +++ | Compound 1.093: ¹H NMR (400 MHz, CD₃OD) δ 9.42 (d, J = 7.0 Hz, 0.8 H), 9.18 (s, 2 H), 7.77-7.70 (m, 4 H), 7.58-7.48 (m, 4 H), 6.93 (dd, J = 2.6, 4.4 Hz, 1 H), 6.85 (d, J = 5.5 Hz, 1 H), 5.00-3.65 (br, 5 H), 2.65-2.40 (m, 2 H); MS: (ES) m/z calculated for $C_{22}H_{20}N_6O$ $[M + H]^+$ 385.2, found 385. |

| Structure | Avg Bind IC50 (nM) | Avg Ser IC50 (nM) | NMR and MS Data |
|---|---|---|---|
| | +++ | +++ | Compound 1.094: $^1$H NMR (400 MHz, DMSO) δ 8.47 (d, J = 7.0 Hz, 1 H), 8.10 (d, J = 2.2 Hz, 1 H), 7.52-7.40 (m, 4 H), 6.93 (d, J = 4.4 Hz, 1 H), 6.87 (d, J = 2.2 Hz, 1 H), 6.80 (d, J = 4.0 Hz, 1 H), 6.60 (dd, J = 2.9, 4.0 Hz, 1 H), 4.62-4.50 (m, 1 H), 4.10-3.70 (m, 4 H), 2.19 (s, 3 H), 2.30-2.00 (m, 2 H); MS; (ES) m/z calculated for $C_{22}H_{21}ClN_6O$ [M + H]$^+$ 421.2, found 421. |
| | +++ | +++ | Compound 1.095: $^1$H NMR (400 MHz, DMSO) δ 8.70 (s, 1 H), 8.53 (d, J = 7.0 Hz, 1 H), 8.10 (dd, J = 5.5, 8.8 Hz, 2 H), 7.53 (d, J = 4.8 Hz, 1 H), 7.49 (s, 1 H), 7.41 (t, J = 8.8 Hz, 1 H), 6.95 (d, J = 4.4 Hz, 1 H), 6.83 (d, J = 4.0 Hz, 1 H), 6.62 (dd, J = 2.6, 4.1 Hz, 1 H), 4.62-4.50 (m, 1 H), 4,10-3.70 (m, 4 H), 2.30-2.00 (m, 2 H); MS: (ES) m/z calculated for $C_{21}H_{18}FN_5O_2$ [M + H]$^+$ 392.2, found 392. |
| | +++ | +++ | Compound 1.096: $^1$H NMR (400 MHz, CD$_3$OD) δ 8.85 (d, J = 6.6 Hz, 1 H), 8.23 (s, 1 H), 8.09-8.05 (m, 2 H), 7.76 (s, 1 H), 7.72 (d, J = 5.9 Hz, 1 H), 7.56 (s, 1 H), 7.23 (t, J = 8.8 Hz, 1 H), 6.93 (dd, J = 2.5, 4.4 Hz, 1 H), 6.85 (d, J = 5.9 Hz, 1 H), 5.00-3.60 (m, 5 H), 2.60-2.35 (m, 2 H); MS: (ES) m/z calculated for $C_{21}H_{18}FN_5OS$ [M + H]$^+$ 408.2, found 408. |
| | +++ | +++ | Compound 1.097: $^1$H NMR (400 MHz, CD$_3$OD) δ 7.68-7.65 (m, 2 H), 7.38 (s, 1 H), 6.76-6.74 (m, 2 H), 4.75-4.65 (m, 1 H), 4.25-4.15 (m, 1 H), 4.06-3.80 (m, 5 H), 3.35-3.20 (m, 3 H), 2.62 (s, 1 H), 2.50-2.30 (m, 2 H)m 1.98-1.90 (m, 2 H), 1.65-1.52 (m, 2 H); MS: (ES) m/z calculated for $C_{21}H_{26}N_6O_2S$ [M + H]$^+$ 427.2, found 427. |
| | +++ | +++ | Compound 1,098: $^1$H NMR (400 MHz, CD$_3$OD) δ 7.76 (s, 1 H), 7.70 (d, J = 5.8 Hz, 1 H), 7.54 (d, J = 3.7 Hz, 1 H), 7.39 (s, 1H), 7.53 (dd, J = 2.5, 4.0 Hz, 1 H), 6.84 (d, J = 5.5 Hz, 1 H), 4.82-4.75 (m, 1 H), 4.70-3.60 (br, 4 H), 3.90-3.80 (m, 2 H), 3.40-3.20 (m, 3 H), 2.52-2.30 (m, 2 H), 1.96-1.90 (m, 2 H), 1.65-1.52 (m, 2 H); MS: (ES) m/z calculated for $C_{20}H_{24}FN_6O_2S$ [M + H]$^+$ 413.2, found 413. |

TABLE 1-continued

Specific Examples

| Structure | Avg Bind IC50 (nM) | Avg Ser IC50 (nM) | NMR and MS Data |
|---|---|---|---|
| | +++ | +++ | Compound 1.099: $^1$H NMR (400 MHz, CD$_3$OD) δ 8.35 (d, J = 2.6 Hz, 1 H), 7.76-7.64 (m, 3 H), 7.53 (dt, J = 6.2, 8.4 Hz, 2 H), 7.13 (d, J = 2.5, 8.4 Hz, 1 H), 6.95 (d, J = 2.6 Hz, 1 H), 6.77-6.73 (m, 2 H), 4.82-4.75 (m, 1 H), 4.30-4.24 (m, 1 H), 4.08-3.92 (m, 3 H), 2.63 (s, 3 H), 2.52-2.30 (m, 2 H); MS: (ES) m/z calculated for C$_{22}$H$_{21}$FN$_6$O [M + H]$^+$ 405.2, found 405. |
| | +++ | + | Compound 1.100: $^1$H NMR (400 MHz, CD$_3$OD) δ 8.36 (d, J = 2.6 Hz, 1 H), 7.90 (dd, J = 2.6, 10.3 Hz, 1 H), 7.72-7.64 (m, 3 H), 7.61 (t, J = 8.0 Hz, 1 H), 6.95 (d, J = 2.6 Hz, 1 H), 6.77-6.73 (m, 2 H), 4.82-4.75 (m, 1 H), 4.30-4.24 (m, 1 H), 4.08-3.92 (m, 3 H), 2.63 (s, 3 H), 2.52-2.30 (m, 2 H); MS: (ES) m/z calculated for C$_{22}$H$_{21}$ClFN$_6$O [M + H]$^+$ 439.2, found 439. |
| | +++ | ++ | Compound 1.101: $^1$H NMR (400 MHz, CD$_3$OD) δ 8.02 (d, J = 2.2 Hz, 1 H), 7.65-7.57 (m, 3 H), 7.54-7.46 (m, 3 H), 6.97 (d, J = 2.2 Hz, 1 H), 6.75-6.72 (m, 2 H), 4.82-4.75 (m, 1 H), 4.28-4.24 (m, 1 H), 4.08-4.00 (m, 1 H), 3.98-3.90 (m, 4 H), 2.61 (s, 3 H), 2.52-2.30 (m, 2 H); MS: (ES) m/z calculated for C$_{24}$H$_{23}$N$_7$O [M + H]$^+$ 426.2, found 426. |
| | +++ | +++ | Compound 1.102: $^1$H NMR (400 MHz, DMSO) δ 8.58 (d, J = 2.6 Hz, 1 H), 8.55 (d, J = 6.9 Hz, 1 H), 7.97 (dd, J = 2.2, 7.0 Hz, 2 H), 7.86 (s, 1 H), 7.75 (d, J = 4.4 Hz, 1 H), 7.58 (dd, J = 2.2, 6.9 Hz, 2 H), 7.50 (s, 1 H), 7.25 (d, J = 4.4 Hz, 1 H), 6.91 (d, J = 2.6 Hz, 1 H), 4.62-4.50 (m, 1 H), 4.50-3.70 (m, 4 H), 2.30-2.00 (m, 2 H); MS: (ES) m/z calculated for C$_{20}$H$_{18}$ClN$_7$O [M + H]$^+$ 408 2, found 408. |
| | +++ | ++ | Compound 1.103: $^1$HNMR (400 MHz, DMSO) δ 8.44 (d, J = 7.3 Hz, 1 H), 8.10 (d, J = 2.2 Hz, 1 H), 7.62 (d, J = 4.8, 2 H), 7.53 (s, 1 H), 7.46-7.40 (m, 2 H), 6.87 (d, J = 4.8 Hz, 1 H), 6.85 (d, J = 2.6 Hz, 1 H), 6.49 (d, J = 2.2 Hz, 1 H), 4.48-4.40 (m, 1 H), 3.70-3.50 (m, 4 H), 2.45 (s, 3 H), 2.20 (s, 3 H), 2.20-1.90 (m, 2H); MS: (ES) m/z calculated for C$_{23}$H$_{23}$ClN$_6$O [M + H]$^+$ 435.2, found 435. |

TABLE 1-continued

Specific Examples

| Structure | Avg Bind IC50 (nM) | Avg Ser IC50 (nM) | NMR and MS Data |
|---|---|---|---|
| | +++ | + | Compound 1.104: ¹H NMR (400 MHz, DMSO) δ 11.38 (s, 1 H), 8.78 (d, J = 7.0 Hz, 1 H), 8.59 (d, J = 3.0 Hz, 1 H), 7.95 (d, J = 7.0, 2 H), 7.81 (m, 2 H), 7.61 (d, J = 8.8 Hz, 2 H), 6.92 (s, 1 H), 6.85 (d, J = 5 5 Hz, 1 H), 6.76 (d, J = 2.2 Hz, 1 H), 4.70-4.65 (m, 1 H), 4.18-3.80 (m, 4 H), 2.48 (s, 3 H), 2.38-2.18 (m, 2 H); MS: (ES) m/z calculated for $C_{22}H_{21}ClN_6O$ [M + H]⁺ 421.2, found 421. |
| | +++ | ++ | Compound 1.105: ¹H NMR (400 MHz, DMSO) δ 11.28 (s, 1 H), 8.82 (d, J = 7.0 Hz, 1 H), 8.33 (s, 1 H), 8.04-8.01 (m, 2 H), 7.82 (m, 2 H), 7.54-7.50 (m, 3 H), 6.86 (d, J = 5.5 Hz, 1 H), 6.76 (d, J = 2.2 Hz, 1 H), 4.75-4.65 (m, 1 H), 4.20-3.60 (m, 4 H), 2.48 (s, 3 H), 2.40-2.20 (m, 2 H); MS: (ES) m/z calculated for $C_{22}H_{21}N_5OS$ [M + H]⁺ 404.2, found 404. |
| | +++ | ++ | Compound 1.106: ¹H NMR (400 MHz, CDCCl₃) δ 7.91 (d, J = 7.3 Hz, 1 H ), 7.82 (s, 1 H), 7.68 (dd, J = 4.4, 8.8 Hz, 2 H), 7.33 (d, J = 4.8 Hz, 1 H), 7.19 (t, J = 8.8 Hz, 3 H), 7.00 (m, 2 H), 6.50 (s, 1 H), 4.75 (s, 1 H), 3.90-3.56 (m, 4 H), 2.57 (s, 3 H), 2.42-2.38 (m, 1 H), 2.02-1.80 (m, 1 H); MS (ES) m/z calculated for $C_{22}H_{21}FN_6O$ [M + H]⁺ 405.2, found 405. |
| | +++ | ++ | Compound 1.107: ¹H NMR (400 MHz, CD₃OD) δ 8.72 (d, J = 8.1 Hz, 1 H), 8.45 (s, 1 H), 8.06 (d, J = 8.1 Hz, 2 H), 7.67 (d, J = 5.5 Hz, 2 H), 7.52 (m, 3 H), 6.76-6.73 (m, 2 H), 4.85-4.75 (m, 1 H), 4.30-4.22 (m, 1 H), 4.10-3.90 (m, 3 H), 2.64 (s, 3 H), 2.55-2.35 (m, 2 H); MS: (ES) m/z calculated for $C_{22}H_{21}N_5O_2$ [M + H]⁺ 388.2, found 388. |
| | +++ | ++ | Compound 1.108: ¹H NMR (400 MHz, CD₃OD) δ 8.22 (s, 1 H), 8.09 (dd, J = 5.1, 8.8 Hz, 2 H), 7.67 (d, J = 5.5 Hz, 2 H), 7.24 (t, J = 8.8 Hz, 2 H), 6.75 (d, J = 5.5 Hz, 2 H), 4.85-4.75 (m, 1 H), 4.30-4.22 (m, 1 H), 4.10-3.90 (m, 3 H), 2.64 (s, 3 H), 2.55-2.35 (m, 2 H); MS: (ES) m/z calculated for $C_{22}H_{20}FN_5OS$ [M + H]⁺ 422 2, found 422. |

TABLE 1-continued

Specific Examples

| Structure | Avg Bind IC50 (nM) | Avg Ser IC50 (nM) | NMR and MS Data |
|---|---|---|---|
| | +++ | ++ | Compound 1.109: ¹H NMR (400 MHz, CD$_3$OD) δ 7.87 (s, 1 H), 7.64 (m, 2 H), 7.40-7.28 (m, 4 H), 6.93 (s, 1 H), 6.74-6.70 (m, 2 H), 4.80-4.70 (m, 1 H), 4.30-4.20 (m, 1 H), 4.10-3.85 (m, 3 H), 2.61 (s, 3 H), 2.50-2.35 (m, 2 H), 2.20 (s, 3 H); MS: (ES) m/z calculated for C$_{23}$H$_{24}$N$_5$O [M + H]$^+$ 401.2, found 401. |
| | +++ | ++ | Compound 1.110: ¹H NMR (400 MHz, CD$_3$OD) δ 9.18 (s, 2 H), 7.77 (d, J = 7.0 Hz, 2 H), 7.67 (d, J = 5.9 Hz, 2 H), 7.57-7.48 (m, 3 H), 6.76-6.72 (m, 2 H), 4.95-4.80 (m, 1 H), 4.32-4.24 (m, 1 H), 4.10-3.90 (m, 3 H), 2.64 (s, 3 H), 2.50-2.35 (m, 2 H); MS: (ES) m/z calculated for C$_{23}$H$_{22}$N$_6$O [M + H]$^+$ 399.2, found 399. |
| | +++ | ++ | Compound 1.111: ¹H NMR (400 MHz, DMSO) δ 9.37 (d, J = 7.0 Hz, 1 H), 8.16 (d, J = 7.0 Hz, 2 H), 7.75-7.62 (m, 4 H), 7.47 (d, J = 2.6 Hz, 1 H), 6.93 (d, J = 4.7 Hz, 1 H), 6.51 (d, J = 2.6 Hz, 1 H), 4.53-4.48 (m, 1 H), 3.80-3.55 (m, 4 H), 2.48 (s, 3 H), 2.28-1.90 (m, 2 H); MS: (ES) m/z calculated for C$_{21}$H$_{20}$N$_6$O$_2$: [M + H]$^+$ 389.2, found 389. |
| | +++ | ++ | Compound 1.112: ¹H NMR (400 MHz, DMSO) δ 9.20 (s, 1 H), 8.61 (m, 2 H), 7.98-7.94 (m, 2 H), 7.74 (d, J = 4.4 Hz, 1 H), 7.59-7.55 (m, 2 H), 7.28 (d, J = 4.8 Hz, 1 H), 6.91 (d, J = 2.6 Hz, 1 H), 4.70-3.55 (m, 5 H), 2.40-2.12 (m, 2 H); MS: (ES) m/z calculated for C$_{19}$H$_{17}$ClN$_8$O [M + H]$^+$ 409.2, found 409. |

TABLE 1-continued

Specific Examples

| Structure | Avg Bind IC50 (nM) | Avg Ser IC50 (nM) | NMR and MS Data |
|---|---|---|---|
| | +++ | +++ | Compound 1.113: ¹H NMR (400 MHz, CD$_3$OD) δ 8.80 (d, J = 5.9 Hz, 1 H), 8.38 (d, J = 2.3 Hz, 1 H), 7.79-7.68 (m, 4 H), 7.59-7.48 (m, 2 H), 7.14 (dt, J = 2.8, 8.6 Hz, 1 H), 6.98 (d, J = 2.4 Hz, 1 H), 6.95 (dd, J = 2.6, 4.4 Hz, 1 H), 6.86 (d, J = 5.5 Hz, 1 H), 4.95-3.70 (br, 5 H), 2.60-2.36 (m, 2 H): MS: (ES) m/z calculated for C$_{21}$H$_{19}$FN$_6$O [M + H]$^+$ 391.2, found 391. |
| | +++ | +++ | Compound 1.114: ¹H NMR (400 MHz, CD$_3$OD) δ 8.37 (d, J = 2.9 Hz, 1 H), 7.91 (dd, J = 2.6, 10.3 Hz, 1 H), 7.77 (s, 1 H), 7.71-7.68 (m, 2 H), 7.61-7.55 (m, 2 H), 6.97 (d, 2.6 Hz, 1 H), 6.92 (dd, J = 2.6, 4.4 Hz, 1 H), 6.84 (d, J = 5.9 Hz, 1 H), 4.95-3.70 (br, 5 H), 2.60-2.36 (m, 2 H); MS: (ES) m/z calculated for C$_{21}$H$_{18}$ClFN$_6$O [M + H]$^+$ 425.2, found 425. |
| | +++ | +++ | Compound 1.115: ¹H NMR (400 MHz, CD$_3$OD) δ 8.03 (d, J = 2.2 Hz, 1 H), 7.75 (s, 1 H), 7.70 (d, J = 5.5 Hz, 1 H), 7.60-7.48 (m, 5 H), 6.98 (d, J = 2.5 Hz, 1 H), 6.91 (dd, J = 2.6, 4.4 Hz, 1 H), 6.82 (d, J = 5.8 Hz, 1 H), 4.95-3.65 (br, 5 H), 3.93 (s, 2 H), 2.55-2.30 (m, 2 H): MS: (ES) m/z calculated for C$_{23}$H$_{21}$N$_7$O [M + H]$^+$ 412.2, found 412. |
| | +++ | ++ | Compound 1.116: ¹H NMR (400 MHz, DMSO) δ 8.68 (s, 1 H), 8.54 (d, J = 6.9 Hz, 1 H), 8.08-8.04 (m, 2 H), 7.66 (d, J = 4.4 Hz, 1 H), 7.47-7.38 (m, 3 H), 6.94 (d, J = 4.4 Hz, 1 H), 6.51 (d, J = 2.2 Hz, 1 H), 4.52-4.46 (m, 1 H), 3.70-3.55 (m, 4 H), 2.48 (s, 3 H), 2.26-1.90 (m, 2 H); MS: (ES) m/z calculated for C$_{22}$H$_{20}$FN$_5$O$_2$ [M + H]$^+$ 406.2, found 406. |
| | +++ | +++ | Compound 1.117: ¹H NMR (400 MHz, DMSO) δ 9.38 (s, 1 H), 8.88 (d, J = 7.3 Hz, 1 H), 7.90 (d, J = 7.3 Hz, 2 H), 7.65 (d, J = 4.7 Hz, 1 H), 7.59 (t, J = 7.3 Hz, 2 H), 7.47-7.43 (m, 2 H), 6.92 (d, J = 4.7 Hz, 1 H), 6.51 (d, J = 2.6 Hz, 1 H), 4.52-4.48 (m, 1 H), 3.75-3.55 (m, 4 H), 2.48 (s, 3 H), 2.26-1.90 (m, 2 H); MS: (ES) m/z calculated for C$_{21}$H$_{21}$N$_7$O [M + H]$^+$ 388.2, found 388. |

TABLE 1-continued

Specific Examples

| Structure | Avg Bind IC50 (nM) | Avg Ser IC50 (nM) | NMR and MS Data |
|---|---|---|---|
| | +++ | +++ | Compound 1.118: $^1$H NMR (400 MHz, CD$_3$OD) δ 8.73 (s, 1 H), 7.76 (d, J = 2.6 Hz, 1 H), 7.70 (d, J = 5.5 Hz, 1 H), 7.55 (d, J = 4.0 Hz, 1 H), 7.50-7.32 (m, 4 H), 6.92 (dd, J = 2.5, 4.4 Hz, 1 H), 6.83 (d, J = 5.9 Hz, 1 H), 4.95-4.80 (m, 1 H), 4.70-3.70 (br, 5 H), 2.60-2.30 (m, 2 H), 2.22 (s, 3 H); MS: (ES) m/z calculated for C$_{21}$H$_{21}$N$_7$O [M + H]$^+$ 388.2, found 388. |
| | +++ | ++ | Compound 1.119: $^1$H NMR (400 MHz, DMSO) δ 9 41 (s, 1 H), 8.92 (d, J = 7.0 Hz, 1 H), 7.94 (d, J = 7.0 Hz, 2 H), 7.66 (d, J = 7.0 Hz, 2 H), 7.50-7.48 (m, 2 H), 6.94 (d, J = 4.8 Hz, 1 H), 6.82 (d, J = 4.4 Hz, 1 H), 6.61 (dd, J = 2.6, 4.4 Hz, 1 H), 4.60-4.58 (m, 1 H), 4.10-3.70 (m, 4 H), 2.26-2.10 (m, 2 H); MS: (ES) m/z calculated for C$_{20}$H$_{18}$ClN$_7$O [M + H]$^+$ 408.2, found 408. |
| | +++ | +++ | Compound 1.120: $^1$H NMR (400 MHz, DMSO) δ 9.38 (s, 1 H), 8.15 (d, J = 7.3 Hz, 1 H), 7.74 (t, J = 7.7 Hz, 2 H), 7.65 (t, J = 7.7 Hz, 2 H), 7.54-7.48 (m, 2 H), 6.95 (d, J = 4.8 Hz, 1 H), 6.83 (d, J = 4.0 Hz, 1 H), 6.62 (dd, J = 2.6, 4.0 Hz, 1 H), 4.62-4.58 (m, 1 H), 4.10-3.80 (m, 4 H), 2.28-2.10 (m, 2 H); MS: (ES) m/z calculated for C$_{20}$H$_{18}$ClN$_7$O [M + H]$^+$ 375.2, found 375. |
| | +++ | +++ | Compound 1.121: $^1$H NMR (400 MHz, DMSO) δ 9.40 (s, 1 H), 8.15 (d, J = 7.0 Hz, 2 H), 7.87 (s, 1 H), 7.76-7.68 (m, 2 H), 7.65 (t, J = 8.0 Hz, 1 H), 7.50 (s, 1 H), 7.26 (d, J = 4.4 Hz, 1 H), 4.62-4.58 (m, 1 H), 4.50-3.80 (br, 4 H), 2.38-2.10 (m, 2 H); MS: (ES) m/z calculated for C$_{19}$H$_{17}$N$_7$O$_2$ [M + H]$^+$ 376 2, found 376. |
| | +++ | +++ | Compound 1.122: $^1$H NMR (400 MHz, DMSO) δ 9.20 (s, 1 H), 8.71 (s, 1 H), 8.63 (d, J = 7.0 Hz, 1 H), 8.07-8.03 (m, 2 H), 7.75 (d, J = 4.4 Hz, 1 H), 7.38 (t, J = 9.0 Hz, 2 H), 7.29 (d, J = 4.4 Hz, 1 H), 4.70-3.50 (br, 5 H), 2.38-2.10 (m, 2 H); MS: (ES) m/z calculated for C$_{19}$H$_{16}$FN$_7$O$_2$ [M + H]$^+$ 394.2, found 394. |

TABLE 1-continued

Specific Examples

| Structure | Avg Bind IC50 (nM) | Avg Ser IC50 (nM) | NMR and MS Data |
|---|---|---|---|
| 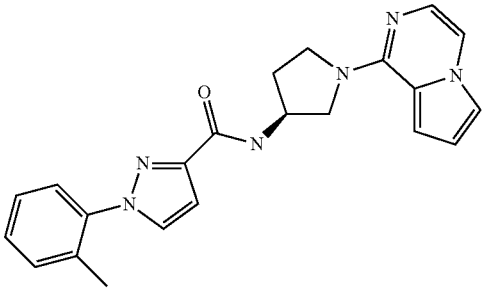 [SMILES: Cc1ccccc1-n1ccc(C(=O)N[C@H]2CCN(c3nccn4cccc34)C2)n1] | +++ | +++ | Compound 1.123: ¹H NMR (400 MHz, CD$_3$OD) δ 8.62 (d, J = 5.9 Hz, 1 H), 7.88 (d, J = 2.5 Hz, 1 H), 7.75 (s, 1 H), 7.70 (d, J = 5.9 Hz, 1 H), 7.54 (d, J = 3.6 Hz, 1 H), 7.40-7.25 (m, 4 H), 6.94 (d, J = 2.2 Hz, 1 H), 6.91 (dd, J = 2.6, 4.4 Hz, 1 H), 6.82 (d, J = 5.5 Hz, 1 H), 4.95-3.65 (br, 5 H), 2.58-2.30 (m, 2 H), 2.20 (s, 3 H); MS: (ES) m/z calculated for C$_{22}$H$_{22}$N$_6$O [M + H]$^+$ 387.2, found 387. |
| 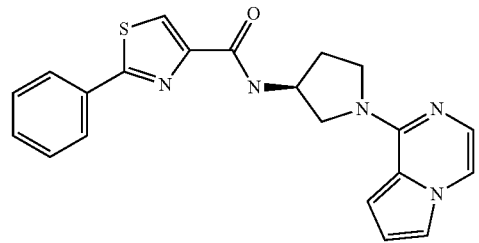 [SMILES: O=C(N[C@H]1CCN(c2nccn3cccc23)C1)c1csc(-c2ccccc2)n1] | +++ | +++ | Compound 1.124: ¹H NMR (400 MHz, CD$_3$OD) δ 8.87 (d, J = 6.7 Hz, 1 H), 8.26 (s, 1 H), 8.07-8.01 (m, 2 H), 7.79 (dd, J = 1.2, 2.7 Hz, 1 H), 7.74 (d, J = 5.5 Hz, 1 H), 7.59 (d, J = 4.3 Hz, 1 H), 7.51-7.46 (m, 3 H), 6.95 (dd, J = 2.3, 4.4 Hz, 1 H), 6.87 (d, J = 5.5 Hz, 1 H), 4.95-3.65 (br, 5 H), 2.60-2.38 (m, 2 H); MS: (ES) m/z calculated for C$_{21}$H$_{19}$N$_5$OS [M + H]$^+$ 390.2, found 390. |
| 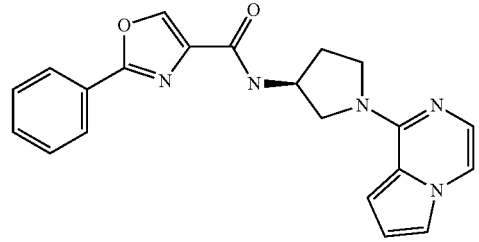 [SMILES: O=C(N[C@H]1CCN(c2nccn3cccc23)C1)c1coc(-c2ccccc2)n1] | +++ | +++ | Compound 1.125: ¹H NMR (400 MHz, CD$_3$OD) δ 8.76 (d, J = 6.6 Hz, 1 H), 8.49 (s, 1 H), 8.10-8.06 (m, 2 H), 7.79 (dd, J = 1.2, 2.4 Hz, 1 H), 7.74 (d, J = 5.5 Hz, 1 H), 7.59-7.50 (m, 4 H), 6.95 (dd, J = 2.7, 4.2 Hz, 1 H), 6.87 (d, J = 5.4 Hz, 1 H), 4.95-3.65 (br, 5 H), 2.60-2.30 (m, 2 H); MS: (ES) m/z calculated for C$_{21}$H$_{19}$N$_5$O$_2$ [M + H]$^+$ 374.2, found 374. |
| 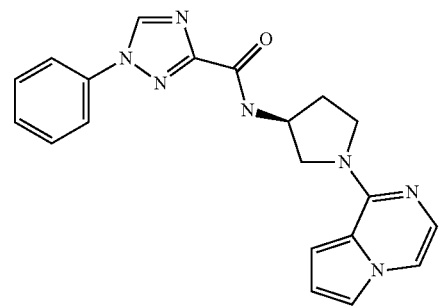 [SMILES: O=C(N[C@H]1CCN(c2nccn3cccc23)C1)c1ncn(-c2ccccc2)n1] | +++ | +++ | Compound 1.126: ¹H NMR (400 MHz, DMSO) δ 11.55 (s, 1 H), 9.35 (s, 1 H), 9.11 (d, J = 7.0 Hz, 2 H), 7.85-7.75 (m, 4 H), 7.55-7.35 (m, 4 H), 6.90-6.80 (m, 2 H), 4.80-3.60 (br, 5 H), 2.38-2.10 (m, 2 H); MS: (ES) m/z calculated for C$_{20}$H$_{19}$N$_7$O [M + H]$^+$ 374.2, found 374. |
| 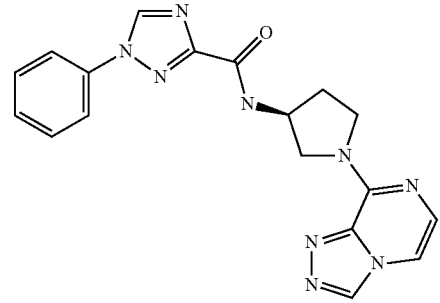 [SMILES: O=C(N[C@H]1CCN(c2nccn3cnnc23)C1)c1ncn(-c2ccccc2)n1] | +++ | +++ | Compound 1.127: ¹H NMR (400 MHz, DMSO) δ 9.40 (s, 1 H), 9.20 (s, 1 H), 9.00 (d, J = 7.0 H, 1 H), 7.90 (d, J = 8.0 Hz, 2H), 7.75 (d, J = 4.7 Hz, 1 H), 7.59 (t, J = 7.3 Hz, 2 H), 7.46 (t, J = 7.3 Hz, 1 H), 7.29 (d, J = 4.4 Hz, 1 H), 4.70-3.50 (br, 5 H), 2.38-2.10 (m, 2 H); MS: (ES) m/z calculated for C$_{18}$H$_{17}$N$_9$O (M + H]$^+$ 4 376.2, found 376. |

TABLE 1-continued

Specific Examples

| Structure | Avg Bind IC50 (nM) | Avg Ser IC50 (nM) | NMR and MS Data |
|---|---|---|---|
| 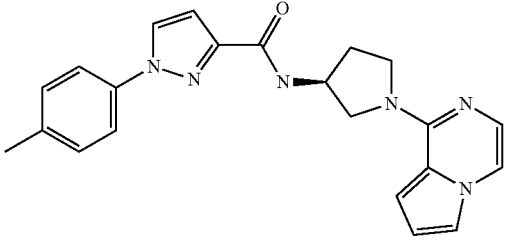 | +++ | +++ | Compound 1.128: $^1$H NMR (400 MHz, CD$_3$OD) δ 8.26 (s, 1 H), 7.87 (dd, J = 4.8, 9.2 Hz, 2H), 7.77 (d, J = 2.6 Hz, 1 H), 7.71 (d, J = 5.5 Hz, 1 H), 7.56 (d, J = 4.4 Hz, 1 H), 7.25 (t, J = 9 2 Hz, 2 H), 6.95 (d, J = 2.5 Hz, 1 H), 6.92 (dd, J = 2.6, 4.4 Hz, 1 H), 6.84 (d, J = 5.5 Hz, 1 H), 4.95-3.65 (br, 5 H), 2.58-2.30 (m, 2 H); MS: (ES) m/z calculated for C$_{21}$H$_{19}$FN$_6$O [M + H]$^+$ 391.2, found 391. |
| 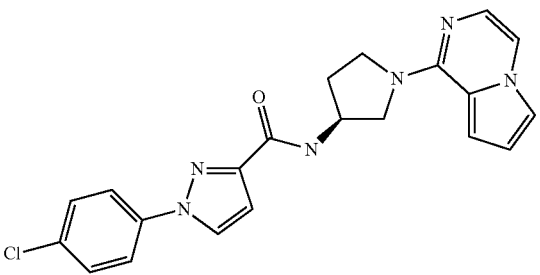 [SMILES: O=C(N[C@H]1CCN(c2nccn3cccc23)C1)c1ccn(-c2ccc(Cl)cc2)n1] | +++ | +++ | Compound 1.129: $^1$H NMR (400 MHz, CD$_3$OD) δ 8.76 (d, J = 6.2 Hz, 1 H), 8.31 (s, 1 H), 7.86 (d, J = 8.8 Hz, 2 H), 7.77 (d, J = 2.5 Hz, 1 H), 7.72 (d, J = 5.5 Hz, 1 H), 7.57 (d, J = 5.5 Hz, 1 H), 7.50 (d, J = 8.8 Hz, 2 H), 6.96 (d, J = 2.5, 1 H), 6.93 (dd, J = 2.6, 7.0 Hz, 1 H), 6.84 (d, J = 5.9 Hz, 1 H), 4.95-4.80 (m, 1 H), 4.70-3.70 (br, 4 H), 2.60-2.30 (m, 2 H); MS: (ES) m/z calculated for C$_{21}$H$_{19}$ClN$_6$O [M + H]$^+$ 407.2, found 407. |

Biological Example 1

To demonstrate that the compounds described above are useful modulators for chemokine binding to CXCR7, the compounds were screened in vitro to determine their ability to displace SDF-1 from the CXCR7 receptor at multiple concentrations. The compounds were combined with cells expressing the CXCR7 receptor (e.g., MCF cells or cells transfected to express CXCR7) in the presence of the 125 I-labeled SDF-1 chemokine as detailed in Determination of IC$_{50}$ values. Reagents and Cells (see below). The ability of the compounds to displace the labeled chemokine from the CXCR7 receptor sites at multiple concentrations was then determined with the screening process.

Compounds that were deemed effective modulators were able to displace at least 50% of the SDF-1 from the CXCR7 receptor at concentrations at or below 15 micromolar (μM) but >2500 nM (+); and more preferably at concentrations from >500 nM to ≤2500 nM (++). At present, especially preferred compounds can displace at least 50% of the SDF-1 from the CXCR7 receptor at concentrations at or below 500 nM (+++). Exemplary compounds that met these criteria are reproduced in Table 1 and the Examples above. In Table 1, Avg Bind IC50 refers to the Buffer Binding Analysis described below, while Avg Ser IC50 refers to the Serum Binding Analysis described below. All compounds were prepared as described in the Examples above, or by related methods substituting readily available starting materials.

1. Determination of IC$_{50}$ values.

Reagents and Cells.

$^{125}$I-labeled SDF-1 was purchased from Perkin-Elmer Life Sciences, Inc. (Boston, Mass.). The MCF-7 (adenocarcinoma; mammary gland) cell line was obtained from the American Type Culture Collection (ATCC, Manassas, Va.) or and was cultured in DMEM (Mediatech, Herndon, Va.) supplemented with 10% fetal bovine serum (FBS) (HyClone Logan, Utah) and bovine insulin (0.01 mg/mL) (Sigma. St. Louis, Mo.) at 37° C. in a humidified incubator at a 5% CO$_2$/air mixture. CXCR7 transfected MDA-MB-435S were produced as described below. MDA-MB-435S human breast cancer line, was purchased from ATCC, and cultured in DMEM/10% FBS medium. The complete coding sequence of the gene encoding CXCR7 (a.k.a. CCXCKR2, hRDC1), was isolated from MCF-7 cells using μMACs mRNA isolation kit (Miltenyi Biotec, Auburn, Calif.). DNA contamination was removed by DNase digestion via RNeasy columns (Qiagen, Inc., Valencia, Calif.) and cDNA was generated using GeneAmp RNA PCR Core Kit (Applied Biosystems, Foster City. Calif.). PCR of cDNA samples was performed using Taq PCR Master Mix kit (Qiagen. Inc.) and hRDC1 primers harboring 5' and 3' Not I sites (hRDC1F 5' GAATGCGGCCGCTATGGATCTGCATCTCTTCGACT-3, hRDC1R 5'-GAATGCGGCCGCTCATTTGGTGCTCT-GCTCCAAG-3') Not I digested PCR product was ligated into Not I digested pcDNA3.1(+)(Invitrogen, Carlsbad, Calif.) and screened for orientation and sequence confirmed. Plasmid DNA was then isolated from overnight bacterial cultures by Maxiprep (Qiagen, Inc.). Plasmid DNA (10 μg) was added to MDA-MB-435s cells and cells were electroporated (0.22 kV, 960 uF) via Gene Pulser (Biorad laboratories, Hercules, Calif.). 48 hr post-electroporation, cells were transferred to selection medium (600 ug/ml G418).

Buffer Binding Analysis.

Target compounds can be tested to determine their ability to bind with CXCR7 sites on MCF-7 and/or MDA-MB-435S CXCR7 transfected cells. Efficiency-maxim/zed radioligand binding using filtration protocols as described in Dairaghi D J, et al., *HHV8-encoded vMIP-I selectively engages chemokine receptor CCR5. Agonist and antagonist profiles of viral chemokines.*, J. Biol. Chem. 1999 Jul. 30; 274(31): 21569-74 and Gosling J. et al., *Cutting edge: identification of a novel chemokine receptor that binds dendritic cell-and T cell-active chemokines including ELC. SLC, and TECK.*, J. Immunol. 2000 Mar. 15; 164(6):2851-6 was used.

In these assays, MCF-7 and/or MDA-MB-435S cells are interrogated with the target compounds and the ability of these compounds to displace $^{125}$I radiolabeled SDF-1 assessed using the protocol described in Dairaghi and Gosling. The target compounds are added to the plate to the indicated concentration and were then incubated with cells followed by the addition of radiolabeled chemokine ($^{125}$I SDF-1) for 3 hr at 4° C. in the following binding medium (25 mM HEPES, 140 mM NaCl, 1 mM CaCl$_2$, 5 mM MgCl$_2$ and 0.2% bovine serum albumin, adjusted to pH 7.1). All assays are then incubated for 3 hrs at 4° C. with gentle agitation. Following incubation in all binding assays, reactions are aspirated onto PEI-treated GF/B glass filters (Packard) using a cell harvester (Packard) and washed twice (25 mM HEPES, 500 mM NaCl, 1 mM CaCl$_2$, 5 mM MgCl$_2$, adjusted to pH 7.1). Scintillant (MicroScint 10, Packard) is added to the wells, and the filters counted in a Packard Topcount scintillation counter. Data are analyzed and plotted using GraphPad Prism (GraphPad Software).

Serum Binding Analysis.

In order to more properly assess the binding efficacy of the compounds, radioligand binding assays were carried out in the presence of 100% human serum to more accurately reflect the in vivo environment. While observed IC50 values are typically lower than those reported for buffer binding assays, the relevance of the assay for ranking of compound efficacy is enhanced. Target compounds were tested to determine their ability to bind with CXCR7 sites on MCF-7 and/or MDA-MB-435S CXCR7 transfected cells. Efficiency-maxim/zed radioligand binding using filtration protocols as described in Dairaghi D J, et al., HHV8-encoded vMIP-I selectively engages chemokine receptor CCR5. Agonist and antagonist profiles of viral chemokines., J. Biol. Chem. 1999 Jul. 30; 274(31): 21569-74 and Gosling J, et al., Cutting edge: identification of a novel chemokine receptor that binds dendritic cell- and T cell-active chemokines including ELC, SLC, and TECK, J. Immunol. 2000 Mar. 15; 164(6):2851-6 was used.

In these assays, MCF-7 and/or MDA-MB-435S cells were interrogated with the target compounds and the ability of these compounds to displace 125 I radiolabeled SDF-1 was assessed using the protocol described in Dairaghi and Gosling. The target compounds were added to the plate to the indicated concentration followed by addition of cells and radiolabeled chemokine (125I SDF-1), both in the following medium (human AB serum with 10 mM HEPES added to stabilize at pH 7.4). All assays were then incubated for 3 hrs at 4° C. with gentle agitation. Following incubation in all binding assays, reactions were aspirated onto PEI-treated GF/B glass filters (Packard) using a cell harvester (Packard) and washed twice (25 mM HEPES, 500 mM NaCl, 1 mM CaCl2, 5 mM MgCl2, adjusted to pH 7.1). Scintillant (MicroScint 10, Packard) was added to the wells, and the filters were counted in a Packard Topcount scintillation counter. Data were analyzed and plotted using GraphPad Prism (GraphPad Software).

Transendothelial Migration Assay:

The compounds of the invention may be further assessed by their ability to inhibit migration of cells in a transendothelial migration assay. In this assay, the ability of a cell to migrate through a layer of endothelial cells towards a chemokine source is analyzed. In one example of this assay 100,000 human umbillic vein endothelial cells (HUVECs, available from Lonza) are plated into the upper chamber of a transwell culture dish with a 5 uM filter pore size (Corning Costar). Medium is added and plates placed in an incubator overnight with 5% CO2 at 37° C. After HUVECs have adhered to the filter overnight to form a monolayer, medium containing chemokine (eg SDF-1, final concentration 10 nM) is added to the lower chamber. Then 500,000 NC-37 cells (available from ATCC) are added to the upper chamber in the presence or absence of the test compound, and plates are returned to the incubator for 3 hours to overnight. Various concentrations of compound may be added to different weels to create a dose response. At the end of this incubation the upper chamber is removed and the cells in the lower chamber are quantified. The cells can be quantified for instance, by labeling with a fluorescent dye such as Cyquant®, (Invitrogen, CA) and then quantifying fluorescence on an appropriate plate reader. Data can be analyzed and plotted using GraphPad Prism (GraphPad Software). The efficacy of the compound is measured as its ability to inhibit the migration of these cells to the lower chamber.

In Vivo Efficacy a) Rabbit Model of Destructive Joint Inflammation

A rabbit LPS study can be conducted essentially as described in Podolin, et al. ibid., Female New Zealand rabbits (approximately 2 kilograms) are treated intra-articularly in both knees with LPS (10 ng). The compound of interest (e.g. formulated in 1% methocel) or vehicle (1% methocel) are dosed orally at a 5 ml/kg dose volume at two times (2 hours before the intra-articular LPS injection and 4 hours after the intra-articular LPS injection). Sixteen hours after the LPS injection, knees are lavaged and cells counts performed. Beneficial effects of treatment are determined by reduction in the number of inflammatory cells recruited to the inflamed synovial fluid of the knee joints. Treatment with the compound of interest results in a significant reduction in recruited inflammatory cells.

b) Evaluation of a Compound of Interest in a Rat Model of Collagen Induced Arthritis A 17 day developing type II collagen arthritis study can be conducted to evaluate the effects of a compound of interest on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3): 857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A compound of interest is dosed daily in a sub-cutaneous manner from day 0 till day 17 at a efficacious dose. Caliper measurements of the ankle joint diameter are taken, and reduced joint swelling is taken as a measure of efficacy.

(c) Evaluation of a Compound of Interest in a Mouse Model of Wound Healing

In the wound healing studies, ICR derived male mice (24±2 g) are used. During the testing period, animals are singly housed in individual cages. Under hexobarbital (90 mg/kg, IP) anesthesia, the shoulder and back region of each animal is shaved. A sharp punch (ID 12 mm) is applied to remove the skin including *panniculus carnosus* and adherent tissues. A test compound or vehicle are each administered topically immediately following cutaneous injury once daily for 10 consecutive days. A positive control, for instance an A2 adenosine receptor agonist (CGS-21680; 10 μg/mouse), may also administered topically daily over the course of the experiment. The wound area, traced onto clear plastic sheets, is measured by use of an Image Analyzer (Life Science Resources Vista, Version 3.0) on days 1, 3, 5, 7, 9 and 11. The percent closure of the wound (%) is calculated, and wound half-closure time (CT50) is determined and analyzed by linear regression using Graph-Pad Prism (Graph Pad Software). Unpaired Student's t test may be applied for comparison between the treated and vehicle groups at each measurement time point. Differences are considered of statistical significance at P<0.05 level.

(d) Evaluation of a Compound of Interest in a Mouse Model of Lung Carcinoma

Many tumor models in animals are known in the art, and may be employed to evaluate a compound of instance. For instance, in a lung carcinoma xenograft study, A549 tumor fragments (30-40 mg) are implanted into the sub cutaneous space in nude mice. Tumors are permitted to grow until approximately 150 mg in size (between 100 and 200 mg) at which point mice are enrolled in the study and treatment begins. Mice are treated with a compound of interest or the vehicle control. Melphalan may be included as a positive control (9 mpk/dose, ip administration, Q4Dx3). Tumors are measured twice weekly with a caliper in two dimensions and converted to tumor mass using the formula for a prolate ellipsoid ($a \times b^2/2$), where a is the longer dimension and b is the shorter dimension, and assuming unit density (1 $mm^3$=1 mg). Body weights may also be measured twice weekly to assess any adverse effects of compound dosing. Antitumor activity is assessed by the delay in tumor growth of the treated group in comparison to the vehicle-treated control group.

(e) Rodent Adoptive Transfer Model of Experimental Autoimmune Encephalomyelitis Rodent EAE is an experimental model of multiple sclerosis (MS) that has been widely used for preclinical testing of numerous agents for the treatment of relapsing remitting and progressive MS. The hallmarks of this model are reliable onset and progression of robust, easily measurable paralysis of tail and limbs, neuronal inflammation, marked demyelination in response to neural antigens.

Mice are injected with the appropriate neuronal antigen (e.g. mylin basic protein, myelin oligodendrocyte glycoprotein, proteolipid protein) in complete Freunds adjuvant at day 0. Immune cells are harvested post CFA/antigen injections and stimulated ex vivo with cytokines and neuronal antigen, to generate a T-cell line with specificity for the neuronal antigen. These cells are then transferred into recipient mice. A compound of interest is dosed daily in a sub-cutaneous, intra-peritoneally, or oral manner from day 0 till end of study at an efficacious dose. Daily observations of degree of paralysis are taken as measures of efficacy.

(f) Evaluation of a Compound of Interest in a Mouse Model of Glioblastoma

Many tumor models in animals are known in the art, and may be employed to evaluate a compound of instance. For instance, in a murine glioblastoma model, $1 \times 10^6$ U251MG cells are implanted by stereotactic injection into the into the brains of nude mice. After 20 days tumors are irradiated with between 1-15 Gy of radiation. Following irradiation mice are treated (eg via subcutaneous, intraperitoneal, oral, parenteral or other route) with compound or vehicle control and tumors are allowed to progress. Tumor growth and/or mortality are monitored for the remainder of the study. Tumors are measured twice weekly with a caliper in two dimensions and converted to tumor mass using the formula for a prolate ellipsoid ($a \times b^2/2$), where a is the longer dimension and b is the shorter dimension, and assuming unit density (1 $mm^3$=1 mg). Body weights may also be measured twice weekly to assess any adverse effects of compound dosing. Antitumor activity is assessed by the delay in tumor growth of the treated group in comparison to the vehicle-treated control group.

(g) Evaluation of a Compound of Interest in a Rat Model of Glioblastoma

Many tumor models in animals are known in the art, and may be employed to evaluate a compound of instance. For instance, in a rat C6 model of glioblastoma, $1 \times 10^6$ C6 cells were implanted by stereotactic injection into the into the brains of Sprague-Dawley rats. After 7 days tumors were irradiated with between 5-20 Gy of radiation. Following irradiation rats were treated (eg via subcutaneous, intraperitoneal, oral, parenteral or other route) with compound or vehicle control and tumors are allowed to progress. Animals were followed until death or loss of >20% weight, or removed for tumor induced neurodeficits eg seizures and immobility in according with appropriate regulations and standards. Compound activity was determined by Kaplan Meier analysis of survival and Compound 1.090 in Table 1 had profound antitumor activity as assessed by the delay in tumor growth of the treated group in comparison to the vehicle treated control group.

(h) Evaluation of a Compound of Interest in a Mouse Model of Hypertension

Many models of pulmonary dysfunction and hypertension in animals are known in the art, and may be employed to evaluate a compound of instance. For instance, in a chronic hypoxia-induced pulmonary hypertension model, newborn mice (FVB/NJ) are randomly exposed to normobaric normoxia (Room Air (RA)) or hypoxia (HA) (FiO2=0.12) for 2 weeks. After 1 week of RA or HA, the mice are treated with the compound of interest eg daily subcutaneous injections of a vehicle or compound from postnatal day 7 to day 14. The degree of pulmonary hypertension can be determined by measuring right ventricular systolic pressure (RVSP). Briefly, a thoracotomy is performed and a 25 gauge needle connected a pressure transducer (Gould Instruments, OH) is inserted into the right ventricle and RSVP recorded. Immediately after RVSP measurements the mice are sacrificed, heart removed and dissected. Right ventricular hypertrophy (RVH) is assessed by the ratio of the weight of right ventricle to the left ventricle+septum (RV/LV+S). Improvements in measurements of RSVP and RVH indicate that the candidate compound has therapeutic capacity.

Validation

Compounds that are initially identified as being of interest by any of the foregoing screening methods can be further tested to validate the apparent activity in vivo. Preferably such studies are conducted with suitable animal models. The basic format of such methods involves administering a lead compound identified during an initial screen to an animal that serves as a disease model for humans and then determining if the disease (e.g., cancer, myocardial infarction, wound healing, inflammatory diseases or other diseases associated with CXCR7) is in fact modulated and/or the disease or condition is ameliorated. The animal models utilized in validation studies generally are mammals of any kind. Specific examples of suitable animals include, but are not limited to, primates, mice, rats and zebrafish.

```
SEQUENCE LISTING
CXCR7 coding sequence
                                         SEQ ID NO: 1
ATGGATCTGCATCTCTTCGACTACTCAGAGCCAGGGAACTTCTCGGACAT
CAGCTGGCCATGCAACAGCAGCGACTGCATCGTGGTGGACACGGTGATGT
GTCCCAACATGCCCAACAAAAGCGTCCTGCTCTACACGCTCTCCTTCATT
TACATTTTCATCTTCGTCATCGGCATGATTGCCAACTCCGTGGTGGTCTG
GGTGAATATCCAGGCCAAGACCACAGGCTATGACACGCACTGCTACATCT
TGAACCTGGCCATTGCCGACCTGTGGGTTGTCCTCACCATCCCAGTCTGG
GTGGTCAGTCTCGTGCAGCACAACCAGTGGCCCATGGGCGAGCTCACGTG
CAAAGTCACACACCTCATCTTCTCCATCAACCTCTTCGGCAGCATTTTCT
TCCTCACGTGCATGAGCGTGGACCGCTACCTCTCCATCACCTACTTCACC
AACACCCCCAGCAGCAGGAAGAAGATGGTACGCCGTGTCGTCTGCATCCT
GGTGTGGCTGCTGGCCTTCTGCGTGTCTCTGCCTGACACCTACTACCTGA
AGACCGTCACGTCTGCGTCCAACAATGAGACCTACTGCCGGTCCTTCTAC
CCCGAGCACAGCATCAAGGAGTGGCTGATCGGCATGGAGCTGGTCTCCGT
TGTCTTGGGCTTTGCCGTTCCCTTCTCCATTATCGCTGTCTTCTACTTCC
TGCTGGCCAGAGCCATCTCGGCGTCCAGTGACCAGGAGAAGCACAGCAGC
CGGAAGATCATCTTCTCCTACGTGGTGGTCTTCCTTGTCTGCTGGCTGCC
CTACCACGTGGCGGTGCTGCTGGACATCTTCTCCATCCTGCACTACATCC
CTTTCACCTGCCGGCTGGAGCACGCCCTCTTCACGGCCCTGCATGTCACA
CAGTGCCTGTCGCTGGTGCACTGCTGCGTCAACCCTGTCCTCTACAGCTT
CATCAATCGCAACTACAGGTACGAGCTGATGAAGGCCTTCATCTTCAAGT
ACTCGGCCAAAACAGGGCTCACCAAGCTCATCGATGCCTCCAGAGTCTCA
GAGACGGAGTACTCTGCCTTGGAGCAGAGCACCAAATGA
CXCR7 amino acid sequence
                                         SEQ ID NO: 2
MDLHLFDYSEPGNFSDISWPCNSSDCIVVDTVMCPNMPNKSVLLYTLSFI
YIFIFVIGMIANSVVVWVNIQAKTTGYDTHCYILNLAIADLWVVLTIPVW
VVSLVQHNQWPMGELTCKVTHLIFSINLFGSIFFLTCMSVDRYLSITYFT
NTPSSRKKMVRRVVCILVWLLAFCVSLPDTYYLKTVISASNNETYCRSFY
PEHSIKEWLIGMELVSVVLGFAVPFSIIAVFYFLLARAISASSDQEKHSS
RKIIFSYVVVFLVCWLPYHVAVLLDIFSILHYIPFTCRLEHALFTALHVT
QCLSLVHCCVNPVLYSFINRNYRYELMKAFIFKYSAKTGLTKLIDASRVS
ETEYSALEQSTK CXCR7.2 coding sequence
                                         SEQ ID NO: 3
ATGGATCTGCACCTCTTCGACTACGCCGAGCCAGGCAACTTCTCGGACAT
CAGCTGGCCATGCAACAGCAGCGACTGCATCGTGGTGGACACGGTGATGT
GTCCCAACATGCCCAACAAAAGCGTCCTGCTCTACACGCTCTCCTTCATT
TACATTTTCATCTTCGTCATCGGCATGATTGCCAACTCCGTGGTGGTCTG
GGTGAATATCCAGGCCAAGACCACAGGCTATGACACGCACTGCTACATCT
TGAACCTGGCCATTGCCGACCTGTGGGTTGTCCTCACCATCCCAGTCTGG
GTGGTCAGTCTCGTGCAGCACAACCAGTGGCCCATGGGCGAGCTCACGTG
CAAAGTCACACACCTCATCTTCTCCATCAACCTCTTCAGCGGCATTTTCT
TCCTCACGTGCATGAGCGTGGACCGCTACCTCTCCATCACCTACTTCACC
AACACCCCCAGCAGCAGGAAGAAGATGGTACGCCGTGTCGTCTGCATCCT
GGTGTGGCTGCTGGCCTTCTGCGTGTCTCTGCCTGACACCTACTACCTGA
AGACCGTCACGTCTGCGTCCAACAATGAGACCTACTGCCGGTCCTTCTAC
CCCGAGCACAGCATCAAGGAGTGGCTGATCGGCATGGAGCTGGTCTCCGT
TGTCTTGGGCTTTGCCGTTCCCTTCTCCATTATCGCTGTCTTCTACTTCC
TGCTGGCCAGAGCCATCTCGGCGTCCAGTGACCAGGAGAAGCACAGCAGC
CGGAAGATCATCTTCTCCTACGTGGTGGTCTTCCTTGTCTGCTGGCTGCC
CTACCACGTGGCGGTGCTGCTGGACATCTTCTCCATCCTGCACTACATCC
CTTTCACCTGCCGGCTGGAGCACGCCCTCTTCACGGCCCTGCATGTCACA
CAGTGCCTGTCGCTGGTGCACTGCTGCGTCAACCCTGTCCTCTACAGCTT
CATCAATCGCAACTACAGGTACGAGCTGATGAAGGCCTTCATCTTCAAGT
ACTCGGCCAAAACAGGGCTCACCAAGCTCATCGATGCCTCCAGAGTGTCG
GAGACGGAGTACTCCGCCTTGGAGCAAAACGCCAAGTGA
CXCR7.2 amino acid sequence
                                         SEQ ID NO: 4
MDLHLFDYAEPGNFSDISWPCNSSDCIVVDTVMCPNMPNKSVLLYTLSFI
YIFIFVIGMIANSVVVWVNIQAKTTGYDTHCYILNLAIADLWVVLTIPVW
VVSLVQHNQWPMGELTCKVTHLIFSINLFSGIFFLTCMSVDRYLSITYFT
NTPSSRKKMVRRVVCILVWLLAFCVSLPDTYYLKTVTSASNNETYCRSFY
PEHSIKEWLIGMELVSVVLGFAVPFSIIAVFYFLLARAISASSDQEKHSS
RKIIFSYVVVFLVCWLPYHVAVLLDIFSILHYIPFTCRLEHALFTALHVT
QCLSLVHCCVNPVLYSFINRNYRYELMKAFIFKYSAKTGLTKLIDASRVS
ETEYSALEQNAK CXCR7.3 coding sequence
                                         SEQ ID NO: 5
ATGGATCTGCATCTCTTCGACTACICAGAGCCAGGGAACTTCTCGGACAT
CAGCTGGCCATGCAACAGCAGCGACTGCATCGTGGTGGACACGGTGATGT
GTCCCAACATGCCCAACAAAAGCGTCCTGCTCTACACGCTCTCCTTCATT
TACATTTTCATCTTCGTCATCGGCATGATTGCCAACTCCGTGGTGGTCTG
GGTGAATATCCAGGCCAAGACCACAGGCTATGACACGCACTGCTACATCT
TGAACCTGGCCATTGCCGACCTGTGGGTTGTCCTCACCATCCCAGTCTGG
GTGGTCAGTCTCGTGCAGCACAACCAGTGGCCCATGGGCGAGCTCACGTG
CAAAGTCACACACCTCATCTTCTCCATCAACCTCTTCGGCAGCATTTTCT
```

-continued

TCCTCACGTGCATGAGCGTGGACCGCTACCTCTCCATCACCTACTTCACC

AACACCCCCAGCAGCAGGAAGAAGATGGTACGCCGTGTCGTCTGCATCCT

GGTGTGGCTGCTGGCCTTCTGCGTGTCTCTGCCTGACACCTACTACCTGA

AGACCGTCACGTCTGCGTCCAACAATGAGACCTACTGCCGGTCCTTCTAC

CCCGAGCACAGCATCAAGGAGTGGCTGATCGGCATGGAGCTGGTCTCCGT

TGTCTTGGGCTTTGCCGTTCCCTTCTCCATTGTCGCTGTCTTCTACTTCC

TGCTGGCCAGAGCCATCTCGGCGTCCAGTGACCAGGAGAAGCACAGCAGC

CGGAAGATCATCTTCTCCTACGTGGTGGTCTTCCTTGTCTGCTGGTTGCC

CTACCACGTGGCGGTGCTGCTGGACATCTTCTCCATCCTGCACTACATCC

CTTTCACCTGCCGGCTGGAGCACGCCCTCTTCACGGCCCTGCATGTCACA

CAGTGCCTGTCGCTGGTGCACTGCTGCGTCAACCCTGTCCTCTACAGCTT

CATCAATCGCAACTACAGGTACGAGCTGATGAAGGCCTTCATCTTCAAGT

ACTCGGCCAAAACAGGGCTCACCAAGCTCATCGATGCCTCCAGAGTCTCA

GAGACGGAGTACTCTGCCTTGGAGCAGAGCACCAAATGA

CXCR7.3 amino acid sequence

SEQ ID NO: 6

MDLHLFDYSEPGNFSDISWPCNSSDCIVVDTVMCPNMPNKSVLLYTLSFI

YIFIFVIGMIANSVVVWVNIQAKTTGYDTHCYILNLAIADLWVVLTIPVW

VVSLVQHNQWPMGELTCKVTHLIFSINLFGSIFFLTCMSVDRYLSITYFT

NTPSSRKKMVRRVVCILVWLLAFCVSLPDTYYLKTVTSASNNETYCRSFY

PEHSIKEWLIGMELVSVVLGFAVPFSIVAVFYFLLARAISASSDQEKHSS

RKIIFSYVVVFLVCWLPYHVAVLLDIFSILHYIPFTCRLEHALFTALHVT

QCLSLVHCCVNPVLYSFINRNYRYELMKAFIFKYSAKTGLTKLIDASRVS

ETEYSALEQSTK

CXCR7.4 coding sequence

SEQ ID NO: 7

ATGGATCTGCATCTCTTCGACTACTCAGAGCCAGGGAACTTCTCGGACAT

CAGCTGGCCATGCAACAGCAGCGACTGCATCGTGGTGGACACGGTGATGT

GTCCCAACATGCCCAACAAAAGCGTCCTGCTCTACACGCTCTCCTTCATT

TACATTTTCATCTTCGTCATCGGCATGATTGCCAACTCCGTGGTGGTCTG

GGTGAATATCCAGGCCAAGACCACAGGCTATGACACGCACTGCTACATCT

TGAACCTGGCCATTGCCGACCTGTGGGTTGTCCTCACCATCCCAGTCTGG

GTGGTCAGTCTCGTGCAGCACAACCAGTGGCCCATGGGCGAGCTCACGTG

CAAAGTCACACACCTCATCTTCTCCATCAACCTCTTCGGCAGCATTTTCT

TCCTCACGTGCATGAGCGTGGACCGCTACCTCTCCATCACCTACTTCACC

AACACCCCCAGCAGCAGGAAGAAGATGGTACGCCGTGTCGTCTGCATCCT

GGTGTGGCTGCTGGCCTTCTGCGTGTCTCTGCCTGACACCTACTACCTGA

AGACCGTCACGTCTGCGTCCAACAATGAGACCTACTGCCGGTCCTTCTAC

CCCGAGCACAGCATCAAGGAGTGGCTGATCGGCATGGAGCTGGTCTCCGT

TGTCTTGGGCTTTGCCGTTCCCTTCTCCATTATCGCTGTCTTCTACTTCC

TGCTGGCCAGAGCCATCTCGGCGTCCAGTGACCAGGAGAAGCACAGCAGC

CGGAAGATCATCTTCTCCTACGTGGTGGTCTTCCTTGTCTGCTGGCTGCC

CTACCACGTGGCGGTGCTGCTGGACATCTTCTCCATCCTGCACTACATCC

CTTTCACCTGCCGGCTGGAGCACGCCCTCTTCACGGCCCTGCATGTCACA

CAGTGCCTGTCGCTGGTGCACTGCTGCGTCAACCCTGTCCTCTACAGCTT

CATCAATCGCAACTACAGGTACGAGCTGATGAAGGCCTTCATCTTCAAGT

ACTCGGCCAAAACAGGGCTCACCAAGCTCATCGATGCCTCCAGAGTCTCA

GAGACGGAGTACTCTGCCTTGGAGCAGAGCACCAAATGA

CXCR7.4 amino acid sequence

SEQ ID NO: 8

MDLHLFDYSEPGNFSDISWPCNSSDCIVVDTVMCPNMPNKSVLLYTLSFI

YIFIFVIGMIANSVVVWVNIQAKTTGYDTHCYILNLAIADLWVVLTIPVW

VVSLVQHNQWPMGELTCKVTHLIFSINLFGSIFFLTCMSVDRYLSITYFT

NTPSSRKKMVRRVVCILVWLLAFCVSLPDTYYLKTVTSASNNETYCRSFY

PEHSIKEWLIGMELVSVVLGFAVPFSIIAVFYFLLARAISASSDQEKHSS

RKIIFSYVVVFLVCWLPYHVAVLLDIFSILHYIPFTCRLEHALFTALHVT

QCLSLVHCCVNPVLYSFINRNYRYELMKAFIFKYSAKTGLTKLIDASRVS

ETEYSALEQSTK

CXCR7.5 coding sequence

SEQ ID NO: 9

ATGGATCTGCATCTCTTCGACTACTCAGAGCCAGGGAACTTCTCGGACAT

CAGCTGGCCGTGCAACAGCAGCGACTGCATCGTGGTGGACACGGTGATGT

GTCCCAACATGCCCAACAAAAGCGTCCTGCTCTACACGCTCTCCTTCATT

TACATTTTCATCTTCGTCATCGGCATGATTGCCAACTCCGTGGTGGTCTG

GGTGAATATCCAGGCCAAGACCACAGGCTATGACACGCACTGCTACATCT

TGAACCTGGCCATTGCCGACCTGTGGGTTGTCCTCACCATCCCAGTCTGG

GTGGTCAGTCTCGTGCAGCACAACCAGTGGCCCATGGGCGAGCTCACGTG

CAAAGTCACACACCTCATCTTCTCCATCAACCTCTTCAGCAGCATTTTCT

TCCTCACGTGCATGAGCGTGGACCGCTACCTCTCCATCACCTACTTCACC

AACACCCCCAGCAGCAGGAAGAAGATGGTACGCCGTGTCGTCTGCATCCT

GGTGTGGCTGCTGGCCTTCTGCGTGTCTCTGCCTGACACCTACTACCTGA

AGACCGTCACGTCTGCGTCCAACAATGAGACCTACTGCCGGTCCTTCTAC

CCCGAGCACAGCATCAAGGAGTGGCTGATCGGCATGGAGCTGGTCTCCGT

TGTCTTGGGCTTTGCCGTTCCCTTCTCCATTATCGCTGTCTTCTACTTCC

TGCTGGCCAGAGCCATCTCGGCGTCCAGTGACCAGGAGAAGCACAGCAGC

CGGAAGATCATCTTCTCCTACGTGGTGGTCTTCCTTGTCTGCTGGTTGCC

CTACCACGTGGCGGTGCTGCTGGACATCTTCTCCATCCTGCACTACATCC

CTTTCACCTGCCGGCTGGAGCACGCCCTCTTCACGGCCCTGCATGTCACA

CAGTGCCTGTCGCTGGTGCACTGCTGCGTCAACCCTGTCCTCTACAGCTT

CATCAATCGCAACTACAGGTACGAGCTGATGAAGGCCTTCATCTTCAAGT

ACTCGGCCAAAACAGGGCTCACCAAGCTCATCGATGCCTCCAGATGCTCA

GAGACGGAGTACTCCGCCTTGGAGCAGAGCACCAAATGA

CXCR7.5 amino acid sequence

SEQ ID NO: 10

MDLHLFDYSEPGNFSDISWPCNSSDCIVVDTVMCPNMPNKSVLLYTLSFI

YIFIFVIGMIANSVVVWVNIQAKTTGYDTHCYILNLAIADLWVVLTIPVW

-continued

VVSLVQHNQWPMGELTCKVTHLIFSINLFSSIFFLTCMSVDRYLSITYFT

NTPSSRKKMVRRVVCILVWLLAFCVSLPDTYYLKTVTSASNNETYCRSFY

PEHSIKEWLIGMELVSVVLGFAVPFSIIAVFYFLLARAISASSDQEKHSS

RKIIFSYVVVFLVCWLPYHVAVLLDIFSILHYIPFTCRLEHALFTALHVT

QCLSLVHCCVNPVLYSFINRNYRYELMKAFIFKYSAKTGLTKLIDASRVS

ETEYSALEQSTK

One of ordinary skill in the art will recognize from the provided description, figures, and examples, that modifications and changes can be made to the various embodiments of the invention without departing from the scope of the invention defined by the following claims and their equivalents.

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A pharmaceutical composition comprising a compound having the formula:

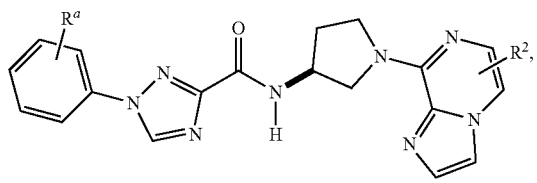

or a pharmaceutically acceptable salt thereof, and a pharmaceutically acceptable excipient, wherein $R^a$ is selected from the group consisting of hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and $-SO_2-C_{1-8}$ alkyl; and $R^2$ is selected from the group consisting of H, halogen, CN, $C_{1-8}$ alkyl, $C_{1-8}$ haloalkyl, $C_{1-8}$ hydroxyalkyl, $-OR^a$, $-CO_2R^a$, $-X-CO_2R^a$, $-NR^aR^b$, $-CONR^aR^b$ and $-X-CONR^aR^b$.

2. The pharmaceutical composition of claim 1, wherein $R^a$ is selected from the group consisting of selected from the group consisting of hydrogen, halogen, cyano, $C_{1-8}$ alkyl and $-SO_2-C_{1-8}$ alkyl.

3. The pharmaceutical composition of claim 1, wherein $R^2$ is selected from the group consisting of H and $C_{1-4}$ alkyl.

4. The pharmaceutical composition of claim 1, wherein $R^a$ is selected from the group consisting of hydrogen, halogen, cyano, $C_{1-8}$ alkyl and $-SO_2-C_{1-8}$ alkyl; and $R^2$ is selected from the group consisting of H and $C_{1-4}$ alkyl.

5. A method of inhibiting the binding of chemokines I-TAC or SDF-1 to a CXCR7 receptor, comprising contacting a compound of formula (I)

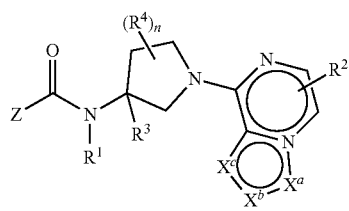

(I)

or a pharmaceutically acceptable salt, hydrate, N-oxide, isotopically enriched or enantiomerically enriched version or a rotamer thereof, wherein each of ring vertices $X^a$, $X^b$ and $X^c$ is independently selected from the group consisting of N, NH, N($R^2$), O, CH and C($R^2$);

the subscript n is 0, 1 or 2;

Z is selected from the group consisting of
(i) monocyclic or fused-bicyclic aryl and heteroaryl, wherein the heteroaryl group has from 1-4 heteroatoms as ring members selected from N, O and S; and wherein said aryl and heteroaryl groups are optionally substituted with from 1 to 5 $R^5$ substituents;
(ii) monocyclic four-, five-, six- or seven-membered ring selected from the group consisting of cycloalkane, and heterocycloalkane, wherein the heterocycloalkane rings have from 1-heteroatoms as ring members selected from N, O and S; and wherein each of said monocyclic Z rings are optionally substituted with from 1 to 3 $R^5$ substituents;

$R^1$ is a member selected from the group consisting of H and $C_{1-8}$ alkyl, wherein the alkyl portion is optionally substituted with halogen, $-NR^aR^b$, $-OR^a$, $-CO_2R^a$, and $-CONR^aR^b$;

each $R^2$ is independently selected from the group consisting of H, halogen, CN, $C_{1-8}$ alkyl, $C_{1-8}$ haloalkyl, $C_{1-8}$ hydroxyalkyl, $-OR^a$, $-CO_2R^a$, $-X-CO_2R^a$, $-NR^aR^b$, $-CONR^aR^b$ and $-X-CONR^aR^b$;

$R^3$ is a member selected from the group consisting of H, $C_{1-8}$ alkyl, $C_{1-8}$ haloalkyl, $C_{1-8}$ hydroxyalkyl, $-CO_2R^a$, $-X-CO_2R^a$, $-CONR^aR^b$ and $-X-CONR^aR^b$;

each $R^4$, when present, is a member independently selected from the group consisting of $C_{1-8}$ alkyl, $C_{1-8}$ haloalkyl, $C_{1-8}$ hydroxyalkyl, $-OR^a$, $-CO_2R^a$, $-X-CO_2R^a$, $-NR^aR^b$, $-CONR^aR^b$ and $-X-CONR^aR^b$;

each $R^5$ is a member independently selected from the group consisting of halogen, CN, $-X-CN$, $C_{1-8}$ alkyl, $C_{3-8}$ cycloalkyl, $C_{3-8}$ cycloalkenyl, $C_{3-5}$ spirocycloalkyl, $C_{2-8}$ alkenyl, $C_{2-8}$ alkynyl, $C_{1-8}$ haloalkyl, $C_{1-8}$ hydroxyalkyl, $-OR^a$, $-CO_2R^a$, $-X-CO_2R^a$, $-NR^aR^b$, $-CONR^aR^b$, $-X-CONR^aR^b$, aryl, 5- or 6-membered heteroaryl, and 3-, 4-, 5- or 6-membered heterocyclic wherein the heteroatoms present as ring vertices of the heteroaryl and heterocyclic rings are selected from N, O and S, and wherein the aryl, heteroaryl and hetereocyclic portions of $R^5$ are optionally further substituted with 1-3 $R^a$;

each $R^a$ and $R^b$ is independently selected from the group consisting of hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and $-SO_2-C_{1-8}$ alkyl;

each X is a $C_{1-4}$ alkylene linking group or a linking group having the formula $-(CH_2)_mO(CH_2)_p-$, wherein the subscripts m and p are integer of from 0 to 5, and m+p is from 0 to 6, wherein any of the methylene portions of X are optionally substituted with one or two methyl groups;

with a cell that expresses the CXCR7 receptor for a time sufficient to inhibit the binding of the chemokines to the CXCR7 receptor.

6. A method for detecting elevated levels of CXCR7 in a sample, said method comprising:
(a) contacting a sample suspected of having elevated levels of CXCR7 with a radiolabeled or detectable form of a compound of Formula (I)

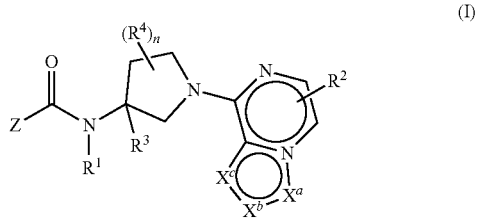

or a pharmaceutically acceptable salt, hydrate, N-oxide, isotopically enriched or enantiomerically enriched version or a rotamer thereof, wherein
each of ring vertices $X^a$, $X^b$ and $X^c$ is independently selected from the group consisting of N, NH, $N(R^2)$, O, CH and $C(R^2)$;
the subscript n is 0, 1 or 2;
Z is selected from the group consisting of
(i) monocyclic or fused-bicyclic aryl and heteroaryl, wherein the heteroaryl group has from 1-4 heteroatoms as ring members selected from N, O and S; and wherein said aryl and heteroaryl groups are optionally substituted with from 1 to 5 $R^5$ substituents;
(ii) monocyclic four-, five-, six- or seven-membered ring selected from the group consisting of cycloalkane, and heterocycloalkane, wherein the heterocycloalkane rings have from 1-heteroatoms as ring members selected from N, O and S; and wherein each of said monocyclic Z rings are optionally substituted with from 1 to 3 $R^5$ substituents;
$R^1$ is a member selected from the group consisting of H and $C_{1-8}$ alkyl, wherein the alkyl portion is optionally substituted with halogen, $-NR^aR^b$, $-OR^a$, $-CO_2R^a$, and $-CONR^aR^b$;
each $R^2$ is independently selected from the group consisting of H, halogen, CN, $C_{1-8}$ alkyl, $C_{1-8}$ haloalkyl, $C_{1-8}$ hydroxyalkyl, $-OR^a$, $-CO_2R^a$, $-X-CO_2R^a$, $-NR^aR^b$, $-CONR^aR^b$ and $-X-CONR^aR^b$;
$R^3$ is a member selected from the group consisting of H, $C_{1-8}$ alkyl, $C_{1-8}$ haloalkyl, $C_{1-8}$ hydroxyalkyl, $-CO_2R^a$, $-X-CO_2R^a$, $-CONR^aR^b$ and $-X-CONR^aR^b$;
each $R^4$, when present, is a member independently selected from the group consisting of $C_{1-8}$ alkyl, $C_{1-8}$ haloalkyl, $C_{1-8}$ hydroxyalkyl, $-OR^a$, $-CO_2R^a$, $-X-CO_2R^a$, $-NR^aR^b$, $-CONR^aR^b$ and $-X-CONR^aR^b$;
each $R^5$ is a member independently selected from the group consisting of halogen, CN, $-X-CN$, $C_{1-8}$ alkyl, $C_{3-8}$ cycloalkyl, $C_{3-8}$ cycloalkenyl, $C_{3-5}$ spirocycloalkyl, $C_{2-8}$ alkenyl, $C_{2-8}$ alkynyl, $C_{1-8}$ haloalkyl, $C_{1-8}$ hydroxyalkyl, $-OR^a$, $-CO_2R^a$, $-X-CO_2R^a$, $-NR^aR^b$, $-CONR^aR^b$, $-X-CONR^aR^b$, aryl, 5- or 6-membered heteroaryl, and 3-, 4-, 5- or 6-membered heterocyclic wherein the heteroatoms present as ring vertices of the heteroaryl and heterocyclic rings are selected from N, O and S, and wherein the aryl, heteroaryl and hetereocyclic portions of $R^5$ are optionally further substituted with 1-3 $R^a$;
each $R^a$ and $R^b$ is independently selected from the group consisting of hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and $-SO_2-C_{1-8}$ alkyl;
each X is a $C_{1-4}$ alkylene linking group or a linking group having the formula $-(CH_2)_mO(CH_2)_p-$, wherein the subscripts m and p are integer of from 0 to 5, and m+p is from 0 to 6, wherein any of the methylene portions of X are optionally substituted with one or two methyl groups;
(b) determining a level of compound that is bound to CXCR7 present in said sample to determine the level of CXCR7 present in said sample; and
(c) comparing the level determined in step (b) with a control sample to determine if elevated levels of CXCR7 are present in said sample.

7. A pharmaceutical composition of claim 1, having the formula:

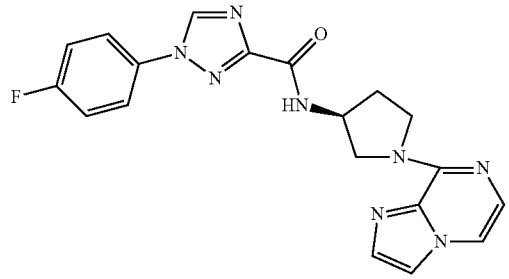 [SMILES: O=C(N[C@H]1CCN(c2nccn3ccnc23)C1)c1ncn(-c2ccc(F)cc2)n1]

or a pharmaceutically acceptable salt thereof.

* * * * *

SEQUENCE LISTING

```
<160> NUMBER OF SEQ ID NOS: 13

<210> SEQ ID NO 1
<211> LENGTH: 1089
<212> TYPE: DNA
<213> ORGANISM: Homo sapiens
<220> FEATURE:
<221> NAME/KEY: CDS
<222> LOCATION: (1)..(1089)
<223> OTHER INFORMATION: G-protein coupled receptor (GPCR) chemokine
      receptor CXCR7, hRDC1, CCXCKR2

<400> SEQUENCE: 1 atg gat ctg cat ctc ttc gac tac tca gag cca ggg aac ttc tcg gac      48
Met Asp Leu His Leu Phe Asp Tyr Ser Glu Pro Gly Asn Phe Ser Asp
1               5                  10                  15 atc agc tgg cca tgc aac agc agc gac tgc atc gtg gtg gac acg gtg      96
Ile Ser Trp Pro Cys Asn Ser Ser Asp Cys Ile Val Val Asp Thr Val
            20                  25                  30 atg tgt ccc aac atg ccc aac aaa agc gtc ctg ctc tac acg ctc tcc     144
Met Cys Pro Asn Met Pro Asn Lys Ser Val Leu Leu Tyr Thr Leu Ser
        35                  40                  45 ttc att tac att ttc atc ttc gtc atc ggc atg att gcc aac tcc gtg     192
Phe Ile Tyr Ile Phe Ile Phe Val Ile Gly Met Ile Ala Asn Ser Val
    50                  55                  60 gtg gtc tgg gtg aat atc cag gcc aag acc aca ggc tat gac acg cac     240
Val Val Trp Val Asn Ile Gln Ala Lys Thr Thr Gly Tyr Asp Thr His
65                  70                  75                  80 tgc tac atc ttg aac ctg gcc att gcc gac ctg tgg gtt gtc ctc acc     288
Cys Tyr Ile Leu Asn Leu Ala Ile Ala Asp Leu Trp Val Val Leu Thr
                85                  90                  95 atc cca gtc tgg gtg gtc agt ctc gtg cag cac aac cag tgg ccc atg     336
Ile Pro Val Trp Val Val Ser Leu Val Gln His Asn Gln Trp Pro Met
            100                 105                 110 ggc gag ctc acg tgc aaa gtc aca cac ctc atc ttc tcc atc aac ctc     384
Gly Glu Leu Thr Cys Lys Val Thr His Leu Ile Phe Ser Ile Asn Leu
        115                 120                 125 ttc ggc agc att ttc ttc ctc acg tgc atg agc gtg gac cgc tac ctc     432
Phe Gly Ser Ile Phe Phe Leu Thr Cys Met Ser Val Asp Arg Tyr Leu
    130                 135                 140 tcc atc acc tac ttc acc aac acc ccc agc agc agg aag aag atg gta     480
Ser Ile Thr Tyr Phe Thr Asn Thr Pro Ser Ser Arg Lys Lys Met Val
145                 150                 155                 160 cgc cgt gtc gtc tgc atc ctg gtg tgg ctg ctg gcc ttc tgc gtg tct     528
Arg Arg Val Val Cys Ile Leu Val Trp Leu Leu Ala Phe Cys Val Ser
                165                 170                 175 ctg cct gac acc tac tac ctg aag acc gtc acg tct gcg tcc aac aat     576
Leu Pro Asp Thr Tyr Tyr Leu Lys Thr Val Thr Ser Ala Ser Asn Asn
```

```
                   180                 185                 190
gag acc tac tgc cgg tcc ttc tac ccc gag cac agc atc aag gag tgg         624
Glu Thr Tyr Cys Arg Ser Phe Tyr Pro Glu His Ser Ile Lys Glu Trp
        195                 200                 205 ctg atc ggc atg gag ctg gtc tcc gtt gtc ttg ggc ttt gcc gtt ccc         672
Leu Ile Gly Met Glu Leu Val Ser Val Val Leu Gly Phe Ala Val Pro
210                 215                 220 ttc tcc att atc gct gtc ttc tac ttc ctg ctg gcc aga gcc atc tcg         720
Phe Ser Ile Ile Ala Val Phe Tyr Phe Leu Leu Ala Arg Ala Ile Ser
225                 230                 235                 240 gcg tcc agt gac cag gag aag cac agc agc cgg aag atc atc ttc tcc         768
Ala Ser Ser Asp Gln Glu Lys His Ser Ser Arg Lys Ile Ile Phe Ser
                245                 250                 255 tac gtg gtg gtc ttc ctt gtc tgc tgg ctg ccc tac cac gtg gcg gtg         816
Tyr Val Val Val Phe Leu Val Cys Trp Leu Pro Tyr His Val Ala Val
            260                 265                 270 ctg ctg gac atc ttc tcc atc ctg cac tac atc cct ttc acc tgc cgg         864
Leu Leu Asp Ile Phe Ser Ile Leu His Tyr Ile Pro Phe Thr Cys Arg
        275                 280                 285 ctg gag cac gcc ctc ttc acg gcc ctg cat gtc aca cag tgc ctg tcg         912
Leu Glu His Ala Leu Phe Thr Ala Leu His Val Thr Gln Cys Leu Ser
290                 295                 300 ctg gtg cac tgc tgc gtc aac cct gtc ctc tac agc ttc atc aat cgc         960
Leu Val His Cys Cys Val Asn Pro Val Leu Tyr Ser Phe Ile Asn Arg
305                 310                 315                 320 aac tac agg tac gag ctg atg aag gcc ttc atc ttc aag tac tcg gcc        1008
Asn Tyr Arg Tyr Glu Leu Met Lys Ala Phe Ile Phe Lys Tyr Ser Ala
                325                 330                 335 aaa aca ggg ctc acc aag ctc atc gat gcc tcc aga gtc tca gag acg        1056
Lys Thr Gly Leu Thr Lys Leu Ile Asp Ala Ser Arg Val Ser Glu Thr
            340                 345                 350 gag tac tct gcc ttg gag cag agc acc aaa tga                            1089
Glu Tyr Ser Ala Leu Glu Gln Ser Thr Lys
        355                 360

<210> SEQ ID NO 2
<211> LENGTH: 362
<212> TYPE: PRT
<213> ORGANISM: Homo sapiens

<400> SEQUENCE: 2

Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

Phe Ile Tyr Ile Phe Ile Phe Val Ile Gly Met Ile Ala Asn Ser Val
    50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
```

```
                130                 135                 140
Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
                195                 200                 205

Leu Ile Gly Met Glu Leu Val Ser Val Val Leu Gly Phe Ala Val Pro
            210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
            275                 280                 285

Leu Glu His Ala Leu Phe Thr Ala Leu His Val Thr Gln Cys Leu Ser
            290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
                340                 345                 350

Glu Tyr Ser Ala Leu Glu Gln Ser Thr Lys
            355                 360

<210> SEQ ID NO 3
<211> LENGTH: 362
<212> TYPE: PRT
<213> ORGANISM: Homo sapiens

<400> SEQUENCE: 3

Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
                20                  25                  30

Met Cys Pro Asn Met Pro Asn Lys Ser Val Leu Leu Tyr Thr Leu Ser
            35                  40                  45

Phe Ile Tyr Ile Phe Ile Phe Val Ile Gly Met Ile Ala Asn Ser Val
        50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
    130                 135                 140
```

| | | | | | | | | | | | | |
|---|---|---|---|---|---|---|---|---|---|---|---|---|
|Ser|Ile|Thr|Tyr|Phe|Thr|Asn|Thr|Pro|Ser|Ser|Arg|Lys|Lys|Met|Val|
|145| | | | |150| | | | |155| | | | |160|

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Phe Leu Val Cys Trp Leu Pro Tyr His Val Ala Val
                260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

<210> SEQ ID NO 4
<211> LENGTH: 1089
<212> TYPE: DNA
<213> ORGANISM: Homo sapiens

<400> SEQUENCE: 4

```
atggatctgc acctcttcga ctacgccgag ccaggcaact tctcggacat cagctggcca      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcagc ggcattttct tcctcacgtg catgagcgtg     420
gaccgctacc tctccatcac ctacttcacc aacacccccca gcagcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggctgcc ctaccacgtg gcggtgctgc tggacatctt ctccatcctg     840
cactacatcc ctttcacctg ccggctggag cacgccctct tcacggccct gcatgtcaca     900
```

```
cagtgcctgt cgctggtgca ctgctgcgtc aaccctgtcc tctacagctt catcaatcgc    960
aactacaggt acgagctgat gaaggccttc atcttcaagt actcggccaa aacagggctc   1020
accaagctca tcgatgcctc cagagtgtcg gagacggagt actccgcctt ggagcaaaac   1080
gccaagtga                                                           1089
```

<210> SEQ ID NO 5
<211> LENGTH: 362
<212> TYPE: PRT
<213> ORGANISM: Homo sapiens

<400> SEQUENCE: 5

```
Met Asp Leu His Leu Phe Asp Tyr Ala Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

Phe Ile Tyr Ile Phe Ile Phe Val Ile Gly Met Ile Ala Asn Ser Val
50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Ser Gly Ile Phe Phe Leu Thr Cys Met Ser Val Asp Arg Tyr Leu
130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
        290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335
```

Lys Thr Gly Leu Thr Lys Leu Ile Asp Ala Ser Arg Val Ser Glu Thr
            340                 345                 350

Glu Tyr Ser Ala Leu Glu Gln Asn Ala Lys
        355                 360

<210> SEQ ID NO 6
<211> LENGTH: 1089
<212> TYPE: DNA
<213> ORGANISM: Homo sapiens

<400> SEQUENCE: 6

```
atggatctgc atctcttcga ctactcagag ccagggaact tctcggacat cagctggcca      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcggc agcattttct tcctcacgtg catgagcgtg     420
gaccgctacc tctccatcac ctacttcacc aacacccccca gcagcaggaa gaagatggta    480
cgccgtgtcg tctgcatcct ggtgtggctg ctggccttct gcgtgtctct gcctgacacc     540
tactacctga gaccgtcac gtctgcgtcc aacaatgaga cctactgccg tcccttctac     600
cccgagcaca gcatcaagga gtggctgatc ggcatggagc tggtctccgt tgtcttgggc     660
tttgccgttc ccttctccat tgtcgctgtc ttctacttcc tgctggccag agccatctcg     720
gcgtccagtg accaggagaa gcacagcagc cggaagatca tcttctccta cgtggtggtc     780
ttccttgtct gctggttgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa aacgggctc    1020
accaagctca tcgatgcctc cagagtctca gagacggagt actctgcctt ggagcagagc   1080
accaaatga                                                            1089
```

<210> SEQ ID NO 7
<211> LENGTH: 362
<212> TYPE: PRT
<213> ORGANISM: Homo sapiens

<400> SEQUENCE: 7

Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

Phe Ile Tyr Ile Phe Ile Phe Val Ile Gly Met Ile Ala Asn Ser Val
    50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

```
Ile Pro Val Trp Val Val Ser Leu Val Gln His Asn Gln Trp Pro Met
            100                 105                 110
Gly Glu Leu Thr Cys Lys Val Thr His Leu Ile Phe Ser Ile Asn Leu
        115                 120                 125
Phe Gly Ser Ile Phe Phe Leu Thr Cys Met Ser Val Asp Arg Tyr Leu
    130                 135                 140
Ser Ile Thr Tyr Phe Thr Asn Thr Pro Ser Ser Arg Lys Lys Met Val
145                 150                 155                 160
Arg Arg Val Val Cys Ile Leu Val Trp Leu Leu Ala Phe Cys Val Ser
                165                 170                 175
Leu Pro Asp Thr Tyr Tyr Leu Lys Thr Val Thr Ser Ala Ser Asn Asn
            180                 185                 190
Glu Thr Tyr Cys Arg Ser Phe Tyr Pro Glu His Ser Ile Lys Glu Trp
        195                 200                 205
Leu Ile Gly Met Glu Leu Val Ser Val Val Leu Gly Phe Ala Val Pro
    210                 215                 220
Phe Ser Ile Val Ala Val Phe Tyr Phe Leu Leu Ala Arg Ala Ile Ser
225                 230                 235                 240
Ala Ser Ser Asp Gln Glu Lys His Ser Ser Arg Lys Ile Ile Phe Ser
                245                 250                 255
Tyr Val Val Val Phe Leu Val Cys Trp Leu Pro Tyr His Val Ala Val
            260                 265                 270
Leu Leu Asp Ile Phe Ser Ile Leu His Tyr Ile Pro Phe Thr Cys Arg
        275                 280                 285
Leu Glu His Ala Leu Phe Thr Ala Leu His Val Thr Gln Cys Leu Ser
    290                 295                 300
Leu Val His Cys Cys Val Asn Pro Val Leu Tyr Ser Phe Ile Asn Arg
305                 310                 315                 320
Asn Tyr Arg Tyr Glu Leu Met Lys Ala Phe Ile Phe Lys Tyr Ser Ala
                325                 330                 335
Lys Thr Gly Leu Thr Lys Leu Ile Asp Ala Ser Arg Val Ser Glu Thr
            340                 345                 350
Glu Tyr Ser Ala Leu Glu Gln Ser Thr Lys
        355                 360

<210> SEQ ID NO 8
<211> LENGTH: 1089
<212> TYPE: DNA
<213> ORGANISM: Homo sapiens

<400> SEQUENCE: 8
atggatctgc atctcttcga ctactcagag ccagggaact tctcggacat cagctggcca      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcggc agcatttttct tcctcacgtg catgagcgtg     420
gaccgctacc tctccatcac ctacttcacc aacaccccca gcagcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg gtccttctac     600
```

```
cccgagcaca gcatcaagga gtggctgatc ggcatggagc tggtctccgt tgtcttgggc    660
tttgccgttc ccttctccat tatcgctgtc ttctacttcc tgctggccag agccatctcg    720
gcgtccagtg accaggagaa gcacagcagc cggaagatca tcttctccta cgtggtggtc    780
ttccttgtct gctggctgcc ctaccacgtg gcggtgctgc tggacatctt ctccatcctg    840
cactacatcc ctttcacctg ccggctggag cacgccctct tcacggccct gcatgtcaca    900
cagtgcctgt cgctggtgca ctgctgcgtc aaccctgtcc tctacagctt catcaatcgc    960
aactacaggt acgagctgat gaaggccttc atcttcaagt actcggccaa acagggctc    1020 accaagctca tcgatgcctc cagagtctca gagacggagt actctgcctt ggagcagagc    1080
accaaatga                                                            1089
```

<210> SEQ ID NO 9
<211> LENGTH: 362
<212> TYPE: PRT
<213> ORGANISM: Homo sapiens

<400> SEQUENCE: 9

```
Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
                20                  25                  30

Met Cys Pro Asn Met Pro Asn Lys Ser Val Leu Leu Tyr Thr Leu Ser
            35                  40                  45

Phe Ile Tyr Ile Phe Ile Phe Val Ile Gly Met Ile Ala Asn Ser Val
        50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285
```

Leu Glu His Ala Leu Phe Thr Ala Leu His Val Thr Gln Cys Leu Ser
            290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
            355                 360

<210> SEQ ID NO 10
<211> LENGTH: 1089
<212> TYPE: DNA
<213> ORGANISM: Homo sapiens

<400> SEQUENCE: 10

```
atggatctgc atctcttcga ctactcagag ccagggaact tctcggacat cagctggccg      60
tgcaacagca gcgactgcat cgtggtggac acggtgatgt gtcccaacat gcccaacaaa     120
agcgtcctgc tctacacgct ctccttcatt tacatttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcagc agcattttct tcctcacgtg catgagcgtg     420
gaccgctacc tctccatcac ctacttcacc aacaccccca gcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg tccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggttgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa aacgggctc    1020
accaagctca tcgatgcctc cagagtctca gagacggagt actccgcctt ggagcagagc    1080
accaaatga                                                            1089
```

<210> SEQ ID NO 11
<211> LENGTH: 362
<212> TYPE: PRT
<213> ORGANISM: Homo sapiens

<400> SEQUENCE: 11

Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

```
Phe Ile Tyr Ile Phe Ile Phe Val Ile Gly Met Ile Ala Asn Ser Val
         50                  55                  60
Val Val Trp Val Asn Ile Gln Ala Lys Thr Thr Gly Tyr Asp Thr His
 65                  70                  75                  80
Cys Tyr Ile Leu Asn Leu Ala Ile Ala Asp Leu Trp Val Val Leu Thr
                 85                  90                  95
Ile Pro Val Trp Val Val Ser Leu Val Gln His Asn Gln Trp Pro Met
            100                 105                 110
Gly Glu Leu Thr Cys Lys Val Thr His Leu Ile Phe Ser Ile Asn Leu
            115                 120                 125
Phe Ser Ser Ile Phe Phe Leu Thr Cys Met Ser Val Asp Arg Tyr Leu
130                 135                 140
Ser Ile Thr Tyr Phe Thr Asn Thr Pro Ser Ser Arg Lys Lys Met Val
145                 150                 155                 160
Arg Arg Val Val Cys Ile Leu Val Trp Leu Leu Ala Phe Cys Val Ser
                165                 170                 175
Leu Pro Asp Thr Tyr Tyr Leu Lys Thr Val Thr Ser Ala Ser Asn Asn
            180                 185                 190
Glu Thr Tyr Cys Arg Ser Phe Tyr Pro Glu His Ser Ile Lys Glu Trp
            195                 200                 205
Leu Ile Gly Met Glu Leu Val Ser Val Val Leu Gly Phe Ala Val Pro
210                 215                 220
Phe Ser Ile Ile Ala Val Phe Tyr Phe Leu Leu Ala Arg Ala Ile Ser
225                 230                 235                 240
Ala Ser Ser Asp Gln Glu Lys His Ser Ser Arg Lys Ile Ile Phe Ser
                245                 250                 255
Tyr Val Val Val Phe Leu Val Cys Trp Leu Pro Tyr His Val Ala Val
            260                 265                 270
Leu Leu Asp Ile Phe Ser Ile Leu His Tyr Ile Pro Phe Thr Cys Arg
            275                 280                 285
Leu Glu His Ala Leu Phe Thr Ala Leu His Val Thr Gln Cys Leu Ser
290                 295                 300
Leu Val His Cys Cys Val Asn Pro Val Leu Tyr Ser Phe Ile Asn Arg
305                 310                 315                 320
Asn Tyr Arg Tyr Glu Leu Met Lys Ala Phe Ile Phe Lys Tyr Ser Ala
                325                 330                 335
Lys Thr Gly Leu Thr Lys Leu Ile Asp Ala Ser Arg Val Ser Glu Thr
            340                 345                 350
Glu Tyr Ser Ala Leu Glu Gln Ser Thr Lys
            355                 360
```

<210> SEQ ID NO 12
<211> LENGTH: 35
<212> TYPE: DNA
<213> ORGANISM: Artificial Sequence
<220> FEATURE:
<223> OTHER INFORMATION: synthetic hRDC1 primer hRCD1F

<400> SEQUENCE: 12
gaatgcggcc gctatggatc tgcatctctt cgact                              35

<210> SEQ ID NO 13
<211> LENGTH: 34
<212> TYPE: DNA

```
<213> ORGANISM: Artificial Sequence
<220> FEATURE:
<223> OTHER INFORMATION: synthetic hRDC1 primer hRCD1R

<400> SEQUENCE: 13
gaatgcggcc gctcatttgg tgctctgctc caag                           34
```